US 8,236,300 B2

(12) United States Patent
Sehgal et al.

(10) Patent No.: US 8,236,300 B2
(45) Date of Patent: *Aug. 7, 2012

(54) IN VIVO AND EX VIVO GENE TRANSFER INTO RENAL TISSUE USING GUTLESS ADENOVIRUS VECTORS

(75) Inventors: Lakshman R. Sehgal, Monarch Beach, CA (US); Jonathan Wong, Palot Alto, CA (US)

(73) Assignee: Biovec, LLC, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/023,322

(22) Filed: Feb. 8, 2011

(65) Prior Publication Data

US 2011/0196023 A1 Aug. 11, 2011

Related U.S. Application Data

(63) Continuation of application No. 12/778,360, filed on May 12, 2010, now Pat. No. 8,048,410, which is a continuation of application No. 12/320,434, filed on Jan. 26, 2009, which is a continuation-in-part of application No. 11/650,478, filed on Jan. 8, 2007, now Pat. No. 7,501,114, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
*A01K 63/00* (2006.01)
*A61K 39/325* (2006.01)
*C07H 21/04* (2006.01)

(52) U.S. Cl. .................. 424/93.6; 424/233.1; 424/23.5; 424/24.1; 424/24.2

(58) Field of Classification Search ........................ None
See application file for complete search history.

(56) References Cited

U.S. PATENT DOCUMENTS

| | | | |
|---|---|---|---|
| 4,826,811 A | 5/1989 | Sehgal et al. |
| 4,868,116 A | 9/1989 | Morgan et al. |
| 5,061,688 A | 10/1991 | Beissinger et al. |
| 5,339,346 A | 8/1994 | White |
| 5,438,041 A | 8/1995 | Zheng et al. |
| 5,449,614 A | 9/1995 | Danos et al. |
| 5,466,668 A | 11/1995 | Glaser et al. |
| 5,639,625 A | 6/1997 | Carson et al. |
| 5,661,033 A | 8/1997 | Ho et al. |
| 5,827,824 A | 10/1998 | Light et al. |
| 5,863,760 A | 1/1999 | Light et al. |
| 5,869,230 A | 2/1999 | Sukhatme |
| 5,916,874 A | 6/1999 | Fujiwara et al. |
| 5,919,619 A | 7/1999 | Tullis |
| 5,981,225 A | 11/1999 | Kochanek et al. |
| 5,985,846 A | 11/1999 | Kochanek et al. |
| 5,994,132 A | 11/1999 | Chamberlain et al. |
| 6,083,750 A | 7/2000 | Chamberlain et al. |
| 6,207,455 B1 | 3/2001 | Chang |
| 6,290,949 B1 | 9/2001 | French et al. |
| 6,328,958 B1 | 12/2001 | Amalfitano et al. |
| 6,334,194 B1 | 12/2001 | Hihara |
| 6,335,011 B1 | 1/2002 | Podsakoff et al. |
| 6,342,214 B1 | 1/2002 | Tryggvason et al. |
| 6,888,047 B1 | 5/2005 | Wu et al. |
| 7,132,277 B1 | 11/2006 | Bett et al. |
| 7,160,539 B2 | 1/2007 | Munn et al. |
| 7,179,459 B2 | 2/2007 | Sehgal et al. |
| 7,481,998 B2 | 1/2009 | Sehgal et al. |
| 7,501,114 B2 | 3/2009 | Sehgal et al. |
| 7,687,058 B2 | 3/2010 | Sehgal et al. |
| 2002/0068713 A1 | 6/2002 | Rade et al. |
| 2002/0081695 A1 | 6/2002 | Bednarik et al. |
| 2002/0193336 A1 | 12/2002 | Elkins et al. |
| 2003/0003077 A1 | 1/2003 | Armendariz Borunda et al. |
| 2003/0185801 A1 | 10/2003 | Vogels et al. |
| 2004/0198683 A1 | 10/2004 | Sehgal et al. |
| 2005/0106124 A1 | 5/2005 | Sehgal et al. |
| 2007/0184027 A1 | 8/2007 | Seghal et al. |
| 2008/0318882 A1 | 12/2008 | Wang et al. |

FOREIGN PATENT DOCUMENTS

| | | |
|---|---|---|
| WO | 96/06933 A1 | 3/1996 |
| WO | 99/14346 A1 | 3/1999 |
| WO | 00/46360 A1 | 8/2000 |
| WO | 01/29058 A1 | 4/2001 |
| WO | 2004/050844 A2 | 6/2004 |

OTHER PUBLICATIONS

Parks, et al., "Effects of stuffer DNA on transgene expression from helper-dependent adenovirus vectors", J. Viral. 70 (10): 8027-8034, Oct. 1999.
GenBank Acc. No. M26434, "Human hypoxanthine phosphoribosyltransferease (HPRT) gene, complete cds", US Natl. Library of Med., Bethesda, MD, USA, Nov. 26, 2001.
Orkin, et al., "Report and Recommendations of the Panel to Assess the NIH Investment in Research on Gene Therapy", US National Institutes of Health, Bethesda, MD, USA, Dec. 7, 1995.
Verma, et al., "Gene therapy—promises, problems and prospects", Nature 389: 239-242,1997.
Rosenberg, et al., "Gene therapist, heal thyself", Science 287: 1751,2000.
Zuckerbraun, B.S., "Vascular gene therapy: a reality of the 21st century", Arch. Surg. 137: 854-861, Jul. 2002.
Esmon, C.T., "Protein C in sepsis", Ann. Med. 34: 598-605, 2002.
Waugh, et al., "Local Overexpression of Thrombomodulin for In Vivo Prevention of Arterial Thrombosis in a Rabbit Model", Circulation Research, vol. 84, No. 1, pp. 84-92, 1999.
Waugh, et al., "Thrombomodulin Overexpression to Limit Neointima Formation", Circulation, vol. 102, No. 3. pp. 332-337, 2000.
Vassalli et al., "Gene therapy for arterial thrombosis", Cardiovascular Research, vol. 19, No. 6, pp. 459-459,1997.

(Continued)

*Primary Examiner* — Richard Schnizer
(74) *Attorney, Agent, or Firm* — Ping Wang, Esq.; Andrews Kurth, LLP

(57) ABSTRACT

A method for treating a renal disease in a subject is disclosed. The method includes administering into a kidney of the subject with an effective amount of a gutless adenoviral vector containing a polynucleotide encoding a therapeutic agent. The gutless adenoviral vector contains the nucleotide sequence of SEQ ID NO:13 or SEQ ID NO:15 and expresses the therapeutic agent in a kidney tissue of the subject.

11 Claims, 18 Drawing Sheets

OTHER PUBLICATIONS

Umana, et al., "Efficient FLPe recombinase enables scalable production of helper-dependent adenoviral vectors with negligible helper-virus contamination", Nature Biotechnology, vol. 19, No. 6, pp. 582-585, 2001.

Wen, et al., "Human Thrombomodulin: Complete eDNA Sequence and Chromosome Localization of the Gene", Biochemistry, vol. 26, pp. 4350-4357, 1987.

Borroni, et al., "Peripheral Blood Abnormalities in Alzheimer Disease: Evidence for Early Endothelial Dysfunction", Alzheimer Disease and Associated Disorders, vol. 16, No. 3, pp. 150-155, 2002.

McKay, et al., "Gene Transfer Therapy in Vascular Disease", Cardiovascular Drug Reviews, vol. 19, No. 3, pp. 245-262, 2001.

Ausbel, et al., (eds) Greene Publishing Associates, "Current Protocols in Molecular Biology", Sections 9.10-9,14.1989.

Ng, et al., "Development of a FLP/fre System for Generating Helper-Dependent Adenoviral Vectors", Molecular Therapy, vol. 3, No. 5, pp. 809-815, 2001.

Bledsoe, et al., "Cytokine production in motor neurons by poliovirus replicon vector gene delivery". Nature Biotechnol., vol. 18. pp. 964-969, 2000.

Chen, et al., "Low-Dose Vaccinia Virus-Mediated Cytokine Gene Therapy of Glioma", Journal of Immunotherapy, vol. D 24, pp. 46-57, 2001.

Chen, et al., "Gene therapy for brain tumors: Regression of experimental gliomas by adenovirus-mediated gene transfer in vivo", Proc. Natl. Acad. Sci. USA, vol. 91, pp. 3054-3057, 1994.

Cui, et al., "Plasmid DNA-Entrapped Nanoparticles Engineered from Microemulsion Precursers: In Vitro and In Vivo Evaluation", Bioconjugate Chem., vol. 13, pp. 1319-1327, 2002.

Curiel, "Strategies to Adapt Adenoviral Vectors for Targeted Delivery", Annals New York Academy of Sciences, vol. 886, pp. 158-171, 1991.

Gossen, et al., "Transcriptional Activation by Tetracyclines in Mammalian Cells", Science, vol. 268, pp. 1766-1769, 1995.

Gossen, et al., "Tight control of gene expression in mammalian cells by tetracycline-responsive promoters", Proc. Natl. Acad. Sci. USA, vol. 89, pp. 5547-5551, 1992.

Fink, et al., "Gene Transfer to Neurons Using Herpes Simplex Virus-Based Vectors", Annual Rev. Neurosci., vol. 19, pp. 265-287, 1996.

Flotte, et al., "Gene Expression from Adeno-associated Virus Vectors in Airway Epithelial Cells", Am. J. Respir. Cell. Mol. Biol., vol. 7, pp. 349-356, 1992.

Green, et al., "A New Scalable Method for the Purification of Recombinant Adenovirus Vectors", Human Gene Therapy, vol. 13, pp. 1921-1934, 2002.

Haj-Ahmand, et al., "Development of a Helper-Independent Human Adenovirus Vector and Its Use in the Transfer of the Herpes Simplex Virus Thymidine Kinase Gene", J. Virol., vol. 57., pp. 267-273, 1986.

Howell, et al., "High-Level Dystrophin Expression After Adenovirus-Mediated Dystrophin Minigene Transfer to Skeletal Muscle of Dystrophic Dogs: Prolongation of Expression with Immunosuppression", Human Gene Therapy, vol. 9, pp. 629-634, 1998.

Kay, et al., "Evidence for gene transfer and expression of factor IX in haemophilia B patients treated with an AAV vector", Nature Genetics, vol. 24, pp. 257-261, 2000.

Kessler, et al., "Gene delivery to skeletal muscle results in sustained expression and systemic delivery of a therapeutic protein", Proc. Natl. Acad. Sci. USA, vol. 96, pp. 14082-14087, 1996.

Kistner, et al., "Doxycycline-mediated quantitative and tissue-specific control of gene expression in transgenic mice", Proc. Natl. Acad. Sci. USA, vol. 93, pp. 10933-10938, 1996.

Magari, et al., "Pharmacologic Control of a Humanized Gene Therapy System Implanted into Nude Mice", J. Clin. Invest., vol. 100, pp. 173-206, 1997.

Miller, "Progress Toward Human Gene Therapy", Blood, vol. 76, pp. 271-278, 1990.

Muzyczka, et al., "Use of Adeno-Associated Virus as a General Transduction Vector for Mammalian Cells", Curro Topics in Micro. and Immunology, vol. 158, pp. 97-129, 1990.

Naldni, et al., "In Vivo Gene Delivery and Stable Transduction of Nondividing Cells by a Lentiviral Vector", Science, vol. 272, pp. 263-267, 1996.

No, et al., "Ecdysone-inducible gene expression in mammalian cells and transgenic mice", Proc. Natl. Acad. Sci. USA, vol. 93, pp. 3346-3351, 1996.

Pruchnic, et al., "The Use of Adeno-Associated Virus to Circumvent the Maturation-Dependent Viral Transduction of Muscle Fibers", Human Gene Therapy, vol. 11, pp. 521-536, 2000.

Ragot, et al., "Efficient adenovirus-mediated transfer of a human minidystrophin gene to skeletal muscle of mdx mice", Nature, vol. 361, pp. 647-650, 1993.

Romano, et al "Latest Developments in Gene Transfer: Achievements, Perspectives, and Controversies Over Therapeutic Applications", Stem Cells, vol. 18, pp. 19-39, 2000.

Ropert, "Liposomes as a gene delivery system", Brazilian Journal of Medical and Biological Research, vol. 32, pp. 163-169, 1999.

Sakhuja, et al., "Optimization of the Generation and Propagation of Gutless Adenoviral Vectors", Human Gene Therapy, vol. 14, pp. 243-254, 2003.

Samulski, et al., "Helper-Free Stocks of Recombinant Adeno-Associated Viruses: Normal Integration Does Not Require Viral Gene Expression", Journal of Virology, vol. 63, No. 9, pp. 3822-3828, 1989.

Schwarze, et al., "In Vivo Protein Transduction Delivery of a Biologically Active Protein into the Mouse", Science, vol. 285, pp. 1569-1572, 1999.

Song, et al., "Sustained secretion of human alpha-1 antitrypsin from murine muscle transduced with adeno-associated virus vectors", Proc. Natl. Acad. Sci. USA, vol. 95, pp. 14348-14384, 1998.

Suzuki, et al., "Structure and expression of human thrombomodulin, a thrombin receptor on endothelium acting as a cofactor for protein C activation", EMBO Journal, vol. 6, pp. 1891-1897, 1987.

Wahlfors, et al., "Evaluation of recombinant alphaviruses as vectors in gene therapy", Gene Therapy, vol. 7, pp. 472-480, 2000.

Wang, et al., "A regulatory system for use in gene transfer", Proc. Natl. Acad. Sci. USA, vol. 91, pp. 8180-8184, 1994.

Wang, et al., "Ligand-inducible and liver-specific target gene expression in transgenic mice", Nature Biotechnology, vol. 15, pp. 239-243, 1997.

Yamashita, et al., "Electroporation-mediated Interleukin-12 Gene Therapy Hepatocellular Carcinoma in the Mice Model", Cancer Research, vol. 61, pp. 1005-1012, 2001.

Ye, et al., "Regulated Delivery of Therapeutic Proteins After In Vivo Somatic Cell Gene Transfer", Science, vol. 283, pp. 88-91, 1999.

Yi, et al., "A Cationic Lipid Emulsion/DNA Complex as a Physically Stable and Serum-Resistant Gene Delivery System", Pharmaceutical Research, vol. 17, No. 3, pp. 314-320, 2000.

Xiao, et al., "Efficient Long-Term Gene Transfer into Muscle Tissue of Immunocompetent Mice by Adeno-Associated Virus Vector", Journal of Virology, vol. 70, No. 11, pp. 8098-8108, 1996.

Xiao, et al., "Adeno-Associated Virus as a Vector for Liver-Directed Gene Therapy", Journal of Virology, vol. 72, No. 12, pp. 10222-10226, 1998.

Zhang, et al., "Long-term expression of human alpha-1 antitrypsin gene in mouse liver achieved by intravenous administration of plasmid DNA using a hydrodynamics-based procedure", Gene Therapy, vol. 7, pp, 1344-1349, 2000

Cui, et al., "Genetic Immunization Using Nanoparticles Engineered from Microemulsion Precursors", Pharmaceutical Research, vol. 19, No. 7, pp. 939-946, 2002.

Kibbe, et al., "Handbook of Pharmaceutical Excipients", 3rd Edition, Pharmaceutical Press London UK, 2000.

Lee, et al., "Crit. Rev. Ther.", Drug Carrier Systems, vol. 14, pp. 173-206, 1997.

Harui, et al., "Vaccination with helper-dependent adenovirus enhances the generation of transgene-specific CTL". Gene Therapy, vol. 11, pp. 1617-1626, 2004.

Johansson, et al., "Adenoviral-Mediated Expression of Porphobilinogen Deaminase in Liver Restores the Metabolic Defect in a Mouse Model of Acute Intermittent Porphyria", Molecular Therapy, vol. 10, pp. 337-343, 2004.

Fu, et al., "Overexpression of SR-BI by Adenoviral Vector Reserves the Fibrate-Induced Hypercholesterolemia of Apolipoprotein E-Deficient Mice", Journal of Biological Chemistry, vol. 278, pp. 52559-52563, 2003.

Brevetti, et al., "Overexpression of endothelial nitric oxide synthase increases skeletal muscle blood flow and oxygenation in severe rat hund limb ischemia", The Society for Vascular Sugery, pp. 820-826, 2003.

Li, et al., J. Vase. Surg. 32: 804-813, 2000.

Tohda, et al., Arteriosclerosis, Thrombosis, and Vascular Biology, 18: 1861-1869, 1998.

Kurosawa, et al., J. Biol. Chem., 263(13): 5993-5996,1988.

Tabuchi, et al., Eur. J. Card. Thor. Surg., 26: 995-1000, 2004.

Miller, et al., Faseb J., 9: 190-199, 1995.

Crystal, Science, 270: 404-410,1995.

Read, et al., Adv. Gen., 53: 19-46, 2005.

Search Result for SEQ 10 No. 13 in U.S. Appl. No. 11/685,474.

Marth, et al., Nature Genetics, 23(4): 452-456, 1999.

Wheelan, et al., Genome Research, 11(11): 1952-1957,2001.

Kibbe, et al., "Gene Therapy for Restenosis", Circ. Res., vol. 86, pp. 829-33, 2000.

Shears, et al., "Efficient Inhibition of Intimal Hyperplasia by Adenovirus-Mediated Inducible Nitric Oxide Synthase Gene Transfer to Rats and Pigs In Vivo", J. Am. Coli. Surg., vol. 187, No. 3, pp. 295-306, 1998.

Ross, "The pathogenesis of atherosclerosis: a perspective for the 1990s", Nature, vol. 362, pp. 801-809. 1993.

Sadler, "Thrombomodulin Structure and Function", Tehomb Haemost, vol. 78, pp. 392-395,1997.

Esmon, "Thrombomodulin as a model of molecular mechanisms that modulate protease specificity and function at the vessel surface", Faseb J., vol. 9, pp. 946-955,1995.

Salomaa, et al., "Soluble thrombomodulin as a predictor of incident coronary heart disease and symptomless carotid artery atherosclerosis in the Atherosclerosis Risk in Communities (ARIC) Study: a case-cohort study", Lancet, vol. 353,pp. 1729-1734, 1999.

Palmer, et al., "Nitric oxide release accounts for the biological activity of enothelium-derived relaxing factor", Nature, vol. 88, pp. 4651-4655,1991.

Kubes, et al., "Nitric oxide: An endogenous modulator of leukocyte adhesion", Proc. Natl. Acad. Sci. USA, vol. 88, pp. 4651-4655.1991.

Steg, et al., "Reduction of Restenosis After Angioplasty in an Atheromatous Rabbit Model by Suicide Gene Therapy", Circulation vol. 96, pp. 401-411,1997.

Van Belle, et al., "Accelerated Endothelialization by Local Deliery of Recombinant Human Vascular Endothelial Growth Factor Reduces In-Stent Intimal Formation", Biochem. and Biophs. Res. Communications, vol. 235, pp. 311-316, 1997.

Salyapongse, et al., "Gene Therapy and Tissue Engineering", Tissue Engineering, vol. 26, No. 4, pp. 663-676,1999.

Kon, et al., "Bone Morphogenetic Protein-2 Stimulates Differentiation of Cultured Spinal Ligament Cells from Patients with Ossification of the Posterior Longitudinal Ligament", Calcif. Tissue Int., vol. 60, pp. 291-296,1997.

Kibbe, et al., J. Vase. Surg., 34: 156-65,2001.

He, et al., PNAS, 95: 2509-2514,1998.

Marmur, et al., "Strand Separation and Specific Recombination in Deoxyribonucleic Acids: Biological Studies", PNAS USA, vol. 46, pp. 453-461,1960.

Doty, et al., "Strand Separation and Specific Recombination in Deoxyribonucleic Acids: Physical Chemical Studies", PNAS USA, vol. 46, pp. 461-476, 1960.

Sambrook, et al., "Analysis of Genomic DNA by Southern Hybridization", Molecular Cloning: A Laboratory Manual, vol. II, pp. 9.31-9.62,1989.

Zushi, et al., "Aspartic acid 349 in the forth epidermal growth factor-like structure of human thrombomodulin plays a role in its Ca(2+)-mediated binding to protein C", The Journal of Biological Chemistry, vol. 266, No. 30, pp. 19886-19889, 1991.

Parks, et al., "A helper-dependent adenovirus vector system: Removal of helper virus by Cre-mediated excision of the viral packaging signal", PNAS, vol. 93, pp. 13565-13570, 1996.

Lieber, at al., "Recombinant Adenoviruses with Large Deletions Generated by Cre-Mediated Excision Exhibit Different Biological Properties Compared with First-Generation Vectors In Vitro and In Vivo", J. Virol., vol. 70, pp. 8944-8960, 1996.

Dittman, et al., "Human Thrombomodulin: Complete eDNA Sequence and Chromosome Localization of the Gene", Biochemistry, vol. 26, pp. 4350-4357,1987.

Beauchamp, et al., "Development of a FLP/frt System for Generating Helper-Dependent Adenoviral Vectors", Molecular Therapy, vol. 3, No. 5, pp. 809-815, 2001.

Nabel, et al., Science, vol. 249, pp. 1285-1288, 1990.

Tsiang, et al., "Functional domains of membrane-bound human thrombomodulin. EGF-like domains four to six and the serine/threonine-rich domain are required for cofactor activity", The Journal of Biological Chemistry. vol. 267. No. 9, pp. 6164-6170, 1992.

Nagashima, et al., "Alanine-scanning mutagenesis of the epidermal growth factor-like domains of human thrombomodulin identifies critical residues for its cofactor activity", The Journal of Biological Chemistry, vol. 268., No. 4,pp. 2888-2892, 1993.

Gerlitz, et al., "Identification of the predominant glycosaminoglycan-attachment site in soluble recombinant human thrombomodulin: potential regulation of functionality by glycosyltransferase competition for serine474", The Biochemical Journal, vol. 295, pp. 131-140,1993.

Lin, et al., "Modulation of glycosaminoglycan additional in naturally expressed and recombinant human thrombomodulin", The Journal of Biological Chemistry, vol. 269, No. 40, pp. 25021-25030,1994.

Adler, et al., "The structure of a 19-residue fragment from the C-loop of the fourth epidermal growth factor-like domain of thrombomodulin", The Journal of Biological Chemistry, vol. 270, No. 40, pp. 23366-23372, 1995.

Weiler-Guettler, et al., "A targeted point mutation in thrombomodulin generated viable mice with a prethrombotic state", The Journal of Clinical Investigation, vol. 101, No. 9, pp. 1983-1991, 1998.

Supplementary European Search Report mailed Aug. 25, 2011 (Application No. EP 07772782.4, based on PCT Application No. PCT/US2007/006371, filed Mar. 14, 2007).

SEQUENCE LISTING

<160> NUMBER OF SEQ ID NOS: 25

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttttg    180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga actagtggat cccccgggct gcaggaattc tgatggctct caaaattcct     420
gcctccttta gggataaaag actttaagac ttttttaacaa aaagaaaaa gaaaaaaaaa     480
attcctgcct cctggtgtac acacacgaa gggttccctc cccttgaatg tgaccaggat     540
ctgtgaaaat aacgggatag ccgctcctgt gattaggtta tgtggtagac tagagcaaga     600
ttctcctgct ggttttgaag aagtcagctg ccatgttgtg agactgtcat gggctagggc     660
atgagccttt aaatatctgg gagcaacccc tggccagcag ccagtgagaa aacgggccct     720
cagtcctaca atcacaagga actaaattct gccaacaacc tgaaggaact ttgaagagga     780
tcatgagtcc cttgattcag cttgatgagc ccctgagcag aggatacagc taacttgtac     840
tagggaagta taaaaaacat gcatgggaat gatatatatc aactttaagg ataattgtca     900
tacttctggg aatgaaggga aagaaatggg gctttagttg tattatgatc tttaatttct     960
caaaaaaaat aagatcagaa gcaaatatgg caaaatgtta atactttgt gggtacgtag     1020
gtattcagca taccctttt tctgagttca aaatatttta taattaaaat gaaatgcagg     1080
ccaggcacag tggctcatgc ctataatacc agcactttgc gaggccgagg tgggaggatg     1140
gcttgaggcc agaccagcct ggccaacatg gcaaacccc atctctactt aaaaaaaaaa     1200
aaactatata tatatatatg tgtgtgtgtg tgtatatata tatgtgtata tatttata     1260
tatgtgtgta tatatatata tgtatatata tttatatatg tgtgtgtata tatatata     1320
cacacacaca catatataca tacatacata cacacacaca cacacacaat tagccaggca     1380
tggtggcgca cacctgtagt cccagctact tgggaggctg agacatgaga attgcttgaa     1440
cctgggaggc agagtagtta gtgagctgag atcataccac tgcactccag cctggtgaca     1500
gagtgagact ctgtcttaaa aaaataaaa attaaaatta aatgcaaaag gtccaagtga     1560
attgaagagg aaagggggtat caaggaaggt tttgtggagg tgacgtttga gctgggtctt     1620
aaatgactta aacatgggat aagaagggag ggaataagga catttcaggt acgagaaata     1680
aggagcaaac agtggaaaca acctaacgtc tgtcaaccag tgaatggata acaaaaatgt     1740
aattcagatg gtatccaact tacgatggtt caacatgaga tttttctgac tttaggatag     1800
atttatcaaa gtagtaaatc catttcaac ttatgatatt ttcaacttca gatgggttta    1860
```

```
tcaggacaca gttgaggaac acctgtctat ccatacaatt tggcaataaa aaggaaatga   1920
gtgcagatat actccacaac atgaatgaac cttgaaaaca ttaagtgaga gaagccagat   1980
acaaaaggcc acatattgta tgattctatt tatacaaaat gtccagaata ggcaaatctt   2040
atagacagca agtaggtaga tgatcagttt gctaggtgct gggggaaggg gaaatgggga   2100
gtgatggcta aggggattgg gtttctttgt ggggcaatga aaatgtttta aaattgagcg   2160
tgataatgat tgcacaatgc tgcatatata tataatctat agattatata tatataaga   2220
gaggctgtta gacagtgata agtgatatat atatatatat acatagagag agagagagag   2280
agagagagag gctgttagtg ataagtgatc aggaaaataa agtattgag gaggaatacg   2340
aagttgacgg tgtgaaaaca tgagatttta ataggatgg ccagggaagg ccttaatgag   2400
aaagtgactt atgagtaaaa caagggatc ctaaaccta gcatgcatca gaatcactcg   2460
gaaacttgtt aaagcatagc ttgctgggcc tcatcacaga tattttgatt cggtaggttc   2520
ttgtctgata ttaatacttt tggtctaggg aaccacattt tgagaaccac tgagctaaag   2580
gaagtaaagg tttcccttag tttactagct ggtaaccta ggaaactgct tagcctctcg   2640
gtgctaagat acaaaatact ttagcacata ataacacatg gaaaatagtc tataaattat   2700
aaatattatt ttttatgtac caaatattac ataagacaaa atctaagcaa gatatata   2760
tatatacata aaatataaga tatatatgta tatattatat atagataaat agagagagag   2820
agttatgttt agaaagaaaa tacttcaaac taaaaaaaga gaggtaggaa gtataccatt   2880
ccattattgg taaaaacaaa ttactaagta gtctttacaa aaaaccaatc tcactccttt   2940
agaacacaag cccaccatta aaactgatgc agaggaattt ctctccctgg cttaccttta   3000
ggatggtgca tactaagtta gaaaagtcat aaatgttata ttaaaagtaa atgtgaactt   3060
acttccacaa tcaagacatt ctagaagaaa aagagaaatg aaaatcagta caatgaataa   3120
aacggtattt ccaattataa gtcaaatcac atcataacaa ccctaaggaa ttatccaaac   3180
tcttgttttt agatgcttta ttatatcaaa ctctccttta aacaagtggc ccatctgctg   3240
ggatttggaa gcctgtaata ctgaaatttt catcataatg gaaatttaa aaacagaatt   3300
tgacccacct gttttaaaa cactttcatt acttaacaag aggtctaatc ttgggcaagt   3360
cttgaaattt ctctggcctt agtttcccat gtgttaaatg aaacttgaag cagttggtct   3420
cttatagtct cctgactcta acattctaag aattatattt gtacaataac tcaaaaatca   3480
cataatttaa tttaccatat ggactccaaa atatattttc tcattaggct aaacttgatc   3540
tgcattttct ggatgtgtcc atattcttgg actacactaa aacatgatac caatgcttcc   3600
tctcaccata aaccctcact tcgctttcta catttaagaa ttttatagct ggaagagtcc   3660
ttaacagaaa ataccatcta ataattaccc ctcaaaatcg agaaagtcct atctgttctt   3720
atgctagtta taagaatgag gcagcatttc acataatggt tataaacact gccacaagaa   3780
gattcatgat gtgttgttta tctgtagctc tcatcatact ctgtcatata actatagcat   3840
taagatttta atgttctata tattcttcta agacagtgtt taccagagta aggcacaaaa   3900
gatccactgg tttgcaagaa agattagaac ttttaaattt tttacctcac cttgtttaat   3960
ctatatttt gtatgtattt tgtaacatat atattattat taccataaat catatataat   4020
ttaaaatgca tatattaggg gtaaatgctc aggaaacttt ttataaattg ggcatgcaaa   4080
tacaagtttg aagactcact gttctaggta ttaaaagtaa agttataacc aagtaaagct   4140
tccacctttt catgtctcaa agcagtttat tgttggaggt aagatctctt agaagcctaa   4200
acaggtccaa gtacagaatg aagtaaggct agcccataac ttgtgcaag caattcatac   4260
```

```
tatttctctc atgctgagct ctcctcagtg aagcagctac tatagacaac tgcagcctat    4320
tggtagccta ttttacaggc aggaaaaaaa ttacttttta ttcaaagtgg aactcaggac    4380
atggggagaa atgaataca aaaaataggg tcaatccaaa ggcacacagc aaatgagtaa    4440
cacagttatg ttttttttccc atttgtatga ggtcccagta aattctaagt aaactgcaaa    4500
tttaataata cactaaaaaa gccatgcaat tgttcaaatg aatcccagca tggtacaagg    4560
agtacagaca ctagagtcta aaaaacaaaa gaatgccatt attgagtttt tgaattatat    4620
caagtagtta catctctact taataaatga gaaaacgag gataagaggc catttgataa    4680
aatgaaaata gccaagaagt ggtattagag acttgaatac aggtattcgg gtccaaagtt    4740
catctgctca atactaact ggggaaaaga gggaaaaata tttatataca tatatatctg    4800
cacacaaaaa taccccccaaa agacaaaatg aggccaggca gggtggctca cacccgtaat    4860
cccggtactt tgggaggctg aggcaggtgg atacctgaga tcaggagttg gagatcagcc    4920
tggtcaacat ggtgaaaccc tgtctctact aaagataaaa aaattagcca ggcatggtgg    4980
cgtgcgcctg taatcccagc tacttgggag tctgaggcag gagaatcact tgaactggga    5040
aggggaggtt gcagtgagcc aagatcgtac tactgcactc cagcctgggc agcagagtga    5100
gactccatca caaaaataaa taaataaata aaatacaatg aaacagaaag ttcaaataat    5160
cccataatct taccaccaag aaataacttt cactcgttat acttattgat ttttccataa    5220
taaatgtact ttactgtgac tatcatgaaa agaaagttat tttagaaaca gagaactgtt    5280
tcagatcaaa tctatgtagt agaacagagc cattaggtgg gaaagacgag atcaaactaa    5340
atctcagaag gcctaaaagg ctaggtccat tccagcacta aaaactgacc agacaagtaa    5400
tggcttcaac agcttctaaa tatggacaaa gcatgctgaa agggaaggac aggtctaaca    5460
gtggtatatg aaatgaacag gaggggcaaa gctcatttct cctctgaagt tttccaaaga    5520
tgctgaggag gacattagtt tgacatgacc ctgatatggg acaagataat ttcacagaag    5580
ttttacatgt taaagttttc ttatagatac tcattcaagt aagcaatgaa cactaaaatc    5640
taaagaaaga aaagagcttt agagtcaggt ctgtattcaa attcaagctc taccacttac    5700
tggttctgtg actttgggca agtctttttaa ccttattaag tcttaatttc ctgatttgta    5760
aaatggggat atcgtctccc tcacaggatt gttgtgaaac ttttatgaga ttaatgcctt    5820
tatatttggc atagtgtaag taaacaataa ctggcagctt caaaaaaaaa aagcagtagc    5880
attccatcat ttattattgg ttactctcaa aaagttttc aatgtactag aagataaata    5940
ttcaaatacc ttaatatctc cattattttc aggtaaacag catgctcctg aacaaccaat    6000
gggtcaacaa ataaattaaa agggaaatct aaaaacatct tgatattaaa ctacatggaa    6060
gcacaatata ccaaaaccaa tggttcacac taggagaatt ttaaggtaca agaaaactct    6120
ttgagatttc ttaaaataat agtatgtctg aatttattga gtgatttacc agaaactgtt    6180
gtaagagctc tacttgcatt atagcactta atcctcttaa ctctatggct gctattatca    6240 acctcacccct aatcacatat gggacacaga gaggttaagt aacttgccca aggtcagagt    6300
taggaagtac taagccatgc tttgaatcag ttgtcaggct ccggaactca cactttcagc    6360
cactacataa tactgctttg ctatcttta ggaaactatg tgagtctacc tcacatagac    6420
tcacataggt ttgttttttt tttttttta aaggctatct tttcccccat caatgttttt    6480
tgaaggatcc caaattagag tcccacagag gcagacagca gtacttgaca atatggacat    6540
ttaaggttaa tgttggattc tactgtcttt ttactacatg acctagggaa cgataattaa    6600
cctagactgc ttccaagggt taaataaccc atttagttat actatgtaaa ttatctctta    6660
```

```
gtgattgatt gaaagcacac tgttactaat tgactcggta tgaagtgctt ttttttcttc    6720
cctttcaaga tacataccct tccagttaaa gttgagagat catctccacc aattactttt    6780
atgtcccctg ttgactggtc attctagtta aaaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt gatgttttta agagtcctaa    7080
aaaatgggtt acatccattt ttaagtgggt agtattataa cagccaccca tcttcaatca    7140
cagtgatttc tgaattgtga gggaagttat tagcatgaca ggtgtctggt tctggccctg    7200
tacgattccc atgagtcaag caaattgtaa gggctggtct atatcacacc caaccccaag    7260
gatatgtccc tcaaaagtct agcccaggcc ccgtcatctt cagcatcatc tgggaaacca    7320
ggtctgatta gtagtccttt aaggaatacc tcttaggctc ccatttttact gctatcacag    7380 aatccaataa aacccttaca ggagattcaa tgggaaatgc tcaacaccca ctgtagttgg    7440
tggtgacaat gaccataatt tggctgtgct ggattcagga cagaaaattt gggtgaaaga    7500
gcaggtgaac aaaagagctt cgacttgccc tagcagagag caagccatac cataccacaa    7560
agccacagca attaacggg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaataaag ccataagtgg actggaagaa aatagagaat tttttttaac    7860
atccgtagaa agggtaaaaa cccaggcatg acatgaacca aaactgaaga ggttctgtaa    7920
caaatacccc ctttttatata ttgggctcca caataagaa cccataggaa aatggagaat    7980
gaacacaaat agacaattta tagaagagaa ggttataagg tgtaaaatta tatctatctg    8040
agaaacaaac actaaacaa tgtgattcta ctgttctccc acccatactg gcaaaactta    8100
agcctgataa tatgctgagg ggaaataagc actcttgttg gtgagagtat taattggcat    8160
agcttctttt gaaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tcttttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca tttttattca    8640
acatttaaac aaatttgtaa cagcaattac atgagtagtg acaatggcgt ttatgagact    8700
tttcactttt atgtgcttct attttttgtta tgcttctata tatacatcca tttattatgg    8760
agtgttactt tcaaaaatca caaatgggcc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
```

```
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttatttt tcttaactct cttgcctggc ctatagccac    9420
catggaagct aataaagaat attaatttaa gagtaatggt atagttcact acattggaat    9480
acaggtataa gtgcctacat tgtacatgaa tggcatacat ggatcaatta ccccaccctgg   9540
gtggccaaag gaactgcgcg aacctccctc cttggctgtc tggaacaagc ttcccactag    9600
atcccttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac ataccccttt aatgtcttta    9840
tttctatttt gtctacctct tcagtctagg tgaaaaaata ggaaggataa tagggaagaa    9900
ctttgtttat gcctacttat ccgcccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggacttt ttttttttatc ggaaaacagt    10260
cattctctca acattcaagc aggccccaag tctaccacac tcaatcacat tttctcttca   10320
tatcataatc tctcaaccat tctctgtcct tttaactgtt tttctatacc ctgatcaaat   10380
gccaacaaaa gtgagaatgt tagaatcatg tattttaga ggtagactgt atctcagata    10440
aaaaaaaagg gcagatattc cattttccaa aatatgtatg cagaaaaaat aagtatgaaa   10500
ggacatatgc tcaggtaaca agttaatttg tttacttgta ttttatgaat tccctaaaac   10560
ctacgtcacc cgccccgttc ccacgccccg cgccacgtca caaactccac cccctcatta   10620
tcatattggc ttcaatccaa aataaggtat attattgatg atgttaatta acatgcatgg   10680
atccatatgc ggtgtgaaat accgcacaga tgcgtaagga gaaataccg catcaggcgc    10740
tcttccgctt cctcgctcac tgactcgctg cgctcggtcg ttcggctgcg gcgagcggta   10800
tcagctcact caaaggcggt aatacggtta tccacagaat caggggataa cgcaggaaag   10860
aacatgtgag caaaaggcca gcaaaaggcc aggaaccgta aaaaggccgc gttgctggcg   10920
ttttccata ggctccgccc ccctgacgag catcacaaaa atcgacgctc aagtcagagg    10980
tggcgaaacc cgacaggact ataaagatac caggcgtttc ccctggaag ctccctcgtg    11040
cgctctcctg ttccgaccct gccgcttacc ggatacctgt ccgcctttct cccttcggga   11100
agcgtggcgc tttctcatag ctcacgctgt aggtatctca gttcggtgta ggtcgttcgc   11160
tccaagctgg gctgtgtgca cgaaccccc gttcagcccg accgctgcgc cttatccggt    11220
aactatcgtc ttgagtccaa cccggtaaga cacgacttat cgccactggc agcagccact   11280
ggtaacagga ttagcagagc gaggtatgta ggcggtgcta cagagttctt gaagtggtgg   11340
cctaactacg gctacactag aaggacagta tttggtatct gcgctctgct gaagccagtt   11400
accttcggaa aaagagttgg tagctcttga tccggcaaac aaaccaccgc tggtagcggt   11460
```

```
ggtttttttg tttgcaagca gcagattacg cgcagaaaaa aaggatctca agaagatcct    11520
ttgatctttt ctacgggtc tgacgctcag tggaacgaaa actcacgtta agggattttg    11580
gtcatgagat tatcaaaaag gatcttcacc tagatccttt taaattaaaa atgaagtttt    11640
aaatcaatct aaagtatata tgagtaaact tggtctgaca gttaccaatg cttaatcagt    11700
gaggcaccta tctcagcgat ctgtctattt cgttcatcca tagttgcctg actcccgtc    11760 gtgtagataa ctacgatacg ggagggctta ccatctggcc ccagtgctgc aatgataccg    11820
cgagacccac gctcaccggc tccagattta tcagcaataa accagccagc cggaagggcc    11880
gagcgcagaa gtggtcctgc aactttatcc gcctccatcc agtctattaa ttgttgccgg    11940
gaagctagag taagtagttc gccagttaat agtttgcgca acgttgttgc cattgctgca    12000
gccatgagat tatcaaaaag gatcttcacc tagatccttt tcacgtagaa agccagtccg    12060
cagaaacggt gctgaccccg gatgaatgtc agctactggg ctatctggac aagggaaaac    12120
gcaagcgcaa agagaaagca ggtagcttgc agtgggctta catggcgata gctagactgg    12180
gcggttttat ggacagcaag cgaaccggaa ttgccagctg gggcgccctc tggtaaggtt    12240
gggaagccct gcaaagtaaa ctggatggct ttcttgccgc caaggatctg atggcgcagg    12300
ggatcaagct ctgatcaaga gacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480 cttttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
gatccggcta cctgcccatt cgaccaccaa gcgaaacatc gcatcgagcg agcacgtact    12780
cggatggaag ccggtcttgt cgatcaggat gatctggacg aagagcatca ggggctcgcg    12840
ccagccgaac tgttcgccag gctcaaggcg agcatgcccg acggcgagga tctcgtcgtg    12900
acccatggcg atgcctgctt gccgaatatc atggtggaaa atggccgctt ttctggattc    12960
atcgactgtg gccggctggg tgtggcggac cgctatcagg acatagcgtt ggctacccgt    13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccaa taggccgaaa tcggcaaaat    13200
cccttataaa tcaaaagaat agaccgagat agggttgagt gttgttccag tttggaacaa    13260
gagtccacta ttaaagaacg tggactccaa cgtcaagggg cgaaaaaccg tctatcaggg    13320
cgatggccca ctacgtgaac catcacccta atcaagtttt tggggtcga ggtgccgtaa    13380 agcactaaat cggaaccctaaagggagccc ccgatttaga gcttgacggg gaaagccggc    13440
gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                      13602
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65              70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
                180                 185                 190

Tyr Gly Thr Pro Phe Ala Ala Arg Gly Ala Asp Phe Gln Ala Leu Pro
    195                 200                 205

Val Gly Ser Ser Ala Ala Val Ala Pro Leu Gly Leu Gln Leu Met Cys
210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
            245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
    275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
            420                 425                 430
```

| | | | | | | | | | | | | | | |
|---|---|---|---|---|---|---|---|---|---|---|---|---|---|---|
| Leu | Asp | Asp | Gly | Phe | Ile | Cys | Thr | Asp | Ile | Asp | Glu | Cys | Glu | Asn | Gly |
| | | 435 | | | | 440 | | | | 445 | | | | | |
| Gly | Phe | Cys | Ser | Gly | Val | Cys | His | Asn | Leu | Pro | Gly | Thr | Phe | Glu | Cys |
| | 450 | | | | | 455 | | | | | 460 | | | | |
| Ile | Cys | Gly | Pro | Asp | Ser | Ala | Leu | Ala | Arg | His | Ile | Gly | Thr | Asp | Cys |
| 465 | | | | | 470 | | | | | 475 | | | | | 480 |
| Asp | Ser | Gly | Lys | Val | Asp | Gly | Gly | Asp | Ser | Gly | Ser | Gly | Glu | Pro | Pro |
| | | | | 485 | | | | | 490 | | | | | 495 | |
| Pro | Ser | Pro | Thr | Pro | Gly | Ser | Thr | Leu | Thr | Pro | Pro | Ala | Val | Gly | Leu |
| | | | 500 | | | | | 505 | | | | | 510 | | |
| Val | His | Ser | Gly | Leu | Leu | Ile | Gly | Ile | Ser | Ile | Ala | Ser | Leu | Cys | Leu |
| | | | 515 | | | | 520 | | | | | 525 | | | |
| Val | Val | Ala | Leu | Leu | Ala | Leu | Leu | Cys | His | Leu | Arg | Lys | Lys | Gln | Gly |
| | | | 530 | | | | | 535 | | | | | 540 | | |
| Ala | Ala | Arg | Ala | Lys | Met | Glu | Tyr | Lys | Cys | Ala | Ala | Pro | Ser | Lys | Glu |
| 545 | | | | | 550 | | | | | 555 | | | | | 560 |
| Val | Val | Leu | Gln | His | Val | Arg | Thr | Glu | Arg | Thr | Pro | Gln | Arg | Leu | |
| | | | | 565 | | | | | 570 | | | | | 575 | |

<210> SEQ ID NO 3
<211> LENGTH: 1725
<212> TYPE: DNA
<213> ORGANISM: Homo sapiens

<400> SEQUENCE: 3

```
atgcttgggg tcctggtcct tggcgcgctg gccctggccg gcctggggtt ccccgcaccc        60
gcagagccgc agccgggtgg cagccagtgc gtcgagcacg actgcttcgc gctctacccg       120
ggccccgcga ccttcctcaa tgccagtcag atctgcgacg gactgcgggg ccacctaatg       180
acagtgcgct cctcggtggc tgccgatgtc atttccttgc tactgaacgg cgacggcggc       240
gttggccgcc ggcgcctctg gatcggcctg cagctgccac ccggctgcgg cgaccccaag       300
cgcctcgggc ccctgcgcgg cttccagtgg gttacgggag acaacaacac cagctatagc       360
aggtgggcac ggctcgacct caatggggct cccctctgcg gccgttgtg cgtcgctgtc        420 tccgctgctg aggccactgt gcccagcgag ccgatctggg aggagcagca gtgcgaagtg       480
aaggccgatg gcttcctctg cgagttccac ttcccagcca cctgcaggcc actggctgtg       540
gagcccggcg ccgcggctgc cgccgtctcg atcacctacg caccccgtt cgcggcccgc        600 ggagcggact tccaggcgct gccggtgggc agctccgccg cggtggctcc cctcggctta       660
cagctaatgt gcaccgcgcc gcccggagcg gtccaggggc actgggccag ggaggcgccg       720
ggcgcttggg actgcagcgt ggagaacggc ggctgcgagc acgcgtgcaa tgcgatccct       780
ggggctcccc gctgccagtg cccagccggc gccgccctgc aggcagacgg cgcgctcctgc      840 accgcatccg cgacgcagtc ctgcaacgac ctctgcgagc acttctgcgt tcccaacccc       900
gaccagccgg gctcctactc gtgcatgtgc gagaccggct accggctggc ggccgaccaa       960
caccggtgcg aggacgtgga tgactgcata ctggagccca gtccgtgtcc gcagcgctgt      1020
gtcaacacac agggtggctt cgagtgccac tgctacccta actacgacct ggtggacggc      1080
gagtgtgtgg agcccgtgga cccgtgcttc agagccaact gcgagtacca gtgccagccc      1140
ctgaaccaaa ctagctacct ctgcgtctgc gccgagggct cgcgcccat tccccacgag      1200 ccgcacaggt gccagatgtt ttgcaaccag actgcctgtc cagccgactg cgaccccaac      1260
acccaggcta gctgtgagtg ccctgaaggc tacatcctgg acgacggttt catctgcacg      1320
```

```
gacatcgacg agtgcgaaaa cggcggcttc tgctccgggg tgtgccacaa cctcccggt    1380 accttcgagt gcatctgcgg gcccgactcg gcccttgccc gccacattgg caccgactgt    1440
gactccggca aggtggacgg tggcgacagc ggctctggcg agcccccgcc cagcccgacg    1500
cccggctcca ccttgactcc tccggccgtg gggctcgtgc attcgggctt gctcataggc    1560
atctccatcg cgagcctgtg cctggtggtg gcgcttttgg cgctcctctg ccacctgcgc    1620
aagaagcagg gcgccgccag ggccaagatg gagtacaagt gcgcggcccc ttccaaggag    1680
gtagtgctgc agcacgtgcg gaccgagcgg acgccgcaga gactc                    1725

<210> SEQ ID NO 4
<211> LENGTH: 649
<212> TYPE: DNA
<213> ORGANISM: Homo sapiens
<220> FEATURE:
<221> NAME/KEY: misc_feature
<222> LOCATION: (1)..(649)
<223> OTHER INFORMATION: n= a, c, g, t, unknown or other

<400> SEQUENCE: 4
tctagacgcg ttgacattga ttattgacta gttattaata gtaatcaatt acgggtcat     60 tagttcatag cccatgatat catatggagt tccgcgttac ataacttacg gtaaatggcc    120
cgcctggctg accgcccaac gacccccgcc cattgacgtc aataatgacg tatgttccca    180
tagtaacgcc aatagggact ttccattgac gtcaatgggt ggagtattta cggtaaactg    240
cccacttggc agtacatcaa gtgtatcata tgccaagtac gccccctat tgacgtcaat    300 gacggtaaat ggcccgcctg gcattatgcc cagtncatga ccttatggga ctttcctact    360
tggcagacat ctacgtatta gtcatcgcta ttaccatggt gatgcggttt tggcagtaca    420
tcaatgggcg tggatagcgg tttgactcac ggggattttc caagtctcca ccccattgac    480
gtcaatggga gtttgttttg gcaccaaaat caacgggact ttccaaaatg tcgtaacaac    540
tccgccccat tgacgcaaat gggcggtagg cgtgtacggt gggaggtcta tataagcaga    600
gctctctggc taactagaga ccccctgctt actggcttat cgagatatc                649

<210> SEQ ID NO 5
<211> LENGTH: 3693
<212> TYPE: DNA
<213> ORGANISM: Homo sapiens

<400> SEQUENCE: 5
ggcagcgcgc agcggcaaga agtgtctggg ctgggacgga caggagaggc tgtcgccatc     60
ggcgtcctgt gcccctctgc tccggcacgg ccctgtcgca gtgcccgcgc tttccccggc    120
gcctgcacgc ggcgcgcctg ggtaacatgc ttggggtcct ggtccttggc gcgctggccc    180
tggccggcct ggggttcccc gcacccgcag agccgcagcc gggtggcagc cagtgcgtcg    240
agcacgactg cttcgcgctc tacccggggcc ccgcgacctt cctcaatgcc agtcagatct    300
gcgacggact gcggggccac ctaatgacag tgcgctcctc ggtggctgcc gatgtcattt    360
ccttgctact gaacgcgac ggcggcgttg gccgccggcg cctctggatc ggcctgcagc    420
tgccacccgg ctgcggcgac cccaagcgcc tcgggcccct gcgcggcttc cagtgggtta    480
cgggagacaa caacaccagc tatagcaggt gggcacggct cgacctcaat ggggctcccc    540
tctgcggccc gttgtgcgtc gctgtctccg ctgctgaggc cactgtgccc agcgagccga    600
tctgggagga gcagcagtgc gaagtgaagg ccgatggctt cctctgcgag ttccacttcc    660
cagccacctg caggccactg gctgtggagc ccggcgccgc ggctgccgcc gtctcgatca    720
```

```
cctacggcac cccgttcgcg gcccgcggag cggacttcca ggcgctgccg gtgggcagct    780
ccgccgcggt ggctcccctc ggcttacagc taatgtgcac cgcgccgccc ggagcggtcc    840
aggggcactg ggccagggag gcgccgggcg cttgggactg cagcgtggag aacggcggct    900
gcgagcacgc gtgcaatgcg atccctgggg ctccccgctg ccagtgccca gccggcgccg    960
ccctgcaggc agacgggcgc tcctgcaccg catccgcgac gcagtcctgc aacgacctct   1020
gcgagcactt ctgcgttccc aaccccgacc agccgggctc ctactcgtgc atgtgcgaga   1080
ccggctaccg gctggcggcc gaccaacacc ggtgcgagga cgtggatgac tgcatactgg   1140
agcccagtcc gtgtccgcag cgctgtgtca acacacaggg tggcttcgag tgccactgct   1200
accctaacta cgacctggtg gacggcgagt gtgtggagcc cgtggacccg tgcttcagag   1260
ccaactgcga gtaccagtgc cagcccctga accaaactag ctacctctgc gtctgcgccg   1320
agggcttcgc gcccattccc cacgagccgc acaggtgcca gatgttttgc aaccagactg   1380
cctgtccagc cgactgcgac cccaacaccc aggctagctg tgagtgccct gaaggctaca   1440
tcctggacga cggtttcatc tgcacggaca tcgacgagtg cgaaaacggc ggcttctgct   1500
ccggggtgtg ccacaacctc cccggtacct tcgagtgcat ctgcgggccc gactcggccc   1560
ttgcccgcca cattggcacc gactgtgact ccggcaaggt ggacggtggc gacagcggct   1620
ctggcgagcc cccgcccagc ccgacgcccg gctccacctt gactcctccg gccgtggggc   1680
tcgtgcattc gggcttgctc ataggcatct ccatcgcgag cctgtgcctg gtggtggcgc   1740
ttttggcgct cctctgccac ctgcgcaaga agcagggcgc cgccagggcc aagatggagt   1800
acaagtgcgc ggcccttcc aaggaggtag tgctgcagca cgtgcggacc gagcggacgc   1860
cgcagagact ctgagcggcc tccgtccagg agcctggctc cgtccaggag cctgtgcctc   1920
ctcaccccca gctttgctac caaagcacct tagctggcat tacagctgga gaagaccctc   1980 cccgcaccccc ccaagctgtt ttcttctatt ccatggctaa ctggcgaggg ggtgattaga   2040
gggaggagaa tgagcctcgg cctcttccgt gacgtcactg gaccactggg caatgatggc   2100
aattttgtaa cgaagacaca gactgcgatt tgtcccaggt cctcactacc gggcgcagga   2160
gggtgagcgt tattggtcgg cagccttctg ggcagacctt gacctcgtgg gctagggatg   2220
actaaaatat ttatttttt taagtattta ggttttgtt tgtttccttt gttcttacct   2280
gtatgtctcc agtatccact ttgcacagct ctccggtctc tctctctcta caaactccca   2340
cttgtcatgt gacaggtaaa ctatcttggt gaattttttt ttcctagccc tctcacattt   2400
atgaagcaag ccccacttat tccccattct tcctagtttt ctcctcccag gaactgggcc   2460
aactcacctg agtcacccta cctgtgcctg accctacttc ttttgctctt agctgtctgc   2520
tcagacagaa cccctacatg aaacagaaac aaaaacacta aaaataaaaa tggccatttg   2580 cttttttcacc agatttgcta atttatcctg aaatttcaga ttcccagagc aaaataattt   2640
taaacaaagg ttgagatgta aaaggtatta aattgatgtt gctggactgt catagaaatt   2700
acacccaaag aggtatttat ctttactttt aaacagtgag cctgaatttt gttgctgttt   2760
tgatttgtac tgaaaaatgg taattgttgc taatcttctt atgcaatttc ctttttttgtt   2820 attattactt attttgaca gtgttgaaaa tgttcagaag gttgctctag attgagagaa   2880
gagacaaaca cctcccagga gacagttcaa gaaagcttca aactgcatga ttcatgccaa   2940
ttagcaattg actgtcactg ttccttgtca ctggtagacc aaaataaaac cagctctact   3000
ggtcttgtgg aattgggagc ttgggaatgg atcctggagg atgcccaatt agggcctagc   3060
cttaatcagg tcctcagaga atttctacca tttcagagag gccttttgga atgtggcccc   3120
```

-continued

| | |
|---|---|
| tgaacaagaa ttggaagctg ccctgcccat gggagctggt tagaaatgca gaatcctagg | 3180 |
| ctccacccca tccagttcat gagaatctat atttaacaag atctgcaggg ggtgtgtctg | 3240 |
| ctcagtaatt tgaggacaac cattccagac tgcttccaat tttctggaat acatgaaata | 3300 |
| tagatcagtt ataagtagca ggccaagtca ggcccttatt ttcaagaaac tgaggaattt | 3360 |
| tctttgtgta gctttgctct ttggtagaaa aggctaggta cacagctcta gacactgcca | 3420 |
| cacagggtct gcaaggtctt tggttcagct aagctaggaa tgaaatcctg cttcagtgta | 3480 |
| tggaaataaa tgtatcatag aaatgtaact tttgtaagac aaaggttttc ctcttctatt | 3540 |
| ttgtaaactc aaaatatttg tacatagtta tttatttatt ggagataatc tagaacacag | 3600 |
| gcaaaatcct tgcttatgac atcacttgta caaaataaac aataacaat gtgaaaaaaa | 3660 |
| aaaaaaaaaa aaaaaaaaaa aaaaaaaaaa aaa | 3693 |

<210> SEQ ID NO 6
<211> LENGTH: 4457
<212> TYPE: DNA
<213> ORGANISM: Homo sapiens
<220> FEATURE:
<221> NAME/KEY: misc_feature
<222> LOCATION: (1)..(4457)
<223> OTHER INFORMATION: n= a, c, g, t, unknown or other

<400> SEQUENCE: 6

| | |
|---|---|
| gtttaaacgg gccctctaga cgcgttgaca ttgattattg actagttatt aatagtaatc | 60 |
| aattacgggg tcattagttc atagcccatg atatcatatg gagttccgcg ttacataact | 120 |
| tacggtaaat ggcccgcctg gctgaccgcc caacgacccc cgcccattga cgtcaataat | 180 |
| gacgtatgtt cccatagtaa cgccaatagg gactttccat tgacgtcaat gggtggagta | 240 |
| tttacggtaa actgcccact tggcagtaca tcaagtgtat catatgccaa gtacgccccc | 300 |
| ctattgacgt caatgacggt aaatggcccg cctggcatta tgcccagtnc atgaccttat | 360 |
| gggactttcc tacttggcag acatctacgt attagtcatc gctattacca tggtgatgcg | 420 |
| gttttggcag tacatcaatg ggcgtggata gcggtttgac tcacggggat ttccaagtc | 480 |
| tccaccccat tgacgtcaat gggagtttgt tttggcacca aaatcaacgg gactttccaa | 540 |
| aatgtcgtaa caactccgcc ccattgacgc aaatgggcgg taggcgtgta cggtgggagg | 600 |
| tctatataag cagagctctc tggctaacta gagaacccct gcttactggc ttatcgagat | 660 |
| atctgcagaa ttcatctgtc gactgctacc ggcagcgcgc agcggcaaga agtgtctggg | 720 |
| ctgggacgga caggagaggc tgtcgccatc ggcgtcctgt gccctctgc tccggcacgg | 780 |
| ccctgtcgca gtgcccgcgc tttccccggc gcctgcacgc ggcgcgcctg ggtaacatgc | 840 |
| ttgggggtcct ggtccttggc gcgctggccc tggccggcct ggggttcccc gcacccgcag | 900 |
| agccgcagcc gggtggcagc cagtgcgtcg agcacgactg cttcgcgctc taccgggcc | 960 |
| ccgcgacctt cctcaatgcc agtcagatct gcgacggact gcggggccac ctaatgacag | 1020 |
| tgcgctcctc ggtggctgcc gatgtcattt ccttgctact gaacggcgac ggcggcgttg | 1080 |
| gccgccggcg cctctggatc ggcctgcagc tgccacccgg ctgcggcgac cccaagcgcc | 1140 |
| tcgggcccct gcgcggcttc cagtgggtta cgggagacaa caacaccagc tatagcaggt | 1200 |
| gggcacggct cgacctcaat ggggctcccc tctgcggccc gttgtgcgtc gctgtctccg | 1260 |
| ctgctgaggc cactgtgccc agcgagccga tctgggagga gcagcagtgc gaagtgaagg | 1320 |
| ccgatggctt cctctgcgag ttccacttcc cagccacctg caggccactg gctgtgggagc | 1380 |
| ccggcgccgc ggctgccgcc gtctcgatca cctacggcac ccgttcgcg gcccgcggag | 1440 |

```
cggacttcca ggcgctgccg gtgggcagct ccgccgcggt ggctcccctc ggcttacagc    1500
taatgtgcac cgcgccgccc ggagcggtcc aggggcactg gccagggag cgccgggcg      1560 cttgggactg cagcgtggag aacggcggct gcgagcacgc gtgcaatgcg atccctgggg    1620
ctccccgctg ccagtgccca gccggcgccg ccctgcaggc agacgggcgc tcctgcaccg    1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggacccg tgcttcagag ccaactgcga gtaccagtgc agcccctga    1980 accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc ccgcccagc ccgacgcccg    2340 gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcaccc ccaagctgtt ttcttctatt    2700
ccatggctaa ctggcgaggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttattttttt taagtattta    2940 ggttttgtt tgtttccttt gttcttacct gtatgtctcc agtatccact ttgcacagct    3000
ctccggtctc tctctctcta caaactccca cttgtcatgt gacaggtaaa ctatcttggt    3060
gaattttttt ttcctagccc tctcacattt atgaagcaag ccccacttat tccccattct    3120
tcctagtttt ctcctcccag gaactgggcc aactcacctg agtcaccta cctgtgcctg    3180 accctacttc ttttgctctt agctgtctgc tcagacagaa cccctacatg aaacagaaac    3240
aaaaacacta aaaataaaaa tggccatttg cttttccacc agatttgcta atttatcctg    3300
aaatttcaga ttcccagagc aaaataattt taaacaaagg ttgagatgta aaggtatta    3360 aattgatgtt gctggactgt catagaaatt acacccaaag aggtatttat ctttactttt    3420
aaacagtgag cctgaatttt gttgctgttt tgatttgtac tgaaaaatgg taattgttgc    3480
taatcttctt atgcaatttc cttttttgtt attattactt attttgaca gtgttgaaaa    3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagt atgcccaatt agggcctagc cttaatcagg tcctcagaga atttctacca    3780
tttcagagag gcctttgga atgtggcccc tgaacaagaa ttggaagctg ccctgcccat    3840
```

-continued

```
gggagctggt tagaaatgca gaatcctagg ctccacccca tccagttcat gagaatctat    3900
atttaacaag atctgcaggg ggtgtgtctg ctcagtaatt tgaggacaac cattccagac    3960
tgcttccaat tttctggaat acatgaaata tagatcagtt ataagtagca ggccaagtca    4020
ggcccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt tgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaa aaaaaaaaa      4380 aaaggtagca gtcgacagat gaattccacc acactggact agtggatccg agctcggtac    4440
caagcttaag tttaaac                                                  4457
```

<210> SEQ ID NO 7
<211> LENGTH: 17534
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: misc_feature
<222> LOCATION: (1)..(17534)
<223> OTHER INFORMATION: n= a, c, g, t, unknown or other

<400> SEQUENCE: 7

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccatttcgc gggaaaactg aataagagga     300
agtgaaatct gaataatttt gtgttactca tagcgcgtaa tactggtacc gcggccgcct    360
cgagtctaga actagtggat cccccaaacg ggccctctag acgcgttgac attgattatt    420
gactagttat taatagtaat caattacggg gtcattagtt catagcccat gatatcatat    480
ggagttccgc gttacataac ttacggtaaa tggcccgcct ggctgaccgc ccaacgaccc    540
ccgcccattg acgtcaataa tgacgtatgt tcccatagta acgccaatag gactttcca    600 ttgacgtcaa tgggtggagt atttacggta aactgcccac ttggcagtac atcaagtgta    660
tcatatgcca gtacgccccc ctattgacg tcaatgacgg taaatggccc gcctggcatt    720
atgcccagtn catgacctta tgggactttc ctacttggca gacatctacg tattagtcat    780
cgctattacc atggtgatgc ggttttggca gtacatcaat gggcgtggat agcggtttga    840
ctcacgggga ttttccaagt ctccacccca ttgacgtcaa tgggagtttg ttttggcacc    900
aaaatcaacg ggactttcca aaatgtcgta acaactccgc cccattgacg caaatgggcg    960
gtaggcgtgt acggtgggag gtctatataa gcagagctct ctggctaact agagaacccc   1020
tgcttactgg cttatcgaga tatctgcaga attcatctgt cgactgctac cggcagcgcg   1080
cagcggcaag aagtgtctgg gctgggacgg acaggagagg ctgtcgccat cggcgtcctg   1140 tgccctctg ctccggcacg gcctgtcgc agtgcccgcg cttccccgg gcctgcacg      1200 cggcgcgcct gggtaacatg cttggggtcc tggtccttgg cgcgctggcc ctggccggcc    1260
tggggttccc cgcacccgca gagccgcagc cgggtggcag ccagtgcgtc gagcacgact    1320
```

```
gcttcgcgct ctacccgggc cccgcgacct tcctcaatgc cagtcagatc tgcgacggac   1380
tgcggggcca cctaatgaca gtgcgctcct cggtggctgc cgatgtcatt tccttgctac   1440
tgaacggcga cggcggcgtt ggccgccggc gcctctggat cggcctgcag ctgccacccg   1500
gctgcggcga ccccaagcgc ctcgggcccc tgcgcggctt ccagtgggtt acgggagaca   1560
acaacaccag ctatagcagg tgggcacggc tcgacctcaa tggggctccc ctctgcggcc   1620
cgttgtgcgt cgctgtctcc gctgctgagg ccactgtgcc cagcgagccg atctgggagg   1680
agcagcagtg cgaagtgaag gccgatggct tcctctgcga gttccacttc ccagccacct   1740
gcaggccact ggctgtggag cccggcgccg cggctgccgc cgtctcgatc acctacggca   1800
ccccgttcgc ggcccgcgga gcggacttcc aggcgctgcc ggtgggcagc tccgccgcgg   1860
tggctcccct cggcttacag ctaatgtgca ccgccgcc cggagcggtc caggggcact   1920
gggccaggga ggcgccggc gcttgggact gcagcgtgga gaacggcggc tgcgagcacg   1980
cgtgcaatgc gatccctggg gctccccgct gccagtgccc agccgcgcc gcctgcagg   2040 cagacgggcg ctcctgcacc gcatccgcga cgcagtcctg caacgacctc tgcgagcact   2100
tctgcgttcc caaccccgac cagccgggct cctactcgtg catgtgcgag accggctacc   2160
ggctggcggc cgaccaacac cggtgcgagg acgtggatga ctgcatactg gagcccagtc   2220
cgtgtccgca gcgctgtgtc aacacacagg gtggcttcga gtgccactgc taccctaact   2280
acgacctggt ggacggcgag tgtgtggagc ccgtggaccc gtgcttcaga gccaactgcg   2340
agtaccagtg ccagccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgccc tgaaggctac atcctggacg   2520 acggttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctggcgagc   2700
ccccgcccag cccgacgccc ggctccacct tgactcctcc ggccgtgggg ctcgtgcatt   2760
cgggcttgct cataggcatc tccatcgcga gcctgtgcct ggtggtggcg ctttggcgc   2820 tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcacccc   3000 agctttgcta ccaaagcacc ttagctggca ttacagctgg agaagaccct ccccgcaccc   3060
cccaagctgt tttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat ttgtcccagg tcctcactac cgggcgcagg agggtgagcg   3240
ttattggtcg gcagccttct gggcagacct tgacctcgtg ggctagggat gactaaaata   3300
tttatttttt ttaagtattt aggttttttgt ttgtttcctt tgttcttacc tgtatgtctc   3360
cagtatccac tttgcacagc tctccggtct ctctctctct acaaactccc acttgtcatg   3420
tgacaggtaa actatcttgg tgaattttt tttcctagcc ctctcacatt tatgaagcaa   3480
gccccactta ttccccattc ttcctagttt tctcctccca ggaactgggc caactcacct   3540
gagtcaccct acctgtgcct gaccctactt cttttgctct tagctgtctg ctcagacaga   3600 accctacat gaaacagaaa caaaacact aaaaataaaa atggccattt gcttttcac   3660 cagatttgct aatttatcct gaaatttcag attcccagag caaaataatt ttaaacaaag   3720
```

```
gttgagatgt aaaaggtatt aaattgatgt tgctggactg tcatagaaat tacacccaaa   3780
gaggtattta tctttacttt taaacagtga gcctgaattt tgttgctgtt ttgatttgta   3840
ctgaaaaatg gtaattgttg ctaatcttct tatgcaattt cctttttgt tattattact    3900 tatttttgac agtgttgaaa atgttcagaa ggttgctcta gattgagaga agagacaaac   3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
gtcctcagag aatttctacc atttcagaga ggccttttgg aatgtggccc ctgaacaaga   4200
attggaagct gccctgccca tgggagctgg ttagaaatgc agaatcctag gctccacccc   4260
atccagttca tgagaatcta tatttaacaa gatctgcagg gggtgtgtct gctcagtaat   4320
ttgaggacaa ccattccaga ctgcttccaa ttttctggaa tacatgaaat atagatcagt   4380
tataagtagc aggccaagtc aggcccttat tttcaagaaa ctgaggaatt ttctttgtgt   4440
agctttgctc tttggtagaa aaggctaggt acacagctct agacactgcc acacagggtc   4500
tgcaaggtct ttggttcagc taagctagga atgaaatcct gcttcagtgt atggaaataa   4560
atgtatcata gaaatgtaac ttttgtaaga caaaggtttt cctcttctat tttgtaaact   4620
caaaatattt gtacatagtt atttatttat tggagataat ctagaacaca ggcaaaatcc   4680
ttgcttatga catcacttgt acaaaataaa caataacaa tgtgaaaaaa aaaaaaaaa    4740 aaaaaaaaaa aaaaaaaaaa aaaggtagc agtcgacaga tgaattccac cacactggac   4800
tagtggatcc gagctcggta ccaagcttaa gtttgggctg caggaattct gatggctctc   4860
aaaattcctg cctcctttag ggataaaaga ctttaagact ttttaacaaa aagaaaaag    4920 aaaaaaaaaa ttcctgcctc ctggtgtaca cacacagaag ggttccctcc ccttgaatgt   4980
gaccaggatc tgtgaaaata acgggatagc cgctcctgtg attaggttat gtggtagact   5040
agagcaagat tctcctgctg gttttgaaga agtcagctgc catgttgtga gactgtcatg   5100
ggctagggca tgagccttta aatatctggg agcaaccct ggccagcagc cagtgagaaa    5160
acgggccctc agtcctacaa tcacaaggaa ctaaattctg ccaacaacct gaaggaactt   5220
tgaagaggat catgagtccc ttgattcagc ttgatgagcc cctgagcaga ggatacagct   5280
aacttgtact agggaagtat aaaaaacatg catgggaatg atatatatca actttaagga   5340
taattgtcat acttctggga atgaagggaa agaaatgggg cttagttgt attatgatct    5400 ttaatttctc aaaaaaaata agatcagaag caaatatggc aaaatgttaa tacttttgtg   5460
ggtacgtagg tattcagcat accctttttt ctgagttcaa aatattttat aattaaaatg   5520
aaatgcaggc caggcacagt ggctcatgcc tataatacca gcactttgcg aggccgaggt   5580
gggaggatgg cttgaggcca gaccagcctg gccaacatgg caaaacccca tctctactta   5640
aaaaaaaaaa aactatatat atatatatgt gtgtgtgt gtatatatat atatgtatat     5700
atatttatat atgtgtgtat atatatatat gtatatatat ttatatatgt gtgtgtatat   5760
atatatatac acacacacac atatatacat acatacatac acacacacac acacacaatt   5820
agccaggcat ggtggcgcac acctgtagtc ccagctactt gggaggctga gacatgagaa   5880
ttgcttgaac ctgggaggca gagtagttag tgagctgaga tcataccact gcactccagc   5940
ctggtgacag agtgagactc tgtcttaaaa aaaataaaaa ttaaattaa atgcaaaagg    6000 tccaagtgaa ttgaagagga aaggggtatc aaggaaggtt ttgtggaggt gacgtttgag   6060
ctgggtctta aatgacttaa acatgggata agaagggagg gaataaggac atttcaggta   6120
```

```
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccagaatag    6480
gcaaatctta tagacagcaa gtaggtagat gatcagtttg ctaggtgctg ggggaagggg    6540
aaatggggag tgatggctaa ggggattggg tttctttgtg gggcaatgaa aatgttttaa    6600
aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagattttat ataggatggc cagggaaggc    6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatactttt ggtctaggga accacatttt gagaaccact    7020
gagctaaagg aagtaaaggt ttcccttagt ttactagctg gtaacactgg cccaggaggc    7080
ctttctggtg accccctaagg aattatccaa actcttgttt ttagatgctt tattatatca    7140
aactctcctt taaacaagtg gcccatctgc tgggatttgg aagcctgtaa tactgaaatt    7200
ttcatcataa tggaattttt aaaaacagaa tttgacccac ctgtttttaa aacactttca    7260
ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500
ggactacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
acttttaaat ttttaccctc accttgttta atctatattt ttgtatgtat tttgtaacat    7920
atatattatt attaccataa atcatatata atttaaaatg catatattag gggtaaatgc    7980
tcaggaaact tttataaaat tgggcatgca aatacaagtt tgaagactca ctgttctagg    8040
tattaaaagt aaagttataa ccaagtaaag cttccacctt ttcatgtctc aaagcagttt    8100
attgttggag gtaagatctc ttagaagcct aaacaggtcc aagtacgaaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280 aattacttt tattcaaagt ggaactcagg acatggggag aaaatgaata caaaaaatag    8340
ggtcaatcca aaggcacaca gcaaatgagt aacacagtta tgtttttttc ccatttgtat    8400
gaggtcccag taaattctaa gtaaactgca aatttaataa tacactaaaa aagccatgca    8460
attgttcaaa tgaatcccag catggtacaa ggagtacaga cactagagtc taaaaaacaa    8520
```

```
aagaatgcca ttattgagtt tttgaattat atcaagtagt tacatctcta cttaataaat   8580
gagaaaaacg aggataagag gccatttgat aaaatgaaaa tagccaagaa gtggtattag   8640
agacttgaat acaggtattc gggtccaaag ttcatctgct caaatactaa ctggggaaaa   8700
gagggaaaaa tatttatata catatatatc tgcacacaaa ataccccca aaagacaaaa   8760 tgaggccagg cagggtggct cacacccgta atcccggtac tttgggaggc tgaggcaggt   8820
ggatacctga gatcaggagt tggagatcag cctggtcaac atggtgaaac cctgtctcta   8880
ctaaagataa aaaaattagc caggcatggt ggcgtgcgcc tgtaatccca gctacttggg   8940
agtctgaggc aggagaatca cttgaactgg aaggggagg ttgcagtgag ccaagatcgt   9000
actactgcac tccagcctgg gcagcagagt gagactccat cacaaaaata aataaataaa   9060
taaaatacaa tgaaacagaa agttcaaata atcccataat cttaccacca agaaataact   9120
ttcactcgtt atacttattg attttttccat aataaatgta ctttactgtg actatcatga   9180
aaagaaagtt atttttagaaa cagagaactg tttcagatca aatctatgta gtagaacaga   9240
gccattaggt gggaaagacg agatcaaact aaatctcaga aggcctaaaa ggctaggtcc   9300
attccagcac taaaaactga ccagacaagt aatggcttca acagcttcta aatatggaca   9360
aagcatgctg aaagggaagg acaggtctaa cagtggtata tgaaatgaac aggaggggca   9420
aagctcattt ctcctctgaa gttttccaaa gatgctgagg aggacattag tttgacatga   9480
ccctgatatg ggacaagata atttcacaga agttttacat gttaaagttt cttatagat   9540 actcattcaa gtaagcaatg aacactaaaa tctaaagaaa gaaagagct ttagagtcag   9600 gtctgtattc aaattcaagc tctaccactt actggttctg tgactttggg caagtctttt   9660
aaccttatta agtcttaatt tcctgatttg taaaatgggg atatcgtctc cctcacagga   9720
ttgttgtgaa acttttatga gattaatgcc tttatatttg gcatagtgta agtaaacaat   9780
aactggcagc ttcaaaaaaa aaaagcagta gcattccatc atttattatt ggttactctc   9840
aaaaagtttt tcaatgtact agaagataaa tattcaaata ccttaatatc tccattattt   9900
tcaggtaaac agcatgctcc tgaacaacca atgggtcaac aaataaatta aagggaaat   9960 ctaaaaacat cttgatatta aactacatgg aagcacaata taccaaaacc aatggttcac  10020
actaggagaa ttttaaggta caagaaaact ctttgagatt tcttaaaata atagtatgtc  10080
tgaatttatt gagtgattta ccagaaactg ttgtaagagc tctacttgca ttatagcact  10140
taatcctctt aactctatgg ctgctattat caacctcacc ctaatcacat atgggacaca  10200
gagaggttaa gtaacttgcc caaggtcaga gttaggaagt actaagccat gctttgaatc  10260
agttgtcagg ctccggaact cacactttca gccactacat aatactgctt tgctatcttt  10320
taggaaacta tgtgagtcta cctcacatag actcacatag gtttgttttt ttttttttt   10380 taaaggctat ctttccccc atcaatgttt tttgaaggat cccaaattag agtcccacag  10440
aggcagacag cagtacttga caatatggac atttaaggtt aatgttggat tctactgtct  10500
ttttactaca tgacctaggg aacgataatt aacctagact gcttccaagg gttaaataac  10560
ccatttagtt atactatgta aattatctct tagtgattga ttgaaagcac actgttacta  10620
attgactcgg tatgaagtgc ttttttttct tcccctttcaa gatacatacc tttccagtta  10680
aagttgagag atcatctcca ccaattactt ttatgtcccc tgttgactgg tcattctagt  10740
taaaaaaaaa aaaaactata tatatatata tctacacaca catatgtata tgtatatcct  10800
tatgtacaca cacaaacttc aaattaaatg agaactagaa gatttgagaa gttagctagc  10860
taatatccat agcattatga tattctaaat gatatgaatt ataagaatta ggtttcctga  10920
```

```
aatgaatgac tagaaaactt tcaagtagag attagtaaaa attaaaaagt cctaatcggc   10980
cattactgat ttgatgtttt taagagtcct aaaaaatggg ttacatccat ttttaagtgg   11040
gtagtattat aacagccacc catcttcaat cacagtgatt tctgaattgt gagggaagtt   11100
attagcatga caggtgtctg gttctggccc tgtacgattc ccatgagtca agcaaattgt   11160
aagggctggt ctatatcaca cccaaccccca aggatatgtc cctcaaaagt ctagcccagg   11220
ccccgtcatc ttcagcatca tctgggaaac caggtctgat tagtagtcct ttaaggaata   11280
cctcttaggc tcccatttta ctgctatcac agaatccaat aaaaccctta caggagattc   11340
aatgggaaat gctcaacacc cactgtagtt ggtggtgaca atgaccataa tttggctgtg   11400
ctggattcag gacagaaaat ttgggtgaaa gagcaggtga acaaaagagc ttcgacttgc   11460
cctagcagag agcaagccat accataccac aaagccacag caattacaac ggtgcagtac   11520
cagcacagta aatgaacaaa gtagagccca gaaacagacc cagaactata tgaggattta   11580
gtatacaata aagatggtat ttcgagtcag tagggaaaag atgaattatt caataaatga   11640
tgtttggcca actagtaacc catttgggaa aaaataaaag tatggtccct acctcacagc   11700
atacacaaaa ataaattcca gacgattaaa atctaaatg taaaaaataa agccataagt   11760
ggactggaag aaaatagaga attttttta acatccgtag aaagggtaaa aacccaggca   11820
tgacatgaac caaaactgaa gaggttctgt aacaaatacc cccttttata tattgggctc   11880
caacaataag aacccatagg aaaatggaga atgaacacaa atagacaatt tatagaagag   11940
aaggttataa ggtgtaaaat tatatctatc tgagaaacaa acactaaaac aatgtgattc   12000
tactgttctc ccacccatac tggcaaaact taagcctgat aatatgctga ggggaaataa   12060
gcactcttgt tggtgagagt attaattggc atagcttctt ttgaaaatga catagcaata   12120
cctgttaaaa ttgcaaacat gcatgtcact taatccagta atcccacttc tgggaatcaa   12180
tgctacaaaa acactgacaa gtatacaaag atacattcaa gagtgttcac tgggccgggt   12240
gcggtggctt catgcctgta atcccaggga ggcagaggca agacgatcgc ttgacccag   12300 gagttcaagg ccagcccgag aaacacagca agaccctgtc tctcttttt ttatttaaaa   12360 aataaatgtt cactgtatca gttgttcaca aaaacaaacc aacatgtcca ttaacaggga   12420
accatttaaa ttaatcaagt tcatctacac aatgtaatac catgcaacta ttaaaaagca   12480
cctgataatc caaagcacac tgagacagaa taatgctatt aaaaacacca agtagtggaa   12540
cactgtgttg cctatgacac catttttatt caacatttaa acaaatttgt aacagcaatt   12600
acatgagtag tgacaatggc gtttatgaga cttttcactt ttatgtgctt ctattttgt   12660 tatgcttcta tatatacatc catttattat ggagtgttac tttcaaaaat cacaaatggg   12720
ccagtattat ttggtgttgc aaggtgagca tatgacttct gatatcaacc tttgcatatt   12780
acttctcaat ttagggaaat tacagacatc ccttattcta actaacttaa aacccagcat   12840
ttcaaacata cagaattgat ggggaaaaaa aagaaagaag aaagaaagaa aaggcaacaa   12900
gcttcagatg acagtgactc acatcaaatt attttataaaa tctgttaaat agtgccatct   12960
tctggagata cctggtatta cagtccaact ccagttgatg tctttacaga gacaagagga   13020
ataaaggaaa aaatattcaa gaactgaaaa gtatggagtc atggaaaaat tgctgtgatc   13080
caaaggctac ggtgatagga caagaaacaa gagaactcca agcagtaaga cactgctgtt   13140
ctattagcat ccaaaccctcc atactcctgt ttgccccaag gctttttaa aaaatagaga   13200 caggatctca ctattttgct caggctggtc ttgaactcct ggactcaagc tatcctcctg   13260
cctcggcctc ctaaagtgcc gagattacag gcttgagtca ccataccctgg ctatttattt   13320
```

```
tttcttaact ctcttgcctg gcctatagcc accatggaag ctaataaaga atattaattt    13380
aagagtaatg gtatagttca ctacattgga atacaggtat aagtgcctac attgtacatg    13440
aatggcatac atgatcaat taccccacct gggtggccaa aggaactgcg cgaacctccc     13500
tccttggctg tctggaacaa gcttcccact agatcccttt actgagtgcc tccctcatct    13560
ttaattatgg ttaagtctag gataacagga ctggcaaagg tgaggggaaa gcttcctcca    13620
gagttgctct accctctcct ctaccgtcct atctcctcac tcctctcagc caaggagtcc    13680
aatctgtcct gaactcagag cgtcactgtc aactacataa aattgccaga gaagctcttt    13740
gggactacaa acacataccc ttaatgtctt tatttctatt ttgtctacct cttcagtcta    13800
ggtgaaaaaa taggaaggat aatagggaag aactttgttt atgcctactt atccgcccct    13860
aggaattttg aaacctctca ggtagcaata agaactgcag catggtatag aaaaagagga    13920
ggaaagctgt atagaaatgc ataataaatg ggcaggaaaa gaactgcttg aacaaacag     13980 ggaggttgaa ctataaggag agaaagcaga gaggctaatc aacaaggctg ggttcccaag    14040
agggcatgat gagactatta ctaaggtagg aattactaag ggctccatgt cccccttagtg    14100 gcttagtact atgtagcttg ctttctgcag tgaacttcag accttcttt taggatccta     14160 gaatggactt ttttttttta tcggaaaaca gtcattctct caacattcaa gcaggcccca    14220
agtctaccac actcaatcac attttctctt catatcataa tctctcaacc attctctgtc    14280
cttttaactg tttttctata ccctgatcaa atgccaacaa aagtgagaat gttagaatca    14340 tgtatttta gaggtagact gtatctcaga taaaaaaaaa gggcagatat tccattttcc    14400
aaaatatgta tgcagaaaaa ataagtatga aaggacatat gctcaggtaa caagttaatt    14460
tgtttacttg tattttatga attccctaaa acctacgtca cccgcccgt tcccacgccc     14520 cgcgccacgt cacaaactcc accccctcat tatcatattg gcttcaatcc aaaataaggt    14580
atattattga tgatgttaat taacatgcat ggatccatat gcggtgtgaa ataccgcaca    14640
gatgcgtaag gagaaaatac cgcatcaggc gctcttccgc ttcctcgctc actgactcgc    14700
tgcgctcggt cgttcggctg cggcgagcgg tatcagctca ctcaaaggcg gtaatacggt    14760
tatccacaga atcaggggat aacgcaggaa agaacatgtg agcaaaaggc cagcaaaagg    14820
ccaggaaccg taaaaaggcc gcgttgctgg cgtttttcca taggctccgc cccccctgacg    14880 agcatcacaa aaatcgacgc tcaagtcaga ggtggcgaaa cccgacagga ctataaagat    14940
accaggcgtt tccccctgga agctccctcg tgcgctctcc tgttccgacc ctgccgctta    15000
ccggatacct gtccgccttt ctcccttcgg gaagcgtggc gctttctcat agctcacgct    15060
gtaggtatct cagttcggtg taggtcgttc gctccaagct gggctgtgtg cacgaacccc    15120
ccgttcagcc cgaccgctgc gccttatccg gtaactatcg tcttgagtcc aacccggtaa    15180
gacacgactt atcgccactg gcagcagcca ctggtaacag gattagcaga gcgaggtatg    15240
taggcggtgc tacagagttc ttgaagtggt ggcctaacta cggctacact agaaggacag    15300
tatttggtat ctgcgctctg ctgaagccag ttaccttcgg aaaaagagtt ggtagctctt    15360
gatccggcaa acaaaccacc gctggtagcg gtggtttttt tgtttgcaag cagcagatta    15420
cgcgcagaaa aaaaggatct caagaagatc ctttgatctt ttctacgggg tctgacgctc    15480
agtggaacga aaactcacgt taagggattt tggtcatgag attatcaaaa aggatcttca    15540
cctagatcct tttaaattaa aaatgaagtt ttaaatcaat ctaaagtata tatgagtaaa    15600
cttggtctga cagttaccaa tgcttaatca gtgaggcacc tatctcagcg atctgtctat    15660
ttcgttcatc catagttgcc tgactccccg tcgtgtagat aactacgata cgggagggct    15720
```

```
taccatctgg ccccagtgct gcaatgatac cgcgagaccc acgctcaccg gctccagatt   15780
tatcagcaat aaaccagcca gccggaaggg ccgagcgcag aagtggtcct gcaactttat   15840
ccgcctccat ccagtctatt aattgttgcc gggaagctag agtaagtagt tcgccagtta   15900
atagtttgcg caacgttgtt gccattgctg cagccatgag attatcaaaa aggatcttca   15960
cctagatcct tttcacgtag aaagccagtc cgcagaaacg gtgctgaccc cggatgaatg   16020
tcagctactg ggctatctgg acaagggaaa acgcaagcgc aaagagaaag caggtagctt   16080
gcagtgggct tacatggcga tagctagact gggcggtttt atggacagca agcgaaccgg   16140
aattgccagc tggggcgccc tctggtaagg ttgggaagcc ctgcaaagta aactggatgg   16200
ctttcttgcc gccaaggatc tgatggcgca ggggatcaag ctctgatcaa gagacaggat   16260
gaggatcgtt tcgcatgatt gaacaagatg gattgcacgc aggttctccg gccgcttggg   16320
tggagaggct attcggctat gactgggcac aacagacaat cggctgctct gatgccgccg   16380
tgttccggct gtcagcgcag gggcgcccgg ttcttttttgt caagaccgac ctgtccggtg   16440
ccctgaatga actgcaagac gaggcagcgc ggctatcgtg gctggccacg acgggcgttc   16500
cttgcgcagc tgtgctcgac gttgtcactg aagcgggaag ggactggctg ctattgggcg   16560
aagtgccggg gcaggatctc ctgtcatctc accttgctcc tgccgagaaa gtatccatca   16620
tggctgatgc aatgcggcgg ctgcatacgc ttgatccggc tacctgccca ttcgaccacc   16680
aagcgaaaca tcgcatcgag cgagcacgta ctcggatgga agccggtctt gtcgatcagg   16740
atgatctgga cgaagagcat caggggctcg cgccagccga actgttcgcc aggctcaagg   16800
cgagcatgcc cgacggcgag gatctcgtcg tgacccatgg cgatgcctgc ttgccgaata   16860
tcatggtgga aaatggccgc ttttctggat tcatcgactg tggccggctg ggtgtggcgg   16920
accgctatca ggacatagcg ttggctaccc gtgatattgc tgaagagctt ggcggcgaat   16980
gggctgaccg cttcctcgtg ctttacggta tcgccgctcc cgattcgcag cgcatcgcct   17040
tctatcgcct tcttgacgag ttcttctgaa ttttgttaaa attttttgtta aatcagctca   17100 ttttttaacc aataggccga aatcggcaaa atcccttata atcaaaaga atagaccgag   17160 atagggttga gtgttgttcc agtttggaac aagagtccac tattaaagaa cgtggactcc   17220
aacgtcaaag ggcgaaaaac cgtctatcag ggcgatggcc cactacgtga accatcaccc   17280
taatcaagtt ttttggggtc gaggtgccgt aaagcactaa atcggaaccc taaagggagc   17340
ccccgattta gagcttgacg gggaaagccg cgaacgtgg cgagaaagga agggaagaaa   17400
gcgaaaggag cgggcgctag ggcgctggca agtgtagcgg tcacgctgcg cgtaaccacc   17460
acacccgccg cgcttaatgc gccgctacag ggcgcgtcca ttcgccattc aggatcgaat   17520
taattcttaa ttaa                                                     17534

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaacactgg cccaggaggc ctttctggtg acccc                               35

<210> SEQ ID NO 9
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
tgaccgggtc ctccggaaag accactgggg att                                    33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagttccttc tgcctggaat ac                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagtcacaa ggatggacta ca                                                22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct       60
acttgccctc tggaaccagc tctagggtca ccacatctct gcttctgagt gcctcctcag      120
acacagtctg tatttcctct tccaagctct catcacaaac attgtgctgt attatatgtt      180
tctgtgtggt cttccttcta tgaggaagcc ttggaaagca ggagacttat tttagtcttc      240
tttatgtttc ttttattccc aacacattat gtctgcccca tagacctttt caataaatga      300
ttattgagtt agtgactcct tttacatgct gacaaatgtg gctcttatta ctccccattt      360
cagtatcaca tatttgtaaa agtgaatcct tcttaatcgt tttacttttc tcctagtaaa      420
ttcctcatct atgcctgtct gctgctgttc tctgtgctgc tggcccttcg tttggatggc      480
atcatacagt ggagttactg ggctgtcttt gctccaatat ggctgtggaa gttaatggtc      540
attgttggag cctcagttgg aactggagtc tgggcacgaa atcctcaata tcggtaatac      600
tgctttatac aacccattgg tctctagcat gagggagcaa tatcttgact tttctcactt      660
ttgatgaagt aaggaccatt ttattttcta cctatctggg gtcttagaac tatagtataa      720
gctaacagat ctcttctgtg ttttttgaaaa tttagtctttt ggtatgtatt ttcttacaaa      780
agcagtgcca tttggggggta agttgccagc cagctcacag atgcctatat aatccaaaat      840
gcacccaaaa tacagaactg gtatgccata ctagactaag cagcatgaaa ccaccctgtt      900
tttaggaaaa gacactcata ttatgtttgg tcatgaaaga tctttctcca atacagtttt      960
ggaactgggg ctccccttgt cccaccctcc tagtcccaga gctttaggac tattagcagt     1020
gtagggaagg tggcttgacc aggagaccat gagtccctga gacagcagct ggggaatgag     1080
gaaagtcaaa gattggatgc cgagaaggaa agcagagcct ttgggggcag gggagagggg     1140
```

```
tacccttttac cgtttccaac tcttgccctc cctgctcttg gatgcctccg ctggcccaaa    1200
ttcctgggag ttgctcacgc cagcatgcaa cctgcttgtt gctgggacct gcgagagtct    1260
ttcccttctc tgccacagag actgtaacta cataaaggga aaaaggggga cttaagactg    1320
ggaggctatt atgaacctcc actgggaaaa tgaggagtac aggaattccc agaaggcagc    1380
tgctcatgtg ggaaaagtgt aaagttgaaa ctaccgcacc tttttttttt tttttttttt    1440
tttttttttt ttgagacaga gtttcgctct tgttgcccag gctggagtgc aatggtgtga    1500
tctcggccca ctgcagcctc cacatcccgg gttcaagtga ttctcctgcc tcggcctcct    1560
gagtagctgg gattacaggc acctgccacc atgcccagct aattttttgt attttagta    1620 gagatagggt ttcaccatgc caggctagtt ttgaactcct gacatcaggt gatccacccg    1680
ccttggcctc ctgaagtgct gggattacag gtgtgagcca ccacgtccgg ccactacatc    1740
aactttttaa attttgtttt actaaatatg aaaatgattc agattgtgta aattacatat    1800
cacatacatg tctaagaact gtaaaacagt tacacagaga gccttggcag gtgagggaca    1860
ttcatgtata gctgtttcag agttcttaga ttttttttga aagattgatg acctgtgtgg    1920
ctgtatgtgt tttattttt tatgagatat tttcagatat ctaatattaa ttgcttctca    1980
aagaatgcaa agttaaataa acatttaggt tctactaatt gatatttaga atatattcaa    2040
acttctcttt gttggtctta tttaagatgt tttgagcaag gaaaggaatt gtgtatgtgg    2100
ggttgaatgt aaggaatgta caggcgtggt cattctcatg ttaacattaa ccagtggaac    2160
atggttgggc cctacaggaa taacctctga tagcattttc tctatgatct aacttccggt    2220
gtatttgtca cccacaatac atgtatatca taaatgttca tctgtatttt gaataaacat    2280
tgtaggcctt tcagatgcat tatagagcct tttcctgatt agcggcctta ccattgctca    2340
attgtagatc tgttaaggtt attgtgcatg atacttagct aattaaactg attttgtttg    2400
agaacagttt taactcttgt tcttctttct ctttcatgtg caggtgttaa tttatcttaa    2460
tggaatagaa aggaaaatga aaatcattta tacgttttat ttgcatttaa aaatagcacc    2520
taacaatagt tactactatc ttgaaatata actggcactt gttcatagaa ctagagttat    2580
ttttataata ttgtgtgaag ggtggtttac atggtttctt gaaaaatgag gatcatgaga    2640 cttaagggggg atttgcctgg ttttagcagc agaagcaaat cagcttgaat aatcttggaa    2700
gtaactcttg ttgttgaatt taaagatgtg aacagaagtg tttatgtaca ttgtcaggga    2760
aataagaact ggctattact tttgagaata tccttatacg gttaaaacat taaattctgg    2820
tttggttgta atgttcattt tgtattatgt agtagttctt cgatgtttca gagattgcct    2880
accaaagctt aggtttaagt tagctttcta cctgatttcc ctttgctttt gtcaaatttt    2940
caagtaaaat tcaaagtata aatataagtt ggtatttgcc ctgaactgct tgcttatagt    3000
ggagattctg aactgagggt gttttcttct tctctcccctt ttttagagca gaaggagaaa    3060
cgtgtgtgga gtttaaagcc atgttgattg cagtgggcat ccacttgctc ttgttgatgt    3120
ttgaagttct ggtctgtgac agaatcgaga gaggaagcca tttctggctc ctggtcttca    3180
tgccgctgtt ctttgtttcc ccggtgtctg ttgcagcttg cgtttgggc tttcgacatg    3240 acaggtcact agaggtgaga tttcatatat ttaagaatgt tttccacttt gggaggtcaa    3300
ggcaggtgga tcacttgagg tcaggagttt gagaccagcc tggccaacat ggtgaaaccc    3360
catctctact aataatacaa aaattagccg ggtgtggtgg catgcgccag taatcccagc    3420
ttctccggag gctgaggcgg gagaatctct tgaacccagg aggcggaggt tgcagtgagc    3480
caagattgaa ccattgcact ccagcctggg tgacagaatg aaactccgtc ttaaaaaaaa    3540
```

```
aaaaaaagaa tgttttcaaa agtaaaatat tttgctcagt tattcagatg tcaatttctt    3600 acccttgtt aggaagagct tgatcattac caactctaca tcatgagaca acaaggcaac    3660
aaaagatgat ggaaataaca attttcttt cttcacttag aacactagct tttcacccag    3720
gacatcagcc ttctcccagc ttcacatcct gtatcaatca gacagaaaca gaactgatag    3780
gttagataca gatatatgta taaagagagt taaggaactg gctcacatta ctgtggggct    3840
ggcaagtctg aaatctccag ggcaggtgaa caggctggag acctaggagg agttgacact    3900
gcagtcctgg cacagaattt tttcctctcc aggaaaccac agttttgct tttaaggcct    3960 tcacctgatt gcatgaggcc cacccatgct atggagggta gtctccttta ttcaaagtca    4020
gtaccttcac tgcaacagca agcttagtgt ttgattaaat aactgggtac tatagcccag    4080
ccaagttgac actcaaaact gaccatctcc ccacctcaga ccccatgatt tagcacctcc    4140
cctgctgtct ggttagctta tcctgatgtg cccctgtgtt tgtttattca ttcaataaac    4200
atttatcaag tatttactag atgccaagcc cttttttccct aagcatagag gatatgcaga    4260
tgaataaaat accaggacta gtaataatag taatgaaagt aattgcagat aacgtttatt    4320
gagcacttac tgtgtgccag gcattgtgcg aggcacatta catgtggtag ttttcttact    4380
aactaactct gtgaggtagg tccagagaag ataagtcatt tgttcatggc cacatgtgaa    4440
ggggcaggac caggattccg tttgagtcag cccgactcta aagcccggc acataactac    4500 ataactgcat agaagctgag ggcccaaagc tgaatactga tgggttgagg ggagaactag    4560
aggctgtaga tgcctggttt tgagccgtgt ggatgaagag tgaagggaga agactgcagt    4620
tggcttagga agtaaacata gcagctgtag ggtgggtcag gcatataagc ctagacccca    4680
ggtatgggcg tgaggggaag gtatgtgac agagggacgg tgatggagca aggccctgtg    4740
ggactcaggg agaatgggac ctagagcacc aggaagggtt tggccttgaa caaggggagc    4800
tattccctga ttttcatgct ggtggaaagg ccacagcatg ggtatagtgg taggtaggag    4860
tgagccgtgg agggagagta tctgatggtc cactttcacc ctccctacaa ttcccagttt    4920
atatcaggga cttgagcatc catggatttt ggtatccaca gggggtcctg gaaccaatcc    4980
cccacagata ctgagggaca actatacaag gactaggact gcattgggcc tgaattacag    5040
aaagtaagtc tttcatatat tcacactcta ggcattcctg cccttggaag aaacaacata    5100
ccaggagctg agctccctcc tcctgtgatg caagaacagt acctatgttg gtgaggggt    5160 ggtctggagt aggctcatac agagatggga aggaggagtt gagggtctgc caggaagccc    5220
tgtgttggga gggaagggat ggcattttg ggacacattg aagcctagag gcaggaaaca    5280
ctccatcagc tgagtggact gtggcgattc agatccgacg ggagcacaag gtggaaagga    5340
aggaactgtg ggagttgaga agagagggag cctctacaga gggattgggg caaatagggg    5400
ccacgtcctc agcccacaga gcatgtgctg aagtgcccca ggcacccag tgcactcaca    5460 gggcaccagg ggatagtgga cattttgagg aaaacagtaa tacctgacat tgttgggac    5520 accatacaaa ctactagctt gaaatagttt acaggtttat ttttaggcca cactgcattc    5580
ctttcagtga cgtcgtatct ttaagaagct gggttttcag cagttgctgt gaaaacaaaa    5640
aaggctaatg ctgtgtgaaa atccgggtga agaacaggta acgagtggga gcaccttgtc    5700
tgattccaag gcgtgggaaa tggtgagcta cctgacaggc acacgcatcc cactgggaat    5760
tagttttggt tatttaagaa taatattaac atttttcttt agatttatat gaattatttt    5820
ttctagtggc tacttagaaa tacttactaa gttagatgta attacttaaa tcagtgcaac    5880
tgttggcatt cccagccaca ttagggattt cttttggcct agaggtctat ggaggaatta    5940
```

```
ctaaattccc catgtaccta tgtactgaga acttttggga agctctgggc ctggtcccag   6000
atttcaattt tgtgggcaag aatgtacttt accagagtga ggagcagcct gcagggcgtt   6060
tgggctggag gcgggaggtt agtaaggggt tgctgaagtg gtaggcggat ggtgccgaag   6120
aaggcctcac taggcagtca tcatcaggat aggaagtggg cacgggattc aggagaaatc   6180
tggactttac agtggacagg atgtggtgac tgaacgtgac agtgtgggaa aaagaatgca   6240
gggtgattcc cgggctcatg gcttgagaaa tgagaccact gttgtgcctc caagtgacat   6300
gggaggctat agaaagtgac atgggaggct atagaaagtg acatgggagg ccatagaaag   6360
tgacatggga ggccatagaa agtgacatgg gaggccatag aaagtgacaa gggaggccat   6420
agaaagtgac atgggaggcc atagtgacat gggaggccat agaaagtgac atgggaggct   6480
atagaaagtg acatgggagg ccatagaaag tgacatggga ggccatagaa agtgacatgg   6540
gaggccatag tgacatggga ggccatagaa agtgacatgg gaggctatag aaagaggaga   6600
tacaaggttc taagtgcagg cgataatgat ctctatttgg gactggcttc atttgaggtg   6660
cctttaggag agccgagtgg cctatgcaca gctgggtctg ctatgcagca ggaaggctaa   6720
gttggagaca gatgtgagaa ctaaccatga aggaggtaat aatgcagacc aagggtctgg   6780
ttgaaatttc ttctccccca gtccagggtg cagcgggtga gtgaaaatat gtgtgtttgt   6840
gtgtctgtct tcctagtcgg gagagaagac tgagtttgtg gctctgcgga gcatcaccat   6900
ttaaggaggg ggaaaaggag acagaaggaa ttaccagaac actccagagg gctccaagac   6960
tgtatggtgg gatctagatg gccaggagga ggggagcaaa aaggaaagag tcatccacag   7020
tatcagtagg atgccagttg aagtgttttt gctgcctccc ggttatcggt gactttgatg   7080
aaagctgtct tctggtggtc atgggggtgg aggccagatc acaaggaagc tgggaatggt   7140
agatgagata gtagggcctt gcatattcat tactgtctcg cagagagaaa cctgaggcta   7200
agaggggtct tggatcaaag gatggggtgg gtttatctgg tttcggggct tttgttttta   7260
atgagaagga gtcatttctg tgctgctagg agggatcaat ggaataggtg gggttaaaga   7320
tacagtacgg aatctacagt tgatggcttg atgtgacaag gtcctcaagg agcctgaaag   7380
gaaggggtgg ggtccaaggg caaaaccgag gtatgagaag aaggatgcac aaggatggtt   7440
tcgagtagac agtattgttg gtagggacat gaaggaagtt tagtggtcta ttgcagctag   7500
cctgtgttcc cagtgaacct ggaaacaagg ttctcatctg tgctcaggcc tcaggccaga   7560
aagggcaagg cagcagaggg gcaaggcagc aggctgagcc ccatttcccc ttgccataat   7620
actgctgtgc ccctctggta ccgaaaatca ggagtttcca gtgcaatata atattataca   7680
agttacactg tattataatg tgtattgtct tttagtgtgt taaccaaatt actgcagtat   7740
taaatgcaaa ttatactttg tttaactgat tcttctcttc attttagtt agaaatcctg   7800 tgttctgtca acattctcca gtttatattc attgccttaa gactggacaa gatcatccac   7860
tggccctggc ttgtatgtaa cttttaaaat ccttaaataa acttcttttt tattataaaa   7920
gtaattcata ttcactgtac aaagcttgga aaagacggac aagcagaagt aatagcctaa   7980
tagtcaccca taatcccacc atgggagat aacatggtta gtgtttttat gtctgtgttt   8040
tatacaaaca gtttggatat aactgtgtgc accattttgt atcctgattt ttttgtttta   8100
atgttgtatc ataaacattt tatcatgtta ataaaggtc tttataaaca tgacttctaa   8160
agtttaattg atacaaaata ttcttcaagt gcatgtatca gaccatcctc ttatttctaa   8220
aatatgtgta ttccattgtt gccagtgttg aatgatttta aatcatactg cagtatatat   8280
gtttatgcat taaaattttt gccttttgtt ttttggttgt tttcttagga aatagtccag   8340
```

```
aaatagtgtt actgagctag aggttgggaa ctatttgaga ttcctatata cgtatactgc   8400
actgccaact tgcttttcca aaagccatac ctggccaggc gcagtggctt acacttacag   8460
tcccagcact ttgggaggcc gaggtgagct gatcacttga gctcaggagt tcgagaccaa   8520
cctgtgcaat gtagcaagac cctgtctcaa agaaaaaaa aaaaaagcca tacccattta   8580
cactcttgct ggtggtggca tctatgtcat gcttctaaac tgtgacttca gttactgggc   8640
atttggttga aattaactgt gaataaatgg gtagatggat gcagagatag aaagataagt   8700
ggcaaggtag aaattagaga acacagtata gattccacta ttaaatgcat ggaaaaaaga   8760
tggagactaa aggcagaaga gttccattgc cactgggagg taaggtcatg ctagtgtttt   8820
tgttcggttt tattttctct gttgtttgat gtataatttt gcatacaata tattttatgt   8880
attaaatata gctacccttta aaaagtgaaa agtatagtaa agaattggga gcagagaaga   8940
aatgaaggga acctaagtat actccatatt taaagatggg aataatcact tctgcccaaa   9000
gtctttgata aaacattcat aataaaaaat attcagtcac tcatcctaca acttcacagt   9060
gctgtatctg gagaatggtc attgggttca aaactgtttc tgttgtgacg tgaaggaaac   9120
atatctaaac aagaccaaat tttttcgtat aagatactgt cagggaaaaa aaagattagt   9180
aattttgaga gctttccaca aatgagaaga aagattttt ctgcccttca tcctctgtag   9240
atcccagttg atgaagcagt ctgagtacat gtttcccata gtgagcaaga gaaacaagg   9300 aagcctattg agatctaaca ttccacccat gaagggaact tcagtaaaaa ggagaatctc   9360
atcacagaat ggggaacggg gaagaaaggc tgtgcataga ctctgcagag aaacctacaa   9420
tcaagaactg gtcaggagaa gtaaaattcg tatgccaact caaatcatag atctaaaaga   9480
aaatgtaaaa ctatagatct gttaggaaat aacataggac agaatctttg gggtttgcaa   9540
ttaggcagag agtacttaga aatggcactg ttaatatggt ccatacgaga gagaaatcat   9600 aaattttggac ttcctcaaaa ttaaaatgaa atgaagacag gccacagact gggagaaaat   9660
atttgcaaag cacacatcaa aacactgact tgcacccaga acatacagag aactcttaaa   9720
aactcaaaac tgcaaaaaga aacacctaaa aattggcaaa agagttgaca atttgcgaag   9780
gggatataca catggcgaaa aagcacagga aaagatgctc aacgccatta caggttaggg   9840
aagacaaact acaaccagga tgagggcccg aaacacatgg cttcagaatg gtgaaactca   9900
gcaacactga cgaggccacg tgcctgggag gatgcagagg aactgggaca ctccagtgtt   9960
actggcggga aggcaggtgg tacgggcact gtagaaaatg gtttggccat ctctgatgca  10020
gttaaaagcg cacttcccgt gggacttggc tgccccactc ctgggtataa gatttacccc  10080
cagagaagtg aaagcgcgca gccttgtaga aacccacaca ccagtgtttg tagcagtctt  10140
gtttgcattt tggatagcgg ccttgtttgg ttttcacaaa ccaccctcag cggacagtca  10200
gataaactgt aggcatccat acaatggaat accactcaga tctgagaggg aacgacctgt  10260
ggatacaggg agggaacaac ttggatgaat ctcattagag acattatgtg gatggcggga  10320
agccagtctc aacaggttac ttgtctcgcg atgccatcta cataaagttc cagcagagac  10380
aaaagtacag tgagagaaca gatcagtgtt tgccggggct aatggtgggg acggtgtgat  10440
agtgaaggga cagcacggag agttttgcag ggtgacagac ctcttctgca tcctgccaac  10500
ggctgtgtga atctacttgt gtgaagactc agggaactca caccaaagga agacggtcac  10560
ttttcctact gtatgataga taattaataa aaagggagaa cggaggagtg tcgtcccagg  10620
aggcagggca ggagggcgaa gacgtgtcac aggggagcct ggccaagtgg cgcccccgga  10680
actcgtcctc tgggcttgtg tgtggatgag acaaggtcta cctggtacga cagggacata  10740
```

```
ctgggaatgc gcccttgccg tggaggcggg gacccggcag cgctacgtat ccagcatcaa    10800
cctgtatcca gcatcaaccc gccaagttca ctaacttggt aggggtgagg ttagggatcc    10860
ttaggagccc aggcagccag actttctggg gagcccattc ccatttgtgt tgccaaagta    10920
cccccagcag gttgtgggaa tgttgcctgt gaagagagtc tgttggggtg agatcttgtg    10980
tgtgtgcaca gggtgacagt tgtgtcccat ttcccgggaa gctgtgatgg cagcagaacc    11040
tagaggagcc tgagagagtg tgggagagtg ggcctctgga agagtagagg ctgcggagcc    11100
aggtgcaggg ctgtctgtca cccaaaggaa gagggactga tgactcactg agcgtgtgtg    11160
tcccctggtg gcagcaggcc ccatagtgaa cataccatac cttttctgtc ctgagcgatg    11220
ctcccagcag tcctgggaga tggaacggtc cttattcggc tcacaggaag gaccgcctta    11280
actggacaga cacagcaagg tgctaaagat gccttccatc agaggccagg ttggaagctc    11340
taaagagact tctcttgctg ttctctcacc caccccagg ttgtgtgtgt cccgctgtgg    11400
attctcatgt cctttctgtg cctggtggtc ctctactaca ttgtgtggtc cgtcttgttc    11460
ttgcgctcta tggatgtgat tgcggacagc gcaggacaca cataaccatg gccctgagct    11520
ggatgaccat cgtcgtgccc cttcttacat ttgaggtaag cgttccacgg gaagcctctt    11580
cagcccctga agcttgcgct tcccctgaca ggattctgca cccctagaaa ggcagcctct    11640
gtccctcgag ctcacagtga gcccactcca ggagagggga gagaacacag ccatctccga    11700
gagggagctt cggtgaaagg agagcatcct tcctttctct tgggggcagc acgtggggct    11760
ggcagggaga agagtgcacc tttttagcca tggtgcctct gtatggctcc agtttccact    11820
ctggggaaag cagagtggga tgtcagattt gtgtattgga gtcacgtgga gaattctaga    11880
atgggagctg ttgactcctt agaacaaaca cccggaggag tttgccataa aactgctggc    11940
actgggaact tttcaagtgg ataggctatt gccgagctct gaagagggac ataaaagctc    12000
atttcgagct ttccccaggg ataggtggtt tcctgccttt ttctggcggt gctgatgttc    12060
cctcttgtgg gagctcacgc gggggtgggg tggtggggag gaactgccta atgaagtctg    12120
gcttccgcct ctgcccattt tcggtgctgg catcaaccgg gactatgtct ctttctttag    12180
attctgctgg ttcacaaact ggatggccac aacgccttct cctgcatccc gatctttgtc    12240 ccccttggc tctcgttgat cacgctgatg gcaaccacat ttggacagaa gggaggaaac    12300
cactgtatgt actcagcatt tcagaagtcc ttggtgtgtg tctgggggg gaccaggggg    12360 tgggggtgg cggatagaag tctaggaagg gatgagtccc cgagggcccc aatttagaag    12420
cttgtgtggg aaagtgaggg ctgaggaaat tctgggacct tctaagggaa gggcatgccg    12480
taactctggt gttctgctgg cctgcaccgg gacttttctc gcagtgcacg ctgccatttg    12540
aggtagaacc agacacggca ggcaacctct cagagatccc gttccctcct ctgcaaaatg    12600
gggatcaaga cagattcttc ccaggcccgg gagggtttga tggaaaatcc acatctccca    12660
cccaaacctg ggattcatcc taggtccctg ttggccgctc tgcctccccc atatccttgc    12720
tgccatcacc cgagtcttgc ctgtcttgcc ttgctaacac tctattcccc tccacctgct    12780
tgctgaggca gacacttcca aaacgatctc tgcagagggt gccttcctgg caaggctgtg    12840
ggctccatgg cacggaagcc cagagcattg cccttcggaa agccagtggg tttgggggca    12900
gggcctcact gcagcccagc agcccgggct gtgcttgctg tttgtgcctc tgcccccctac    12960 cccgcacccg ggagcaggga gggcttgcac cgagctgaca ctccagtagc ctacagagag    13020
gagtagtggg actgggaaag tggctttaag gtggctccat gagttcaggc cccctcctgg    13080
ccaacccgtg catgactacc gccctcacgg attccagagg gtgacagaaa tcttgttctt    13140
```

```
gggtggcact gtcatccatg agtttatcct ggctggagaa gattagcgga agacaccgta   13200
gtctgcgcac cacagatatt ttgagactca ctggagcagt agttctcaaa tttgggcatc   13260
cagcagaatc ccaaaagggc caggaaaagg ggaccgctgg agcccaccct agcccgactc   13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaaagttaa caggaaggtc   13560
agttgagcct cgtgtgtgaa ataaaaaatt cttatttttc agggtggttt ggtatccgca   13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtaccctct tccccgtcag acccactggg agatggctgc   14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tccaggtcg tggctggggc agtcagtagg aactgtaact atgtctctga   14340
tgcaccacgt gtttagacac agcacagtcc tttttctgt tcctactgtg gaagtagttt   14400
ctctttgggc atgctgacag cagttttttca tagcctcacg gatgagccct ttctacggga   14460
gtgactccat gcttgtatac agagtattta tacaaatgtt ttagcatctt catatgcggt   14520
gttaacccct agttctgtac agcatattct gttcaagtat tttttttacaa gcttgtgctg   14580
taggcacatg ccttctgctg cagaagtgga cgcccgtggc acactccccc ccccccccg   14640
tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
tcctgcctga aaacaaatag gtcctttgct gaaaagaggg taaaaaaaga gctttgatct   15060
tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca gcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
```

```
ttgccacact tgttactgct taggaggctt tctggagtgt tccttgggtg ctacgacaat   15600
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg attttcagtc ctgtgggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
cggccgggtt gagcatcagc agtctgtttg cagacccctc actgtcaccc cctgagccag   16140
tgcgccttgg gccctgcggt caggatgtct caagcgtgga ggcatcaccg gttcgtggca   16200
gtctctggaa ggtcactgag ctctgtgccc agaatcgagt cggggagtc tgtgcagagg   16260 tggccctgtg tgtgggggaca gtgtgtgaca cagacactgc tttggatgga cacctctccc   16320
gtgacctcct agcatccaat cccaaaggaa caactgttgc agagatggac cgctggacac   16380
aaacccacgt gcgtttctct ggagacactg gccaaggaaa acaaaacatg ctcgaaggcc   16440
aacagctgca tgccccaccg cgatgtgacc gcagacaccc ggggtgtaga agggtctctg   16500
cctggtgggg ggacacgtgc aggccgagga gaggcaggaa ggaggctgcc tccgactccc   16560
cactggactg catggcgacg gcgtgtggtg gggcagtcag ctaagccatt tgcctaaggg   16620
gctgtcgggc atctgcgtgc tggggaccga cagtgtgggt gtgttaggag gatctgtatg   16680
gagcacattg ctgcctctgg ctaggacagg gtggaaaggg tggcgtggct acagcctgac   16740
ccatgggcac cgtcctaccc tttgttctgt gcttccgagt gtcagtcatg gctggggtc   16800 tgtgggccca tgactcagac ggtgagctct gaccttcctg agccagggct ttgctgtagt   16860
tgtgcctggc tcaggagctc taggacaagg ggaccgctcc aggtctgcat ctacggtgtg   16920
gcagggcccc tcggcactct tgtgcactag tgtcatcttt cccattgaaa tgactgtgag   16980
gaccagaatg tgcacatgca gatgggcagc tacttgtctg ccttggccct ttattacaca   17040
acttgctggg ggtggagatg ccacccccg gcagtcagag ccccttatg atgtcatggg   17100 gctggttaca tgactgccaa ggggtgctgc tggccacact gcactagcaa gtttgccaga   17160
tggaggacaa gcgatcattg agtatggctc gctgtgaaga aagaaattcg agaggacagg   17220
atcatggctt ggaaagggtg ccttcccte cccagttgca gtcagagacc taccttcacc   17280
cagcagatcc ttcccctgcc tgggacgacc cggggtccac tgggagccct aacttgaggc   17340
tgctgacaga agaaatcgct ttccaacctc tggccgagga agcttcgttc agaaggccgc   17400
accctgacgg tgacgtcccg ccccagggag aagataatct cctctccctc cccttttccac   17460 agaaactgtg gagactggtc agcagcaacc agttttcgtc catctggtgg gatgacagtg   17520
gggcttgtag agtgatcaat caaaaactct ttgaaaagga gattctcaaa agggacgtcg   17580
cacacaaagt gtttgccaca acttcgataa agagcttctt ccgccagcta aacttgtatg   17640
gcttccgaaa acggcgtcaa tgcactttca ggaccttcac ccgcattttc tccgcaaaaa   17700
ggctggtctc catcttgaat aaggtaatga acgacaagcc tctggagggg ttaagtcggt   17760
gggctctggg gcctggtcgg gtgaagtcc caggactgcc tcctgggaag tgggcgacct   17820
caggcagggt gtgggccat cgctgtgggc ctgtgtcccc ctctgggtgg aggtgacatg   17880
aactaagagt gaatgtgggg agagggctga ggatggtgcg ggcccctctc gagtgtgtaa   17940
```

| aatatcacag gtgccaagta gccgtatctg cgtgtcgtcc tccccggggc cagccatgtc | 18000 |
| atctggtggt tgctgtgtcc ccctgactcc acagcacatt accctgtgag gtgagcaggc | 18060 |
| caggggagtc tggtatttgt accactgtca ccctagctgg tgtctggaga ggtgctcaag | 18120 |
| tggaagcact gaagggcgcc tggcgcagga ggtgcagatg ctcctgctgc ccttggtagg | 18180 |
| tgggcccctg gtgtggaaga gccagtaccc agggcctcca acccagccgg ggtgcattct | 18240 |
| gttgccagct gacactgcat gggggaggcc cagaatcttc ttccctcctg gtctgcaact | 18300 |
| tcaaagaccc tttccgccgg ccatggacac cctaatctgc cattttgagg cttttttccaa | 18360 |
| gacggaaagg cccgccacaa cttggtaaac cttgacgatg tgaacgcgag tccccagctt | 18420 |
| cctttgggga ctgggacctt ttccagaaag gcctcctggg ccagtagagt tctcttgcac | 18480 |
| aggggcgtag atggttggta gttgtagtcc atccttgtga cttg | 18524 |

<210> SEQ ID NO 13
<211> LENGTH: 7695
<212> TYPE: DNA
<213> ORGANISM: Homo sapiens

<400> SEQUENCE: 13

| ggcccaggag gcctttctgg aaaaggtccc agtccccaaa ggaagctggg gactcgcgtt | 60 |
| cacatcgtca aggtttacca agttgtggcg ggcctttccg tcttggaaaa agcctcaaaa | 120 |
| tggcagatta gggtgtccat ggccggcgga aagggtcttt gaagttgcag accaggaggg | 180 |
| aagaagattc tgggcctccc ccatgcagtg tcagctggca acagaatgca ccccggctgg | 240 |
| gttggaggcc ctgggtactg gctcttccac accaggggcc cacctaccaa gggcagcagg | 300 |
| agcatctgca cctcctgcgc caggcgccct tcagtgcttc cacttgagca cctctccaga | 360 |
| caccagctag ggtgacagtg gtacaaatac cagactcccc tggcctgctc acctcacagg | 420 |
| gtaatgtgct gtggagtcag ggggacacag caaccaccag atgacatggc tggccccggg | 480 |
| gaggacgaca cgcagatacg gctacttggc acctgtgata ttttacacac tcgagagggg | 540 |
| cccgcaccat cctcagccct ctccccacat tcactcttag ttcatgtcac ctccacccag | 600 |
| aggggggacac aggcccacag cgatggcccc acaccctgcc tgaggtcgcc cacttcccag | 660 |
| gaggcagtcc tgggacttcc acccgaccag gccccagagc ccaccgactt aacccctcca | 720 |
| gaggcttgtc gttcattacc ttattcaaga tggagaccag ccttttttgcg gagaaaatgc | 780 |
| gggtgaaggt cctgaaagtg cattgacgcc gttttcggaa gccatacaag tttagctggc | 840 |
| ggaagaagct ctttatcgaa gttgtggcaa acactttgtg tgcgacgtcc cttttgagaa | 900 |
| tctccttttc aaagagtttt tgattgatca ctctacaagc cccactgtca tcccaccaga | 960 |
| tggacgaaaa ctggttgctg ctgaccagtc tccacagttt ctgtggaaag ggagggaga | 1020 |
| ggagattatc ttctccctgg ggcgggacgt caccgtcagg gtgcggcctt ctgaacgaag | 1080 |
| cttcctcggc cagaggttgg aaagcgattt cttctgtcag cagcctcaag ttagggctcc | 1140 |
| cagtggaccc cgggtcgtcc caggcagggg aaggatctgc tgggtgaagg taggtctctg | 1200 |
| actgcaactg gggagggaaa ggcaccccttt ccaagccatg atcctgtcct ctcgaatttc | 1260 |
| tttcttcaca gcgagccata tcaatgatc gcttgtcctc catctggcaa acttgctagt | 1320 |
| gcagtgtggc cagcagcacc ccttggcagt catgtaacca gccccatgac atcataaagg | 1380 |
| ggctctgact gccgggggggt ggcatctcca cccccagcaa gttgtgtaat aaagggccaa | 1440 |
| ggcagacaag tagctgccca tctgcatgtg cacattctgg tcctcacagt catttcaatg | 1500 |
| ggaaagatga cactagtgca caagagtgcc gaggggccct gccacaccgt agatgcagac | 1560 |

```
ctggagcggt ccccttgtcc tagagctcct gagccaggca caactacagc aaagccctgg   1620
ctcaggaagg tcagagctca ccgtctgagt catgggccca cagacccag cacatgactg   1680 acactcggaa gcacagaaca aagggtagga cggtgcccat gggtcaggct gtagccacgc   1740 cacccttttcc accctgtcct agccagaggc agcaatgtgc tccatacaga tcctcctaac   1800
acacccacac tgtcggtccc cagcacgcag atgcccgaca gcccttagg caaatggctt   1860 agctgactgc cccaccacac gccgtcgcca tgcagtccag tggggagtcg gaggcagcct   1920
ccttcctgcc tctcctcggc ctgcacgtgt ccccccacca ggcagagacc cttctacacc   1980
ccgggtgtct gcggtcacat cgcggtgggg catgcagctg ttggccttcg agcatgtttt   2040
gttttccttg gccagtgtct ccagagaaac gcacgtgggt ttgtgtccag cggtccatct   2100
ctgcaacagt tgttcctttg ggattggatg ctaggaggtc acgggagagg tgtccatcca   2160
aagcagtgtc tgtgtcacac actgtcccca cacacagggc cacctctgca cagactcccc   2220
cgactcgatt ctgggcacag agctcagtga ccttccagag actgccacga accggtgatg   2280
cctccacgct tgagacatcc tgaccgcagg gcccaaggcg cactggctca gggggtgaca   2340
gtgaggggtc tgcaaacaga ctgctgatgc tcaacccggc cgctgccgag ctgtgtgact   2400
tgggcacgtc acttaacctc tctcggcctc tgtctcctcc cggggataag agtagtagca   2460
cctgcttccc ggggctgtga ggatccagtg ggacgtatag gaactagcga ggcaccggca   2520
gttgggtcag agctactgtt gtcacttcac aaggcatttt cttcaacagc aagtcggaaa   2580
tctcatgagc ctaaggcaga atccacctgt ggcctctggt tacaacccac aggactgaaa   2640
atccttccag ccacagcaac tggtgaattt cctggtcaat tgccacaagt catgagctga   2700
accccacttg agtttcagtt caggcagaac tctagagacg actagggcaa gctagacagc   2760
gactgcagag ccttttgttg cagcgtgagc agtcctcagc tgttgacatc actggggagc   2820
aaacgaggac caggagcggt gaaaggacag tgtctgctgc agattgtcgt agcacccaag   2880
gaacactcca gaaagcctcc taagcagtaa caagtgtggc aaggtgtagc ccagccaaca   2940
gtggcatctg cgaggcgtcc cctccttcct cccactaccc cgtatacccct gggacctgtg   3000 cactgaagga ctcattctaa aggctgtgcc cctgcagccg ccagcctcac tcactggctg   3060
cctgtgccag ctagagattt cttccctctg aggctggctg agaggaccac tccagtttcc   3120
tggcccatcc agcaaagaag atacacatca tgcacgtgta aaatgaggaa ccggtttatt   3180
gaacagctta aggagagcaa aaatagtggc tttagctaca ttttttacac actgagcagg   3240
aaagtctaaa ccatcccgtt ccctgtacc ccaaagagaa cagggcttgc tggaggccag   3300
tgccaagggc ggagtcgtgc tcgcagcaga cttgaattaa ccccatgtag gccggcgagc   3360
agttgcccgc gtgaaaacac caccctcttc tcctggctga aagatcaaa gctcttttt   3420 taccctcttt tcagcaaagg acctatttgt tttcaggcag gaggatgtta aacttgcagc   3480
ctctgacaca cggtggaacc tgcagtgctt ggagaaacgg cacgcacacg tgaaaacatc   3540
atgcctactc caaagccttc ttgttgctgg caggagggaa gcttgagact ttccacgca   3600 tagtcgtgac ccgcgtggcc gtttctgctc tcagcaacat tctctagtgt tccggcttca   3660
agcagcgctt gtcaggtttg aagctagcca ctattctgag aacgtcagaa aagcatggac   3720
catctcttgc ttggtgttgc cgttgtgca gtagcagcta ctacgtacct gcacgagttc   3780
cagggcagaa gtggcaatgt cccatgaagg cgtggcaccc cacgggggggg gggggggagt   3840 gtgccacggg cgtccacttc tgcagcagaa ggcatgtgcc tacagcacaa gcttgtaaaa   3900
aaatacttga acagaatatg ctgtacagaa ctaggggtta acaccgcata tgaagatgct   3960
```

```
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatactttt gattgggatt    4260
tcagcaccgt atagacagat gttccttctg ggggcctggc aagcagccat ctcccagtgg    4320
gtctgacggg gaagaggggt acctggagcc cctcccagac agacggtaat cccacccctg    4380
ttctcacact cttcctggca tccgcatctg ctggcacaca cccccgtcac ctgccacttc    4440
cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560
gaaggcggag agagtgcgtc ccagtccact taagctctgt ccccggaagt ggcatctaat    4620
ctggcatttc gatatttaat ttgggaggtg ggagcacata cttcccaggg ctctgggtaa    4680
tgaccaccct ggccttcttt cgaaacatgg gtgcgatttt aggggctcc ggaactgggg    4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaattttt atttcacaca cgaggctcaa ctgaccttcc tgttaacttt    4920
ctttccgtaa caagaagttt cactcctaca atgtcataac atactttatc cagactcctg    4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt cccctttttcc tggcccttttt gggattctgc tggatgccca aatttgagaa    5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtaggggg cagaggcaca    5520
aacagcaagc acagcccggg ctgctgggct gcagtgaggc cctgccccca aacccactgg    5580
ctttccgaag ggcaatgctc tgggcttccg tgccatggag cccacagcct tgccaggaag    5640
gcaccctctg cagagatcgt tttggaagtg tctgcctcag caagcaggtg gaggggaata    5700
gagtgttagc aaggcaagac aggcaagact cgggtgatgg cagcaaggat atggggagg    5760 cagagcggcc aacagggacc taggatgaat cccaggtttg ggtgggagat gtggattttc    5820
catcaaaccc tcccgggcct gggaagaatc tgtcttgatc cccatttttgc agaggaggga    5880 acgggatctc tgagaggttg cctgccgtgt ctggttctac ctcaaatggc agcgtgcact    5940
gcgagaaaag tcccggtgca ggccagcaga acaccagagt tacggcatgc ccttccctta    6000
gaaggtccca gaatttcctc agccctcact ttccacaca agcttctaaa ttggggccct    6060
cggggactca tcccttccta gacttctatc cgccaccccc cacccctggg tccccccca    6120 gacacacacc aaggacttct gaaatgctga gtacatacag tggtttcctc ccttctgtcc    6180
aaatgtggtt gccatcagcg tgatcaacga gagccaaagg gggacaaaga tcgggatgca    6240
ggagaaggcg ttgtggccat ccagtttgtg aaccagcaga atctaaagaa agagacatag    6300
tcccggttga tgccagcacc gaaaatgggc agaggcggaa gccagacttc attaggcagt    6360
```

| | |
|---|---|
| tcctccccac cacccccaccc ccgcgtgagc tcccacaaga gggaacatca gcaccgccag | 6420 |
| aaaaaggcag gaaaccacct atccctgggg aaagctcgaa atgagctttt atgtccctct | 6480 |
| tcagagctcg gcaatagcct atccacttga aaagttccca gtgccagcag ttttatggca | 6540 |
| aactcctccg ggtgtttgtt ctaaggagtc aacagctccc attctagaat tctccacgtg | 6600 |
| actccaatac acaaatctga catcccactc tgctttcccc agagtggaaa ctggagccat | 6660 |
| acagaggcac catggctaaa aaggtgcact cttctccctg ccagcccac gtgctgcccc | 6720 |
| caagagaaag gaaggatgct ctcctttcac cgaagctccc tctcggagat ggctgtgttc | 6780 |
| tctcccctct cctggagtgg gctcactgtg agctcgaggg acagaggctg cctttctagg | 6840 |
| ggtgcagaat cctgtcaggg gaagcgcaag cttcagggc tgaagaggct tcccgtggaa | 6900 |
| cgcttacctc aaatgtaaga aggggcacga cgatggtcat ccagctcagg gccatggtta | 6960 |
| tgtgtgtcct gcgctgtccg caatcacatc catagagcgc aagaacaaga cggaccacac | 7020 |
| aatgtagtag aggaccacca ggcacagaaa ggacatgaga atcccagcg ggacacacac | 7080 |
| aacctggggg tgggtgagag aacagcaaga gaagtctctt tagagcttcc aacctggcct | 7140 |
| ctgatggaag gcatctttag caccttgctg tgtctgtcca gttaaggcgg tccttcctgt | 7200 |
| gagccgaata aggaccgttc catctcccag gactgctggg agcatcgctc aggacagaaa | 7260 |
| aggtatggta tgttcactat gggggcctgct gccaccaggg acacacacg ctcagtgagt | 7320 |
| catcagtccc tcttcctttg ggtgacagac agccctgcac ctggctccgc agcctctact | 7380 |
| cttccagagg cccactctcc cacactctct caggctcctc taggttctgc tgccatcaca | 7440 |
| gcttcccggg aaatgggaca caactgtcac cctgtgcaca cacacaagat ctcaccccaa | 7500 |
| cagactctct tcacaggcaa cattcccaca acctgctggg ggtactttgg caacacaaat | 7560 |
| gggaatgggc tccccagaaa gtctggctgc ctgggctcct aaggatccct aacctcaccc | 7620 |
| ctaccaagtt agtgaacttg gcgggttgat gctggataca ggttgatgct ggatacgtag | 7680 |
| cgctgccggg tgacc | 7695 |

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14

| | |
|---|---|
| gggcgaattg ggcccgacgt cgcatgctcc cggccgccat ggcggccgcg ggaattcgat | 60 |
| atcactagtg aattcgcggc cggcgattgg gcccgacgtc gcatgctccc ggccgccatg | 120 |
| gcggccgcgg gaattcgatt ccttaattaa gtcgactggg acccaaactt tggagtcgtt | 180 |
| gacagatgtg acaggtgaag cctgggatga catcgccaaa aatgcaacgt ctcactcatt | 240 |
| gtcactactc ccagggctca gtcgtcactg ggaaaatct ccagaaggta gcgcgggcca | 300 |
| aggtgacagg tgtctgccaa gatctgcccg ccagactccc gggcggcgcg ctccctccct | 360 |
| gcaggccttc agcccgtcag catccccttc ctcggggccc tgctcactcc cagcctccat | 420 |
| cccccctgcca tctcctccgc cggtcgcgtg cggacacaag gatggggacc tcccagcgag | 480 |
| gagcgctctg ggcggggctc cggacgcatg cgcggccctc gtacggaagc ccggaaggag | 540 |
| gggcaggggg cggtggctca ggtttctccg ggcggcggcg gcggcggcgg cggcgacggc | 600 |
| gacggcgacg gcagcgggga cggcagcagt agcgggagca gcagcgtgga cgcggctggc | 660 |

```
gctggcgcca tgaacccgct gtaaggcgca ggctgtgcag cacggggtgc gggggaggag    720
gaggaggacg ccgcggtgaa gttctccgcc atgaacctga ggggcctctt ccaggacttc    780
aacccgaggt gaggcggcgt cgttggcgcc cccgggagtc cgcgctgcgg gctcgggcgc    840
gggctggtgt tcggctccgg ggaggcacgg cgggcgagat gctgcagccc gaggacccgg    900
gcgcctgccc gagcctccct gcgggtgcaa gcggtcccca ggcaaaacag tcggcctcgg    960
cgcccgcccg cttcctcctc ccgtgcccgg tgctttcagc ccctgcccgg ccacggccgg   1020
aagggcccgg ccgcgagccc cgtcctgccc caagggaacc ccattctttt ctgcttgctg   1080
tccctcattg gtgtcccaac ttcttcgtct cggttccatc ctcttctgcg ccgctgcggg   1140
ccctccattc tccgcgtcag ggccgtctca ctcgacccaa caccoctacc cccaccccag   1200
ctgtttcctc cagttcctcg cagtccttgg ggttttcctt gggtttatgc ccatccctct   1260
cttgtttgct tctttgttga acggatacct gaaacactgt tgaatccttg gagtcagtgt   1320
cggggtatgg caataccctta tataatgcat ttctgggtga gcctgatcat tttccatact   1380
cattttctca tcagtcttca ctacaagttt atttgcagga agtagatatt gctgtccttc   1440
ttttccagat ggggaacacc cagtggacag tgtggagaaa acactggcta agcactcaag   1500
cgcctgtcct tgcacttgcc cgactgtttt gtaactgttc tttaccccag gctgtgagct   1560
ccctgaagct gagaccatct cctgctcatc tcagtgtccc cagcgcctcc cacccaccgt   1620
atctggcaca tagtaggcac atataaaatg tttgtggaac taaactgagc ccaaagactt   1680
ggattggaga cgaggccata tgtaactggg tgattctctg cccttctttg gcccttctgt   1740
aaaatgagga gttggcctaa ctgatctctt aaatgcacta ctctccgaaa ggagtatccg   1800
tttcccttat ttgccagttg ggaagacgtg ctcagtaaat atttgtgtgc tgtaacctat   1860
gttaggtgct ttagatgctg gcggtctcag catggggtga agaagggctt gtacacttaa   1920
gatgccttac agtactgtgc agtgctgtac tgcgggggcc aactctgggg acctatgcct   1980
tggctgcttg ttgaggatga aaggaagttt tagggggagta tttgtatgtt gagggtgcag   2040
tctccctagg gatggtgaca ttttaacttg tgagtcattg tgactttgta tgtgcccttt   2100
ttccactttg agttcatgtt ctggttagga gtgccagtgt ctctaacacg gtgcagacat   2160
tatcattgtt ggcttcgaag gcatagagga ggtaacagaa ctaactgcag tcccttcctc   2220
tgctgcatca gggggttaag attggtctgc agggtagtag ggttggtgct gtggctggac   2280
aagccctgta tgtcttctat ttggagatgg tgataagaaa gttaagtaaa aactgaattg   2340
ttttgtgccc ttgggcaact cacttatcta ttgttttatc tgtagaatga gtataatctc   2400
tcagtggggt agggaggcca attaaggatt gattacaaag tgccttacaa atagaaagct   2460
acagtgactt gtttgcaagg tgacagagaa ttcagaagcc tcaagaaact gccttaagtg   2520
atcaaacagg ctaacggagt tgccaaagca aaatagtgct gcactgatac tacctttaac   2580
cgttttttcc tttagccctt ttccccccaa aaaattagt atatgaaatt acagtgaaat    2640
acctggtatc taagcagatt tatagtaatt ctcaacatat tcatcaatct cttaattcta   2700
cctgcattaa aatgtatttc tacctgaaaa gtttaaggt cttttatact gtgccatttt    2760
cctgattcat tgttgccaga ggtagtgagt tccttaattt tacagatatt tcaagaggac   2820
attggccagg tattattggt aaatcagatt tgtttttta gctggtagtg tttcacctct    2880
cctgagcact cctagttttt gacagtgtgc tttagtctcc ttccatgctg aggaaggcct   2940
tctctatagg agaaagaaaa ctgaggggtg tacacaggaa gttaccttat gctggggact   3000
caaaccttga tgctactgct tgctcccctg cctctatttt tgaaccaatt caacatctcc   3060
```

```
ctcctacccc aggaccttgt cacacactgt tctctttacc aggaatgttt ccctctcttt    3120
tcctctcctc cagacctagt gaactcctat ttatcctcac ttggcacttg ctaagggaag    3180
cattcctgac ttccctgacc agatttactg ctccctgttt ctacagttcc tgtagtattt    3240
actactcctc catcatagtg catatttgta cccttgtgtc tgtctggatg cttatttgat    3300
taatacctgc ctcccccact aaactttaag ctccatgggg tcaaggccgt gactgtgtca    3360
gtatcgtagc ctgcatactt ggaatagtac ctggctcaat aaatatttgt ggagtaaata    3420
actgaataac tctccagagc ctataagata aatctagagc tgctgctttc aatcactgct    3480
ttcctggtgg tctgtggcct ggttctcttt cttctcacac tcttcccacc ttcagagtgc    3540
agccattgct ttggagagat gggagagaac atggcactaa ggcagaatat ggctatattt    3600
actttgaaga gcatgtcttt gtcatagaaa tagtcactgt catggtttgg tgggtcccaa    3660
ggcatgggtc atggctccag atcccctttc cagccttttg gatcttggta agtctgaacc    3720
cactgctgcg ttggcaaggc tctggaaact atagtgacag agaatgattc acaagtgtca    3780
acactcagat gtacagggct gccagctgac ccactctacc tatttccatc tggcactgaa    3840
ctggttgatc atgaacttct tttcataatt gcttttagt tatgcaggtt aagacatgcc    3900
gaaacagatg taccggaccc acaaacaagt ccttccttga atgcctgagg cttcctaaca    3960
gtgaaagagc cctgttctta gagtaggcaa actgattctg aggcattgta ggtggtaggg    4020
atctggtagt aggtagcatt aggtgggctc ccggcactca ccatggagcc ttgaaatttt    4080
ctgctacttt gggggagttg ctggttcaga gaaggccctt ccaccctggt agccatgtgg    4140
cactggaagg ctgtgaaaac tctgctgggc cttcttagtc atctgttgtg agctcctgat    4200
gggagtgtgg tgtatccctc aggtgtgcta gactggaaca aaggctgaga agtgttgctc    4260
tgggggttcc aacttgtggg catggggtac tgatgagatc agtagtgttt ggagacttct    4320
gtatgctcca tcttcagaag acattctgga gtccatataa gttatcttgt ctcttgtttg    4380
aagcaggaaa aaggaatgcg attgctggta atatagttca ctaaagtcag ctacctggcc    4440
tctaacagtt atttgcaaag tatattataa cattgattcc tcaaacatct agattcctat    4500
ctcgtgccaa gtgatgtact aggtgctcta agtacaaaaa taaaggaata tagtcctcct    4560
ctcaatgcgt aagcctagtg gaagaagcag aaatgaaagg gaaataagaa ttcaatagag    4620
tatgaggcat tacagtgaaa gaaaccaaat gtcttagaag tacaaatggc agagctacta    4680
attctgtctc gagcaggcag ggaagagtct atagtggaaa tgacttttga gctagatttt    4740
gaattgagct agtcttttga gccagacttt tgagctagaa ttgtagggtt gtcatcagac    4800
cagagagtag gaagggtacc ttgtgaggaa gagagagaga gatcagattg ttactgtgtc    4860
tatgtagaaa aggaagacat aagaaactcc attttgatct gtactaagaa aaattgtttc    4920
tgctttgaga tgctgttaac ctgtaacttt agtcccaacc ctgtgctcac agaaacctgt    4980
gctgtaatga atcaaggttt aatggattta gggctgtgca ggatgtacct tgttaacaat    5040
atgtttgcag gcagtatgct tggtaaaagt catcgccatt ctccattctc gattaaccag    5100
ggacacagtg cactgcggaa ggccgcaggg acatctgccc aagaaagcct gggtattgtc    5160
caaggtttcc ccccactgag acagcctgag atatggcctt gtgggaaagg aaagacctta    5220
ccaccccccca gcccgacacc cgtaaagtgt ctgtgctgag gaggagtagt gaaagagcgg    5280
ggcctctttg cagttgagat aagaggaagg cttctgtctc ctgctcatcc ctgggaatgg    5340
aatgtctctg tgtaaagctg accattccca ttcgttctat tctgagatag gagaaaacca    5400
ccctgtggct ggaggcgaag tatgctggca gcaatactgc tctgttactc tttgctacac    5460
```

```
tgagttgttt gggtaaagag aaacataaat ctagcctgcg tgcacatcca ggcacagtac    5520 cttccttga acttattcat gatacagatt cctttgctca cgtttccctg ctgaccttct    5580
ccccacctgt tgccctgcta cactcccctc gctaagatag taaaaataat gatcagtaaa    5640
tactgaggta actcagaggc tagcgctggt gcgggtcctc cgtatgctga gtgccggtcc    5700
cctgggccca ctgttctttc tctatacttt gtttctgtgt cttatttctt ttctcagtct    5760
cgtcccacct gacgagaaat acccacaggt gtggaggggc tggccccttt cagtatctca    5820
gaagggacaa agtacacaaa ggcatggggt catgatagtg cctggtatgt tcaggtagtg    5880
aagaggtcca tgtggtatga gcactgcaga tgatatgtgt cgtatgaatt aaaaatacat    5940
agttactgca aatagttttt acaggttatt gtttttaaga aagcagtatc taatgcacga    6000
gtgtactgtc agtactgtca atgaactact taccactcaa gtgactgctt acgcgtcgaa    6060
tcactagtga attcgcggcc gcctgcaggt cgaccatatg ggagagctcc caacgcgttg    6120
gatgcatagc ttgagtattc tatagtgtca cctaaatagc ttggcgtaat catggtcata    6180
gctgtttcct gtgtgaaatt gttatccgct cacaattcca cacaacatac gagccggaag    6240
cataaagtgt aaagcctggg gtgcctaatg agtgagctaa ctcacattaa ttgcgttgcg    6300
ctcactgccc gctttccagt cgggaaacct gtcgtgccag ctgcattaat gaatcggcca    6360
acgcgcgggg agaggcggtt tgcgtattgg gcgctcttcc gcttcctcgc tcactgactc    6420
gctgcgctcg tcgttcggc tgcggcgagc ggtatcagct cactcaaagg cggtaatacg    6480
gttatccaca gaatcagggg ataacgcagg aaagaacatg tgagcaaaag gccagcaaaa    6540
ggccaggaac cgtaaaaagg ccgcgttgct ggcgtttttc cataggctcc gcccccctga    6600
cgagcatcac aaaaatcgac gctcaagtca gaggtggcga aacccgacag gactataaag    6660
ataccaggcg tttccccctg gaagctccct cgtgcgctct cctgttccga ccctgccgct    6720
taccggatac ctgtccgcct ttctcccttc gggaagcgtg cgctttctc atagctcacg    6780 ctgtaggtat ctcagttcgg tgtaggtcgt tcgctccaag ctgggctgtg tgcacgaacc    6840
ccccgttcag cccgaccgct gcgccttatc cggtaactat cgtcttgagt ccaacccggt    6900
aagacacgac ttatcgccac tggcagcagc cactggtaac aggattagca gagcgaggta    6960
tgtaggcggt gctacagagt tcttgaagtg gtggcctaac tacggctaca ctagaagaac    7020
agtatttggt atctgcgctc tgctgaagcc agttaccttc ggaaaaagag ttggtagctc    7080
ttgatccggc aaacaaacca ccgctggtag cggtggtttt tttgtttgca agcagcagat    7140
tacgcgcaga aaaaaaggat ctcaagaaga tcctttgatc ttttctacgg ggtctgacgc    7200
tcagtggaac gaaaactcac gttaagggat tttggtcatg agattatcaa aaaggatctt    7260
cacctagatc cttttaaatt aaaaatgaag ttttaaatca atctaaagta tatatgagta    7320
aacttggtct gacagttacc aatgcttaat cagtgaggca cctatctcag cgatctgtct    7380
atttcgttca tccatagttg cctgactccc cgtcgtgtag ataactacga tacgggaggg    7440
cttaccatct ggccccagtg ctgcaatgat accgcgagac ccacgctcac cggctccaga    7500
tttatcagca ataaaccagc cagccggaag ggccgagcgc agaagtggtc ctgcaacttt    7560
atccgcctcc atccagtcta ttaattgttg ccgggaagct agagtaagta gttcgccagt    7620
taatagtttg cgcaacgttg ttgccattgc tacaggcatc gtggtgtcac gctcgtcgtt    7680
tggtatggct tcattcagct ccggttccca acgatcaagg cgagttacat gatccccat    7740 gttgtgcaaa aaagcggtta gctccttcgg tcctccgatc gttgtcagaa gtaagttggc    7800
cgcagtgtta tcactcatgg ttatggcagc actgcataat tctcttactg tcatgccatc    7860
```

| | |
|---|---|
| cgtaagatgc ttttctgtga ctggtgagta ctcaaccaag tcattctgag aatagtgtat | 7920 |
| gcggcgaccg agttgctctt gcccggcgtc aatacgggat aataccgcgc cacatagcag | 7980 |
| aactttaaaa gtgctcatca ttggaaaacg ttcttcgggg cgaaaactct caaggatctt | 8040 |
| accgctgttg agatccagtt cgatgtaacc cactcgtgca cccaactgat cttcagcatc | 8100 |
| ttttactttc accagcgttt ctgggtgagc aaaaacagga aggcaaaatg ccgcaaaaaa | 8160 |
| gggaataagg gcgacacgga aatgttgaat actcatactc ttccttttc aatattattg | 8220 |
| aagcatttat cagggttatt gtctcatgag cggatacata tttgaatgta tttagaaaaa | 8280 |
| taaacaaata ggggttccgc gcacatttcc ccgaaaagtg ccacctgatg cggtgtgaaa | 8340 |
| taccgcacag atgcgtaagg agaaaatacc gcatcaggaa attgtaagcg ttaatatttt | 8400 |
| gttaaaattc gcgttaaatt tttgttaaat cagctcattt tttaaccaat aggccgaaat | 8460 |
| cggcaaaatc ccttataaat caaaagaata gaccgagata gggttgagtg ttgttccagt | 8520 |
| ttggaacaag agtccactat taagaacgt ggactccaac gtcaaagggc gaaaaaccgt | 8580 |
| ctatcagggc gatggcccac tacgtgaacc atcaccctaa tcaagttttt tggggtcgag | 8640 |
| gtgccgtaaa gcactaaatc ggaaccctaa agggagcccc cgatttagag cttgacgggg | 8700 |
| aaagccggcg aacgtggcga gaaggaagg gaagaaagcg aaaggagcgg gcgctagggc | 8760 |
| gctggcaagt gtagcggtca cgctgcgcgt aaccaccaca cccgccgcgc ttaatgcgcc | 8820 |
| gctacagggc gcgtccattc gccattcagg ctgcgcaact gttgggaagg gcgatcggtg | 8880 |
| cgggcctctt cgctattacg ccagctggcg aaagggggat gtgctgcaag gcgattaagt | 8940 |
| tgggtaacgc cagggttttc ccagtcacga cgttgtaaaa cgacggccag tgaattgtaa | 9000 |
| tacgactcac tata | 9014 |

<210> SEQ ID NO 15
<211> LENGTH: 5954
<212> TYPE: DNA
<213> ORGANISM: Homo sapiens

<400> SEQUENCE: 15

| | |
|---|---|
| ggccgcggga attcgattcc ttaattaagt cgactgggac ccaaactttg gagtcgttga | 60 |
| cagatgtgac aggtgaagcc tgggatgaca tcgccaaaaa tgcaacgtct cactcattgt | 120 |
| cactactccc agggctcagt cgtcactggg gaaaatctcc agaaggtagc gcgggccaag | 180 |
| gtgacaggtg tctgccaaga tctgcccgcc agactcccgg gcggcgcgct ccctccctgc | 240 |
| aggccttcag cccgtcagca tccccttcct cggggccctg ctcactccca gcctccatcc | 300 |
| ccctgccatc tcctccgccg gtcgcgtgcg gacacaagga tggggacctc ccagcgagga | 360 |
| gcgctctggg cggggctccg gacgcatgcg cggccctcgt acggaagccc ggaaggaggg | 420 |
| gcagggggcg gtggctcagg tttctccggg cggcggcggc ggcggcggcg gcgacggcga | 480 |
| cggcgacggc agcggggacg gcagcagtag cgggagcagc agcgtggacg cggctggcgc | 540 |
| tggcgccatg aacccgctgt aaggcgcagg ctgtgcagca cggggtgcgg gggaggagga | 600 |
| ggaggacgcc gcggtgaagt ctccgccat gaacctgagg ggcctcttcc aggacttcaa | 660 |
| cccgaggtga gcggcgtcg ttggcgcccc cgggagtccg cgctgcgggc tcgggcgcgg | 720 |
| gctggtgttc ggctccgggg aggcacggcg ggcgagatgc tgcagcccga ggacccgggc | 780 |
| gcctgcccga gctccctgc gggtgcaagc ggtccccagg caaaacagtc ggcctcggcg | 840 |
| cccgccgct tcctcctccc gtgccgggtg ctttcagccc ctgccggcc acggccgaa | 900 |
| gggcccggcc gcgagcccg tcctgcccca agggaacccc attctttct gcttgctgtc | 960 |

```
cctcattggt gtcccaactt cttcgtctcg gttccatcct cttctgcgcc gctgcgggcc    1020
ctccattctc cgcgtcaggg ccgtctcact cgacccaaca cccctacccc caccccagct    1080
gtttcctcca gttcctcgca gtccttgggg ttttccttgg gtttatgccc atccctctct    1140
tgtttgcttc tttgttgaac ggatacctga aacactgttg aatccttgga gtcagtgtcg    1200
gggtatggca ataccttata taatgcattt ctgggtgagc ctgatcattt ccatactca    1260
ttttctcatc agtcttcact acaagtttat ttgcaggaag tagatattgc tgtccttctt    1320
ttccagatgg ggaacaccca gtggacagtg tggagaaaac actggctaag cactcaagcg    1380
cctgtccttg cacttgcccg actgttttgt aactgttctt tacccaggcc tgtgagctcc    1440
ctgaagctga gaccatctcc tgctcatctc agtgtcccca gcgcctccca cccaccgtat    1500
ctggcacata gtaggcacat ataaaatgtt tgtggaacta aactgagccc aaagacttgg    1560
attggagacg aggccatatg taactgggtg attctctgcc cttcttttggc ccttctgtaa    1620
aatgaggagt tggcctaact gatctcttaa atgcactact ctccgaaagg agtatccgtt    1680
tcccttattt gccagttggg aagacgtgct cagtaaatat ttgtgtgctg taacctatgt    1740
taggtgcttt agatgctggc ggtctcagca tggggtgaag aagggcttgt acacttaaga    1800
tgccttacag tactgtgcag tgctgtactg cgggggccaa ctctggggac ctatgccttg    1860
gctgcttgtt gaggatgaaa ggaagtttta ggggagtatt tgtatgttga gggtgcagtc    1920
tccctaggga tggtgacatt ttaacttgtg agtcattgtg actttgtatg tgcccttatt    1980
ccactttgag ttcatgttct ggttaggagt gccagtgtct ctaacacggt gcagacatta    2040
tcattgttgg cttcgaaggc atagaggagg taacagaact aactgcagtc ccttcctctg    2100
ctgcatcagg gggttaagat tggtctgcag ggtagtaggg ttggtgctgt ggctggacaa    2160
gccctgtatg tcttctattt ggagatggtg ataagaaagt taagtaaaaa ctgaattgtt    2220
ttgtgccctt gggcaactca cttatctatt gttttatctg tagaatgagt ataatctctc    2280
agtggggtag ggaggccaat taaggattga ttacaaagtg ccttacaaat agaaagctac    2340
agtgacttgt ttgcaaggtg acagagaatt cagaagcctc aagaaactgc cttaagtgat    2400
caaacaggct aacggagttg ccaaagcaaa atagtgctgc actgatacta cctttaaccg    2460
ttttttcctt tagcccttttt ccccccaaaa aaattagtat atgaaattac agtgaaatac    2520
ctggtatcta agcagattta tagtaattct caacatattc atcaatctct taattctacc    2580
tgcattaaaa tgtatttcta cctgaaaagt ttaaaggtct tttatactgt gccattttcc    2640
tgattcattg ttgccagagg tagtgagttc cttaatttta cagatatttc aagaggacat    2700
tggccaggta ttattggtaa atcagatttg ttttttttagc tggtagtgtt tcacctctcc    2760
tgagcactcc tagttttga cagtgtgctt tagtctcctt ccatgctgag gaaggccttc    2820
tctataggag aaagaaaact gagggtgta cacaggaagt taccttatgc tggggactca    2880
aaccttgatg ctactgcttt gctccctgcc tctattttg aaccaattca acatctccct    2940
cctaccccag gaccttgtca cacactgttc tctttaccag gaatgtttcc ctctcttttc    3000
ctctcctcca gacctagtga actcctattt atcctcactt ggcacttgct aagggaagca    3060
ttcctgactt ccctgaccag atttactgct ccctgtttct acagttcctg tagtatttac    3120
tactcctcca tcatagtgca tatttgtacc cttgtgtctg tctggatgct tatttgatta    3180
atacctgcct ccccccactaa actttaagct ccatgggtc aaggccgtga ctgtgtcagt    3240
atcgtagcct gcatacttgg aatagtacct ggctcaataa atatttgtgg agtaaataac    3300
tgaataactc tccagagcct ataagataaa tctagagctg ctgctttcaa tcactgcttt    3360
```

```
cctggtggtc tgtggcctgg ttctctttct tctcacactc ttcccacctt cagagtgcag    3420
ccattgcttt ggagagatgg gagagaacat ggcactaagg cagaatatgg ctatatttac    3480
tttgaagagc atgtctttgt catagaaata gtcactgtca tggtttggtg ggtcccaagg    3540
catgggtcat ggctccagat ccccttttcca gccttttgga tcttggtaag tctgaaccca   3600
ctgctgcgtt ggcaaggctc tggaaactat agtgacagag aatgattcac aagtgtcaac    3660
actcagatgt acaggctgc cagctgaccc actctaccta tttccatctg gcactgaact     3720
ggttgatcat gaacttcttt tcataattgc tttttagtta tgcaggttaa gacatgccga    3780
aacagatgta ccggacccac aaacaagtcc ttccttgaat gcctgaggct tcctaacagt    3840
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgtttgaa    4260
gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga aataagaatt caatagagta    4500
tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagacttttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
ctttgagatg ctgttaacct gtaactttag tcccaaccct gtgctcacag aaacctgtgc    4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaaggaa agaccttacc    5100
accccccagc ccgacacccg taaagtgtct gtgctgagga ggagtagtga aagagcgggg    5160 cctcttgca gttgagataa gaggaaggct tctgtctcct gctcatccct gggaatggaa      5220
tgtctctgtg taaagctgac cattcccatt cgttctattc tgagatagga gaaaccacc     5280 ctgtggctgg aggcgaagta tgctggcagc aatactgctc tgttactctt tgctacactg    5340
agttgtttgg gtaaagagaa acataaatct agcctgcgtg cacatccagg cacagtacct    5400
ttccttgaac ttattcatga tacagattcc tttgctcacg tttccctgct gaccttctcc    5460
ccacctgttg ccctgctaca ctcccctcgc taagatagta aaataatga tcagtaaata     5520 ctgaggtaac tcagaggcta cgcgctggtgc gggtcctccg tatgctgagt gccggtcccc   5580
tgggcccact gttctttctc tatactttgt ttctgtgtct tatttctttt ctcagtctcg    5640
tcccacctga cgagaaatac ccacaggtgt ggaggggctg gcccctttca gtatctcaga    5700
agggacaaag tacacaaagg catgggggtca tgatagtgcc tggtatgttc aggtagtgaa    5760
```

-continued

| | |
|---|---:|
| gaggtccatg tggtatgagc actgcagatg atatgtgtcg tatgaattaa aaatacatag | 5820 |
| ttactgcaaa tagttttac aggttattgt ttttaagaaa gcagtatcta atgcacgagt | 5880 |
| gtactgtcag tactgtcaat gaactactta ccactcaagt gactgcttac gcgtcgaatc | 5940 |
| actagtgaat tcgc | 5954 |

<210> SEQ ID NO 16
<211> LENGTH: 30756
<212> TYPE: DNA
<213> ORGANISM: Homo sapiens
<220> FEATURE:
<221> NAME/KEY: misc_feature
<222> LOCATION: (1)..(30756)
<223> OTHER INFORMATION: n= a, c, g, t, unknown or other
<400> SEQUENCE: 16

| | |
|---|---:|
| gtacggaagc ccggaaggag gggcaggggg cggtggctca ggtttctccg ggcggcggcg | 60 |
| gcggcggcgg cggcgacggc gacgcgacg gcagcgggga cggcagcagt agcgggagca | 120 |
| gcagcgtgga cgcggctggc gctggcgcca tgaacccgct gtaaggcgca ggctgtgcag | 180 |
| cacggggtgc gggggaggag gaggaggacg ccgcggtgaa gttctccgcc atgaacctga | 240 |
| ggggcctctt ccaggacttc aacccgaggt gaggcggcgt cgttggcgcc cccgggagtc | 300 |
| cgcgctgcgg gctcgggcgc gggctggtgt tcggctccgg ggaggcacgg cgggcgagat | 360 |
| gctgcagccc gaggacccgg gcgcctgccc gagcctccct gcgggtgcaa gcggtcccca | 420 |
| ggcaaaacag tcggcctcgg cgcccgcccg cttcctcctc ccgtgcccgg tgctttcagc | 480 |
| ccctgcccgg ccacggccgg aagggcccgg ccgcgagccc cgtcctgccc caagggaacc | 540 |
| ccattctttt ctgcttgctg tccctcattg gtgtcccaac ttcttcgtct cggttccatc | 600 |
| ctcttctgcg ccgctgcggg ccctccattc tccgcgtcag ggccgtctca ctcgacccaa | 660 |
| caccctacc cccaccccag ctgtttcctc cagttcctcg cagtccttgg ggttttcctt | 720 |
| gggtttatgc ccatccctct cttgtttgct tctttgttga acggataccct gaaacactgt | 780 |
| tgaatccttg gagtcagtgt cggggtatgg caataccctta tataatgcat ttctgggtga | 840 |
| gcctgatcat tttccatact cattttctca tcagtcttca ctacaagttt atttgcagga | 900 |
| agtagatatt gctgtccttc ttttccagat ggggaacacc cagtggacag tgtggagaaa | 960 |
| acactggcta agcactcaag cgcctgtcct tgcacttgcc cgactgtttt gtaactgttc | 1020 |
| tttaccccag gctgtgagct ccctgaagct gagaccatct cctgctcatc tcagtgtccc | 1080 |
| cagcgcctcc cacccaccgt atctggcaca tagtaggcac atataaaatg tttgtggaac | 1140 |
| taaactgagc ccaaagactt ggattggaga cgaggccata tgtaactggg tgattctctg | 1200 |
| cccttctttg gcccttctgt aaaatgagga gttggcctaa ctgatctctt aaatgcacta | 1260 |
| ctctccgaaa ggagtatccg tttcccttat ttgccagttg ggaagacgtg ctcagtaaat | 1320 |
| atttgtgtgc tgtaacctat gttaggtgct ttagatgctg gcggtctcag catgggtga | 1380 |
| agaagggctt gtacacttaa gatgccttac agtactgtgc agtgctgtac tgcgggggcc | 1440 |
| aactctgggg acctatgcct tggctgcttg ttgaggatga aaggaagttt taggggagta | 1500 |
| tttgtatgtt gagggtgcag tctccctagg gatggtgaca ttttaacttg tgagtcattg | 1560 |
| tgactttgta tgtgccctta ttccactttg agttcatgtt ctggttagga gtgccagtgt | 1620 |
| ctctaacacg gtgcagacat tatcattgtt ggcttcgaag gcatagagga ggtaacagaa | 1680 |
| ctaactgcag tcccttcctc tgctgcatca ggggggttaag attggtctgc agggtagtag | 1740 |
| ggttggtgct gtggctggac aagccctgta tgtcttctat ttggagatgg tgataagaaa | 1800 |

```
gttaagtaaa aactgaattg ttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagccctt ttcccccaa aaaaattagt     2100
atatgaaatt acagtgaaat acctggtatc taagcagatt tatagtaatt ctcaacatat    2160
tcatcaatct cttaattcta cctgcattaa aatgtatttc tacctgaaaa gtttaaggt     2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagaccctagt gaactcctat ttatcctcac   2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atccccttc cagccttttg     3180
gatcttggta agtctgaacc cactgctgcg ttggcaaggc tctggaaact atagtgacag    3240
agaatgattc acaagtgtca acactcagat gtacagggc gccagctgac ccactctacc     3300
tatttccatc tggcactgaa ctggttgatc atgaacttct tttcataatt gcttttagt     3360
tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt gggggagttg ctggttcaga gaaggcccctt   3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catggggtac tgatgagatc    3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
```

```
tgacttttga gctagatttt gaattgagct agtcttttga gccagacttt tgagctagaa    4260
ttgtagggtt gtcatcagac cagagagtag aagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggtttcc ccccactgag acagcctgag atatggcctt    4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggagggc    5280 tggcccttt cagtatctca gaaggacaa agtacacaaa ggcatgggt catgatagtg    5340 cctggtatgt tcaggtagtg aagaggtcca tgtggtatga gcactgcaga tgatatgtgt    5400
cgtatgaatt aaaaatacat agttactgca aatagttttt acaggttatt gtttttaaga    5460
aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg accccgccc attgacgtca    5760 ataatgacgt atgttcccat agtaacgcca tagggactt tccattgacg tcaatgggtg    5820
gagtatttac ggtaaactgc ccacttggca gtacatcaag tgtatcatat gccaagtacg    5880 ccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa cccctgctta ctggcttatc    6240
gagatatctg cagaattcat ctgtcgactc ctaccggcag cgcgcagcgg caagaagtgt    6300
ctgggctggg acggacagga gaggctgtcg ccatcggcgt cctgtgcccc tctgctccgg    6360 cacgccctg tcgcagtgcc cgcgcttttcc ccggcgcctg cacgcggcgc gcctgggtaa    6420
catgcttggg gtcctggtcc ttggcgcgct ggccctggcc ggcctggggt tccccgcacc    6480
cgcagagccg cagccgggtg gcagccagtg cgtcgagcac gactgcttcg cgctctaccc    6540
gggccccgcg accttcctca atgccagtca gatctgcgac ggactgcggg gccacctaat    6600
```

```
gacagtgcgc tcctcggtgg ctgccgatgt catttccttg ctactgaacg gcgacggcgg    6660
cgttggccgc cggcgcctct ggatcggcct gcagctgcca cccggctgcg gcgaccccaa    6720
gcgcctcggg ccctgcgcg gcttccagtg ggttacggga gacaacaaca ccagctatag    6780
caggtgggca cggctcgacc tcaatggggc tccctctgc ggcccgttgt gcgtcgctgt     6840
ctccgctgct gaggccactg tgcccagcga ccgatctgg gaggagcagc agtgcgaagt     6900
gaaggccgat ggcttcctct gcgagttcca cttcccagcc acctgcaggc cactggctgt    6960
ggagcccggc gccgcggctg ccgccgtctc gatcacctac ggcaccccgt tcgcggcccg    7020
cggagcggac ttccaggcgc tgccggtggg cagctccgcc gcggtggctc ccctcggctt    7080
acagctaatg tgcaccgcgc cgcccggagc ggtccagggg cactgggcca gggaggcgcc    7140
gggcgcttgg gactgcagcg tggagaacgc cggctgcgag cacgcgtgca atgcgatccc    7200
tggggctccc cgctgccagt gcccagccgg cgccgccctg caggcagacg ggcgctcctg    7260
caccgcatcc gcgacgcagt cctgcaacga cctctgcgag cacttctgcg ttcccaaccc    7320
cgaccagccg ggctcctact cgtgcatgtg cgagaccggc taccggctgg cggccgacca    7380
acaccggtgc gaggacgtgg atgactgcat actggagccc agtccgtgtc cgcagcgctg    7440
tgtcaacaca cagggtggct tcgagtgcca ctgctaccct aactacgacc tggtggacgg    7500
cgagtgtgtg gagcccgtgg accgtgcttc cagagccaac tgcgagtacc agtgccagcc    7560
cctgaaccaa actagctacc tctgcgtctg cgccgagggc ttcgcgccca ttccccacga    7620
gccgcacagg tgccagatgt tttgcaacca gactgcctgt ccagccgact gcgaccccaa    7680
cacccaggct agctgtgagt gccctgaagg ctacatcctg gacgacggtt tcatctgcac    7740
ggacatcgac gagtgcgaaa acggcggctt ctgctccggg gtgtgccaca acctccccgg    7800
taccttcgag tgcatctgcg ggcccgactc ggcccttgcc cgccacattg gcaccgactg    7860
tgactccggc aagtggacg gtggcgacag cggctctggc gagcccccgc ccagcccgac    7920
gcccggctcc accttgactc ctccggccgt ggggctcgtg cattcgggct tgctcatagg    7980
catctccatc gcgagcctgt gcctggtggt ggcgcttttg gcgctcctct gccacctgcg    8040
caagaagcag ggcgccgcca gggccaagat ggagtacaag tgcgcggccc cttccaagga    8100
ggtagtgctg cagcacgtgc ggaccgagcg gacgccgcag agactctgag cggcctccgt    8160
ccaggagcct ggctccgtcc aggagcctgt gcctcctcac ccccagcttt gctaccaaag    8220
caccttagct ggcattacag ctggagaaga ccctccccgc accccccaag ctgttttctt    8280
ctattccatg gctaactggc gaggggtga ttagagggag gagaatgagc ctcggcctct     8340
tccgtgacgt cactggacca ctgggcaatg atggcaattt tgtaacgaag acacagactg    8400
cgatttgtcc caggtcctca ctaccgggcg caggagggtg agcgttattg gtcggcagcc    8460
ttctgggcag accttgacct cgtgggctag ggatgactaa atatttatt tttttaagt     8520
atttaggttt ttgtttgttt cctttgttct tacctgtatg tctccagtat ccactttgca    8580
cagctctccg gtctctctct ctctacaaac tcccacttgt catgtgacag gtaaactatc    8640
ttggtgaatt ttttttttcct agccctctca cattatgaa gcaagcccca cttattcccc     8700
attcttccta gttttctcct cccaggaact gggccaactc acctgagtca ccctacctgt    8760
gcctgacccct acttcttttg ctcttagctg tctgctcaga cagaacccct acatgaaaca    8820
gaaacaaaaa cactaaaaat aaaaatggcc atttgctttt tcaccagatt tgctaattta    8880
tcctgaaatt tcagattccc agagcaaaat aattttaaac aaaggttgag atgtaaaagg    8940
tattaaattg atgttgctgg actgtcatag aaattacacc caaagaggta tttatcttta    9000
```

```
cttttaaaca gtgagcctga attttgttgc tgttttgatt tgtactgaaa aatggtaatt    9060
gttgctaatc ttcttatgca atttccttt ttgttattat tacttatttt tgacagtgtt    9120
gaaaatgttc agaaggttgc tctagattga gagaagagac aaacacctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg gcccctgaac aagaattgga agctgccctg    9420
cccatgggag ctggttagaa atgcagaatc ctaggctcca ccccatccag ttcatgagaa    9480
tctatattta acaagatctg caggggtgt gtctgctcag taatttgagg acaaccattc    9540
cagactgctt ccaattttct ggaatacatg aaatatagat cagttataag tagcaggcca    9600
agtcaggccc ttatttttcaa gaaactgagg aattttcttt gtgtagctt gctctttggt    9660 agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaa aaaaaaaaa aaaaaaaaa    9960 aaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gactttttaa caaaaagaa aagaaaaaa aaaattcctg   10140 cctcctggtg tacacacaca gaagggttcc ctcccttga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag gcatgagcc   10320 tttaaatatc tgggagcaac ccctggccag cagccagtga gaaaacgggc cctcagtcct   10380
acaatcacaa ggaactaaat tctgccaaca acctgaagga actttgaaga ggatcatgag   10440
tcccttgatt cagcttgatg agcccctgag cagaggatac agctaacttg tactaggaa   10500 gtataaaaaa catgcatggg aatgatatat atcaacttta aggataattg tcatacttct   10560
gggaatgaag ggaaagaaat ggggctttag ttgtattatg atctttaatt tctcaaaaaa   10620 ataagatca gaagcaaata tggcaaaatg ttaatacttt tgtgggtacg taggtattca   10680
gcatacccct ttttctgagt tcaaaatatt ttataattaa aatgaaatgc aggccaggca   10740
cagtggctca tgcctataat accagcactt tgcgaggccg aggtgggagg atggcttgag   10800
gccagaccag cctggccaac atggcaaaac cccatctcta cttaaaaaaa aaaaactat   10860 atatatatat atgtgtgtgt gtgtgtatat atatatatgt atatatattt atatatgtgt   10920
gtatatatat atatgtatat atatttatat atgtgtgtgt atatatatat atacacacac   10980
acacatatat acatacatac atacacacac acacacacac aattagccag gcatggtggc   11040
gcacacctgt agtcccagct acttgggagg ctgagacatg agaattgctt gaacctggga   11100
ggcagagtag ttagtgagct gagatcatac cactgcactc cagcctggtg acagagtgag   11160
actctgtctt aaaaaaaata aaaattaaaa ttaaatgcaa aaggtccaag tgaattgaag   11220
aggaaagggg tatcaaggaa ggttttgtgg aggtgacgtt tgagctgggt cttaaatgac   11280
ttaaacatgg gataagaagg gagggaataa ggacatttca ggtacgagaa ataaggagca   11340
aacagtggaa acaacctaac gtctgtcaac cagtgaatgg ataacaaaaa tgtaattcag   11400
```

```
atggtatcca acttacgatg gttcaacatg agattttct gactttagga tagatttatc   11460
aaagtagtaa atccattttc aacttatgat attttcaact tcagatgggt ttatcaggac   11520
acagttgagg aacacctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctggggaa gggaaatgg ggagtgatgg   11760
ctaaggggat tgggtttctt tgtggggcaa tgaaaatgtt ttaaaattga gcgtgataat   11820
gattgcacaa tgctgcatat atatataatc tatagattat atatatataa agagaggctg   11880
ttagacagtg ataagtgata tatatatata tatacataga gagagagaga gagagagaga   11940
gaggctgtta gtgataagtg atcaggaaaa taaaagtatt gaggaggaat acgaagttga   12000
cggtgtgaaa acatgagatt ttatatagga tggccaggga aggccttaat gagaaagtga   12060
cttatgagta aaaacaaggg atcctaaacc ttagcatgca tcagaatcac tcggaaactt   12120
gttaaagcat agcttgctgg gcctcatcac agatattttg attcggtagg ttcttgtctg   12180
atattaatac ttttggtcta gggaaccaca ttttgagaac cactgagcta aggaagtaa    12240
aggtttccct tagtttacta gctggtaaca ctggcccagg aggcctttct ggaaaaggtc   12300
ccagtcccca aaggaagctg gggactcgcg ttcacatcgt caaggtttac caagttgtgg   12360
cgggcctttc cgtcttggaa aaagcctcaa aatggcagat taggtgtcc atggccggcg    12420
gaaagggtct ttgaagttgc agaccaggag ggaagaagat tctgggcctc ccccatgcag   12480
tgtcagctgg caacagaatg cacccccggct gggttggagg ccctgggtac tggctcttcc   12540
acaccagggg cccacctacc aagggcagca ggagcatctg cacctcctgc gccaggcgcc   12600
cttcagtgct tccacttgag cacctctcca gacaccagct agggtgacag tggtacaaat   12660
accagactcc cctggcctgc tcacctcaca gggtaatgtg ctgtggagtc aggggggacac  12720
agcaaccacc agatgacatg gctggccccg ggaggacga cacgcagata cggctacttg    12780
gcacctgtga tattttacac actcgagagg ggcccgcacc atcctcagcc ctctccccac   12840
attcactctt agttcatgtc acctccaccc agaggggac acaggcccac agcgatggcc    12900
ccacaccctg cctgaggtcg cccacttccc aggaggcagt cctgggactt ccacccgacc   12960
aggcccaga gcccaccgac ttaacccctc cagaggcttg tcgttcatta ccttattcaa    13020
gatggagacc agccttttttg cggagaaaat gcgggtgaag gtcctgaaag tgcattgacg   13080
ccgttttcgg aagccataca agtttagctg gcggaagaag ctctttatcg aagttgtggc   13140
aaacactttg tgtgcgacgt ccctttgag aatctccttt tcaaagagtt tttgattgat    13200
cactctacaa gccccactgt catcccacca gatggacgaa aactggttgc tgctgaccag   13260
tctccacagt ttctgtggaa aggggaggga gaggagatta tcttctccct ggggcgggac   13320
gtcaccgtca gggtgcggcc ttctgaacga agcttcctcg gccagaggtt ggaaagcgat   13380
ttcttctgtc agcagcctca agttagggct cccagtggac cccgggtcgt cccaggcagg   13440
ggaaggatct gctgggtgaa ggtaggtctc tgactgcaac tggggaggga aaggcaccct   13500
ttccaagcca tgatcctgtc ctctcgaatt tctttcttca cagcgagcca tactcaatga   13560
tcgcttgtcc tccatctggc aaacttgcta gtgcagtgtg gccagcagca ccccttggca   13620
gtcatgtaac cagccccatg acatcataaa ggggctctga ctgccggggg gtggcatctc   13680
cacccccagc aagttgtgta ataaaggggc aaggcagaca agtagctgcc catctgcatg   13740
tgcacattct ggtcctcaca gtcatttcaa tgggaaagat gacactagtg cacaagagtg   13800
```

```
ccgaggggcc ctgccacacc gtagatgcag acctggagcg gtccccttgt cctagagctc   13860
ctgagccagg cacaactaca gcaaagccct ggctcaggaa ggtcagagct caccgtctga   13920
gtcatgggcc cacagacccc agcacatgac tgacactcgg aagcacagaa caaagggtag   13980
gacggtgccc atgggtcagg ctgtagccac gccacccttt ccaccctgtc ctagccagag   14040
gcagcaatgt gctccataca gatcctccta acacaccac actgtcggtc cccagcacgc   14100
agatgcccga cagcccctta ggcaaatggc ttagctgact gccccaccac acgccgtcgc   14160
catgcagtcc agtggggagt cggaggcagc ctccttcctg cctctcctcg gcctgcacgt   14220 gtcccccac caggcagaga cccttctaca ccccgggtgt ctgcggtcac atcgcggtgg    14280
ggcatgcagc tgttggcctt cgagcatgtt ttgttttcct tggccagtgt ctccagagaa   14340
acgcacgtgg gtttgtgtcc agcggtccat ctctgcaaca gttgttcctt gggattgga    14400 tgctaggagg tcacgggaga ggtgtccatc caaagcagtg tctgtgtcac acactgtccc   14460
cacacacagg gccacctctg cacagactcc cccgactcga ttctgggcac agagctcagt   14520
gaccttccag agactgccac gaaccggtga tgcctccacg cttgagacat cctgaccgca   14580
gggcccaagg cgcactggct cagggggtga cagtgagggg tctgcaaaca gactgctgat   14640
gctcaacccg gccgctgccg agctgtgtga cttgggcacg tcacttaacc tctctcggcc   14700
tctgtctcct cccggggata agagtagtag cacctgcttc ccggggctgt gaggatccag   14760
tgggacgtat aggaactagc gaggcaccgg cagttgggtc agagctactg ttgtcacttc   14820
acaaggcatt tcttcaaca gcaagtcgga atctcatga gcctaaggca gaatccacct     14880
gtggcctctg gttacaaccc acaggactga aaatccttcc agccacagca actggtgaat   14940
ttcctggtca attgccacaa gtcatgagct gaacccact tgagtttcag ttcaggcaga    15000
actctagaga cgactagggc aagctagaca gcgactgcag agccttttgt tgcagcgtga   15060
gcagtcctca gctgttgaca tcactgggga gcaaacgagg accaggagcg gtgaaaggac   15120
agtgtctgct gcagattgtc gtagcaccca aggaacactc cagaaagcct cctaagcagt   15180
aacaagtgtg gcaaggtgta gcccagccaa cagtggcatc tgcgaggcgt ccctccttc    15240 ctcccactac cccgtatacc ctgggacctg tgcactgaag gactcattct aaaggctgtg   15300
cccctgcagc cgccagcctc actcactggc tgcctgtgcc agctagagat ttctttcctc   15360
tgaggctggc tgagaggacc actccagttt cctggcccat ccagcaaaga agatacacat   15420
catgcacgtg taaatgagg aaccggttta ttgaacagct taaggagagc aaaaatagtg    15480
gctttagcta cattttttac acactgagca ggaaagtcta aaccatcccg ttcccctgta   15540
ccccaaagag aacagggctt gctggaggcc agtgccaagg gcggagtcgt gctcgcagca   15600
gacttgaatt aaccccatgt aggccggcga gcagttgccc gcgtgaaaac accaccctct   15660
tctcctggct gagaagatca aagctctttt tttaccctct tttcagcaaa ggacctattt   15720
gttttcaggc aggaggatgt taaacttgca gcctctgaca cacggtggaa cctgcagtgc   15780
ttggagaaac ggcacgcaca cgtgaaaaca tcatgcctac tccaaagcct tcttgttgct   15840
ggcaggaggg aagcttgaga ctttcccacg catagtcgtg acccgcgtgg ccgtttctgc   15900
tctcagcaac attctctagt gttccggctt caagcagcgc ttgtcaggtt tgaagctagc   15960
cactattctg agaacgtcag aaaagcatgg accatctctt gcttggtgtt gccgttgtgg   16020
cagtagcagc tactacgtac ctgcacgagt tccagggcag aagtggcaat gtcccatgaa   16080
ggcgtggcac cccacggggg ggggggggga gtgtgccacg ggcgtccact tctgcagcag   16140
aaggcatgtg cctacagcac aagcttgtaa aaaaatactt gaacagaata tgctgtacag   16200
```

```
aactaggggt taacaccgca tatgaagatg ctaaaacatt tgtataaata ctctgtatac   16260
aagcatggag tcactcccgt agaaagggct catccgtgag gctatgaaaa actgctgtca   16320
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta aacaatactt ttgattggga tttcagcacc gtatagacag atgttccttc   16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca caccccgtc acctgccact ccgcgtccc gtcgtggtga gtggctgata   16740
ggcgctggat gcaaacaagg catgagatgg acgtacctgg agacccagct ccagtactgg   16800
ttctggtctg cggggtgaac gaggggcag aggaaggcgg agagagtgcg tcccagtcca   16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttaggggggct ccggaactgg ggtctcttcg gtttcttcat tatcttcgtg   17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctagggtg ggctccagcg gtcccctttt cctggccctt   17460
ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttgccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gttttggaag   17940
tgtctgcctc agcaagcagg tggagggaa tagagtgtta gcaaggcaag acaggcaaga   18000
ctcgggtgat ggcagcaagg atatggggga ggcagagcgg ccaacaggga cctaggatga   18060
atcccaggtt tgggtgggag atgtggattt tccatcaaac cctcccgggc ctgggaagaa   18120
tctgtcttga tccccatttt gcagaggagg gaacgggatc tctgagaggt tgcctgccgt   18180
gtctggttct acctcaaatg gcagcgtgca ctgcgagaaa agtcccggtg caggccagca   18240
gaacaccaga gttacggcat gcccttccct tagaaggtcc cagaatttcc tcagccctca   18300 cttttcccaca caagcttcta aattggggcc ctcggggact catcccttcc tagacttcta   18360
tccgccaccc cccaccccct ggtccccccc cagacacaca ccaaggactt ctgaaatgct   18420
gagtacatac agtggtttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaagagacat agtcccggtt gatgccagca ccgaaaatgg   18600
```

```
gcagaggcgg aagccagact tcattaggca gttcctcccc accaccccac ccccgcgtga   18660
gctcccacaa gagggaacat cagcaccgcc agaaaaaggc aggaaaccac ctatccctgg   18720
ggaaagctcg aaatgagctt ttatgtccct cttcagagct cggcaatagc ctatccactt   18780
gaaaagttcc cagtgccagc agttttatgg caaactcctc cgggtgtttg ttctaaggag   18840
tcaacagctc ccattctaga attctccacg tgactccaat acacaaatct gacatcccac   18900
tctgctttcc ccagagtgga aactggagcc atacagaggc accatggcta aaaaggtgca   18960
ctcttctccc tgccagcccc acgtgctgcc cccaagagaa aggaaggatg ctctcctttc   19020
accgaagctc cctctcggag atggctgtgt tctctcccct ctcctggagt gggctcactg   19080
tgagctcgag ggacagaggc tgcctttcta ggggtgcaga atcctgtcag gggaagcgca   19140
agcttcaggg gctgaagagg cttcccgtgg aacgcttacc tcaaatgtaa gaaggggcac   19200
gacgatggtc atccagctca gggccatggt tatgtgtgtc ctgcgctgtc cgcaatcaca   19260
tccatagagc gcaagaacaa gacggaccac acaatgtagt agaggaccac caggcacaga   19320
aaggacatga gaatccacag cgggacacac acaacctggg ggtgggtgag agaacagcaa   19380
gagaagtctc tttagagctt ccaacctggc ctctgatgga aggcatcttt agcaccttgc   19440
tgtgtctgtc cagttaaggc ggtccttcct gtgagccgaa taaggaccgt tccatctccc   19500
aggactgctg ggagcatcgc tcaggacaga aaaggtatgg tatgttcact atggggcctg   19560
ctgccaccag gggacacaca cgctcagtga gtcatcagtc cctcttcctt tgggtgacag   19620
acagccctgc acctggctcc gcagcctcta ctcttccaga ggcccactct cccacactct   19680
ctcaggctcc tctaggttct gctgccatca cagcttcccg ggaaatggga cacaactgtc   19740
accctgtgca cacacacaag atctcacccc aacagactct cttcacaggc aacattccca   19800
caacctgctg ggggtacttt ggcaacacaa atgggaatgg gctccccaga aagtctggct   19860
gcctgggctc ctaaggatcc ctaacctcac ccctaccaag ttagtgaact tggcgggttg   19920
atgctggata caggttgatg ctggatacgt agcgctgccg ggtcgtgacc cctaaggaat   19980
tatccaaact cttgttttta gatgctttat tatatcaaac tctcctttaa acaagtggcc   20040
catctgctgg gatttggaag cctgtaatac tgaaattttc atcataatgg aaattttaaa   20100
aacagaattt gacccacctg tttttaaaac actttcatta cttaacaaga ggtctaatct   20160
tgggcaagtc ttgaaattc tctggcctta gtttcccatg tgttaaatga acttgaagc    20220 agttggtctc ttatagtctc ctgactctaa cattctaaga attatatttg tacaataact   20280 caaaatcac ataatttaat ttaccatatg gactccaaaa tatattttct cattaggcta    20340
aacttgatct gcattttctg gatgtgtcca tattcttgga ctacactaaa acatgatacc   20400
aatgcttcct ctcaccataa accctcactt cgctttctac atttaagaat tttatagctg   20460
gaagagtcct taacagaaaa taccatctaa taattacccc tcaaaatcga gaaagtccta   20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagattttaa tgttctatat attcttctaa gacagtgttt accagagtaa   20700
ggcacaaaag atccactggt ttgcaagaaa gattagaact tttaaatttt ttacctcacc   20760
ttgtttaatc tatattttg tatgtatttt gtaacatata tattattatt accataaatc    20820
atatataatt taaaatgcat atattagggg taaatgctca ggaaactttt tataaattgg   20880
gcatgcaaat acaagtttga agactcactg ttctaggtat taaaagtaaa gttataacca   20940
agtaaagctt ccacctttc atgtctcaaa gcagtttatt gttggaggta agatctctta    21000
```

```
gaagcctaaa caggtccaag tacagaatga agtaaggcta gcccataact tgtggcaagc    21060
aattcatact atttctctca tgctgagctc tcctcagtga agcagctact atagacaact    21120
gcagcctatt ggtagcctat tttacaggca ggaaaaaaat tacttttat tcaaagtgga     21180 actcaggaca tggggagaaa atgaatacaa aaataggt caatccaaag gcacacagca      21240
aatgagtaac acagttatgt ttttttccca tttgtatgag gtcccagtaa attctaagta    21300
aactgcaaat ttaataatac actaaaaaag ccatgcaatt gttcaaatga atcccagcat    21360
ggtacaagga gtacagacac tagagtctaa aaaacaaaag aatgccatta ttgagttttt    21420
gaattatatc aagtagttac atctctactt aataaatgag aaaaacgagg ataagaggcc    21480
atttgataaa atgaaaatag ccaagaagtg gtattagaga cttgaataca ggtattcggg    21540
tccaaagttc atctgctcaa atactaactg ggaaaagag ggaaaaatat ttatatacat      21600
atatatctgc acacaaaaat accccaaaa gacaaaatga ggccaggcag ggtggctcac      21660
acccgtaatc ccggtacttt gggaggctga ggcaggtgga tacctgagat caggagttgg    21720
agatcagcct ggtcaacatg gtgaaaccct gtctctacta aagataaaaa aattagccag    21780
gcatggtggc gtgcgcctgt aatcccagct acttgggagt ctgaggcagg agaatcactt    21840
gaactgggaa ggggaggttg cagtgagcca agatcgtact actgcactcc agcctgggca    21900
gcagagtgag actccatcac aaaaataaat aaataaataa aatacaatga aacagaaagt    21960
tcaaataatc ccataatctt accaccaaga aataactttc actcgttata cttattgatt    22020
tttccataat aaatgtactt tactgtgact atcatgaaaa gaaagttatt ttagaaacag    22080
agaactgttt cagatcaaat ctatgtagta gaacagagcc attaggtggg aaagacgaga    22140
tcaaactaaa tctcagaagg cctaaaaggc taggtccatt ccagcactaa aaactgacca    22200
gacaagtaat ggcttcaaca gcttctaaat atggacaaag catgctgaaa gggaaggaca    22260
ggtctaacag tggtatatga aatgaacagg aggggcaaag ctcatttctc ctctgaagtt    22320
ttccaaagat gctgaggagg acattagttt gacatgaccc tgatatggga caagataatt    22380
tcacagaagt tttacatgtt aaagttttct tatagatact cattcaagta agcaatgaac    22440
actaaaatct aaagaaagaa aagagcttta gagtcaggtc tgtattcaaa ttcaagctct    22500
accacttact ggttctgtga ctttgggcaa gtcttttaac cttattaagt cttaatttcc    22560
tgatttgtaa aatggggata tcgtctccct cacaggattg ttgtgaaact tttatgagat    22620
taatgccttt atatttggca tagtgtaagt aaacaataac tggcagcttc aaaaaaaaaa    22680
agcagtagca ttcatcatt tattattggt tactctcaaa aagttttca atgtactaga      22740 agataaatat tcaaatacct taatatctcc attattttca ggtaaacagc atgctcctga    22800
acaaccaatg ggtcaacaaa taattaaaa gggaaatcta aaaacatctt gatattaaac      22860
tacatggaag cacaatatac caaaaccaat ggttcacact aggagaattt taaggtacaa    22920
gaaaactctt tgagatttct taaaataata gtatgtctga atttattgag tgatttacca    22980
gaaactgttg taagagctct acttgcatta tagcacttaa tcctcttaac tctatggctg    23040
ctattatcaa cctcacccta atcacatatg ggacacagag aggttaagta acttgcccaa    23100
ggtcagagtt aggaagtact aagccatgct ttgaatcagt tgtcaggctc cggaactcac    23160
actttcagcc actacataat actgcttttgc tatcttttag gaaactatgt gagtctacct    23220
cacatagact cacataggtt tgttttttttt ttttttttaa aggctatctt tcccccatc    23280 aatgtttttt gaaggatccc aaattagagt cccacagagg cagacagcag tacttgcaaa    23340
tatggacatt taaggttaat gttggattct actgtctttt tactacatga cctagggaac    23400
```

```
gataattaac ctagactgct tccaagggtt aaataaccca tttagttata ctatgtaaat   23460
tatctcttag tgattgattg aaagcacact gttactaatt gactcggtat gaagtgcttt   23520
tttttcttcc ctttcaagat acataccttt ccagttaaag ttgagagatc atctccacca   23580 attacttta tgtcccctgt tgactggtca ttctagttaa aaaaaaaaaa aactatatat   23640
atatatatct acacacacat atgtatatgt atatccttat gtacacacac aaacttcaaa   23700
ttaaatgaga actagaagat ttgagaagtt agctagctaa tatccatagc attatgatat   23760
tctaaatgat atgaattata agaattaggt ttcctgaaat gaatgactag aaaactttca   23820
agtagagatt agtaaaaatt aaaaagtcct aatcggccat tactgatttg atgttttaa   23880 gagtcctaaa aaatgggtta catccatttt taagtgggta gtattataac agccacccat   23940
cttcaatcac agtgatttct gaattgtgag ggaagttatt agcatgacag gtgtctggtt   24000
ctggccctgt acgattccca tgagtcaagc aaattgtaag ggctggtcta tatcacaccc   24060
aaccccaagg atatgtccct caaaagtcta gcccaggccc cgtcatcttc agcatcatct   24120
gggaaaccag gtctgattag tagtcctta aggaataccct cttaggctcc cattttactg   24180
ctatcacaga atccaataaa acccttacag gagattcaat gggaaatgct caacacccac   24240
tgtagttggt ggtgacaatg accataattt ggctgtgctg gattcaggac agaaaatttg   24300
ggtgaaagag caggtgaaca aaagagcttc gacttgccct agcagagagc aagccatacc   24360
ataccacaaa gccacagcaa ttcaacggt gcagtaccag cacagtaaat gaacaaagta   24420
gagcccagaa acagacccag aactatatga ggatttagta tacaataaag atggtatttc   24480
gagtcagtag ggaaaagatg aattattcaa taaatgatgt ttggccaact agtaacccat   24540
ttgggaaaaa ataaaagtat ggtccctacc tcacagcata cacaaaaata aattccagac   24600
ggattaaaat ctaaatgtaa aaaataaagc cataagtgga ctggaagaaa atagagaatt   24660 tttttaaca tccgtagaaa gggtaaaaac ccaggcatga catgaaccaa aactgaagag   24720
gttctgtaac aaataccccc ttttatatat tgggctccaa caataagaac ccataggaaa   24780
atggagaatg aacacaaata gacaatttat agaagagaag gttataaggt gtaaaattat   24840
atctatctga gaaacaaaca ctaaaacaat gtgattctac tgttctccca cccatactgg   24900
caaaacttaa gcctgataat atgctgaggg gaaataagca ctcttgttgg tgagagtatt   24960
aattggcata gcttctttg aaaatgacat agcaatacct gttaaaattg caaacatgca   25020
tgtcacttaa tccagtaatc ccacttctgg gaatcaatgc tacaaaaaca ctgacaagta   25080
tacaaagata cattcaagag tgttcactgg gccgggtgcg gtggcttcat gcctgtaatc   25140
ccagggaggc agaggcaaga cgatcgcttg accccaggag ttcaaggcca gcccgagaaa   25200
cacagcaaga ccctgtctct cttttttta tttaaaaaat aaatgttcac tgtatcagtt   25260
gttcacaaaa acaaaccaac atgtccatta acagggaacc atttaaatta atcaagttca   25320
tctacacaat gtaataccat gcaactatta aaaagcacct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcacttta tgtgcttcta tttttgttat gcttctatat atacatccat   25560
ttattatgga gtgttacttt caaaaatcac aaatgggcca gtattatttg gtgttgcaag   25620
gtgagcatat gacttctgat atcaaccttt gcatattact tctcaattta gggaaattac   25680
agacatccct tattctaact aacttaaaac ccagcatttc aaacatacag aattgatggg   25740
gaaaaaaaag aaagaagaaa gaaagaaaag gcaacaagct tcagatgaca gtgactcaca   25800
```

```
tcaaattatt tataaaatct gttaaatagt gccatcttct ggagatacct ggtattacag   25860
tccaactcca gttgatgtct ttacagagac aagaggaata aaggaaaaaa tattcaagaa   25920
ctgaaaagta tggagtcatg gaaaaattgc tgtgatccaa aggctacggt gataggacaa   25980
gaaacaagag aactccaagc agtaagacac tgctgttcta ttagcatcca aacctccata   26040
ctcctgtttg ccccaaggct tttttaaaaa atagagacag gatctcacta ttttgctcag   26100
gctggtcttg aactcctgga ctcaagctat cctcctgcct cggcctccta aagtgccgag   26160
attacaggct tgagtcacca tacctggcta tttattttt cttaactctc ttgcctggcc    26220
tatagccacc atggaagcta ataagaata ttaatttaag agtaatggta tagttcacta    26280
cattggaata caggtataag tgcctacatt gtacatgaat ggcatacatg gatcaattac   26340
cccacctggg tggccaaagg aactgcgcga acctccctcc ttggctgtct ggaacaagct   26400
tcccactaga tcccttact gagtgcctcc ctcatcttta attatggtta agtctaggat     26460
aacaggactg gcaaaggtga ggggaaagct tcctccagag ttgctctacc ctctcctcta   26520
ccgtcctatc tcctcactcc tctcagccaa ggagtccaat ctgtcctgaa ctcagagcgt   26580
cactgtcaac tacataaaat tgccagagaa gctctttggg actacaaaca catcccctta   26640
atgtctttat ttctattttg tctacctctt cagtctaggt gaaaaaatag gaaggataat  26700
agggaagaac tttgtttatg cctacttatc cgccccctagg aattttgaaa acctctaggt  26760
agcaataaga actgcagcat ggtatagaaa aagaggagga aagctgtata gaaatgcata   26820
ataaatgggc aggaaaagaa ctgcttggaa caaacaggga ggttgaacta taaggagaga   26880
aagcagagag gctaatcaac aaggctgggt tcccaagagg gcatgatgag actattacta   26940
aggtaggaat tactaagggc tccatgtccc cttagtggct tagtactatg tagcttgctt   27000
tctgcagtga acttcagacc cttcttttag gatcctagaa tggactttt tttttatcg     27060 gaaaacagtc attctctcaa cattcaagca ggccccaagt ctaccacact caatcacatt    27120
ttctcttcat atcataatct ctcaaccatt ctctgtcctt taactgtttt ttctataccc   27180
tgatcaaatg ccaacaaaag tgagaatgtt agaatcatgt atttttagag gtagactgta   27240
tctcagataa aaaaaagggg cagatattcc attttccaaa atatgtatgc agaaaaaata   27300
agtatgaaag gacatatgct caggtaacaa gttaatttgt ttacttgtat tttatgaatt   27360
ccctaaaacc tacgtcaccc gccccgttcc cacgccccgc gccacgtcac aaactccacc   27420
ccctcattat catattggct tcaatccaaa ataaggtata ttattgatga tgttaattaa   27480
catgcatgga tccatatgcg gtgtgaaata ccgcacagat gcgtaaggag aaaataccgc   27540
atcaggcgct cttccgcttc ctcgctcact gactcgctgc gctcggtcgt tcggctgcgg   27600
cgagcggtat cagctcactc aaaggcggta atacggttat ccacagaatc aggggataac   27660
gcaggaaaga acatgtgagc aaaaggccag caaaaggcca ggaaccgtaa aaaggccgcg   27720
ttgctggcgt ttttccatag gctccgcccc cctgacgagc atcacaaaaa tcgacgctca   27780
agtcagaggt ggcgaaaccc gacaggacta taaagatacc aggcgtttcc ccctggaagc   27840
tccctcgtgc gctctcctgt tccgaccctg ccgcttaccg gatacctgtc cgcctttctc   27900
ccttcgggaa gcgtggcgct ttctcatagc tcacgctgta ggtatctcag ttcggtgtag   27960
gtcgttcgct ccaagctggg ctgtgtgcac gaacccccg ttcagcccga ccgctgcgcc     28020
ttatccggta actatcgtct tgagtccaac ccggtaagac acgacttatc gccactggca   28080
gcagccactg gtaacaggat tagcagagcg aggtatgtag gcggtgctac agagttcttg   28140
aagtggtggc ctaactacgg ctacactaga aggacagtat ttggtatctg cgctctgctg   28200
```

```
aagccagtta ccttcggaaa aagagttggt agctcttgat ccggcaaaca aaccaccgct   28260
ggtagcggtg gttttttttgt ttgcaagcag cagattacgc gcagaaaaaa aggatctcaa   28320
gaagatcctt tgatcttttc tacggggtct gacgctcagt ggaacgaaaa ctcacgttaa   28380
gggattttgg tcatgagatt atcaaaaagg atcttcacct agatcctttt aaattaaaaa   28440
tgaagtttta aatcaatcta agtatatat gagtaaactt ggtctgacag ttaccaatgc   28500
ttaatcagtg aggcacctat ctcagcgatc tgtctatttc gttcatccat agttgcctga   28560
ctccccgtcg tgtagataac tacgatacgg gagggcttac catctggccc cagtgctgca   28620
atgataccgc gagacccacg ctcaccggct ccagatttat cagcaataaa ccagccagcc   28680
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgacccegg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg gaagccctg caaagtaaac tggatggctt tcttgccgcc aaggatctga   29100
tggcgcaggg gatcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc ttttgtcaa gaccgacctg tccggtgccc tgaatgaact gcaagacgag   29340
gcagcgcggc tatcgtggct ggccacgacg ggcgttcctt gcgcagctgt gctcgacgtt   29400
gtcactgaag cgggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata gaccgagata gggttgagtg ttgttccagt   30060
ttggaacaag agtccactat taagaacgt ggactccaac gtcaaagggc gaaaaaccgt   30120
ctatcagggc gatggcccac tacgtgaacc atcaccctaa tcaagttttt tggggtcgag   30180
gtgccgtaaa gcactaaatc ggaaccctaa agggagcccc cgatttagag cttgacgggg   30240
aaagccggcg aacgtggcga gaaggaagg gaagaaagcg aaaggagcgg cgctagggc   30300 gctggcaagt gtagcggtca cgctgcgcgt aaccaccaca cccgccgcgc ttaatgcgcc   30360
gctacagggc gcgtccattc gccattcagg atcgaattaa ttcttaatta acatcatcaa   30420 taatataccct tattttggat tgaagccaat atgataatga ggggtggag tttgtgacgt   30480 ggcgcgggc gtgggaacgg ggcgggtgac gtagtagtgt ggcggaagtg tgatgttgca   30540
agtgtggcgg aacacatgta agcgacggat gtggcaaaag tgacgttttt ggtgtgcgcc   30600
```

```
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                              30756

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      Foward PCR primer (containing a Fse I restriction site)

<400> SEQUENCE: 17
tatttattgg ccggccgcgt taagatacat tgatgag                             37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      Reverse PCR primer (containing a Sbf I restriction site)

<400> SEQUENCE: 18
tatttattcc tgcaggtcgt aggtcaaggt agtaga                              36

<210> SEQ ID NO 19
<211> LENGTH: 1224
<212> TYPE: DNA
<213> ORGANISM: Rattus norvegicus

<400> SEQUENCE: 19
atgcctcaca gtcaaatatc tcctgcagaa ggctctagaa ggatccttga agaataccac     60
atagatgaag atgtgggctt tgctctacca catccactgg aggagctgcc tgatacgtac    120
agaccttgga tccttgtggc tagaaatctg cctaagctga ttgagaatgg gaagctccga    180
gaagaagtcg agaagctgcc cacactgcgc accgaagaac tgaggggaca caggttacag    240
cgcctggcac atttggccct ggggtacatc accatggcgt atgtgtggaa ccagggggat    300
gatgatattc gaaaggtgct gccccgcaat cttgccgttc cctactgcga gctctcggag    360
aagctggggc tgcctcccat tctgtcttac gcagactgcg tcctggcaaa ctggaagaaa    420
aaggacccca tgggcccat gacatacgag aacatggaca ttctgttctc gtttcctggt    480
ggggactgcg ataaaggctt cttcctggtc tctctaatgg tggaaatcgc agcttctcct    540
gcaatcaaag caattcctac tgtatccagt gcagtagagc atcaagaccc gaaagcactg    600
gagaaggcac tgtgtagtat agctgccagt ctggagaaag ccaaggaaat ttttaagagg    660
atgcgtgact tcgtggatcc agacaccttt ttccacgttc ttcgcatata tttgtctggt    720
tggaagggca accctaagct gccggagggt ctgctgtacg agggcgtctg ggacaccccc    780
aaaaaatttt caggggggcag tgcaggccag agcagcatct ttcagagtct tgatgtcctt    840
ctgggaataa agcatgacgt tggtgaagga tctgctgcag aattcctcca ggaaatgaga    900
gagtacatgc ctccagccca ccggaacttc ctctcctcct tagagtcagc tcccccagtc    960
cgtgagtttg tcattttaag acgcaatgaa gacttgaagg aggcttataa tgagtgtgtg   1020
aatggcctgg tctccctcag aatgttccac ctctcgatag tagatactta cattgtgaag   1080
ccttcgaagc agaagcccat gggtggccac aagtcagaag agcctcaaa cacgaaaaac   1140 agagggactg gggtactga cgtcatgaat ttcctgagga gtgtgaaaga tacaaccaag   1200
```

```
aaagcccttc tgagttggcc ttag                                              1224
```

<210> SEQ ID NO 20
<211> LENGTH: 1212
<212> TYPE: DNA
<213> ORGANISM: Homo sapiens

<400> SEQUENCE: 20

```
atggcacacg ctatggaaaa ctcctggaca atcagtaaag agtaccatat tgatgaagaa     60
gtgggctttg ctctgccaaa tccacaggaa aatctacctg atttttataa tgactggatg    120
ttcattgcta acatctgcc tgatctcata gagtctggcc agcttcgaga aagagttgag    180
aagttaaaca tgctcagcat tgatcatctc acagaccaca agtcacagcg ccttgcacgt    240
ctagttctgg gatgcatcac catggcatat gtgtggggca aaggtcatgg agatgtccgt    300
aaggtcttgc caagaaatat tgctgttcct tactgccaac tctccaagaa actggaactg    360
cctcctatt tggtttatgc agactgtgtc ttggcaaact ggaagaaaaa ggatcctaat    420
aagcccctga cttatgagaa catggacgtt ttgttctcat ttcgtgatgg agactgcagt    480
aaaggattct tcctggtctc tctattggtg gaaatagcag ctgcttctgc aatcaaagta    540
attcctactg tattcaaggc aatgcaaatg caagaacggg acactttgct aaaggcgctg    600
ttggaaatag cttcttgctt ggagaaagcc cttcaagtgt ttcaccaaat ccacgatcat    660
gtgaacccaa aagcattttt cagtgttctt cgcatatatt tgtctggctg aaaaggcaac    720
ccccagctat cagacggtct ggtgtatgaa gggttctggg aagacccaaa ggagtttgca    780
ggggcagtg caggccaaag cagcgtctt cagtgctttg acgtcctgct gggcatccag    840
cagactgctg gtggaggaca tgctgctcag ttcctccagg acatgagaag atatatgcca    900
ccagctcaca ggaacttcct gtgctcatta gagtcaaatc cctcagtccg tgagtttgtc    960
ctttcaaaag gtgatgctgg cctgcgggaa gcttatgacg cctgtgtgaa agctctggtc   1020
tccctgagga gctaccatct gcaaatcgtg actaagtaca tcctgattcc tgcaagccag   1080
cagccaaagg agaataagac ctctgaagac ccttcaaaac tggaagccaa aggaactgga   1140
ggcactgatt taatgaattt cctgaagact gtaagaagta caactgagaa atcccttttg   1200
aaggaaggtt aa                                                         1212
```

<210> SEQ ID NO 21
<211> LENGTH: 2440
<212> TYPE: DNA
<213> ORGANISM: Artificial Sequence
<220> FEATURE:
<223> OTHER INFORMATION: Description of Artificial Sequence: Rat IDO
      expression cassette
<220> FEATURE:
<221> NAME/KEY: misc_feature
<222> LOCATION: (1)..(2440)
<223> OTHER INFORMATION: n= a, c, g, t, unknown or other

<400> SEQUENCE: 21

```
tatttattcc tgcaggtcgt aggtcaaggt agtagagttt gcgggcagga cggggcgacc     60
atcaatgctg gagcccatca cattctgacg caccccggcc catgggggca tgcgcgttgt    120
caaatatgag ctcacaatgc ttccatcaaa cgagttggtg ctcatggcgg cggcggctgc    180
tgcaaaacag atacaaaact acataagacc cccaccttat atattctttc caccccttan    240
nntaatagta atcaattacg gggtcattag ttcatagccc atatatggag ttccgcgttg    300
gtaaatggcc cgcctggctg accgcccaac gacccccgcc cattgacgtc aataatgacg    360
tatgttccca tagtaacgcc aatagggact ttccattgac gtcaatgggt ggagtattta    420
```

```
cggtaaactg cccacttggc agtacatcaa gtgtatcata tgccaagtac gcccctatt       480 gacgtcaatg acggtaaatg cccgcctgg cattatgccc agtacatgac cttatgggac      540
tttcctactt ggcagtacat ctacgtatta gtcatcgcta ttaccatggt gatgcggttt     600
tggcagtaca tcaatgggcg tggatagcgg tttgactcac ggggatttcc aagtctccac    660
cccattgacg tcaatgggag tttgttttgg caccaaaatc aacgggactt tccaaaatgt    720
cgtaacaact ccgccccatt gacgcaaatg gcggtaggc gtgtacggtg ggaggtctat     780
ataagcagag ctggtttagt gaaccgtcag atccgctaga gatctggtac cgtcgacgcg   840
gccgcgggaa ttcgattatg cctcacagtc aaatatctcc tgcagaaggc tctagaagga   900
tccttgaaga ataccacata gatgaagatg tgggctttgc tctaccacat ccactggagg   960
agctgcctga tacgtacaga ccttggatcc ttgtggctag aaatctgcct aagctgattg  1020
agaatgggaa gctccgagaa gaagtcgaga agctgcccac actgcgcacc gaagaactga  1080
ggggacacag gttacagcgc ctggcacatt tggccctggg gtacatcacc atggcgtatg  1140
tgtggaaccg aggggatgat gatattcgaa aggtgctgcc ccgcaatctt gccgttccct  1200
actgcgagct ctcggagaag ctggggctgc ctcccattct gtcttacgca gactgcgtcc  1260
tggcaaactg gaagaaaaag gaccccaatg ggcccatgac atacgagaac atggacattc  1320
tgttctcgtt tcctgtgggg gactgcgata aggcttctt cctggtctct ctaatggtgg   1380
aaatcgcagc ttctcctgca atcaaagcaa ttcctactgt atccagtgca gtagagcatc  1440
aagacccgaa agcactggag aaggcactgt gtagtatagc tgccagtctg gagaaagcca  1500
aggaaatttt taagaggatg cgtgacttcg tggatccaga cacctttttc cacgttcttc   1560
gcatatattt gtctggttgg aagggcaacc ctaagctgcc ggagggtctg ctgtacgagg   1620
gcgtctggga cacccccaaa aaattttcag ggggcagtgc aggccagagc agcatctttc  1680
agagtcttga tgtccttctg ggaataaagc atgacgttgg tgaaggatct gctgcagaat  1740
tcctccagga aatgagagag tacatgcctc agcccaccg gaacttcctc tcctccttag   1800
agtcagctcc cccagtccgt gagtttgtca ttttaagacg caatgaagac ttgaaggagg  1860
cttataatga gtgtgtgaat ggcctggtct ccctcagaat gttccacctc tcgatagtag  1920
atacttacat tgtgaagcct tcgaagcaga agcccatggg tggccacaag tcagaagagc  1980
cctcaaacac ggaaaacaga gggactgggg gtactgacgt catgaatttc ctgaggagtg  2040
tgaaagatac aaccaagaaa gcccttctga gttggcctta gaatcactag ataagatatc  2100
cgatcnntgg agttcgtgac cgccgccggg atcactctcg gcatggacga gctgtacaag  2160
tccggactca gatccaccgg atctagntaa ctgatcataa tcagccatac cacatttgta  2220
gaggttttac ttgctttaaa aaacctccca cacctccccc tgaacctgaa acataaaatg  2280
aatgcaattg ttgttgttaa cttgtttatt gcagcttata atggttacaa ataaagcaat  2340
agcatcacaa atttcacaaa taaagcattt ttttcactgc attctagttg tggtttgtcc  2400
aaactcatca atgtatctta acgcggccgg ccaataaata                          2440
```

<210> SEQ ID NO 22
<211> LENGTH: 2387
<212> TYPE: DNA
<213> ORGANISM: Artificial Sequence
<220> FEATURE:
<223> OTHER INFORMATION: Description of Artificial Sequence: Human IDO
      expression cassette
<220> FEATURE:
<221> NAME/KEY: misc_feature
<222> LOCATION: (1)..(2387)

<223> OTHER INFORMATION: n= a, c, g, t, unknown or other

<400> SEQUENCE: 22

```
tatttattcc tgcaggtcgt aggtcaaggt agtagagttt gcgggcagga cggggcgacc      60
atcaatgctg gagcccatca cattctgacg caccccggcc catggggggca tgcgcgttgt     120
caaatatgag ctcacaatgc ttccatcaaa cgagttggtg ctcatggcgg cggcggctgc     180
tgcaaaacag atacaaaact acataagacc cccaccttat atattctttc ccacccttan     240
nntaatagta atcaattacg gggtcattag ttcatagccc atatatggag ttccgcgtta     300
cataacttac ggtaaatggc ccgcctggct gaccgcccaa cgaccccgc ccattgacgt       360
caataatgac gtatgttccc atagtaacgc caatagggac tttccattga cgtcaatggg     420
tggagtattt acggtaaact gcccacttgg cagtacatca agtgtatcat atgccaagta     480
cgccccctat tgacgtcaat gacggtaaat ggcccgcctg gcattatgcc cagtacatga     540
ccttatggga ctttcctact tggcagtaca tctacgtatt agtcatcgct attaccatgg     600
tgatgcggtt ttggcagtac atcaatgggc gtggatagcg gtttgactca cggggatttc     660
caagtctcca ccccattgac gtcaatggga gtttgttttg gcaccaaaat caacgggact     720
ttccaaaatg tcgtaacaac tccgccccat tgacgcaaat gggcggtagg cgtgtacggt     780
gggaggtcta tataagcaga gctggtttag tgaaccgtca gatccgctag agatctccag     840
aggagcagac tacaagaatg gcacacgcta tggaaaactc ctggacaatc agtaaagagt     900
accatattga tgaagaagtg ggctttgctc tgccaaatcc acaggaaaat ctacctgatt     960
tttataatga ctggatgttc attgctaaac atctgcctga tctcatagag tctggccagc    1020
ttcgagaaag agttgagaag ttaaacatgc tcagcattga tcatctcaca gaccacaagt    1080
cacagcgcct tgcacgtcta gttctgggat gcatcaccat ggcatatgtg tggggcaaag    1140
gtcatggaga tgtccgtaag gtcttgccaa gaaatattgc tgttccttac tgccaactct    1200
ccaagaaact ggaactgcct cctatttttgg tttatgcaga ctgtgtcttg gcaaactgga    1260
agaaaaagga tcctaataag cccctgactt atgagaacat ggacgttttg ttctcatttc    1320
gtgatggaga ctgcagtaaa ggattcttcc tggtctctct attggtggaa atagcagctg    1380
cttctgcaat caaagtaatt cctactgtat tcaaggcaat gcaaatgcaa gaacgggaca    1440
cttttgctaaa ggcgctgttg gaaatagctt cttgcttgga gaaagccctt caagtgtttc    1500
accaaatcca cgatcatgtg aacccaaaag cattttttcag tgttcttcgc atatatttgt    1560
ctggctggaa aggcaacccc cagctatcag acggtctggt gtatgaaggg ttctgggaag    1620
acccaaagga gtttgcaggg ggcagtgcag gccaaagcag cgtctttcag tgctttgacg    1680
tcctgctggg catccagcag actgctggtg gaggacatgc tgctcagttc ctccaggaca    1740
tgagaagata tatgccacca gctcacagga acttcctgtg ctcattagag tcaaatccct    1800
cagtccgtga gtttgtcctt tcaaaaggtg atgctggcct gcgggaagct tatgacgcct    1860
gtgtgaaagc tctggtctcc ctgaggagct accatctgca aatcgtgact aagtacatcc    1920
tgattcctgc aagccagcag ccaaaggaga ataagacctc tgaagaccct tcaaaactgg    1980
aagccaaagg aactggaggc actgattttaa tgaatttcct gaagactgta agaagtacaa    2040
ctgagaaatc cctttttgaag gaaggttaat gtaacccaac aagagcactc gagcctaagc    2100
ttctagataa gatatccgat ccaccggatc tagataactg atcataatca gccataccac    2160
atttgtagag gttttacttg ctttaaaaaa cctcccacac ctcccccctga acctgaaaca    2220
taaaatgaat gcaattgttg ttgttaactt gtttattgca gcttataatg gttacaaata    2280
```

| | |
|---|---|
| aagcaatagc atcacaaatt tcacaaataa agcattttt tcactgcatt ctagttgtgg | 2340 |
| tttgtccaaa ctcatcaatg tatcttaacg cggccggcca ataaata | 2387 |

<210> SEQ ID NO 23
<211> LENGTH: 30756
<212> TYPE: DNA
<213> ORGANISM: Artificial Sequence
<220> FEATURE:
<223> OTHER INFORMATION: Description of Artificial Sequence: Synthetic gutless backbone
<220> FEATURE:
<221> NAME/KEY: misc_feature
<222> LOCATION: (1)..(30756)
<223> OTHER INFORMATION: n=a, c, g, t, unknown or other

<400> SEQUENCE: 23

| | |
|---|---|
| gtacggaagc ccggaaggag gggcaggggg cggtggctca ggtttctccg ggcggcggcg | 60 |
| gcggcggcgg cggcgacggc gacgcgacg gcagcgggga cggcagcagt agcgggagca | 120 |
| gcagcgtgga cgcggctggc gctggcgcca tgaacccgct gtaaggcgca ggctgtgcag | 180 |
| cacggggtgc gggggaggag gaggaggacg ccgcggtgaa gttctccgcc atgaacctga | 240 |
| ggggcctctt ccaggacttc aacccgaggt gaggcggcgt cgttggcgcc ccgggagtc | 300 |
| cgcgctgcgg gctcgggcgc gggctggtgt tcggctccgg ggaggcacgg cgggcgagat | 360 |
| gctgcagccc gaggacccgg gcgcctgccc gagcctccct gcgggtgcaa gcggtcccca | 420 |
| ggcaaaacag tcggcctcgg cgcccgcccg cttcctcctc ccgtgcccgg tgctttcagc | 480 |
| ccctgcccgg ccacggccgg aagggcccgg ccgcagcccc cgtcctgccc caagggaacc | 540 |
| ccattctttt ctgcttgctg tccctcattg gtgtcccaac ttcttcgtct cggttccatc | 600 |
| ctcttctgcg ccgctgcggg ccctccattc tccgcgtcag ggccgtctca ctcgacccaa | 660 |
| caccctacc cccacccag ctgtttcctc cagttcctcg cagtccttgg ggttttcctt | 720 |
| gggtttatgc ccatccctct cttgtttgct tctttgttga acggatacct gaaacactgt | 780 |
| tgaatccttg gagtcagtgt cggggtatgg caatacctta tataatgcat ttctgggtga | 840 |
| gcctgatcat tttccatact cattttctca tcagtcttca ctacaagttt atttgcagga | 900 |
| agtagatatt gctgtccttc ttttccagat ggggaacacc cagtggacag tgtggagaaa | 960 |
| acactggcta agcactcaag cgcctgtcct tgcacttgcc cgactgtttt gtaactgttc | 1020 |
| tttaccccag gctgtgagct ccctgaagct gagaccatct cctgctcatc tcagtgtccc | 1080 |
| cagcgcctcc cacccaccgt atctggcaca tagtaggcac atataaaatg tttgtggaac | 1140 |
| taaactgagc ccaaagactt ggattggaga cgaggccata tgtaactggg tgattctctg | 1200 |
| cccttctttg gcccttctgt aaaatgagga gttggcctaa ctgatctctt aaatgcacta | 1260 |
| ctctccgaaa ggagtatccg tttcccttat ttgccagttg ggaagacgtg ctcagtaaat | 1320 |
| atttgtgtgc tgtaacctat gttaggtgct ttagatgctg gcggtctcag catgggtga | 1380 |
| agaagggctt gtacacttaa gatgccttac agtactgtgc agtgctgtac tgcggggcc | 1440 |
| aactctgggg acctatgcct tggctgcttg ttgaggatga aaggaagttt taggggagta | 1500 |
| tttgtatgtt gagggtgcag tctccctagg gatggtgaca ttttaacttg tgagtcattg | 1560 |
| tgactttgta tgtgccctta ttccactttg agttcatgtt ctggttagga gtgccagtgt | 1620 |
| ctctaacacg gtgcagacat tatcattgtt ggcttcgaag gcatagagga ggtaacagaa | 1680 |
| ctaactgcag tcccttcctc tgctgcatca gggggttaag attggtctgc agggtagtag | 1740 |
| ggttggtgct gtggctggac aagccctgta tgtcttctat ttggagatgg tgataagaaa | 1800 |
| gttaagtaaa aactgaattg ttttgtgccc ttgggcaact cacttatcta ttgttttatc | 1860 |

```
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagcccctt ttcccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgtttttttta   2340
gctggtagtg tttcacctct cctgagcact cctagttttt gacagtgtgc tttagtctcc   2400
ttccatgctg aggaaggcct tctctatagg agaaagaaaa ctgagggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atccccttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gcttttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
```

```
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggttttcc ccccactgag acagcctgag atatggcctt    4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttccttga acttattcat gatacagatt cctttgctca    5040
cgtttccctg ctgaccttct ccccacctgt tgccctgcta cactcccctc gctaagatag    5100
taaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggaggggc    5280
tggcccctt cagtatctca gaagggacaa agtacacaaa ggcatggggt catgatagtg    5340
cctggtatgt tcaggtagtg aagaggtcca tgtggtatga gcactgcaga tgatatgtgt    5400
cgtatgaatt aaaaatacat agttactgca aatagttttt acaggttatt gttttaaga    5460
aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg accccgccc attgacgtca    5760
ataatgacgt atgttcccat agtaacgcca tagggacttt ccattgacg tcaatgggtg    5820
gagtatttac ggtaaactgc ccacttggca gtacatcaag tgtatcatat gccaagtacg    5880
ccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggattttcc    6060
aagtctccac cccattgacg tcaatgggag tttgttttgg caccaaaatc aacgggactt    6120
tccaaaatgt cgtaacaact ccgccccatt gacgcaaatg gcggtaggc gtgtacggtg    6180
ggaggtctat ataagcagag ctctctggct aactagagaa cccctgctta ctggcttatc    6240
gagatatctg cagaattcat ctgtcgactc ctaccggcag cgcgcagcgg caagaagtgt    6300
ctgggctggg acggacagga gaggctgtcg ccatcggcgt cctgtgcccc tctgctccgg    6360
cacggccctg tcgcagtgcc cgcgcttttcc ccggcgcctg cacgcggcgc gcctgggtaa    6420
catgcttggg gtcctggtcc ttggcgcgct ggccctggcc ggcctgggt tccccgcacc    6480
cgcagagccg cagccgggtg gcagccagtg cgtcgagcac gactgcttcg cgctctaccc    6540
gggcccgcg accttcctca atgccagtca gatctgcgac ggactgcggg ccacctaat    6600
gacagtgcgc tcctcggtgg ctgccgatgt catttccttg ctactgaacg gcgacggcgg    6660
```

```
cgttggccgc cggcgcctct ggatcggcct gcagctgcca cccggctgcg gcgaccccaa   6720
gcgcctcggg cccctgcgcg gcttccagtg ggttacggga gacaacaaca ccagctatag   6780
caggtgggca cggctcgacc tcaatggggc tccctctgc ggcccgttgt gcgtcgctgt    6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcaccccgt tcgcggcccg   7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca caggggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacgttt catctgcac    7740 ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagccccgc ccagcccgac   7920 gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac ccccagcttt gctaccaaag   8220
caccttagct ggcattacag ctggagaaga ccctccccgc acccccaag ctgtttctct    8280 ctattccatg gctaactggc gaggggggtga ttagagggag gagaatgagc ctcggcctct   8340
tccgtgacgt cactggacca ctgggcaatg atggcaattt tgtaacgaag acacagactg   8400
cgatttgtcc caggtcctca ctaccgggcg caggaggtg agcgttattg gtcggcagcc   8460
ttctgggcag accttgacct cgtgggctag ggatgactaa aatatttatt tttttaagt    8520 atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttttcct agccctctca catttatgaa gcaagcccca cttattcccc   8700
attcttccta gttttctcct cccaggaact gggccaactc acctgagtca ccctacctgt   8760
gcctgaccct acttcttttg ctcttagctg tctgctcaga cagaacccct acatgaaaca   8820
gaaacaaaaa cactaaaaat aaaatggcc atttgctttt tcaccagatt tgctaattta    8880
tcctgaaatt tcagattccc agagcaaat aattttaaac aaaggttgag atgtaaaagg    8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
```

```
gttgctaatc ttcttatgca atttcctttt ttgttattat tacttatttt tgacagtgtt    9120
gaaaatgttc agaaggttgc tctagattga gagaagagac aaacacctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg gcccctgaac aagaattgga agctgccctg    9420
cccatgggag ctggttagaa atgcagaatc ctaggctcca ccccatccag ttcatgagaa    9480
tctatattta acaagatctg caggggggtgt gtctgctcag taatttgagg acaaccattc    9540
cagactgctt ccaattttct ggaatacatg aaatatagat cagttataag tagcaggcca    9600
agtcaggccc ttatttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaa aaaaaaaaa aaaaaaaaa    9960 aaaaaaaagg tagcagtcga cagatgaatt ccaccacact ggactagtgg atccgagctc    10020
ggtaccaagc ttaagtttgg gctgcaggaa ttctgatggc tctcaaaatt cctgcctcct    10080
ttagggataa aagactttaa gacttttttaa caaaaaagaa aaagaaaaaa aaaattcctg    10140
cctcctggtg tacacacaca gaagggttcc ctccccttga atgtgaccag gatctgtgaa    10200
aataacggga tagccgctcc tgtgattagg ttatgtggta gactagagca agattctcct    10260
gctggttttg aagaagtcag ctgccatgtt gtgagactgt catgggctag gcatgagcc    10320 tttaaatatc tgggagcaac ccctggccag cagccagtga aaaacgggc cctcagtcct    10380 acaatcacaa ggaactaaat tctgccaaca acctgaagga actttgaaga ggatcatgag    10440
tcccttgatt cagcttgatg agcccctgag cagaggatac agctaacttg tactagggaa    10500
gtataaaaaa catgcatggg aatgatatat atcaacttta aggataattg tcatacttct    10560
gggaatgaag ggaaagaaat ggggctttag ttgtattatg atctttaatt tctcaaaaaa    10620
aataagatca gaagcaaata tggcaaaatg ttaatacttt tgtgggtacg taggtattca    10680
gcataccctt ttttctgagt tcaaaatatt ttataattaa aatgaaatgc aggccaggca    10740
cagtggctca tgcctataat accagcactt tgcgaggccg aggtgggagg atggcttgag    10800
gccagaccag cctggccaac atggcaaaac cccatctcta cttaaaaaaa aaaaaactat    10860
atatatatat atgtgtgtgt gtgtgtatat atatatatgt atatatattt atatatgtgt    10920
gtatatatat atatgtatat atatttatat atgtgtgtgt atatatatat atacacacac    10980
acacatatat acatacatac atacacacac acacacacac aattagccag gcatggtggc    11040
gcacacctgt agtcccagct acttgggagg ctgagacatg agaattgctt gaacctggga    11100
ggcagagtag ttagtgagct gagatcatac cactgcactc cagcctggtg acagagtgag    11160
actctgtctt aaaaaaaata aaaattaaaa ttaaatgcaa aaggtccaag tgaattgaag    11220
aggaaagggg tatcaaggaa ggttttgtgg aggtgacgtt tgagctgggt cttaaatgac    11280
ttaaacatgg gataagaagg gagggaataa ggacatttca ggtacgagaa ataaggagca    11340
aacagtggaa acaacctaac gtctgtcaac cagtgaatgg ataacaaaaa tgtaattcag    11400
atggtatcca acttacgatg gttcaacatg agatttttct gactttagga tagatttatc    11460
```

```
aaagtagtaa atccattttc aacttatgat attttcaact tcagatgggt ttatcaggac    11520
acagttgagg aacacctgtc tatccataca atttggcaat aaaaaggaaa tgagtgcaga    11580
tatactccac aacatgaatg aaccttgaaa acattaagtg agagaagcca gatacaaaag    11640
gccacatatt gtatgattct atttatacaa aatgtccaga ataggcaaat cttatagaca    11700
gcaagtaggt agatgatcag tttgctaggt gctgggggaa ggggaaatgg ggagtgatgg    11760
ctaaggggat tgggtttctt tgtggggcaa tgaaaatgtt ttaaaattga gcgtgataat    11820
gattgcacaa tgctgcatat atatataatc tatagattat atatatataa agagaggctg    11880
ttagacagtg ataagtgata tatatatata tatacataga gagagagaga gagagagaga    11940
gaggctgtta gtgataagtg atcaggaaaa taaaagtatt gaggaggaat acgaagttga    12000
cggtgtgaaa acatgagatt ttatatagga tggccaggga aggccttaat gagaaagtga    12060
cttatgagta aaaacaaggg atcctaaacc ttagcatgca tcagaatcac tcggaaactt    12120
gttaaagcat agcttgctgg gcctcatcac agatattttg attcggtagg ttcttgtctg    12180
atattaatac ttttggtcta gggaaccaca ttttgagaac cactgagcta aggaagtaa    12240 aggtttccct tagtttacta gctggtaaca ctggcccagg aggcctttct ggaaaaggtc    12300
ccagtcccca aggaagctg gggactcgcg ttcacatcgt caaggtttac caagttgtgg    12360
cgggcctttc cgtcttggaa aaagcctcaa aatggcagat tagggtgtcc atggccggcg    12420
gaaagggtct ttgaagttgc agaccaggag ggaagaagat tctgggcctc ccccatgcag    12480
tgtcagctgg caacagaatg caccccggct gggttggagg ccctgggtac tggctcttcc    12540
acaccagggg cccacctacc aagggcagca ggagcatctg cacctcctgc gccaggcgcc    12600
cttcagtgct tccacttgag cacctctcca gacaccagct agggtgacag tggtacaaat    12660
accagactcc cctggcctgc tcacctcaca gggtaatgtg ctgtggagtc aggggacac    12720 agcaaccacc agatgacatg gctggccccg ggaggacga cacgcagata cggctacttg    12780
gcacctgtga tattttacac actcgagagg ggcccgcacc atcctcagcc ctctccccac    12840
attcactctt agttcatgtc acctccaccc agaggggggac acaggcccac agcgatggcc    12900
ccacaccctg cctgaggtcg cccacttccc aggaggcagt cctgggactt ccacccgacc    12960 aggcccaga gccaccgac ttaaccccctc cagaggcttg tcgttcatta ccttattcaa    13020
gatggagacc agccttttg cggagaaaat gcgggtgaag gtcctgaaag tgcattgacg    13080
ccgttttcgg aagccataca agtttagctg gcggaagaag ctctttatcg aagttgtggc    13140
aaacactttg tgtgcgacgt cccttttgag aatctccttt tcaaagagtt tttgattgat    13200
cactctacaa gccccactgt catcccacca gatggacgaa aactggttgc tgctgaccag    13260
tctccacagt ttctgtggaa aggggaggga gaggagatta tcttctccct ggggcgggac    13320
gtcaccgtca gggtgcggcc ttctgaacga agcttcctcg gccagaggtt ggaaagcgat    13380
ttcttctgtc agcagcctca agttagggct cccagtggac cccgggtcgt cccaggcagg    13440
ggaaggatct gctgggtgaa ggtaggtctc tgactgcaac tggggaggga aaggcaccct    13500
ttccaagcca tgatcctgtc ctctcgaatt tctttcttca cagcgagcca tactcaatga    13560
tcgcttgtcc tccatctggc aaacttgcta gtgcagtgtg ccagcagca ccccttggca    13620 gtcatgtaac cagcccccatg acatcataaa ggggctctga ctgccggggg gtggcatctc    13680 caccccccagc aagttgtgta ataaagggcc aaggcagaca agtagctgcc catctgcatg    13740
tgcacattct ggtcctcaca gtcatttcaa tgggaaagat gacactagtg cacaagagtg    13800
ccgaggggcc ctgccacacc gtagatgcag acctggagcg gtcccccttgt cctagagctc    13860
```

```
ctgagccagg cacaactaca gcaaagccct ggctcaggaa ggtcagagct caccgtctga   13920
gtcatgggcc cacagacccc agcacatgac tgacactcgg aagcacagaa caaagggtag   13980
gacggtgccc atgggtcagg ctgtagccac gccacccttt ccaccctgtc ctagccagag   14040
gcagcaatgt gctccataca gatcctccta acacacccac actgtcggtc cccagcacgc   14100
agatgcccga cagcccctta ggcaaatggc ttagctgact gccccaccac acgccgtcgc   14160
catgcagtcc agtggggagt cggaggcagc ctccttcctg cctctcctcg gcctgcacgt   14220 gtcccccac caggcagaga cccttctaca ccccgggtgt ctgcggtcac atcgcggtgg    14280
ggcatgcagc tgttggcctt cgagcatgtt ttgttttcct tggccagtgt ctccagagaa   14340
acgcacgtgg gtttgtgtcc agcggtccat ctctgcaaca gttgttcctt tgggattgga   14400
tgctaggagg tcacgggaga ggtgtccatc caaagcagtg tctgtgtcac acactgtccc   14460
cacacacagg gccacctctg cacagactcc cccgactcga ttctgggcac agagctcagt   14520
gaccttccag agactgccac gaaccggtga tgcctccacg cttgagacat cctgaccgca   14580
gggcccaagg cgcactggct caggggtga cagtgagggg tctgcaaaca gactgctgat    14640
gctcaacccg gccgctgccg agctgtgtga cttgggcacg tcacttaacc tctctcggcc   14700
tctgtctcct cccggggata agagtagtag cacctgcttc ccggggctgt gaggatccag   14760
tgggacgtat aggaactagc gaggcaccgg cagttgggtc agagctactg ttgtcacttc   14820
acaaggcatt ttcttcaaca gcaagtcgga aatctcatga gcctaaggca gaatccacct   14880
gtggcctctg gttacaaccc acaggactga aaatccttcc agccacagca actggtgaat   14940
ttcctggtca attgccacaa gtcatgagct gaaccccact tgagtttcag ttcaggcaga   15000
actctagaga cgactagggc aagctagaca gcgactgcag agccttttgt tgcagcgtga   15060
gcagtcctca gctgttgaca tcactgggga gcaaacgagg accaggagcg gtgaaaggac   15120
agtgtctgct gcagattgtc gtagcaccca aggaacactc cagaaagcct cctaagcagt   15180
aacaagtgtg gcaaggtgta gcccagccaa cagtggcatc tgcgaggcgt cccctccttc   15240
ctcccactac cccgtatacc ctgggacctg tgcactgaag gactcattct aaaggctgtg   15300
cccctgcagc cgccagcctc actcactggc tgcctgtgcc agctagagat ttcttttcctc   15360 tgaggctggc tgagaggacc actccagttt cctggcccat ccagcaaaga agatacacat   15420
catgcacgtg taaaatgagg aaccggttta ttgaacagct taaggagagc aaaaatagtg   15480
gctttagcta cattttttac acactgagca ggaaagtcta aaccatcccg ttcccctgta   15540
ccccaaagag aacagggctt gctggaggcc agtgccaagg gcggagtcgt gctcgcagca   15600
gacttgaatt aaccccatgt aggccggcga gcagttgccc gcgtgaaaac accaccctct   15660
tctcctggct gagaagatca aagctctttt tttaccctct tttcagcaaa ggacctattt   15720
gttttcaggc aggaggatgt taaacttgca gcctctgaca cacggtggaa cctgcagtgc   15780
ttggagaaac ggcacgcaca cgtgaaaaca tcatgcctac tccaaagcct tcttgttgct   15840
ggcaggaggg aagcttgaga ctttcccacg catagtcgtg acccgcgtgg ccgtttctgc   15900
tctcagcaac attctctagt gttccggctt caagcagcgc ttgtcaggtt tgaagctagc   15960
cactattctg agaacgtcag aaaagcatgg accatctctt gcttggtgtt gccgttgtgg   16020
cagtagcagc tactacgtac ctgcacgagt tccagggcag aagtggcaat gtcccatgaa   16080
ggcgtggcac cccacggggg gggggggga gtgtgccacg ggcgtccact tctgcagcag   16140
aaggcatgtg cctacagcac aagcttgtaa aaaaatactt gaacagaata tgctgtacag   16200
aactaggggt taacaccgca tatgaagatg ctaaaacatt tgtataaata ctctgtatac   16260
```

```
aagcatggag tcactcccgt agaaagggct catccgtgag gctatgaaaa actgctgtca   16320
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta acaatactt ttgattggga tttcagcacc gtatagacag atgttccttc    16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca caccccgtc acctgccact tccgcgtccc gtcgtggtga gtggctgata    16740
ggcgctggat gcaaacaagg catgagatgg acgtacctgg agacccagct ccagtactgg   16800
ttctggtctg cggggtgaac gaggggggcag aggaaggcgg agagagtgcg tcccagtcca  16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttaggggct ccggaactgg ggtctcttcg gtttcttcat tatcttcgtg    17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctagggtg ggctccagcg gtccccttt cctggccctt     17460 ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggt ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gttttggaag   17940
tgtctgcctc agcaagcagg tggaggggaa tagagtgtta gcaaggcaag acaggcaaga   18000
ctcgggtgat ggcagcaagg atatggggga ggcagagcgg ccaacaggga cctaggatga   18060
atcccaggtt tgggtgggag atgtggattt tccatcaaac cctcccgggc ctgggaagaa   18120
tctgtcttga tccccatttt gcagaggagg gaacgggatc tctgagaggt tgcctgccgt   18180
gtctggttct acctcaaatg gcagcgtgca ctgcagaaaa agtcccggtg caggccagca   18240
gaacaccaga gttacggcat gcccttccct tagaaggtcc cagaatttcc tcagccctca   18300
ctttcccaca caagcttcta aattgggcc ctcgggact catcccttcc tagacttcta     18360
tccgccaccc cccacccccct ggtccccccc cagacacaca ccaaggactt ctgaaatgct   18420
gagtacatac agtggtttcc tcccttctgt ccaaatgtgt ttgccatcag cgtgatcaac   18480
gagagccaaa ggggacaaa gatcgggatg caggagaagg cgttgtggcc atccagtttg     18540
tgaaccagca gaatctaaag aaaagagacat agtcccggtt gatgccagca ccgaaaatgg   18600
gcagaggcgg aagccagact tcattaggca gttcctcccc accaccccac cccgcgtga    18660
```

```
gctcccacaa gagggaacat cagcaccgcc agaaaaaggc aggaaaccac ctatccctgg   18720
ggaaagctcg aaatgagctt ttatgtccct cttcagagct cggcaatagc ctatccactt   18780
gaaaagttcc cagtgccagc agttttatgg caaactcctc cgggtgtttg ttctaaggag   18840
tcaacagctc ccattctaga attctccacg tgactccaat acacaaatct gacatcccac   18900
tctgctttcc ccagagtgga aactggagcc atacagaggc accatggcta aaaaggtgca   18960
ctcttctccc tgccagcccc acgtgctgcc cccaagagaa aggaaggatg ctctcctttc   19020
accgaagctc cctctcggag atggctgtgt tctctcccct ctcctggagt gggctcactg   19080
tgagctcgag ggacagaggc tgcctttcta ggggtgcaga atcctgtcag gggaagcgca   19140
agcttcaggg gctgaagagg cttcccgtgg aacgcttacc tcaaatgtaa gaaggggcac   19200
gacgatggtc atccagctca gggccatggt tatgtgtgtc ctgcgctgtc cgcaatcaca   19260
tccatagagc gcaagaacaa gacggaccac acaatgtagt agaggaccac caggcacaga   19320
aaggacatga gaatccacag cgggacacac acaacctggg ggtgggtgag agaacagcaa   19380
gagaagtctc tttagagctt ccaacctggc ctctgatgga aggcatcttt agcaccttgc   19440
tgtgtctgtc cagttaaggc ggtccttcct gtgagccgaa taaggaccgt tccatctccc   19500
aggactgctg ggagcatcgc tcaggacaga aaaggtatgg tatgttcact atggggcctg   19560
ctgccaccag gggacacaca cgctcagtga gtcatcagtc cctcttcctt tgggtgacag   19620
acagccctgc acctggctcc gcagcctcta ctcttccaga ggcccactct cccacactct   19680
ctcaggctcc tctaggttct gctgccatca cagcttcccg ggaaatggga cacaactgtc   19740
accctgtgca cacacacaag atctcacccc aacagactct cttcacaggc aacattccca   19800
caacctgctg ggggtacttt ggcaacacaa atgggaatgg gctccccaga aagtctggct   19860
gcctgggctc ctaaggatcc ctaacctcac ccctaccaag ttagtgaact tggcgggttg   19920
atgctggata caggttgatg ctggatacgt agcgctgccg ggtcgtgacc cctaaggaat   19980
tatccaaact cttgttttta gatgctttat tatatcaaac tctcctttaa acaagtggcc   20040
catctgctgg gatttggaag cctgtaatac tgaaattttc atcataatgg aaattttaaa   20100
aacagaattt gacccacctg tttttaaaac actttcatta cttaacaaga ggtctaatct   20160
tgggcaagtc ttgaaatttc tctggcctta gtttcccatg tgttaaatga aacttgaagc   20220
agttggtctc ttatagtctc ctgactctaa cattctaaga attatatttg tacaataact   20280
caaaaatcac ataatttaat ttaccatatg gactccaaaa tatattttct cattaggcta   20340
aacttgatct gcattttctg gatgtgtcca tattcttgga ctacactaaa acatgatacc   20400
aatgcttcct ctcaccataa accctcactt cgctttctac atttaagaat tttatagctg   20460
gaagagtcct taacagaaaa taccatctaa taattacccc tcaaaatcga gaaagtccta   20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagatttaa tgttctatat attcttctaa gacagtgttt accagagtaa   20700
ggcacaaaag atccactggt ttgcaagaaa gattagaact tttaaatttt ttacctcacc   20760
ttgtttaatc tatattttg tatgtatttt gtaacatata tattattatt accataaatc   20820
atatataatt taaaatgcat atattagggg taaatgctca ggaaactttt tataaattgg   20880
gcatgcaaat acaagtttga agactcactg ttctaggtat taaaagtaaa gttataacca   20940
agtaaagctt ccacctttc atgtctcaaa gcagttatt gttggaggta agatctctta   21000
gaagcctaaa caggtccaag tacagaatga agtaaggcta gcccataact tgtggcaagc   21060
```

```
aattcatact atttctctca tgctgagctc tcctcagtga agcagctact atagacaact  21120
gcagcctatt ggtagcctat tttacaggca ggaaaaaaat tacttttat tcaaagtgga   21180
actcaggaca tggggagaaa atgaatacaa aaaatagggt caatccaaag gcacacagca  21240
aatgagtaac acagttatgt ttttttccca tttgtatgag gtcccagtaa attctaagta  21300
aactgcaaat ttaataatac actaaaaaag ccatgcaatt gttcaaatga atcccagcat  21360
ggtacaagga gtacagacac tagagtctaa aaaacaaaag aatgccatta ttgagttttt  21420
gaattatatc aagtagttac atctctactt aataaatgag aaaaacgagg ataagaggcc  21480
atttgataaa atgaaaatag ccaagaagtg gtattagaga cttgaataca ggtattcggg  21540
tccaaagttc atctgctcaa atactaactg gggaaaagag ggaaaaatat ttatatacat  21600
atatatctgc acacaaaaat accccaaaa gacaaaatga ggccaggcag ggtggctcac   21660
acccgtaatc ccggtacttt gggaggctga ggcaggtgga tacctgagat caggagttgg  21720
agatcagcct ggtcaacatg gtgaaaccct gtctctacta aagataaaaa aattagccag  21780
gcatggtggc gtgcgcctgt aatcccagct acttgggagt ctgaggcagg agaatcactt  21840
gaactgggaa ggggaggttg cagtgagcca agatcgtact actgcactcc agcctgggca  21900
gcagagtgag actccatcac aaaaataaat aaataaataa aatacaatga aacagaaagt  21960
tcaaataatc ccataatctt accaccaaga aataactttc actcgttata cttattgatt  22020
tttccataat aaatgtactt tactgtgact atcatgaaaa gaaagttatt ttagaaacag  22080
agaactgttt cagatcaaat ctatgtagta gaacagagcc attaggtggg aaagacgaga  22140
tcaaactaaa tctcagaagg cctaaaaggc taggtccatt ccagcactaa aaactgacca  22200
gacaagtaat ggcttcaaca gcttctaaat atggacaaag catgctgaaa gggaaggaca  22260
ggtctaacag tggtatatga aatgaacagg aggggcaaag ctcatttctc ctctgaagtt  22320
ttccaaagat gctgaggagg acattagttt gacatgaccc tgatatggga caagataatt  22380
tcacagaagt tttacatgtt aaagtttct tatagatact cattcaagta agcaatgaac   22440
actaaaatct aaagaaagaa aagagcttta gagtcaggtc tgtattcaaa ttcaagctct  22500
accacttact ggttctgtga ctttgggcaa gtcttttaac cttattaagt cttaatttcc  22560
tgatttgtaa aatggggata tcgtctccct cacaggattg ttgtgaaact tttatgagat  22620
taatgccttt atatttggca tagtgtaagt aaacaataac tggcagcttc aaaaaaaaaa  22680
agcagtagca ttccatcatt tattattggt tactctcaaa aagttttca atgtactaga   22740
agataaatat tcaaatacct taatatctcc attattttca ggtaaacagc atgctcctga  22800
acaaccaatg ggtcaacaaa taaattaaaa gggaaatcta aaaacatctt gatattaaac  22860
tacatggaag cacaatatac caaaaccaat ggttcacact aggagaattt taaggtacaa  22920
gaaaactctt tgagatttct taaaataata gtatgtctga atttattgag tgatttacca  22980
gaaactgttg taagagctct acttgcatta tagcacttaa tcctcttaac tctatggctg  23040
ctattatcaa cctcacccta atcacatatg ggacacagag aggttaagta acttgcccaa  23100
ggtcagagtt aggaagtact aagccatgct ttgaatcagt tgtcaggctc cggaactcac  23160
actttcagcc actacataat actgctttgc tatcttttag gaaactatgt gagtctacct  23220
cacatagact cacataggtt tgtttttttt tttttttaa aggctatctt ttcccccatc   23280
aatgtttttt gaaggatccc aaattagagt cccacagagg cagacagcag tacttgacaa  23340
tatggacatt taaggttaat gttggattct actgtctttt tactacatga cctagggaac  23400
gataattaac ctagactgct tccaagggtt aaataaccca tttagttata ctatgtaaat  23460
```

```
tatctcttag tgattgattg aaagcacact gttactaatt gactcggtat gaagtgcttt    23520 ttttcttcc  ctttcaagat acatacctt  ccagttaaag ttgagagatc atctccacca    23580
attactttta tgtccctgt  tgactggtca ttctagttaa aaaaaaaaaa aactatatat    23640
atatatatct acacacacat atgtatatgt atatccttat gtacacacac aaacttcaaa    23700
ttaaatgaga actagaagat ttgagaagtt agctagctaa tatccatagc attatgatat    23760
tctaaatgat atgaattata agaattaggt ttcctgaaat gaatgactag aaaactttca    23820
agtagagatt agtaaaaatt aaaaagtcct aatcggccat tactgatttg atgtttttaa    23880
gagtcctaaa aaatgggtta catccatttt taagtgggta gtattataac agccacccat    23940
cttcaatcac agtgatttct gaattgtgag ggaagttatt agcatgacag gtgtctggtt    24000
ctggccctgt acgattccca tgagtcaagc aaattgtaag ggctggtcta tatcacaccc    24060
aaccccaagg atatgtccct caaaagtcta gcccaggccc cgtcatcttc agcatcatct    24120
gggaaaccag gtctgattag tagtccttta aggaatacct cttaggctcc cattttactg    24180
ctatcacaga atccaataaa acccttacag gagattcaat gggaaatgct caacacccac    24240
tgtagttggt ggtgacaatg accataattt ggctgtgctg gattcaggac agaaaatttg    24300
ggtgaaagag caggtgaaca aaagagcttc gacttgccct agcagagagc aagccatacc    24360
ataccacaaa gccacagcaa ttacaacggt gcagtaccag cacagtaaat gaacaaagta    24420
gagcccagaa acagacccag aactatatga ggatttagta tacaataaag atggtatttc    24480
gagtcagtag ggaaaagatg aattattcaa taaatgatgt ttggccaact agtaacccat    24540
ttgggaaaaa ataaaagtat ggtccctacc tcacagcata cacaaaaata aattccagac    24600
ggattaaaat ctaaatgtaa aaaataaagc cataagtgga ctggaagaaa atagagaatt    24660 tttttaaca  tccgtagaaa gggtaaaaac ccaggcatga catgaaccaa aactgaagag    24720
gttctgtaac aaatacccccc ttttatatat tgggctccaa caataagaac ccataggaaa    24780
atggagaatg aacacaaata gacaatttat agaagagaag gttataaggt gtaaaattat    24840
atctatctga gaaacaaaca ctaaaacaat gtgattctac tgttctccca cccatactgg    24900
caaaacttaa gcctgataat atgctgaggg gaaataagca ctcttgttgg tgagagtatt    24960
aattggcata gcttcttttg aaaatgacat agcaatacct gttaaaattg caaacatgca    25020
tgtcacttaa tccagtaatc ccacttctgg gaatcaatgc tacaaaaaca ctgacaagta    25080
tacaaagata cattcaagag tgttcactgg gccgggtgcg gtggcttcat gcctgtaatc    25140
ccagggaggc agaggcaaga cgatcgcttg accccaggag ttcaaggcca gcccgagaaa    25200
cacagcaaga ccctgtctct cttttttta  tttaaaaaat aaatgttcac tgtatcagtt    25260
gttcacaaaa acaaaccaac atgtccatta acagggaacc atttaaatta atcaagttca    25320
tctacacaat gtaataccat gcaactatta aaaagcacct gataatccaa agcacactga    25380
gacagaataa tgctattaaa aacaccaagt agtggaacac tgtgttgcct atgacaccat    25440
ttttattcaa catttaaaca aatttgtaac agcaattaca tgagtagtga caatggcgtt    25500
tatgagactt ttcactttta tgtgcttcta ttttgttat  gcttctatat atacatccat    25560
ttattatgga gtgttacttt caaaaatcac aaatgggcca gtattatttg gtgttgcaag    25620
gtgagcatat gacttctgat atcaacccttt gcatattact tctcaattta gggaaattac    25680
agacatccct tattctaact aacttaaaac ccagcatttc aaacatacag aattgatggg    25740
gaaaaaaaag aaagaagaaa gaaagaaaag gcaacaagct tcagtgaca  gtgactcaca    25800 tcaaattatt tataaaatct gttaaatagt gccatcttct ggagatacct ggtattacag    25860
```

| | |
|---|---|
| tccaactcca gttgatgtct ttacagagac aagaggaata aaggaaaaaa tattcaagaa | 25920 |
| ctgaaaagta tggagtcatg gaaaaattgc tgtgatccaa aggctacggt gataggacaa | 25980 |
| gaaacaagag aactccaagc agtaagacac tgctgttcta ttagcatcca aacctccata | 26040 |
| ctcctgtttg ccccaaggct tttttaaaaa atagagacag gatctcacta ttttgctcag | 26100 |
| gctggtcttg aactcctgga ctcaagctat cctcctgcct cggcctccta aagtgccgag | 26160 |
| attacaggct tgagtcacca tacctggcta tttatttttt cttaactctc ttgcctggcc | 26220 |
| tatagccacc atggaagcta ataaagaata ttaatttaag agtaatggta tagttcacta | 26280 |
| cattggaata caggtataag tgcctacatt gtacatgaat ggcatacatg gatcaattac | 26340 |
| cccacctggg tggccaaagg aactgcgcga acctccctcc ttggctgtct ggaacaagct | 26400 |
| tcccactaga tccctttact gagtgcctcc ctcatcttta attatggtta agtctaggat | 26460 |
| aacaggactg gcaaaggtga ggggaaagct tcctccagag ttgctctacc ctctcctcta | 26520 |
| ccgtcctatc tcctcactcc tctcagccaa ggagtccaat ctgtcctgaa ctcagagcgt | 26580 |
| cactgtcaac tacataaaat tgccagaaga gctcttgggg actacaaaca catacccttα | 26640 |
| atgtctttat ttctattttg tctacctctt cagtctaggt gaaaaatag gaaggataat | 26700 |
| agggaagaac tttgtttatg cctacttatc cgccctagg aattttgaaa acctctaggt | 26760 |
| agcaataaga actgcagcat ggtatagaaa aagaggagga aagctgtata gaaatgcata | 26820 |
| ataaatgggc aggaaaagaa ctgcttggaa caaacaggga ggttgaacta taaggagaga | 26880 |
| aagcagagag gctaatcaac aaggctgggt tcccaagagg gcatgatgag actattacta | 26940 |
| aggtaggaat tactaagggc tccatgtccc cttagtggct tagtactatg tagcttgctt | 27000 |
| tctgcagtga acttcagacc cttcttttag gatcctagaa tggacttttt tttttatcg | 27060 |
| gaaacagtc attctctcaa cattcaagca ggccccaagt ctaccacact caatcacatt | 27120 |
| ttctcttcat atcataatct ctcaaccatt ctctgtcctt ttaactgttt ttctataccc | 27180 |
| tgatcaaatg ccaacaaaag tgagaatgtt agaatcatgt atttttagag gtagactgta | 27240 |
| tctcagataa aaaaaagg cagatattcc attttccaaa atatgtatgc agaaaaaata | 27300 |
| agtatgaaag gacatatgct caggtaacaa gttaatttgt ttacttgtat tttatgaatt | 27360 |
| ccctaaaacc tacgtcaccc gccccgttcc cacgccccgc gccacgtcac aaactccacc | 27420 |
| ccctcattat catattggct tcaatccaaa ataaggtata ttattgatga tgttaattaa | 27480 |
| catgcatgga tccatatgcg gtgtgaaata ccgcacagat gcgtaaggag aaaataccgc | 27540 |
| atcaggcgct cttccgcttc ctcgctcact gactcgctgc gctcggtcgt tcggctgcgg | 27600 |
| cgagcggtat cagctcactc aaaggcggta atacggttat ccacagaatc agggggataac | 27660 |
| gcaggaaaga acatgtgagc aaaaggccag caaaaggcca ggaaccgtaa aaaggccgcg | 27720 |
| ttgctggcgt ttttccatag gctccgcccc cctgacgagc atcacaaaaa tcgacgctca | 27780 |
| agtcagaggt ggcgaaaccc gacaggacta taaagatacc aggcgtttcc ccctggaagc | 27840 |
| tccctcgtgc gctctcctgt tccgaccctg ccgcttaccg gatacctgtc cgcctttctc | 27900 |
| ccttcgggaa gcgtggcgct ttctcatagc tcacgctgta ggtatctcag ttcggtgtag | 27960 |
| gtcgttcgct ccaagctggg ctgtgtgcac gaaccccccg ttcagcccga ccgctgcgcc | 28020 |
| ttatccggta actatcgtct tgagtccaac ccggtaagac acgacttatc gccactggca | 28080 |
| gcagccactg gtaacaggat tagcagagcg aggtatgtag gcggtgctac agagttcttg | 28140 |
| aagtggtggc ctaactacgg ctacactaga aggacagtat ttggtatctg cgctctgctg | 28200 |
| aagccagtta ccttcggaaa aagagttggt agctcttgat ccggcaaaca aaccaccgct | 28260 |

```
ggtagcggtg gttttttttgt ttgcaagcag cagattacgc gcagaaaaaa aggatctcaa   28320
gaagatcctt tgatcttttc tacggggtct gacgctcagt ggaacgaaaa ctcacgttaa   28380
gggattttgg tcatgagatt atcaaaaagg atcttcacct agatcctttt aaattaaaaa   28440
tgaagtttta aatcaatcta agtatatat gagtaaactt ggtctgacag ttaccaatgc    28500
ttaatcagtg aggcacctat ctcagcgatc tgtctatttc gttcatccat agttgcctga   28560
ctccccgtcg tgtagataac tacgatacgg gagggcttac catctggccc cagtgctgca   28620
atgataccgc gagacccacg ctcaccggct ccagatttat cagcaataaa ccagccagcc   28680
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgacccgg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg gaagccctg caaagtaaac tggatggctt tcttgccgcc aaggatctga   29100
tggcgcaggg gatcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc ttttttgtcaa gaccgacctg tccggtgccc tgaatgaact gcaagacgag   29340
gcagcgcggc tatcgtggct ggccacgacg ggcgttcctt gcgcagctgt gctcgacgtt   29400
gtcactgaag cgggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata accgagata gggttgagtg ttgttccagt    30060
ttggaacaag agtccactat taaagaacgt ggactccaac gtcaaagggc gaaaaaccgt   30120
ctatcagggc gatggcccac tacgtgaacc atcaccctaa tcaagttttt tggggtcgag   30180
gtgccgtaaa gcactaaatc ggaaccctaa agggagcccc cgatttagag cttgacgggg   30240
aaagccggcg aacgtggcga gaaaggaagg gaagaaagcg aaaggagcgg cgctagggc    30300 gctggcaagt gtagcggtca cgctgcgcgt aaccaccaca cccgccgcgc ttaatgcgcc   30360
gctacagggc gcgtccattc gccattcagg atcgaattaa ttcttaatta acatcatcaa   30420
taatatacct tattttggat tgaagccaat atgataatga gggggtggag tttgtgacgt   30480
ggcgcggggc gtgggaacgg ggcgggtgac gtagtagtgt ggcggaagtg tgatgttgca   30540
agtgtggcgc aacacatgta agcgacggat gtggcaaaag tgacgttttt ggtgtgcgcc   30600
ggtgtacaca ggaagtgaca attttcgcgc ggttttaggc ggatgttgta gtaaatttgg   30660
```

```
gcgtaaccga gtaagatttg gccattttcg cgggaaaact gaataagagg aagtgaaatc   30720
tgaataattt tgtgttactc atagcgcgta atactg                             30756

<210> SEQ ID NO 24
<211> LENGTH: 32392
<212> TYPE: DNA
<213> ORGANISM: Artificial Sequence
<220> FEATURE:
<223> OTHER INFORMATION: Description of Artificial Sequence: Synthetic
      PrIDO-final
<220> FEATURE:
<221> NAME/KEY: misc_feature
<222> LOCATION: (1)..(32392)
<223> OTHER INFORMATION: n= a, c, g, t , unknown or other

<400> SEQUENCE: 24
gtacggaagc ccggaaggag gggcaggggg cggtggctca ggtttctccg ggcggcggcg     60
gcggcggcgg cggcgacggc gacgcgacg gcagcgggga cggcagcagt agcgggagca    120
gcagcgtgga cgcggctggc gctggcgcca tgaacccgct gtaaggcgca ggctgtgcag   180
cacggggtgc gggggaggag gaggaggacg ccgcggtgaa gttctccgcc atgaacctga   240
ggggcctctt ccaggacttc aacccgaggt gaggcggcgt cgttggcgcc cccgggagtc   300
cgcgctgcgg gctcgggcgc gggctggtgt tcggctccgg ggaggcacgg cgggcgagat   360
gctgcagccc gaggacccgg gcgcctgccc gagcctccct gcgggtgcaa gcggtcccca   420
ggcaaaacag tcggcctcgg cgcccgcccg cttcctcctc ccgtgcccgg tgctttcagc   480
ccctgcccgg ccacggccgg aagggcccgg ccgcgagccc cgtcctgccc caagggaacc   540
ccattctttt ctgcttgctg tccctcattg gtgtcccaac ttcttcgtct cggttccatc   600
ctcttctgcg ccgctgcggg ccctccattc tccgcgtcag ggccgtctca ctcgacccaa   660 caccctacc cccaccccag ctgtttcctc cagttcctcg cagtccttgg ggttttcctt   720
gggtttatgc ccatccctct cttgtttgct tctttgttga acggatacct gaaacactgt   780
tgaatccttg gagtcagtgt cggggtatgg caatacctta tataatgcat ttctgggtga   840
gcctgatcat tttccatact cattttctca tcagtcttca ctacaagttt atttgcagga   900
agtagatatt gctgtccttc ttttccagat ggggaacacc cagtggacag tgtggagaaa   960
acactggcta agcactcaag cgccgtgtcct tgcacttgcc cgactgtttt gtaactgttc  1020
tttaccccag gctgtgagct ccctgaagct gagaccatct cctgctcatc tcagtgtccc  1080
cagcgcctcc cacccaccgt atctggcaca tagtaggcac atataaaatg tttgtggaac  1140
taaactgagc ccaaagactt ggattggaga cgaggccata tgtaactggg tgattctctg  1200
cccttctttg gcccttctgt aaaatgagga gttggcctaa ctgatctctt aaatgcacta  1260
ctctccgaaa ggagtatccg tttcccttat ttgccagttg ggaagacgtg ctcagtaaat  1320
atttgtgtgc tgtaacctat gttaggtgct ttagatgctg gcggtctcag catgggtga   1380 agaagggctt gtacacttaa gatgccttac agtactgtgc agtgctgtac tgcgggggcc  1440
aactctgggg acctatgcct tggctgcttg ttgaggatga aaggaagttt taggggagta  1500
tttgtatgtt gagggtgcag tctccctagg gatggtgaca ttttaacttg tgagtcattg  1560
tgactttgta tgtgccctta ttccactttg agttcatgtt ctggttagga gtgccagtgt  1620
ctctaacacg gtgcagacat tatcattgtt ggcttcgaag gcatagagga ggtaacagaa  1680
ctaactgcag tcccttcctc tgctgcatca gggggttaag attggtctgc agggtagtag  1740
ggttggtgct gtggctggac aagccctgta tgtcttctat ttggagatgg tgataagaaa  1800
```

```
gttaagtaaa aactgaattg ttttgtgccc ttgggcaact cacttatcta ttgttttatc   1860
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagccctt ttccccccaa aaaattagt   2100 atatgaaatt acagtgaaat acctggtatc taagcagatt tatagtaatt ctcaacatat   2160
tcatcaatct cttaattcta cctgcattaa aatgtatttc tacctgaaaa gtttaaggt   2220 cttttatact gtgccatttt cctgattcat tgttgccaga ggtagtgagt tccttaatttt  2280 tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagaccctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atccccttc cagccttttg   3180 gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gcttttagt   3360 tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt attgcaaag tatattataa cattgattcc   3960
tcaaacatct agattcctat ctcgtgccaa gtgatgtact aggtgctcta agtacaaaaa   4020 taaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
```

```
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggttttcc ccccactgag acagcctgag atatggcctt    4680
gtgggaaagg aaagacctta ccacccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac ctttccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggagggc    5280 tggcccttt cagtatctca gaagggacaa agtacacaaa ggcatgggt catgatagtg    5340 cctggtatgt tcaggtagtg aagaggtcca tgtggtatga gcactgcaga tgatatgtgt    5400
cgtatgaatt aaaaatacat agttactgca aatagttttt acaggttatt gttttttaaga    5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgtatc atatggagtt ccgcgttaca    5700
taacttacgg taaatggccc gcctggctga ccgcccaacg acccccgccc attgacgtca    5760
ataatgacgt atgttcccat agtaacgcca tagggactt tccattgacg tcaatgggtg    5820
gagtatttac ggtaaactgc ccacttggca gtacatcaag tgtatcatat gccaagtacg    5880 ccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg gcggtaggc gtgtacggtg    6180 ggaggtctat ataagcagag ctctctggct aactagagaa cccctgctta ctggcttatc    6240
gagatatctg cagaattcat ctgtcgactc taccggcag cgcgcagcgg caagaagtgt    6300
ctgggctggg acggacagga gaggctgtcg ccatcggcgt cctgtgcccc tctgctccgg    6360 cacgccctg tcgcagtgcc cgcgcttttcc ccggcgcctg cacgcggcgc gcctgggtaa    6420
catgcttggg gtcctggtcc ttggcgcgct ggccctggcc ggccgcgtta agatacattg    6480
atgagtttgg acaaaccaca actagaatgc agtgaaaaaa atgctttatt tgtgaaattt    6540
gtgatgctat tgctttattt gtaaccatta taagctgcaa taaacaagtt aacaacaaca    6600
```

```
attgcattca ttttatgttt caggttcagg gggaggtgtg ggaggttttt taaagcaagt    6660
aaaacctcta caaatgtggt atggctgatt atgatcagtt anctagatcc ggtggatctg    6720
agtccggact tgtacagctc gtccatgccg agagtgatcc cggcggcggt cacgaactcc    6780
anngatcgga tatcttatct agtgattcta aggccaactc agaagggctt tcttggttgt    6840
atctttcaca ctcctcagga aattcatgac gtcagtaccc ccagtccctc tgttttccgt    6900
gtttgagggc tcttctgact tgtggccacc catgggcttc tgcttcgaag gcttcacaat    6960
gtaagtatct actatcgaga ggtggaacat tctgagggag accaggccat tcacacactc    7020
attataagcc tccttcaagt cttcattgcg tcttaaaatg acaaactcac ggactggggg    7080
agctgactct aaggaggaga ggaagttccg gtgggctgga ggcatgtact ctctcatttc    7140
ctggaggaat tctgcagcag atccttcacc aacgtcatgc tttattccca gaaggacatc    7200
aagactctga agatgctgc tctggcctgc actgccccct gaaaattttt tggggggtgtc    7260
ccagacgccc tcgtacagca gaccctccgg cagcttaggg ttgcccttcc aaccagacaa    7320
atatatgcga agaacgtgga aaaaggtgtc tggatccacg aagtcacgca tcctcttaaa    7380
aatttccttg gctttctcca gactggcagc tatactacac agtgccttct ccagtgcttt    7440
cgggtcttga tgctctactg cactggatac agtaggaatt gctttgattg caggagaagc    7500
tgcgatttcc accattagag agaccaggaa gaagccttta tcgcagtccc caccaggaaa    7560
cgagaacaga atgtccatgt tctcgtatgt catgggccca ttggggtcct ttttcttcca    7620
gtttgccagg acgcagtctg cgtaagacag aatgggaggc agcccagct tctccgagag    7680
ctcgcagtag ggaacggcaa gattgcgggg cagcaccttt cgaatatcat catcccctcg    7740
gttccacaca tacgccatgg tgatgtaccc cagggccaaa tgtgccaggc gctgtaacct    7800
gtgtcccctc agttcttcgg tgcgcagtgt gggcagcttc tcgacttctt ctcggagctt    7860
cccattctca atcagcttag gcagatttct agccacaagg atccaaggtc tgtacgtatc    7920
aggcagctcc tccagtggat gtggtagagc aaagcccaca tcttcatcta tgtggtattc    7980
ttcaaggatc cttctagagc cttctgcagg agatatttga ctgtgaggca taatcgaatt    8040
cccgcggccg cgtcgacggt accagatctc tagcggatct gacggttcac taaaccagct    8100
ctgcttatat agacctccca ccgtacacgc ctaccgccca tttgcgtcaa tggggcggag    8160
ttgttacgac attttggaaa gtcccgttga ttttggtgcc aaaacaaact cccattgacg    8220
tcaatggggt ggagacttgg aaatccccgt gagtcaaacc gctatccacg cccattgatg    8280
tactgccaaa accgcatcac catggtaata gcgatgacta tacgtagat gtactgccaa    8340
gtaggaaagt cccataaggt catgtactgg gcataatgcc aggcgggcca tttaccgtca    8400
ttgacgtcaa tagggggcgt acttggcata tgatacactt gatgtactgc caagtgggca    8460
gtttaccgta atactccac ccattgacgt caatggaaag tccctattgg cgttactatg    8520
ggaacatacg tcattattga cgtcaatggg cggggtcgt tgggcggtca gccaggcggg    8580
ccatttacca acgcggaact ccatatatgg gctatgaact aatgaccccg taattgatta    8640
ctattannnt aagggtggga aagaatatat aaggtggggg tcttatgtag ttttgtatct    8700
gttttgcagc agccgccgcc gccatgagca ccaactcgtt tgatggaagc attgtgagct    8760
catatttgac aacgcgcatg cccccatggg ccggggtgcg tcagaatgtg atgggctcca    8820
gcattgatgg tcgccccgtc ctgcccgcaa actctactac cttgacctac gacctgcagg    8880
cagacgggcg ctcctgcacc gcatccgcga cgcagtcctg caacgacctc tgcgagcact    8940
tctgcgttcc caacccgac cagccgggct cctactcgtg catgtgcgag accggctacc    9000
```

```
ggctggcggc cgaccaacac cggtgcgagg acgtggatga ctgcatactg gagcccagtc   9060
cgtgtccgca gcgctgtgtc aacacacagg gtggcttcga gtgccactgc tacccTAACT   9120
acgacctggt ggacggcgag tgtgtggagc ccgtggaccc gtgcttcaga gccaactgcg   9180
agtaccagtg ccagccccTG aaccaaacta gctacctctg cgtctgcgcc gagggcttcg   9240
cgcccaTTCC ccacgagccg cacaggtgcc agatgtttTG caaccagact gcctgtccag   9300
ccgactgcga ccccaacacc caggctagct gtgagtgccc tgaaggctac atcctggacg   9360
acggtttcat ctgcacggac atcgacgagt gcgaaaacgg cggcttctgc tccggggtgt   9420
gccacaacct ccccggtacc ttcgagtgca tctgcgggcc cgactcggcc cttgcccgcc   9480
acattggcac cgactgtgac tccggcaagg tggacggtgg cgacagcggc tctggcgagc   9540
ccccgcccag cccgacgccc ggctccacct tgactcctcc ggccgtgggg ctcgtgcatt   9600
cgggcttgct cataggcatc tccatcgcga gcctgtgcct ggtggtggcg cttttggcgc   9660
tcctctgcca cctgcgcaag aagcagggcg ccgccagggc caagatggag tacaagtgcg   9720
cggcccctTC caaggaggta gtgctgcagc acgtgcggac cgagcggacg ccgcagagac   9780
tctgagcggc ctccgtccag gagcctggct ccgtccagga gcctgtgcct cctcacccCC   9840
agctttgcta ccaaagcacc ttagctggca ttacagctgg agaagaccct ccccgcaccc   9900
cccaagctgt tttcttctat tccatggcta actggcgagg gggtgattag agggaggaga   9960
atgagcctcg gcctcttccg tgacgtcact ggaccactgg gcaatgatgg caattttgta  10020
acgaagacac agactgcgat ttgtcccagg tcctcactac cgggcgcagg agggtgagcg  10080
ttattggtcg gcagccttct gggcagacct tgacctcgtg ggctagggat gactaaaata  10140
ttTATTTTTT ttaagtattt aggttttTGT ttgttTCCTT tgttcttacc tgtatgtctc  10200
cagtatccac tttgcacagc tctccggtct ctctctctct acaaactccc acttgtcatg  10260
tgacaggtaa actatcttgg tgaatttTTT tttcctagcc ctctcacatt tatgaagcaa  10320
gccccactta ttcccattc ttcctagttt tctcctccca ggaactgggc caactcacct  10380
gagtcaccct acctgtgcct gaccctactt cttttgctct tagctgtctg ctcagacaga  10440
accCCTACAT gaaacagaaa caaaacact aaaaataaaa atggccattt gctttttcac  10500
cagatttgct aattTATCCT gaaatttcag attcccagag caaaataatt ttaaacaaag  10560
gttgagatgt aaaaggtatt aaattgatgt tgctggactg tcatagaaat tacacccaaa  10620
gaggtattta tctttacttt taaacagtga gcctgaattt tgttgctgtt ttgattTGTA  10680
ctgaaaaatg gtaattgttg ctaatcttct tatgcaattt cctttttTGT tattattact  10740
tattttTGAC agtgttgaaa atgttcagaa ggttgctcta gattgagaga agagacaaac  10800
acctcccagg agacagttca agaaagcttc aaactgcatg attcatgcca attagcaatt  10860
gactgtcact gttccttgtc actggtagac caaaataaaa ccagctctac tggtcttgtg  10920
gaattgggag cttgggaatg gatcctggag gatgcccaat tagggcctag ccttaatcag  10980
gtcctcagag aatttctacc atttcagaga ggccttTTGG aatgtggccc ctgaacaaga  11040
attggaagct gccctgccca tgggagctgg ttagaaatgc agaatcctag gctccacccc  11100
atccagttca tgagaatcta taTTTAACAA gatctgcagg gggtgtgtct gctcagtaat  11160
ttgaggacaa ccattccaga ctgcttccaa ttttctggaa tacatgaaat atagatcagt  11220
tataagtagc aggccaagtc aggcccttat tttcaagaaa ctgaggaatt ttctttgtgt  11280
agctttgctc tttggtagaa aaggctaggt acacagctct agacactgcc acacagggtc  11340
tgcaaggtct ttggttcagc taagctagga atgaaatcct gcttcagtgt atggaaataa  11400
```

```
atgtatcata gaaatgtaac ttttgtaaga caaaggtttt cctcttctat tttgtaaact   11460
caaaatattt gtacatagtt atttatttat tggagataat ctagaacaca ggcaaaatcc   11520
ttgcttatga catcacttgt acaaaataaa caaataacaa tgtgaaaaaa aaaaaaaaaa   11580
aaaaaaaaaa aaaaaaaaaa aaaggtagc agtcgacaga tgaattccac cacactggac    11640
tagtggatcc gagctcggta ccaagcttaa gtttgggctg caggaattct gatggctctc   11700
aaaattcctg cctcctttag ggataaaaga ctttaagact ttttaacaaa aagaaaaag    11760 aaaaaaaaaa ttcctgcctc ctggtgtaca cacacagaag ggttccctcc ccttgaatgt   11820
gaccaggatc tgtgaaaata acgggatagc cgctcctgtg attaggttat gtggtagact   11880
agagcaagat tctcctgctg gttttgaaga agtcagctgc catgttgtga gactgtcatg   11940
ggctagggca tgagcctta aatatctggg agcaacccct ggccagcagc cagtgagaaa    12000
acgggccctc agtcctacaa tcacaaggaa ctaaattctg ccaacaacct gaaggaactt   12060
tgaagaggat catgagtccc ttgattcagc ttgatgagcc cctgagcaga ggatacagct   12120
aacttgtact agggaagtat aaaaaacatg catgggaatg atatatatca actttaagga   12180
taattgtcat acttctggga atgaaggaa agaaatgggg ctttagttgt attatgatct    12240
ttaatttctc aaaaaaaata agatcagaag caaatatggc aaaatgttaa tactttgtg    12300 ggtacgtagg tattcagcat acccttttt ctgagttcaa aatattttat aattaaaatg    12360
aaatgcaggc caggcacagt ggctcatgcc tataatacca gcactttgcg aggccgaggt   12420
gggaggatgg cttgaggcca gaccagcctg gccaacatgg caaaacccca tctctactta   12480
aaaaaaaaaa aactatatat atatatatgt gtgtgtgtgt gtatatatat atatgtatat   12540
atatttatat atgtgtgtat atatatatat gtatatatat ttatatatgt gtgtgtatat   12600
atatatatac acacacacac atatatacat acatacatac acacacacac acacacaatt   12660
agccaggcat ggtggcgcac acctgtagtc ccagctactt gggaggctga acatgagaa    12720 ttgcttgaac ctgggaggca gagtagttag tgagctgaga tcataccact gcactccagc   12780
ctggtgacag agtgagactc tgtcttaaaa aaaataaaaa ttaaaattaa atgcaaaagg   12840
tccaagtgaa ttgaagagga aaggggtatc aaggaaggtt ttgtggaggt gacgtttgag   12900
ctgggtctta aatgacttaa acatgggata agaagggagg gaataaggac atttcaggta   12960
cgagaaataa ggagcaaaca gtggaaacaa cctaacgtct gtcaaccagt gaatggataa   13020
caaaaatgta attcagatgg tatccaactt acgatggttc aacatgagat ttttctgact   13080
ttaggataga tttatcaaag tagtaaatcc attttcaact tatgatattt tcaacttcag   13140
atgggtttat caggacacag ttgaggaaca cctgtctatc catacaattt ggcaataaaa   13200
aggaaatgag tgcagatata ctccacaaca tgaatgaacc ttgaaaacat taagtgagag   13260
aagccagata caaaaggcca catattgtat gattctattt atacaaaatg tccagaatag   13320
gcaaatctta tagacagcaa gtaggtagat gatcagtttg ctaggtgctg ggggaagggg   13380
aaatggggag tgatggctaa ggggattggg tttctttgtg gggcaatgaa aatgttttaa   13440
aattgagcgt gataatgatt gcacaatgct gcatatatat ataatctata gattatatat   13500
atataaagag aggctgttag acagtgataa gtgatatata tatatatata catagagaga   13560
gagagagaga gagagagagg ctgttagtga taagtgatca ggaaaataaa agtattgagg   13620
aggaatacga agttgacggt gtgaaaacat gagatttat ataggatggc cagggaaggc    13680
cttaatgaga aagtgactta tgagtaaaaa caagggatcc taaaccttag catgcatcag   13740
aatcactcgg aaacttgtta aagcatagct tgctgggcct catcacagat attttgattc   13800
```

```
ggtaggttct tgtctgatat taatacttttt ggtctaggga accacatttt gagaaccact   13860
gagctaaagg aagtaaaggt ttcccttagt ttactagctg gtaacactgg cccaggaggc   13920
ctttctggaa aaggtcccag tccccaaagg aagctgggga ctcgcgttca catcgtcaag   13980
gtttaccaag ttgtggcggg cctttccgtc ttggaaaaag cctcaaaatg gcagattagg   14040
gtgtccatgg ccggcggaaa gggtctttga agttgcagac caggagggaa gaagattctg   14100
ggcctccccc atgcagtgtc agctggcaac agaatgcacc ccggctgggt tggaggccct   14160
gggtactggc tcttccacac caggggccca cctaccaagg gcagcaggag catctgcacc   14220
tcctgcgcca ggcgcccttc agtgcttcca cttgagcacc tctccagaca ccagctaggg   14280
tgacagtggt acaaatacca gactcccctg gcctgctcac ctcacagggt aatgtgctgt   14340
ggagtcaggg ggacacagca accaccagat gacatggctg gccccgggga ggacgacacg   14400
cagatacggc tacttggcac ctgtgatatt ttacacactc gagaggggcc cgcaccatcc   14460
tcagccctct ccccacattc actcttagtt catgtcacct ccaccagag ggggacacag   14520
gcccacagcg atggccccac accctgcctg aggtcgccca cttcccagga ggcagtcctg   14580
ggacttccac ccgaccaggc cccagagccc accgacttaa cccctccaga ggcttgtcgt   14640
tcattacctt attcaagatg gagaccagcc tttttgcgga gaaaatgcgg gtgaaggtcc   14700
tgaaagtgca ttgacgccgt tttcggaagc catacaagtt tagctggcgg aagaagctct   14760
ttatcgaagt tgtggcaaac actttgtgtg cgacgtccct tttgagaatc tccttttcaa   14820
agagttttttg attgatcact ctacaagccc cactgtcatc ccaccagatg gacgaaaact   14880
ggttgctgct gaccagtctc cacagtttct gtggaaaggg gagggagagg agattatctt   14940
ctccctgggg cgggacgtca ccgtcagggt gcggccttct gaacgaagct tcctcggcca   15000
gaggttggaa agcgatttct tctgtcagca gcctcaagtt agggctccca gtggaccccg   15060
ggtcgtccca ggcaggggaa ggatctgctg ggtgaaggta ggtctctgac tgcaactggg   15120
gagggaaagg caccctttcc aagccatgat cctgtcctct cgaatttctt tcttcacagc   15180
gagccatact caatgatcgc ttgtcctcca tctggcaaac ttgctagtgc agtgtggcca   15240
gcagcacccc ttggcagtca tgtaaccagc cccatgacat cataaagggg ctctgactgc   15300
cggggggtgg catctccacc cccagcaagt tgtgtaataa agggccaagg cagacaagta   15360
gctgccatc tgcatgtgca cattctggtc ctcacagtca tttcaatggg aaagatgaca   15420
ctagtgcaca agagtgccga ggggccctgc cacaccgtag atgcagacct ggagcggtcc   15480
ccttgtccta gagctcctga gccaggcaca actacagcaa agccctggct caggaaggtc   15540
agagctcacc gtctgagtca tgggcccaca gaccccagca catgactgac actcggaagc   15600
acagaacaaa gggtaggacg gtgccatgg gtcaggctgt agccacgcca ccctttccac   15660
cctgtcctag ccagaggcag caatgtgctc catacagatc ctcctaacac acccacactg   15720
tcggtcccca gcacgcagat gcccgacagc cccttaggca aatggcttag ctgactgccc   15780
caccacacgc cgtcgccatg cagtccagtg gggagtcgga ggcagcctcc ttcctgcctc   15840
tcctcggcct gcacgtgtcc ccccaccagg cagagaccct tctacacccc gggtgtctgc   15900
ggtcacatcg cggtggggca tgcagctgtt ggccttcgag catgtttttgt tttccttggc   15960
cagtgtctcc agagaaacgc acgtgggttt tgtgtccagcg gtccatctct gcaacagttg   16020
ttcctttggg attggatgct aggaggtcac gggagaggtg tccatccaaa gcagtgtctg   16080
tgtcacacac tgtccccaca cacagggcca cctctgcaca gactcccccg actcgattct   16140
gggcacagag ctcagtgacc ttccagagac tgccacgaac cggtgatgcc tccacgcttg   16200
```

```
agacatcctg accgcagggc ccaaggcgca ctggctcagg gggtgacagt gaggggtctg   16260
caaacagact gctgatgctc aacccggccg ctgccgagct gtgtgacttg ggcacgtcac   16320
ttaacctctc tcggcctctg tctcctcccg gggataagag tagtagcacc tgcttcccgg   16380
ggctgtgagg atccagtggg acgtatagga actagcgagg caccggcagt tgggtcagag   16440
ctactgttgt cacttcacaa ggcattttct tcaacagcaa gtcggaaatc tcatgagcct   16500
aaggcagaat ccacctgtgg cctctggtta aacccacag dactgaaaat ccttccagcc   16500
aaggcagaat ccacctgtgg cctctggtta caacccacag gactgaaaat ccttccagcc   16560
acagcaactg gtgaatttcc tggtcaattg ccacaagtca tgagctgaac cccacttgag   16620
tttcagttca ggcagaactc tagagacgac tagggcaagc tagacagcga ctgcagagcc   16680
ttttgttgca gcgtgagcag tcctcagctg ttgacatcac tggggagcaa acgaggacca   16740
ggagcggtga aaggacagtg tctgctgcag attgtcgtag cacccaagga acactccaga   16800
aagcctccta agcagtaaca agtgtggcaa ggtgtagccc agccaacagt ggcatctgcg   16860
aggcgtcccc tccttcctcc cactaccccg tataccctgg gacctgtgca ctgaaggact   16920
cattctaaag gctgtgcccc tgcagccgcc agcctcactc actggctgcc tgtgccagct   16980
agagatttct ttcctctgag gctggctgag gaccactc cagtttcctg gcccatccag     17040
caaagaagat acacatcatg cacgtgtaaa atgaggaacc ggtttattga acagcttaag   17100
gagagcaaaa atagtggctt tagctacatt ttttacacac tgagcaggaa agtctaaacc   17160
atcccgttcc cctgtacccc aaagagaaca gggcttgctg gaggccagtg ccaagggcgg   17220
agtcgtgctc gcagcagact tgaattaacc ccatgtaggc cggcgagcag ttgcccgcgt   17280
gaaaacacca ccctcttctc ctggctgaga agatcaaagc tctttttta ccctcttttc    17340
agcaaaggac ctatttgttt tcaggcagga ggatgttaaa cttgcagcct ctgacacacg   17400
gtggaacctg cagtgcttgg agaaacggca cgcacacgtg aaaacatcat gcctactcca   17460
aagccttctt gttgctggca ggagggaagc ttgagacttt cccacgcata gtcgtgaccc   17520
gcgtggccgt ttctgctctc agcaacattc tctagtgttc cggcttcaag cagcgcttgt   17580
caggtttgaa gctagccact attctgagaa cgtcagaaaa gcatggacca tctcttgctt   17640
ggtgttgccg ttgtggcagt agcagctact acgtacctgc acgagttcca gggcagaagt   17700
ggcaatgtcc catgaaggcg tggcacccca cggggggggg ggggagtgt gccacgggcg    17760
tccacttctg cagcagaagg catgtgccta cagcacaagc ttgtaaaaaa atacttgaac   17820
agaatatgct gtacagaact aggggttaac accgcatatg aagatgctaa acatttgta    17880
taaatactct gtatacaagc atggagtcac tcccgtagaa agggctcatc cgtgaggcta   17940
tgaaaaactg ctgtcagcat gcccaaagag aaactacttc cacagtagga acagaaaaaa   18000
ggactgtgct gtgtctaaac acgtggtgca tcagagacat agttacagtt cctactgact   18060
gccccagcca cgacctggga gtgctgagga cctgggagtg ctcagcgagc tgcaggaggt   18120
cagccctgtg gagaaataca tttctaaaca atacttttga ttgggatttc agcaccgtat   18180
agacagatgt tccttctggg ggcctggcaa gcagccatct cccagtgggt ctgacgggga   18240
agaggggtac ctggagcccc tcccagacag acggtaatcc cacccctgtt ctcacactct   18300
tcctggcatc cgcatctgct ggcacacacc cccgtcacct gccacttccg cgtcccgtcg   18360
tggtgagtgg ctgataggcg ctggatgcaa acaaggcatg agatggacgt acctggagac   18420
ccagctccag tactggttct ggtctgcggg gtgaacgagg gggcagagga aggcggagag   18480
agtgcgtccc agtccactta agctctgtcc ccggaagtgg catctaatct ggcatttcga   18540
tatttaattt gggaggtggg agcacatact tcccagggct ctgggtaatg accaccctgg   18600
```

-continued

```
ccttctttcg aaacatgggt gcgattttag ggggctccgg aactgggtc tcttcggttt      18660
cttcattatc ttcgtgatgg agatcatagg aaatgtttcc atattctcgt agaaatggga      18720
agatttcaag cagaaactga cagaaatctt tgcggatacc aaaccaccct gaaaaataag      18780
aattttttat ttcacacacg aggctcaact gaccttcctg ttaactttct ttccgtaaca      18840
agaagtttca ctcctacaat gtcataacat actttatcca gactcctgag tcacaaagcc      18900
tgaacagggc ttgagtaccc aaaatgggga agaagtgcaa atgctagctc tgtggtgctt      18960
ggagtggggt tcccggaccg gcagggacag cgtccacggg gcctagttag ggatgccatt      19020
ctcgggcccc agcccagacc tccagaaact gagtcgggct agggtgggct ccagcggtcc      19080
ccttttcctg gcccttttgg gattctgctg gatgcccaaa tttgagaact actgctccag      19140
tgagtctcaa aatatctgtg gtgcgcagac tacggtgtct tccgctaatc ttctccagcc      19200
aggataaact catggatgac agtgccaccc aagaacaaga tttctgtcac cctctggaat      19260
ccgtgagggc ggtagtcatg cacgggttgg ccaggagggg gcctgaactc atggagccac      19320
cttaaagcca ctttcccagt cccactactc ctctctgtag gctactggag tgtcagctcg      19380
gtgcaagccc tccctgctcc cgggtgcggg gtaggggggca gaggcacaaa cagcaagcac      19440
agcccgggct gctgggctgc agtgaggccc tgcccccaaa cccactggct ttccgaaggg      19500
caatgctctg ggcttccgtg ccatggagcc cacagccttg ccaggaaggc accctctgca      19560
gagatcgttt tggaagtgtc tgcctcagca agcaggtgga ggggaataga gtgttagcaa      19620
ggcaagacag gcaagactcg ggtgatggca gcaaggatat gggggaggca gagcggccaa      19680
cagggaccta ggatgaatcc caggtttggg tgggagatgt ggattttcca tcaaaccctc      19740
ccgggcctgg gaagaatctg tcttgatccc cattttgcag aggagggaac gggatctctg      19800
agaggttgcc tgccgtgtct ggttctacct caaatggcag cgtgcactgc gagaaaagtc      19860
ccggtgcagg ccagcagaac accagagtta cggcatgccc ttcccttaga aggtcccaga      19920
atttcctcag ccctcacttt cccacacaag cttctaaatt ggggccctcg gggactcatc      19980
ccttcctaga cttctatccg ccaccccca cccctggtc cccccccaga cacacaccaa      20040
ggacttctga aatgctgagt acatacagtg gtttcctccc ttctgtccaa atgtggttgc      20100
catcagcgtg atcaacgaga gccaaagggg gacaaagatc gggatgcagg agaaggcgtt      20160
gtggccatcc agtttgtgaa ccagcagaat ctaaagaaag agacatagtc ccggttgatg      20220
ccagcaccga aaatgggcag aggcggaagc cagacttcat taggcagttc ctccccacca      20280
ccccacccc gcgtgagctc ccacaagagg gaacatcagc accgccagaa aaaggcagga      20340
aaccacctat ccctggggaa agctcgaaat gagcttttat gtccctcttc agagctcggc      20400
aatagcctat ccacttgaaa agttcccagt gccagcagtt ttatggcaaa ctcctccggg      20460
tgtttgttct aaggagtcaa cagctcccat tctagaattc tccacgtgac tccaatacac      20520
aaatctgaca tcccactctg ctttccccag agtggaaact ggagccatac agaggcacca      20580
tggctaaaaa ggtgcactct tctccctgcc agcccacgt gctgccccca agagaaagga      20640
aggatgctct cctttcaccg aagctccctc tcggagatgg ctgtgttctc tcccctctcc      20700
tggagtgggc tcactgtgag ctcgagggac agaggctgcc tttctagggg tgcagaatcc      20760
tgtcagggga agcgcaagct tcaggggctg aagaggcttc ccgtggaacg cttacctcaa      20820
atgtaagaag gggcacgacg atggtcatcc agctcagggc catggttatg tgtgtcctgc      20880
gctgtccgca atcacatcca tagagcgcaa gaacaagacg gaccacacaa tgtagtagag      20940
gaccaccagg cacagaaagg acatgagaat ccacagcggg acacacacaa cctgggggtg      21000
```

```
ggtgagagaa cagcaagaga agtctcttta gagcttccaa cctggcctct gatggaaggc    21060
atctttagca ccttgctgtg tctgtccagt taaggcggtc cttcctgtga gccgaataag    21120
gaccgttcca tctcccagga ctgctgggag catcgctcag gacagaaaag gtatggtatg    21180
ttcactatgg ggcctgctgc caccagggga cacacacgct cagtgagtca tcagtccctc    21240
ttcctttggg tgacagacag ccctgcacct ggctccgcag cctctactct tccagaggcc    21300
cactctccca cactctctca ggctcctcta ggttctgctg ccatcacagc ttcccgggaa    21360
atgggacaca actgtcaccc tgtgcacaca cacaagatct caccccaaca gactctcttc    21420
acaggcaaca ttcccacaac ctgctggggg tactttggca acacaaatgg gaatgggctc    21480
cccagaaagt ctggctgcct gggctcctaa ggatccctaa cctcacccct accaagttag    21540
tgaacttggc gggttgatgc tggatacagg ttgatgctgg atacgtagcg ctgccgggtc    21600
gtgaccccta aggaattatc caaactcttg ttttагatg ctttattata tcaaactctc    21660
ctttaaacaa gtgcccatc tgctgggatt tggaagcctg taatactgaa attttcatca    21720
taatggaaat tttaaaaaca gaatttgacc cacctgtttt taaaacactt tcattactta    21780
acaagaggtc taatcttggg caagtcttga aatttctctg gccttagttt cccatgtgtt    21840
aaatgaaact tgaagcagtt ggtctcttat agtctcctga ctctaacatt ctaagaatta    21900
tatttgtaca ataactcaaa aatcacataa tttaatttac catatggact ccaaaatata    21960
ttttctcatt aggctaaact tgatctgcat tttctggatg tgtccatatt cttggactac    22020
actaaaacat gataccaatg cttcctctca ccataaaccc tcacttcgct ttctacattt    22080 aagaattta tagctggaag agtccttaac agaaaatacc atctaataat taccccctcaa    22140 aatcgagaaa gtcctatctg ttcttatgct agttataaga atgaggcagc atttcacata    22200
atggttataa acactgccac aagaagattc atgatgtgtt gtttatctgt agctctcatc    22260
atactctgtc atataactat agcattaaga ttttaatgtt ctatatattc ttctaagaca    22320
gtgtttacca gagtaaggca caaaagatcc actggtttgc aagaaagatt agaacttta    22380 aattttttac ctcaccttgt ttaatctata tttttgtatg tattttgtaa catatatatt    22440
attattacca taaatcatat ataatttaaa atgcatatat tagggtaaa tgctcaggaa    22500 actttttata aattgggcat gcaaatacaa gtttgaagac tcactgttct aggtattaaa    22560
agtaaagtta taaccaagta aagcttccac cttttcatgt ctcaaagcag tttattgttg    22620
gaggtaagat ctcttagaag cctaaacagg tccaagtaca gaatgaagta aggctagccc    22680
ataacttgtg gcaagcaatt catactattt ctctcatgct gagctctcct cagtgaagca    22740
gctactatag acaactgcag cctattggta gcctatttta caggcaggaa aaaaattact    22800
ttttattcaa agtggaactc aggacatggg gagaaaatga atacaaaaaa tagggtcaat    22860
ccaaaggcac acagcaaatg agtaacacag ttatgttttt ttcccatttg tatgaggtcc    22920
cagtaaattc taagtaaact gcaaatttaa taatacacta aaaaagccat gcaattgttc    22980
aaatgaatcc cagcatggta caaggagtac agacactaga gtctaaaaaa caaaagaatg    23040
ccattattga gttttgaat tatatcaagt agttacatct ctacttaata aatgagaaaa    23100
acgaggataa gaggccattt gataaaatga aaatagccaa gaagtggtat tagagacttg    23160
aatacaggta ttcgggtcca aagttcatct gctcaaatac taactgggga aaagagggaa    23220
aaatatttat atacatatat atctgcacac aaaaataccc ccaaaagaca aatgaggcc    23280 aggcagggtg gctcacaccc gtaatcccgg tactttggga ggctgaggca ggtggatacc    23340
tgagatcagg agttggagat cagcctggtc aacatggtga aaccctgtct ctactaaaga    23400
```

```
taaaaaaatt agccaggcat ggtggcgtgc gcctgtaatc ccagctactt gggagtctga   23460
ggcaggagaa tcacttgaac tgggaagggg aggttgcagt gagccaagat cgtactactg   23520
cactccagcc tgggcagcag agtgagactc catcacaaaa ataaataaat aaataaaata   23580
caatgaaaca gaaagttcaa ataatcccat aatcttacca ccaagaaata actttcactc   23640
gttatactta ttgattttc cataataaat gtactttact gtgactatca tgaaaagaaa   23700
gttattttag aaacagagaa ctgtttcaga tcaaatctat gtagtagaac agagccatta   23760
ggtgggaaag acgagatcaa actaaatctc agaaggccta aaaggctagg tccattccag   23820
cactaaaaac tgaccagaca agtaatggct tcaacagctt ctaaatatgg acaaagcatg   23880
ctgaaaggga aggacaggtc taacagtggt atatgaaatg aacaggaggg gcaaagctca   23940
tttctcctct gaagttttcc aaagatgctg aggaggacta tagttgaca tgaccctgat   24000 atgggacaag ataatttcac agaagtttta catgttaaag ttttcttata gatactcatt   24060
caagtaagca atgaacacta aaatctaaag aaagaaaaga gctttagagt caggtctgta   24120
ttcaaattca agctctacca cttactggtt ctgtgacttt gggcaagtct tttaacctta   24180
ttaagtctta atttcctgat ttgtaaaatg gggatatcgt ctccctcaca ggattgttgt   24240
gaaactttta tgagattaat gcctttatat ttggcatagt gtaagtaaac aataactggc   24300
agcttcaaaa aaaaaagca gtagcattcc atcatttatt attggttact ctcaaaaagt   24360
ttttcaatgt actagaagat aaatattcaa ataccttaat atctccatta ttttcaggta   24420
aacagcatgc tcctgaacaa ccaatgggtc aacaaataaa ttaaaaggga aatctaaaaa   24480
catcttgata ttaaactaca tggaagcaca atataccaaa accaatggtt cacactagga   24540
gaattttaag gtacaagaaa actctttgag atttcttaaa ataatagtat gtctgaattt   24600
attgagtgat ttaccagaaa ctgttgtaag agctctactt gcattatagc acttaatcct   24660
cttaactcta tggctgctat tatcaacctc accctaatca catatgggac acagagaggt   24720
taagtaactt gcccaaggtc agagttagga agtactaagc catgctttga atcagttgtc   24780
aggctccgga actcacactt tcagccacta cataatactg ctttgctatc ttttaggaaa   24840
ctatgtgagt ctacctcaca tagactcaca taggtttgtt tttttttttt ttttaaaggc   24900
tatcttttcc cccatcaatg ttttttgaag gatcccaaat tagagtccca cagaggcaga   24960
cagcagtact tgacaaatatg gacatttaag gttaatgttg gattctactg tctttttact   25020
acatgaccta gggaacgata attaacctag actgcttcca agggttaaat aacccattta   25080
gttatactat gtaaattatc tcttagtgat tgattgaaag cacactgtta ctaattgact   25140
cggtatgaag tgctttttt tcttcccttt caagatacat acctttccag ttaaagttga   25200
gagatcatct ccaccaatta cttttatgtc ccctgttgac tggtcattct agttaaaaaa   25260
aaaaaaaact atatatatat atatctacac acacatatgt atatgtatat ccttatgtac   25320
acacacaaac ttcaaattaa atgagaacta gaagatttga gaagttagct agctaatatc   25380
catagcatta tgatattcta aatgatatga attataagaa ttaggttttcc tgaaatgaat   25440 gactagaaaa ctttcaagta gagattagta aaaattaaaa agtcctaatc ggccattact   25500
gatttgatgt ttttaagagt cctaaaaaat gggttacatc cattttaag tgggtagtat   25560 tataacagcc acccatcttc aatcacagtg atttctgaat tgtgagggaa gttattagca   25620
tgacaggtgt ctggttctgg ccctgtacga ttcccatgag tcaagcaaat tgtaagggct   25680
ggtctatatc acacccaacc ccaaggatat gtccctcaaa agtctagccc aggcccgtc   25740 atcttcagca tcatctggga aaccaggtct gattagtagt cctttaagga atacctctta   25800
```

```
ggctcccatt ttactgctat cacagaatcc aataaaaccc ttacaggaga ttcaatggga  25860
aatgctcaac acccactgta gttggtggtg acaatgacca taatttggct gtgctggatt  25920
caggacagaa aatttgggtg aaagagcagg tgaacaaaag agcttcgact tgccctagca  25980
gagagcaagc cataccatac cacaaagcca cagcaattac aacggtgcag taccagcaca  26040
gtaaatgaac aaagtagagc ccagaaacag acccagaact atatgaggat ttagtataca  26100
ataaagatgg tatttcgagt cagtagggaa agatgaatt  attcaataaa tgatgtttgg  26160
ccaactagta acccatttgg gaaaaaataa agtatggtc  cctacctcac agcatacaca  26220
aaaataaatt ccagacggat taaaatctaa atgtaaaaaa taaagccata agtggactgg  26280
aagaaaatag agaattttt  ttaacatccg tagaaagggt aaaaacccag gcatgacatg  26340
aaccaaaact gaagaggttc tgtaacaaat acccccttt  atatattggg ctccaacaat  26400
aagaacccat aggaaaatgg agaatgaaca caaatagaca atttatagaa gagaaggtta  26460
taaggtgtaa aattatatct atctgagaaa caaacactaa aacaatgtga ttctactgtt  26520
ctcccaccca tactggcaaa acttaagcct gataatatgc tgaggggaaa taagcactct  26580
tgttggtgag agtattaatt ggcatagctt cttttgaaaa tgacatagca atacctgtta  26640
aaattgcaaa catgcatgtc acttaatcca gtaatcccac ttctgggaat caatgctaca  26700
aaaacactga caagtataca aagatacatt caagagtgtt cactgggccg ggtgcggtgg  26760
cttcatgcct gtaatcccag ggaggcagag gcaagacgat cgcttgaccc caggagttca  26820
aggccagccc gagaaacaca gcaagaccct gtctctcttt tttttattta aaaaataaat  26880
gttcactgta tcagttgttc acaaaaacaa accaacatgt ccattaacag ggaaccattt  26940
aaattaatca agttcatcta cacaatgtaa taccatgcaa ctattaaaaa gcacctgata  27000
atccaaagca cactgagaca gaataatgct attaaaaaca ccaagtagtg gaacactgtg  27060
ttgcctatga caccatttt  attcaacatt taaacaaatt tgtaacagca attacatgag  27120
tagtgacaat ggcgtttatg agacttttca cttttatgtg cttctattt  tgttatgctt  27180 ctatatatac atccatttat tatggagtgt tactttcaaa aatcacaaat gggccagtat  27240
tatttggtgt tgcaaggtga gcatatgact tctgatatca acctttgcat attacttctc  27300 aattaggga  aattacagac atcccttatt ctaactaact taaaacccag catttcaaac  27360
atacagaatt gatggggaaa aaaagaaag  aagaaagaaa gaaaaggcaa caagcttcag  27420
atgacagtga ctcacatcaa attatttata aaatctgtta aatagtgcca tcttctggag  27480
atacctggta ttacagtcca actccagttg atgtctttac agagacaaga ggaataaagg  27540
aaaaaatatt caagaactga aaagtatgga gtcatggaaa aattgctgtg atccaaaggc  27600
tacggtgata ggacaagaaa caagagaact ccaagcagta agacactgct gttctattag  27660
catccaaacc tccatactcc tgtttgcccc aaggcttttt taaaaaatag agacaggatc  27720
tcactatttt gctcaggctg gtcttgaact cctggactca agctatcctc ctgcctcggc  27780
ctcctaaagt gccgagatta caggcttgag tcaccatacc tggctattta tttttcttta  27840
actctcttgc ctggcctata gccaccatgg aagctaataa agaatattaa tttaagagta  27900
atggtatagt tcactacatt ggaatacagg tataagtgcc tacattgtac atgaatggca  27960
tacatggatc aattaccca  cctgggtggc caaggaact  gcgcgaacct ccctccttgg  28020
ctgtctggaa caagcttccc actagatccc tttactgagt gcctccctca tctttaatta  28080
tggttaagtc taggataaca ggactggcaa aggtgagggg aaagcttcct ccagagttgc  28140
tctaccctct cctctaccgt cctatctcct cactcctctc agccaaggag tccaatctgt  28200
```

```
cctgaactca gagcgtcact gtcaactaca taaaattgcc agagaagctc tttgggacta    28260
caaacacata cccttaatgt ctttatttct attttgtcta cctcttcagt ctaggtgaaa    28320
aaataggaag gataataggg aagaactttg tttatgccta cttatccgcc cctaggaatt    28380
ttgaaaacct ctaggtagca ataagaactg cagcatggta tagaaaaaga ggaggaaagc    28440
tgtatagaaa tgcataataa atgggcagga aaagaactgc ttggaacaaa cagggaggtt    28500
gaactataag gagagaaagc agagaggcta atcaacaagg ctgggttccc aagagggcat    28560
gatgagacta ttactaaggt aggaattact aagggctcca tgtcccctta gtggcttagt    28620
actatgtagc ttgcttctg cagtgaactt cagacccttc ttttaggatc ctagaatgga    28680
cttttttttt ttatcggaaa acagtcattc tctcaacatt caagcaggcc caagtctac    28740 cacactcaat cacattttct cttcatatca taatctctca accattctct gtcctttaa    28800 ctgtttttct ataccctgat caaatgccaa caaaagtgag aatgttagaa tcatgtattt    28860
ttagaggtag actgtatctc agataaaaaa aaagggcaga tattccattt tccaaaatat    28920
gtatgcagaa aaaataagta tgaaaggaca tatgctcagg taacaagtta atttgtttac    28980
ttgtatttta tgaattccct aaaacctacg tcacccgccc cgttcccacg ccccgcgcca    29040
cgtcacaaac tccacccct cattatcata ttggcttcaa tccaaaataa ggtatattat    29100
tgatgatgtt aattaacatg catggatcca tatgcggtgt gaaataccgc acagatgcgt    29160
aaggagaaaa taccgcatca ggcgctcttc cgcttcctcg ctcactgact cgctgcgctc    29220
ggtcgttcgg ctgcggcgag cggtatcagc tcactcaaag gcggtaatac ggttatccac    29280
agaatcaggg gataacgcag gaaagaacat gtgagcaaaa ggccagcaaa aggccaggaa    29340
ccgtaaaaag gccgcgttgc tggcgttttt ccataggctc cgcccccctg acgagcatca    29400
caaaaatcga cgctcaagtc agaggtggcg aaacccgaca ggactataaa gataccaggc    29460
gtttccccct ggaagctccc tcgtgcgctc tcctgttccg accctgccgc ttaccggata    29520
cctgtccgcc tttctccctt cgggaagcgt ggcgctttct catagctcac gctgtaggta    29580
tctcagttcg gtgtaggtcg ttcgctccaa gctgggctgt gtgcacgaac cccccgttca    29640
gcccgaccgc tgcgccttat ccggtaacta tcgtcttgag tccaacccgg taagacacga    29700
cttatcgcca ctggcagcag ccactggtaa caggattagc agagcgaggt atgtaggcgg    29760
tgctacagag ttcttgaagt ggtggcctaa ctacggctac actagaagga cagtatttgg    29820
tatctgcgct ctgctgaagc cagttacctt cggaaaaaga gttggtagct cttgatccgg    29880
caaacaaacc accgctggta gcggtggttt ttttgtttgc aagcagcaga ttacgcgcag    29940
aaaaaaagga tctcaagaag atcctttgat cttttctacg gggtctgacg ctcagtggaa    30000
cgaaaactca cgttaaggga ttttggtcat gagattatca aaaaggatct tcacctagat    30060
ccttttaaat taaaatgaa gttttaaatc aatctaaagt atatatgagt aaacttggtc    30120
tgacagttac caatgcttaa tcagtgaggc acctatctca gcgatctgtc tatttcgttc    30180
atccatagtt gcctgactcc ccgtcgtgta gataactacg atacgggagg gcttaccatc    30240
tggccccagt gctgcaatga taccgcgaga cccacgctca ccggctccag atttatcagc    30300
aataaaccag ccagccggaa gggccgagcg cagaagtggt cctgcaactt tatccgcctc    30360
catccagtct attaattgtt gccgggaagc tagagtaagt agttcgccag ttaatagttt    30420
gcgcaacgtt gttgccattg ctgcagccat gagattatca aaaaggatct tcacctagat    30480
ccttttcacg tagaaagcca gtccgcagaa acggtgctga ccccggatga atgtcagcta    30540
ctgggctatc tggacaaggg aaaacgcaag cgcaaagaga aagcaggtag cttgcagtgg    30600
```

```
gcttacatgg cgatagctag actgggcggt tttatggaca gcaagcgaac cggaattgcc  30660
agctggggcg ccctctggta aggttgggaa gccctgcaaa gtaaactgga tggctttctt  30720
gccgccaagg atctgatggc gcaggggatc aagctctgat caagagacag gatgaggatc  30780
gtttcgcatg attgaacaag atggattgca cgcaggttct ccggccgctt gggtggagag  30840
gctattcggc tatgactggg cacaacagac aatcggctgc tctgatgccg ccgtgttccg  30900
gctgtcagcg caggggcgcc cggttctttt tgtcaagacc gacctgtccg gtgccctgaa  30960
tgaactgcaa gacgaggcag cgcggctatc gtggctggcc acgacgggcg ttccttgcgc  31020
agctgtgctc gacgttgtca ctgaagcggg aagggactgg ctgctattgg gcgaagtgcc  31080
ggggcaggat ctcctgtcat ctcaccttgc tcctgccgag aaagtatcca tcatggctga  31140
tgcaatgcgg cggctgcata cgcttgatcc ggctacctgc ccattcgacc accaagcgaa  31200
acatcgcatc gagcgagcac gtactcggat ggaagccggt cttgtcgatc aggatgatct  31260
ggacgaagag catcagggc tcgcgccagc cgaactgttc gccaggctca aggcgagcat  31320
gcccgacggc gaggatctcg tcgtgaccca tggcgatgcc tgcttgccga atatcatggt  31380
ggaaaatggc cgcttttctg gattcatcga ctgtggccgg ctgggtgtgg cggaccgcta  31440
tcaggacata gcgttggcta cccgtgatat tgctgaagag cttggcggcg aatgggctga  31500
ccgcttcctc gtgctttacg gtatcgccgc tcccgattcg cagcgcatcg ccttctatcg  31560
ccttcttgac gagttcttct gaattttgtt aaaattttg ttaaatcagc tcatttttta  31620
accaataggc cgaaatcggc aaaatcccctt ataaatcaaa agaatagacc gagataggt  31680
tgagtgttgt tccagtttgg aacaagagtc cactattaaa gaacgtggac tccaacgtca  31740
aagggcgaaa aaccgtctat cagggcgatg gcccactacg tgaaccatca ccctaatcaa  31800
gttttttggg gtcgaggtgc cgtaaagcac taaatcggaa ccctaaaggg agcccccgat  31860
ttagagcttg acggggaaag ccggcgaacg tggcgagaaa ggaagggaag aaagcgaaag  31920
gagcgggcgc tagggcgctg gcaagtgtag cggtcacgct gcgcgtaacc accacacccg  31980
ccgcgcttaa tgcgccgcta cagggcgcgt ccattcgcca ttcaggatcg aattaattct  32040
taattaacat catcaataat ataccttatt ttggattgaa gccaatatga taatgagggg  32100
gtggagtttg tgacgtggcg cggggcgtgg gaacggggcg ggtgacgtag tagtgtggcg  32160
gaagtgtgat gttgcaagtg tggcggaaca catgtaagcg acggatgtgg caaaagtgac  32220
gttttttggtg tgcgccggtg tacacaggaa gtgacaattt tcgcgcggtt ttaggcggat  32280
gttgtagtaa atttgggcgt aaccgagtaa gatttggcca ttttcgcggg aaaactgaat  32340
aagaggaagt gaaatctgaa taattttgtg ttactcatag cgcgtaatac tg         32392
```

<210> SEQ ID NO 25
<211> LENGTH: 32339
<212> TYPE: DNA
<213> ORGANISM: Artificial Sequence
<220> FEATURE:
<223> OTHER INFORMATION: Description of Artificial Sequence: Synthetic PhIDO-final
<220> FEATURE:
<221> NAME/KEY: misc_feature
<222> LOCATION: (1)..(32339)
<223> OTHER INFORMATION: n= a, c, g, t, unknown or other

<400> SEQUENCE: 25

```
gtacggaagc ccggaaggag gggcaggggg cggtggctca ggtttctccg ggcggcggcg      60
gcggcggcgg cggcgacggc gacgcgcacg gcagcgggga cggcagcagt agcgggagca     120
gcagcgtgga cgcggctggc gctggcgcca tgaacccgct gtaaggcgca ggctgtgcag     180
```

```
cacggggtgc gggggaggag gaggaggacg ccgcggtgaa gttctccgcc atgaacctga    240
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660
cacccctacc cccaccccag ctgtttcctc cagttcctcg cagtccttgg ggttttcctt    720
gggtttatgc ccatccctct cttgtttgct tctttgttga acggatacct gaaacactgt    780
tgaatccttg gagtcagtgt cggggtatgg caatacctta tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgccgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gcccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg cggtctcag catggggtga    1380 agaagggctt gtacacttaa gatgccttac agtactgtgc agtgctgtac tgcggggggcc    1440 aactctgggg acctatgcct tggctgcttg ttgaggatga aaggaagttt taggggagta    1500
tttgtatgtt gagggtgcag tctccctagg gatggtgaca ttttaacttg tgagtcattg    1560
tgactttgta tgtgcccctta ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagcccctt ttccccccaa aaaaattagt    2100
atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccctga tgctactgct ttgctccctg cctctatttt    2520
tgaaccaatt caacatctcc ctcctacccc aggaccttgt cacacactgt tctctttacc    2580
```

```
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gcttttagt    3360 tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt ggggagttg ctggttcaga gaaggccctt    3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
```

```
tgcacatcca ggcacagtac ctttccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggagggc     5280 tggcccctt   cagtatctca gaagggacaa agtacacaaa ggcatgggt catgatagtg    5340 cctggtatgt tcaggtagtg aagaggtcca tgtggtatga gcactgcaga tgatatgtgt    5400
cgtatgaatt aaaaatacat agttactgca aatagttttt acaggttatt gttttaaga    5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca acgggccct ctagacgcgt tgacattgat tattgactag ttattaatag    5640
taatcaatta cggggtcatt agttcatagc ccatgtatc atatggagtt ccgcgttaca    5700
taacttacgg taaatggccc gcctggctga ccgcccaacg acccccgccc attgacgtca    5760
ataatgacgt atgttcccat agtaacgcca atagggactt tccattgacg tcaatgggtg    5820
gagtatttac ggtaaactgc ccacttggca gtacatcaag tgtatcatat gccaagtacg    5880 ccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggattttcc    6060 aagtctccac cccattgacg tcaatgggag tttgttttgg caccaaaatc aacgggactt    6120
tccaaaatgt cgtaacaact ccgccccatt gacgcaaatg gcggtaggc gtgtacggtg    6180 ggaggtctat ataagcagag ctctctggct aactagagaa cccctgctta ctggcttatc    6240
gagatatctg cagaattcat ctgtcgactg ctaccggcag cgcgcagcgg caagaagtgt    6300
ctgggctggg acggacagga gaggctgtcg ccatcggcgt cctgtgcccc tctgctccgg    6360 cacgccctg tcgcagtgcc cgcgctttcc ccggcgcctg cacgcggcgc gcctgggtaa    6420
catgcttggg gtcctggtcc ttggcgcgct ggccctggcc ggccgcgtta agatacattg    6480
atgagtttgg acaaaccaca actagaatgc agtgaaaaaa atgctttatt tgtgaaattt    6540
gtgatgctat tgctttattt gtaaccatta taagctgcaa taaacaagtt aacaacaaca    6600
attgcattca tttatgtttt caggttcagg gggaggtgtg ggaggttttt taaagcaagt    6660
aaaacctcta caaatgtggt atggctgatt atgatcagtt atctagatcc ggtggatcgg    6720
atatcttatc tagaagctta ggctcgagtg ctcttgttgg gttacattaa ccttccttca    6780
aaagggattt ctcagttgta cttcttacag tcttcaggaa attcattaaa tcagtgcctc    6840
cagttccttt ggcttccagt tttgaagggt cttcagaggt cttattctcc tttggctgct    6900
ggcttgcagg aatcaggatg tacttagtca cgatttgcag atggtagctc ctcagggaga    6960
ccagagcttt cacacaggcg tcataagctt cccgcaggcc agcatcacct tttgaaagga    7020
caaactcacg gactgaggga tttgactcta atgagcacag aagttcctg tgagctggtg     7080 gcatatatct tctcatgtcc tggaggaact gagcagcatg tcctccacca gcagtctgct    7140
ggatgcccag caggacgtca aagcactgaa agacgctgct ttggcctgca ctgccccctg    7200
caaactcctt tgggtcttcc cagaacccctt catacaccag accgtctgat agctgggggt    7260
tgcctttcca gccagacaaa tatatgcgaa gaacactgaa aaatgctttt gggttcacat    7320
gatcgtggat ttggtgaaac acttgaaggg cttctccaa gcaagaagct atttccaaca    7380
```

```
gcgcctttag caaagtgtcc cgttcttgca tttgcattgc cttgaataca gtaggaatta   7440
ctttgattgc agaagcagct gctatttcca ccaatagaga gaccaggaag aatcctttac   7500
tgcagtctcc atcacgaaat gagaacaaaa cgtccatgtt ctcataagtc aggggcttat   7560
taggatcctt tttcttccag tttgccaaga cacagtctgc ataaaccaaa ataggaggca   7620
gttccagttt cttggagagt tggcagtaag gaacagcaat atttcttggc aagaccttac   7680
ggacatctcc atgacctttg ccccacacat atgccatggt gatgcatccc agaactagac   7740
gtgcaaggcg ctgtgacttg tggtctgtga gatgatcaat gctgagcatg tttaacttct   7800
caactctttc tcgaagctgg ccagactcta tgagatcagg cagatgttta gcaatgaaca   7860
tccagtcatt ataaaaatca ggtagatttt cctgtggatt tggcagagca aagcccactt   7920
cttcatcaat atggtactct ttactgattg tccaggagtt ttccatagcg tgtgccattc   7980
ttgtagtctg ctcctctgga gatctctagc ggatctgacg gttcactaaa ccagctctgc   8040
ttatatagac ctcccaccgt acacgcctac cgcccatttg cgtcaatggg gcggagttgt   8100
tacgacattt tggaaagtcc cgttgatttt ggtgccaaaa caaactccca ttgacgtcaa   8160
tggggtggag acttggaaat ccccgtgagt caaaccgcta ccacgcccca ttgatgtact   8220
gccaaaaccg catcaccatg gtaatagcga tgactaatac gtagatgtac tgccaagtag   8280
gaaagtccca taaggtcatg tactgggcat aatgccaggc gggccattta ccgtcattga   8340
cgtcaatagg gggcgtactt ggcatatgat acacttgatg tactgccaag tgggcagttt   8400
accgtaaata ctccacccat tgacgtcaat ggaaagtccc tattggcgtt actatgggaa   8460
catacgtcat tattgacgtc aatgggcggg ggtcgttggg cggtcagcca ggcgggccat   8520
ttaccgtaag ttatgtaacg cggaactcca tatatgggct atgaactaat gaccccgtaa   8580
ttgattacta ttannntaag ggtgggaaag aatatataag gtgggggtct tatgtagttt   8640
tgtatctgtt ttgcagcagc cgccgccgcc atgagcacca actcgtttga tggaagcatt   8700
gtgagctcat atttgacaac gcgcatgccc ccatgggccg gggtgcgtca gaatgtgatg   8760
ggctccagca ttgatggtcg ccccgtcctg cccgcaaact ctactacctt gacctacgac   8820
ctgcaggcag acgggcgctc ctgcaccgca tccgcgacgc agtcctgcaa cgacctctgc   8880
gagcacttct gcgttcccaa ccccgaccag ccgggctcct actcgtgcat gtgcgagacc   8940
ggctaccggc tggcggccga ccaacaccgg tgcgaggacg tggatgactg catactggag   9000
cccagtccgt gtccgcagcg ctgtgtcaac acacagggtg gcttcgagtg ccactgctac   9060
cctaactacg acctggtgga cggcgagtgt gtggagcccg tggacccgtg cttcagagcc   9120
aactgcgagt accagtgcca gcccctgaac caaactagct acctctgcgt ctgcgccgag   9180
ggcttcgcgc ccattcccca cgagccgcac aggtgccaga tgttttgcaa ccagactgcc   9240
tgtccagccg actgcgaccc caacacccag gctagctgtg agtgccctga aggctacatc   9300
ctggacgacg gtttcatctg cacggacatc gacgagtgcg aaaacggcgg cttctgctcc   9360
ggggtgtgcc acaacctccc cggtaccttc gagtgcatct gcgggcccga ctcggccctt   9420
gcccgccaca ttggcaccga ctgtgactcc ggcaaggtgg acgtggcga cagcggctct   9480
ggcgagcccc cgcccagccc gacgcccggc tccaccttga ctcctccggc cgtggggctc   9540
gtgcattcgg gcttgctcat aggcatctcc atcgcgagcc tgtgcctggt ggtggcgctt   9600
ttggcgctcc tctgccacct gcgcaagaag cagggcgccg ccaggcgcaa gatggagtac   9660
aagtgcgcg cccttccaa ggaggtagtg ctgcagcacg tgcggaccga gcggacgccg   9720
cagagactct gagcggcctc cgtccaggag cctggctccg tccaggagcc tgtgcctcct   9780
```

```
cacccccagc tttgctacca aagcaccttta gctggcatta cagctggaga agaccctccc    9840
cgcaccccc  aagctgtttt cttctattcc atggctaact ggcgaggggg tgattagagg    9900
gaggagaatg agcctcggcc tcttccgtga cgtcactgga ccactgggca atgatggcaa    9960
ttttgtaacg aagacacaga ctgcgatttg tcccaggtcc tcactaccgg gcgcaggagg   10020
gtgagcgtta ttggtcggca gccttctggg cagaccttga cctcgtgggc tagggatgac   10080
taaaatattt attttttta agtatttagg tttttgtttg tttcctttgt tcttacctgt   10140
atgtctccag tatccacttt gcacagctct ccggtctctc tctctctaca aactcccact   10200
tgtcatgtga caggtaaact atcttggtga atttttttt cctagccctc tcacatttat    10260
gaagcaagcc ccacttattc cccattcttc ctagttttct cctcccagga actgggccaa   10320
ctcacctgag tcaccctacc tgtgcctgac cctacttctt ttgctcttag ctgtctgctc   10380
agacagaacc cctacatgaa acagaaacaa aaacactaaa aataaaaatg gccatttgct   10440
ttttcaccag atttgctaat ttatcctgaa atttcagatt cccagagcaa ataaatttta   10500
aacaaaggtt gagatgtaaa aggtattaaa ttgatgttgc tggactgtca tagaaattac   10560
acccaaagag gtatttatct ttacttttaa acagtgagcc tgaattttgt tgctgttttg   10620
atttgtactg aaaaatggta attgttgcta atcttcttat gcaatttcct ttttgttat    10680
tattacttat ttttgacagt gttgaaaatg ttcagaaggt tgctctagat tgagagaaga   10740
gacaaacacc tcccaggaga cagttcaaga aagcttcaaa ctgcatgatt catgccaatt   10800
agcaattgac tgtcactgtt ccttgtcact ggtagaccaa aataaaacca gctctactgg   10860
tcttgtggaa ttgggagctt gggaatggat cctggaggat gcccaattag ggcctagcct   10920
taatcaggtc ctcagagaat ttctaccatt tcagagaggc cttttggaat gtggcccctg   10980
aacaagaatt ggaagctgcc ctgcccatgg gagctggtta gaaatgcaga atcctaggct   11040
ccaccccatc cagttcatga gaatctatat ttaacaagat ctgcagggggg tgtgtctgct   11100
cagtaatttg aggacaacca ttccagactg cttccaattt tctggaatac atgaaatata   11160
gatcagttat aagtagcagg ccaagtcagg cccttatttt caagaaactg aggaattttc   11220
tttgtgtagc tttgctcttt ggtagaaaag gctaggtaca cagctctaga cactgccaca   11280
cagggtctgc aaggtctttg gttcagctaa gctaggaatg aaatcctgct tcagtgtatg   11340
gaaataaatg tatcatagaa atgtaacttt tgtaagacaa aggttttcct cttctatttt   11400
gtaaactcaa aatatttgta catagttatt tatttattgg agataatcta gaacacaggc   11460
aaaatccttg cttatgacat cacttgtaca aaataaacaa ataacaatgt gaaaaaaaaa   11520
aaaaaaaaaa aaaaaaaaaa aaaaaaaaaa aggtagcagt cgacagatga attccaccac   11580
actggactag tggatccgag ctcggtacca agcttaagtt tgggctgcag gaattctgat   11640
ggctctcaaa attcctgcct cctttaggga taaaagactt taagactttt taacaaaaaa   11700
gaaaagaaa  aaaaaaattc ctgcctcctg gtgtacacac acagaagggt tccctcccct   11760
tgaatgtgac caggatctgt gaaaataacg ggatagccgc tcctgtgatt aggttatgtg   11820
gtagactaga gcaagattct cctgctggtt ttgaagaagt cagctgccat gttgtgagac   11880
tgtcatgggc tagggcatga gccttttaaat atctgggagc aaccctggc  cagcagccag   11940
tgagaaaacg ggccctcagt cctacaatca caaggaacta aattctgcca acaacctgaa   12000
ggaactttga agaggatcat gagtcccttg attcagcttg atgagcccct gagcagagga   12060
tacagctaac ttgtactagg gaagtataaa aaacatgcat gggaatgata tatatcaact   12120
ttaaggataa ttgtcatact tctgggaatg aagggaaaga aatgggcctt tagttgtatt   12180
```

```
atgatcttta atttctcaaa aaaaataaga tcagaagcaa atatggcaaa atgttaatac   12240
ttttgtgggt acgtaggtat tcagcatacc cttttttctg agttcaaaat attttataat   12300
taaaatgaaa tgcaggccag gcacagtggc tcatgcctat aataccagca ctttgcgagg   12360
ccgaggtggg aggatggctt gaggccagac cagcctggcc aacatggcaa accccatct   12420 ctacttaaaa aaaaaaaaac tatatatata tatgtgtg tgtgtgtgta tatatatata   12480
tgtatatata tttatatatg tgtgtatata tatatatgta tatatattta tatatgtgtg   12540
tgtatatata tatatacaca cacacacata tatacataca tacatacaca cacacacaca   12600
cacaattagc caggcatggt ggcgcacacc tgtagtccca gctacttggg aggctgagac   12660
atgagaattg cttgaacctg ggaggcagag tagttagtga gctgagatca taccactgca   12720
ctccagcctg gtgacagagt gagactctgt cttaaaaaaa ataaaaatta aaattaaatg   12780
caaaaggtcc aagtgaattg aagaggaaag gggtatcaag gaaggttttg tggaggtgac   12840
gtttgagctg ggtcttaaat gacttaaaca tgggataaga agggagggaa taaggacatt   12900
tcaggtacga gaataagga gcaaacagtg gaaacaacct aacgtctgtc aaccagtgaa   12960
tggataacaa aaatgtaatt cagatggtat ccaacttacg atggttcaac atgagatttt   13020
tctgacttta ggatagattt atcaaagtag taaatccatt ttcaacttat gatattttca   13080
acttcagatg ggtttatcag gacacagttg aggaacacct gtctatccat acaatttggc   13140
aataaaaagg aaatgagtgc agatatactc cacaacatga atgaaccttg aaaacattaa   13200
gtgagagaag ccagatacaa aaggccacat attgtatgat tctatttata caaaatgtcc   13260
agaataggca aatcttatag acagcaagta ggtagatgat cagtttgcta ggtgctgggg   13320 gaagggaaa tggggagtga tggctaaggg gattgggttt ctttgtgggg caatgaaaat   13380
gttttaaaat tgagcgtgat aatgattgca caatgctgca tatatatata atctatagat   13440
tatatatata taaagagagg ctgttagaca gtgataagtg atatatatat atatatacat   13500
agagagagag agagagagag agagaggctg ttagtgataa gtgatcagga aaataaaagt   13560
attgaggagg aatacgaagt tgacggtgtg aaaacatgag attttatata ggatggccag   13620
ggaaggcctt aatgagaaag tgacttatga gtaaaaacaa gggatcctaa accttagcat   13680
gcatcagaat cactcggaaa cttgttaaag catagcttgc tgggcctcat cacagatatt   13740
ttgattcggt aggttcttgt ctgatattaa tacttttggt ctagggaacc acattttgag   13800
aaccactgag ctaaaggaag taaaggtttc ccttagttta ctagctggta acactggccc   13860
aggaggcctt tctggaaaag gtcccagtcc ccaaaggaag ctggggactc gcgttcacat   13920
cgtcaaggtt taccaagttg tggcgggcct ttccgtcttg gaaaaagcct caaaatggca   13980
gattagggtg tccatggccg gcggaaaggg tctttgaagt tgcagaccag gagggaagaa   14040
gattctgggc ctcccccatg cagtgtcagc tggcaacaga atgcaccccg gctgggttgg   14100
aggccctggg tactggctct tccacaccag gggcccacct accaagggca gcaggagcat   14160
ctgcacctcc tgcgccaggc gcccttcagt gcttccactt gagcacctct ccagacacca   14220
gctagggtga cagtggtaca aataccagac tcccctggcc tgctcacctc acagggtaat   14280
gtgctgtgga gtcagggga cacagcaacc accagatgac atggctggcc ccggggagga   14340
cgacacgcag atacggctac ttggcacctg tgatatttta cacactcgag aggggcccgc   14400
accatcctca gccctctccc cacattcact cttagttcat gtcacctcca cccagagggg   14460
gacacaggcc cacagcgatg gccccacacc ctgcctgagg tcgcccactt cccaggaggc   14520
agtcctggga cttccacccg accaggcccc agagcccacc gacttaaccc ctccagaggc   14580
```

```
ttgtcgttca ttaccttatt caagatggag accagccttt ttgcggagaa aatgcgggtg   14640
aaggtcctga aagtgcattg acgccgtttt cggaagccat acaagtttag ctggcggaag   14700
aagctcttta tcgaagttgt ggcaaacact ttgtgtgcga cgtccctttt gagaatctcc   14760 tttttcaaaga gttttttgatt gatcactcta caagccccac tgtcatccca ccagatggac   14820
gaaaactggt tgctgctgac cagtctccac agtttctgtg aaaggggag ggagaggaga   14880 ttatcttctc cctggggcgg gacgtcaccg tcagggtgcg gccttctgaa cgaagcttcc   14940
tcggccagag gttggaaagc gatttcttct gtcagcagcc tcaagttagg gctcccagtg   15000
gaccccgggt cgtcccaggc aggggaagga tctgctgggt gaaggtaggt ctctgactgc   15060
aactggggag ggaaaggcac cctttccaag ccatgatcct gtcctctcga atttcttttct   15120 tcacagcgag ccatactcaa tgatcgcttg tcctccatct ggcaaacttg ctagtgcagt   15180
gtggccagca gcacccccttg gcagtcatgt aaccagcccc atgacatcat aaaggggctc   15240
tgactgccgg ggggtggcat ctccacccc agcaagttgt gtaataaagg gccaaggcag   15300
acaagtagct gcccatctgc atgtgcacat tctggtcctc acagtcattt caatgggaaa   15360
gatgacacta gtgcacaaga gtgccgaggg gccctgccac accgtagatg cagacctgga   15420
gcggtcccct tgtcctagag ctcctgagcc aggcacaact acagcaaagc cctggctcag   15480
gaaggtcaga gctcaccgtc tgagtcatgg gcccacagac cccagcacat gactgacact   15540
cggaagcaca gaacaaaggg taggacggtg cccatgggtc aggctgtagc cacgccaccc   15600 tttccacccct gtcctagcca gaggcagcaa tgtgctccat acagatcctc ctaacacacc   15660
cacactgtcg gtccccagca cgcagatgcc cgacagcccc ttaggcaaat ggcttagctg   15720
actgccccac cacacgccgt cgccatgcag tccagtgggg agtcggaggc agcctccttc   15780
ctgcctctcc tcggcctgca cgtgtccccc caccaggcag agaccttct acaccccggg   15840 tgtctgcgt cacatcgcgg tggggcatgc agctgttggc cttcgagcat gtttttgtttt   15900 ccttggccag tgtctccaga gaaacgcacg tgggtttgtg tccagcggtc catctctgca   15960
acagttgttc ctttgggatt ggatgctagg aggtcacggg agaggtgtcc atccaaagca   16020
gtgtctgtgt cacacactgt ccccacacac agggccacct ctgcacagac tcccccgact   16080
cgattctggg cacagagctc agtgaccttc cagagactgc cacgaaccgg tgatgcctcc   16140
acgcttgaga catcctgacc gcagggccca aggcgcactg gctcagggg tgacagtgag   16200 gggtctgcaa acagactgct gatgctcaac ccggccgctg ccgagctgtg tgacttgggc   16260
acgtcactta acctctctcg gcctctgtct cctcccgggg ataagagtag tagcacctgc   16320
ttcccggggc tgtgaggatc cagtgggacg tataggaact agcgaggcac cggcagttgg   16380
gtcagagcta ctgttgtcac ttcacaaggc attttcttca acagcaagtc ggaaatctca   16440
tgagcctaag gcagaatcca cctgtggcct ctggttacaa cccacaggac tgaaaatcct   16500
tccagccaca gcaactggtg aatttcctgg tcaattgcca caagtcatga gctgaacccc   16560
acttgagttt cagttcaggc agaactctag agacgactag ggcaagctag acagcgactg   16620
cagagccttt tgttgcagcg tgagcagtcc tcagctgttg acatcactgg ggagcaaacg   16680
aggaccagga gcggtgaaag gacagtgtct gctgcagatt gtcgtagcac ccaaggaaca   16740
ctccagaaag cctcctaagc agtaacaagt gtggcaaggt gtagcccagc caacagtggc   16800
atctgcgagg cgtcccctcc ttcctcccac taccccgtat accctgggac ctgtgcactg   16860
aaggactcat tctaaaggct gtgccctgc agccgccagc ctcactcact ggctgcctgt   16920
gccagctaga gatttctttc ctctgaggct ggctgagagg accactccag tttcctggcc   16980
```

```
catccagcaa agaagataca catcatgcac gtgtaaaatg aggaaccggt ttattgaaca      17040
gcttaaggag agcaaaaata gtggctttag ctacattttt tacacactga gcaggaaagt      17100
ctaaaccatc ccgttcccct gtaccccaaa gagaacaggg cttgctggag gccagtgcca      17160
agggcggagt cgtgctcgca gcagacttga attaacccca tgtaggccgg cgagcagttg      17220
cccgcgtgaa acaccaccc tcttctcctg gctgagaaga tcaaagctct ttttttaccc       17280
tcttttcagc aaaggaccta tttgttttca ggcaggagga tgttaaactt gcagcctctg      17340
acacacggtg gaacctgcag tgcttggaga acggcacgc acacgtgaaa acatcatgcc       17400
tactccaaag ccttcttgtt gctggcagga gggaagcttg agactttccc acgcatagtc      17460
gtgacccgcg tggccgtttc tgctctcagc aacattctct agtgttccgg cttcaagcag      17520
cgcttgtcag gtttgaagct agccactatt ctgagaacgt cagaaaagca tggaccatct      17580
cttgcttggt gttgccgttg tggcagtagc agctactacg tacctgcacg agttccaggg      17640
cagaagtggc aatgtcccat gaaggcgtgg caccccacgg gggggggggg ggagtgtgcc      17700
acgggcgtcc acttctgcag cagaaggcat gtgcctacag cacaagcttg taaaaaaata      17760
cttgaacaga atatgctgta cagaactagg ggttaacacc gcatatgaag atgctaaaac      17820
atttgtataa atactctgta tacaagcatg gagtcactcc cgtagaaagg gctcatccgt      17880
gaggctatga aaaactgctg tcagcatgcc caaagagaaa ctacttccac agtaggaaca      17940
gaaaaaagga ctgtgctgtg tctaaacacg tggtgcatca gagacatagt tacagttcct      18000
actgactgcc ccagccacga cctgggagtg ctgaggacct gggagtgctc agcgagctgc      18060
aggaggtcag ccctgtggag aaatacattt ctaaacaata cttttgattg ggatttcagc      18120
accgtataga cagatgttcc ttctgggggc ctggcaagca gccatctccc agtgggtctg      18180
acggggaaga ggggtacctg gagccctcc cagacagacg gtaatcccac ccctgttctc       18240
acactcttcc tggcatccgc atctgctggc acacacccc gtcacctgcc acttccgcgt       18300
cccgtcgtgg tgagtggctg ataggcgctg gatgcaaaca aggcatgaga tggacgtacc      18360
tggagaccca gctccagtac tggttctggt ctgcggggtg aacgaggggg cagaggaagg      18420
cggagagagt gcgtcccagt ccacttaagc tctgtccccg gaagtggcat ctaatctggc      18480
atttcgatat ttaatttggg aggtgggagc acatacttcc cagggctctg ggtaatgacc      18540
accctggcct tctttcgaaa catgggtgcg attttagggg gctccggaac tggggtctct      18600
tcggtttctt cattatcttc gtgatggaga tcataggaaa tgtttccata ttctcgtaga      18660
aatgggaaga tttcaagcag aaactgacag aaatctttgc ggataccaaa ccaccctgaa      18720
aaataagaat ttttattc acacacgagg ctcaactgac cttcctgtta actttctttc        18780
cgtaacaaga agtttcactc ctacaatgtc ataacatact ttatccagac tcctgagtca      18840
caaagcctga acagggcttg agtacccaaa atggggaaga agtgcaaatg ctagctctgt      18900
ggtgcttgga gtgggttcc cggaccggca gggacagcgt ccacggggcc tagttaggga      18960
tgccattctc gggccccagc ccagacctcc agaaactgag tcgggctagg gtgggctcca      19020
gcggtcccct tttcctggcc cttttgggat tctgctggat gcccaaattt gagaactact      19080
gctccagtga gtctcaaaat atctgtggtg cgcagactac ggtgtcttcc gctaatcttc      19140
tccagccagg ataaactcat ggatgacagt gccacccaag aacaagattt ctgtcaccct      19200
ctggaatccg tgggcggt agtcatgcac gggttggcca ggaggggcc tgaactcatg        19260 gagccacctt aaagccactt tcccagtccc actactcctc tctgtaggct actggagtgt      19320
cagctcggtg caagccctcc ctgctcccgg gtgcggggta gggggcagag gcacaaacag      19380
```

-continued

```
caagcacagc ccgggctgct gggctgcagt gaggccctgc ccccaaaccc actggctttc    19440
cgaagggcaa tgctctgggc ttccgtgcca tggagcccac agccttgcca ggaaggcacc    19500
ctctgcagag atcgttttgg aagtgtctgc ctcagcaagc aggtggaggg gaatagagtg    19560
ttagcaaggc aagacaggca agactcgggt gatggcagca aggatatggg ggaggcagag    19620
cggccaacag ggacctagga tgaatcccag gtttgggtgg gagatgtgga ttttccatca    19680
aaccctcccg ggcctgggaa gaatctgtct tgatccccat tttgcagagg agggaacggg    19740
atctctgaga ggttgcctgc cgtgtctggt tctacctcaa atggcagcgt gcactgcgag    19800
aaaagtcccg gtgcaggcca gcagaacacc agagttacgg catgcccttc ccttagaagg    19860
tcccagaatt tcctcagccc tcactttccc acacaagctt ctaaattggg gccctcgggg    19920
actcatccct tcctagactt ctatccgcca ccccccaccc cctggtcccc cccagacac     19980
acaccaagga cttctgaaat gctgagtaca tacagtggtt tcctcccttc tgtccaaatg    20040
tggttgccat cagcgtgatc aacgagagcc aaagggggac aaagatcggg atgcaggaga    20100
aggcgttgtg gccatccagt ttgtgaacca gcagaatcta agaaagaga catagtcccg     20160
gttgatgcca gcaccgaaaa tgggcagagg cggaagccag acttcattag gcagttcctc    20220
cccaccaccc caccccgcg tgagctccca aagagggaa catcagcacc gccagaaaaa      20280
ggcaggaaac cacctatccc tggggaaagc tcgaaatgag cttttatgtc cctcttcaga    20340
gctcggcaat agcctatcca cttgaaaagt tcccagtgcc agcagtttta tggcaaactc    20400
ctccgggtgt ttgttctaag gagtcaacag ctcccattct agaattctcc acgtgactcc    20460
aatacacaaa tctgacatcc cactctgctt tccccagagt ggaaactgga gccatacaga    20520
ggcaccatgg ctaaaaaggt gcactcttct ccctgccagc cccacgtgct gcccccaaga    20580
gaaaggaagg atgctctcct ttcaccgaag ctccctctcg gagatggctg tgttctctcc    20640
cctctcctgg agtgggctca ctgtgagctc gagggacaga ggctgccttt ctaggggtgc    20700
agaatcctgt caggggaagc gcaagcttca ggggctgaag aggcttcccg tggaacgctt    20760
acctcaaatg taagaagggg cacgacgatg gtcatccagc tcagggccat ggttatgtgt    20820
gtcctgcgct gtccgcaatc acatccatag agcgcaagaa caagacggac cacacaatgt    20880
agtagaggac caccaggcac agaaaggaca tgagaatcca cagcgggaca cacacaacct    20940
gggggtgggt gagagaacag caagagaagt ctctttagag cttccaacct ggcctctgat    21000
ggaaggcatc tttagcacct tgctgtgtct gtccagttaa ggcggtcctt cctgtgagcc    21060
gaataaggac cgttccatct cccaggactg ctgggagcat cgctcaggac agaaaaggta    21120
tggtatgttc actatggggc ctgctgccac caggggacac acacgctcag tgagtcatca    21180
gtccctcttc ctttgggtga cagacagccc tgcacctggc tccgcagcct ctactcttcc    21240
agaggcccac tctcccacac tctctcaggc cctctaggt tctgctgcca tcacagcttc      21300
ccgggaaatg ggacacaact gtcaccctgt gcacacacac aagatctcac cccaacagac    21360
tctcttcaca gcaacattc ccacaacctg ctggggtac tttggcaaca caatgggaa       21420
tgggctcccc agaaagtctg gctgcctggg ctcctaagga tccctaacct caccccctacc  21480
aagttagtga acttgcggg ttgatgctgg atacaggttg atgctggata cgtagcgctg     21540
ccgggtcgtg acccctaagg aattatccaa actcttgttt ttagatgctt tattatatca   21600
aactctcctt taaacaagtg gcccatctgc tgggatttgg aagcctgtaa tactgaaatt    21660
ttcatcataa tggaaatttt aaaaacagaa tttgacccac ctgttttttaa aacactttca    21720
ttacttaaca agaggtctaa tcttgggcaa gtcttgaaat ttctctggcc ttagttttccc   21780
```

```
atgtgttaaa tgaaacttga agcagttggt ctcttatagt ctcctgactc taacattcta   21840
agaattatat ttgtacaata actcaaaaat cacataattt aatttaccat atggactcca   21900
aaatatattt tctcattagg ctaaacttga tctgcatttt ctggatgtgt ccatattctt   21960
ggactacact aaaacatgat accaatgctt cctctcacca taaaccctca cttcgctttc   22020
tacatttaag aattttatag ctggaagagt ccttaacaga aaataccatc taataattac   22080
ccctcaaaat cgagaaagtc ctatctgttc ttatgctagt tataagaatg aggcagcatt   22140
tcacataatg gttataaaca ctgccacaag aagattcatg atgtgttgtt tatctgtagc   22200
tctcatcata ctctgtcata taactatagc attaagattt taatgttcta tatattcttc   22260
taagacagtg tttaccagag taaggcacaa aagatccact ggtttgcaag aaagattaga   22320
acttttaaat tttttacctc accttgttta atctatattt ttgtatgtat tttgtaacat   22380
atatattatt attaccataa atcatatata atttaaaatg catatattag gggtaaatgc   22440
tcaggaaact ttttataaat tgggcatgca aatacaagtt tgaagactca ctgttctagg   22500
tattaaaagt aaagttataa ccaagtaaag cttccacctt ttcatgtctc aaagcagttt   22560
attgttggag gtaagatctc ttagaagcct aaacaggtcc aagtacagaa tgaagtaagg   22620
ctagcccata acttgtggca agcaattcat actatttctc tcatgctgag ctctcctcag   22680
tgaagcagct actatagaca actgcagcct attggtagcc tattttacag gcaggaaaaa   22740
aattactttt tattcaaagt ggaactcagg acatggggag aaaatgaata caaaaaatag   22800
ggtcaatcca aaggcacaca gcaaatgagt aacacagtta tgttttttc ccatttgtat   22860 gaggtcccag taaattctaa gtaaactgca aatttaataa tacactaaaa aagccatgca   22920
attgttcaaa tgaatcccag catggtacaa ggagtacaga cactagagtc taaaaaacaa   22980
aagaatgcca ttattgagtt tttgaattat atcaagtagt tacatctcta cttaataaat   23040
gagaaaaacg aggataagag gccatttgat aaaatgaaaa tagccaagaa gtggtattag   23100
agacttgaat acaggtattc gggtccaaag ttcatctgct caaatactaa ctggggaaaa   23160
gagggaaaaa tatttatata catatatatc tgcacacaaa ataccccca aaagacaaaa   23220 tgaggccagg cagggtggct cacacccgta atcccggtac tttgggaggc tgaggcaggt   23280
ggatacctga gatcaggagt tggagatcag cctggtcaac atggtgaaac cctgtctcta   23340
ctaaagataa aaaattagc caggcatggt ggcgtgcgcc tgtaatccca gctacttggg   23400
agtctgaggc aggagaatca cttgaactgg gaaggggagg ttgcagtgag ccaagatcgt   23460
actactgcac tccagcctgg gcagcagagt gagactccat cacaaaaata aataaataaa   23520
taaaatacaa tgaaacagaa agttcaaata atcccataat cttaccacca agaaataact   23580
ttcactcgtt atacttattg attttccat aataaatgta ctttactgtg actatcatga   23640
aaagaaagtt atttagaaa cagagaactg tttcagatca aatctatgta gtagaacaga   23700
gccattaggt gggaaagacg agatcaaact aaatctcaga aggcctaaaa ggctaggtcc   23760
attccagcac taaaaactga ccagacaagt aatggcttca acagcttcta aatatggaca   23820
aagcatgctg aaagggaagg acaggtctaa cagtggtata tgaaatgaac aggagggca   23880 aagctcattt ctcctctgaa gttttccaaa gatgctgagg aggacattag tttgacatga   23940
ccctgatatg ggacaagata atttcacaga agttttacat gttaaagttt tcttatagat   24000
actcattcaa gtaagcaatg aacactaaaa tctaaagaaa gaaagagct ttagagtcag   24060 gtctgtattc aaattcaagc tctaccactt actggttctg tgactttggg caagtctttt   24120
aaccttatta agtcttaatt tcctgatttg taaaatgggg atatcgtctc cctcacagga   24180
```

```
ttgttgtgaa acttttatga gattaatgcc tttatatttg gcatagtgta agtaaacaat    24240
aactggcagc ttcaaaaaaa aaaagcagta gcattccatc atttattatt ggttactctc    24300 aaaaagttt  tcaatgtact agaagataaa tattcaaata ccttaatatc tccattattt    24360
tcaggtaaac agcatgctcc tgaacaacca atgggtcaac aaataaatta aagggaaat     24420 ctaaaaacat cttgatatta aactacatgg aagcacaata taccaaaacc aatggttcac    24480
actaggagaa ttttaaggta caagaaaact ctttgagatt tcttaaaata atagtatgtc    24540
tgaatttatt gagtgattta ccagaaactg ttgtaagagc tctacttgca ttatagcact    24600
taatcctctt aactctatgg ctgctattat caacctcacc ctaatcacat atgggacaca    24660
gagaggttaa gtaacttgcc caaggtcaga gttaggaagt actaagccat gctttgaatc    24720
agttgtcagg ctccggaact cacactttca gccactacat aatactgctt tgctatcttt    24780
taggaaacta tgtgagtcta cctcacatag actcacatag gtttgttttt ttttttttt     24840 taaaggctat cttttccccc atcaatgttt tttgaaggat cccaaattag agtcccacag    24900
aggcagacag cagtacttga caatatggac atttaaggtt aatgttggat tctactgtct    24960
ttttactaca tgacctaggg aacgataatt aacctagact gcttccaagg gttaaataac    25020
ccatttagtt atactatgta aattatctct tagtgattga ttgaaagcac actgttacta    25080
attgactcgg tatgaagtgc ttttttttct tcccttcaa gatacatacc tttccagtta    25140
aagttgagag atcatctcca ccaattactt ttatgtcccc tgttgactgg tcattctagt    25200
taaaaaaaaa aaaactata tatatatata tctacacaca catatgtata tgtatatcct     25260
tatgtacaca cacaaacttc aaattaaatg agaactagaa gatttgagaa gttagctagc    25320
taatatccat agcattatga tattctaaat gatatgaatt ataagaatta ggtttcctga    25380
aatgaatgac tagaaaactt tcaagtagag attagtaaaa attaaaagt cctaatcggc      25440 cattactgat ttgatgtttt taagagtcct aaaaaatggg ttacatccat ttttaagtgg    25500
gtagtattat aacagccacc catcttcaat cacagtgatt tctgaattgt gagggaagtt    25560
attagcatga caggtgtctg gttctggccc tgtacgattc ccatgagtca agcaaattgt    25620
aagggctggt ctatatcaca cccaacccca aggatatgtc cctcaaaagt ctagcccagg    25680
ccccgtcatc ttcagcatca tctgggaaac caggtctgat tagtagtcct ttaaggaata    25740
cctcttaggc tcccatttta ctgctatcac agaatccaat aaaacccta caggagattc      25800 aatgggaaat gctcaacacc cactgtagtt ggtggtgaca atgaccataa tttggctgtg    25860
ctggattcag gacagaaaat ttgggtgaaa gagcaggtga acaaaagagc ttcgacttgc    25920
cctagcagag agcaagccat accataccac aaagccacag caattacaac ggtgcagtac    25980
cagcacagta aatgaacaaa gtagagccca gaaacagacc cagaactata tgaggattta    26040
gtatacaata aagatggtat ttcgagtcag tagggaaaag atgaattatt caataaatga    26100
tgtttggcca actagtaacc catttgggaa aaaataaaag tatggtccct acctcacagc    26160
atacacaaaa ataaattcca gacggattaa aatctaaatg taaaaaataa agccataagt    26220
ggactggaag aaaatagaga attttttta acatccgtag aaagggtaaa aacccaggca     26280
tgacatgaac caaaactgaa gaggttctgt aacaaatacc ccctttttata tattgggctc    26340 caacaataag aacccatagg aaaatggaga atgaacacaa atagacaatt tatagaagag    26400
aaggttataa ggtgtaaaat tatatctatc tgagaaacaa acactaaaac aatgtgattc    26460
tactgttctc ccacccatac tggcaaaact taagcctgat aatatgctga ggggaaataa    26520
gcactcttgt tggtgagagt attaattggc atagcttctt ttgaaaatga catagcaata    26580
```

```
cctgttaaaa ttgcaaacat gcatgtcact taatccagta atcccacttc tgggaatcaa    26640
tgctacaaaa acactgacaa gtatacaaag atacattcaa gagtgttcac tgggccgggt    26700
gcggtggctt catgcctgta atcccaggga ggcagaggca agacgatcgc ttgaccccag    26760
gagttcaagg ccagcccgag aaacacagca agaccctgtc tctctttttt ttatttaaaa    26820
aataaatgtt cactgtatca gttgttcaca aaaacaaacc aacatgtcca ttaacaggga    26880
accatttaaa ttaatcaagt tcatctacac aatgtaatac catgcaacta ttaaaaagca    26940
cctgataatc caaagcacac tgagacagaa taatgctatt aaaaacacca agtagtggaa    27000
cactgtgttg cctatgacac catttttatt caacatttaa acaaatttgt aacagcaatt    27060
acatgagtag tgacaatggc gtttatgaga cttttcactt ttatgtgctt ctattttgt     27120 tatgcttcta tatatacatc catttattat ggagtgttac tttcaaaaat cacaaatggg    27180
ccagtattat ttggtgttgc aaggtgagca tatgacttct gatatcaacc tttgcatatt    27240
acttctcaat ttagggaaat tacagacatc ccttattcta actaacttaa aacccagcat    27300
ttcaaacata cagaattgat ggggaaaaaa aagaagaag aaagaaagaa aaggcaacaa     27360
gcttcagatg acagtgactc acatcaaatt atttataaaa tctgttaaat agtgccatct    27420
tctggagata cctggtatta cagtccaact ccagttgatg tctttacaga gacaagagga    27480 ataaggaaa aaatattcaa gaactgaaaa gtatggagtc atggaaaaat tgctgtgatc     27540
caaaggctac ggtgatagga caagaaacaa gagaactcca agcagtaaga cactgctgtt    27600
ctattagcat ccaaacctcc atactcctgt ttgccccaag gcttttttaa aaaatagaga    27660
caggatctca ctattttgct caggctggtc ttgaactcct ggactcaagc tatcctcctg    27720
cctcggcctc ctaaagtgcc gagattacag gcttgagtca ccatacctgg ctatttattt    27780
tttcttaact ctcttgcctg gcctatagcc accatggaag ctaataaaga atattaattt    27840
aagagtaatg gtatagttca ctacattgga atacaggtat aagtgcctac attgtacatg    27900
aatggcatac atggatcaat taccccacct gggtggccaa aggaactgcg cgaacctccc    27960
tccttggctg tctggaacaa gcttcccact agatcccttt actgagtgcc tccctcatct    28020
ttaattatgg ttaagtctag gataacagga ctggcaaagg tgaggggaaa gcttcctcca    28080
gagttgctct accctctcct ctaccgtcct atctcctcac tcctctcagc caaggagtcc    28140
aatctgtcct gaactcagag cgtcactgtc aactacataa aattgccaga gaagctcttt    28200
gggactacaa acacataccc ttaatgtctt tatttctatt ttgtctacct cttcagtcta    28260
ggtgaaaaaa taggaaggat aatagggaag aactttgttt atgcctactt atccgcccct    28320
aggaattttg aaaacctcta ggtagcaata agaactgcag catggtatag aaaaagagga    28380
ggaaagctgt atagaaatgc ataataaatg ggcaggaaaa gaactgcttg aacaaacag     28440 ggaggttgaa ctataaggag agaaagcaga gaggctaatc aacaaggctg ggttcccaag    28500
agggcatgat gagactatta ctaaggtagg aattactaag ggctccatgt cccccttagtg   28560 gcttagtact atgtagcttg ctttctgcag tgaacttcag acccttcttt taggatccta    28620
gaatggactt tttttttta tcggaaaaca gtcattctct caacattcaa gcaggcccca    28680
agtctaccac actcaatcac attttctctt catatcataa tctctcaacc attctctgtc    28740
cttttaactg ttttttctata ccctgatcaa atgccaacaa aagtgagaat gttagaatca    28800
tgtattttta gaggtagact gtatctcaga taaaaaaaaa gggcagatat tccattttcc    28860
aaaatatgta tgcagaaaaa ataagtatga aaggacatat gctcaggtaa caagttaatt    28920
tgtttacttg tattttatga attccctaaa acctacgtca cccgccccgt tcccacgccc    28980
```

```
cgcgccacgt cacaaactcc acccectcat tatcatattg gcttcaatcc aaaataaggt   29040
atattattga tgatgttaat taacatgcat ggatccatat gcggtgtgaa ataccgcaca   29100
gatgcgtaag gagaaaatac cgcatcaggc gctcttccgc ttcctcgctc actgactcgc   29160
tgcgctcggt cgttcggctg cggcgagcgg tatcagctca ctcaaaggcg gtaatacggt   29220
tatccacaga atcaggggat aacgcaggaa agaacatgtg agcaaaaggc cagcaaaagg   29280
ccaggaaccg taaaaaggcc gcgttgctgg cgtttttcca taggctccgc cccctgacg    29340
agcatcacaa aaatcgacgc tcaagtcaga ggtggcgaaa cccgacagga ctataaagat   29400
accaggcgtt ccccctgga agctccctcg tgcgctctcc tgttccgacc ctgccgctta    29460
ccggatacct gtccgccttt ctcccttcgg gaagcgtggc gctttctcat agctcacgct   29520
gtaggtatct cagttcggtg taggtcgttc gctccaagct gggctgtgtg cacgaacccc   29580
ccgttcagcc cgaccgctgc gccttatccg gtaactatcg tcttgagtcc aacccggtaa   29640
gacacgactt atcgccactg gcagcagcca ctggtaacag gattagcaga gcgaggtatg   29700
taggcggtgc tacagagttc ttgaagtggt ggcctaacta cggctacact agaaggacag   29760
tatttggtat ctgcgctctg ctgaagccag ttaccttcgg aaaaagagtt ggtagctctt   29820
gatccggcaa acaaaccacc gctggtagcg gtggtttttt tgtttgcaag cagcagatta   29880
cgcgcagaaa aaaaggatct caagaagatc ctttgatctt ttctacgggg tctgacgctc   29940
agtggaacga aaactcacgt taagggattt tggtcatgag attatcaaaa aggatcttca   30000
cctagatcct tttaaattaa aaatgaagtt ttaaatcaat ctaaagtata tatgagtaaa   30060
cttggtctga cagttaccaa tgcttaatca gtgaggcacc tatctcagcg atctgtctat   30120
ttcgttcatc catagttgcc tgactccccg tcgtgtagat aactacgata cgggagggct   30180
taccatctgg ccccagtgct gcaatgatac cgcgagaccc acgctcaccg gctccagatt   30240
tatcagcaat aaaccagcca gccggaaggg ccgagcgcag aagtggtcct gcaactttat   30300
ccgcctccat ccagtctatt aattgttgcc gggaagctag agtaagtagt tcgccagtta   30360
atagtttgcg caacgttgtt gccattgctg cagccatgag attatcaaaa aggatcttca   30420
cctagatcct tttcacgtag aaagccagtc cgcagaaacg gtgctgaccc cggatgaatg   30480
tcagctactg ggctatctgg acaagggaaa acgcaagcgc aaagagaaag caggtagctt   30540
gcagtgggct tacatggcga tagctagact gggcggtttt atggacagca agcgaaccgg   30600
aattgccagc tggggcgccc tctggtaagg ttgggaagcc ctgcaaagta actggatgg    30660
ctttcttgcc gccaaggatc tgatggcgca ggggatcaag ctctgatcaa gagacaggat   30720
gaggatcgtt tcgcatgatt gaacaagatg gattgcacgc aggttctccg gccgcttggg   30780
tggagaggct attcggctat gactgggcac aacagacaat cggctgctct gatgccgccg   30840
tgttccggct gtcagcgcag gggcgcccgg ttcttttgt caagaccgac ctgtccggtg    30900
ccctgaatga actgcaagac gaggcagcgc ggctatcgtg gctggccacg acgggcgttc   30960
cttgcgcagc tgtgctcgac gttgtcactg aagcgggaag ggactggctg ctattgggcg   31020
aagtgccggg gcaggatctc ctgtcatctc accttgctcc tgccgagaaa gtatccatca   31080
tggctgatgc aatgcggcgg ctgcatacgc ttgatccggc tacctgccca ttcgaccacc   31140
aagcgaaaca tcgcatcgag cgagcacgta ctcggatgga agccggtctt gtcgatcagg   31200
atgatctgga cgaagagcat caggggctcg cgccagccga actgttcgcc aggctcaagg   31260
cgagcatgcc cgacggcgag gatctcgtcg tgacccatgg cgatgcctgc ttgccgaata   31320
tcatggtgga aaatggccgc ttttctggat tcatcgactg tggccggctg ggtgtggcgg   31380
```

```
accgctatca ggacatagcg ttggctaccc gtgatattgc tgaagagctt ggcggcgaat    31440
gggctgaccg cttcctcgtg ctttacggta tcgccgctcc cgattcgcag cgcatcgcct    31500
tctatcgcct tcttgacgag ttcttctgaa ttttgttaaa atttttgtta aatcagctca    31560 tttttttaacc aataggccga aatcggcaaa atcccttata aatcaaaaga atagaccgag   31620
atagggttga gtgttgttcc agtttggaac aagagtccac tattaaagaa cgtggactcc    31680
aacgtcaaag ggcgaaaaac cgtctatcag ggcgatggcc cactacgtga accatcaccc    31740
taatcaagtt ttttgggggtc gaggtgccgt aaagcactaa atcggaaccc taaagggagc   31800
ccccgattta gagcttgacg gggaaagccg gcgaacgtgg cgaaaagga agggaagaaa     31860 gcgaaaggag cgggcgctag ggcgctggca agtgtagcgg tcacgctgcg cgtaaccacc    31920
acacccgccg cgcttaatgc gccgctacag ggcgcgtcca ttcgccattc aggatcgaat    31980
taattcttaa ttaacatcat caataatata ccttattttg gattgaagcc aatatgataa    32040 tgaggggggtg gagtttgtga cgtggcgcgg ggcgtgggaa cggggcgggt gacgtagtag   32100
tgtggcggaa gtgtgatgtt gcaagtgtgg cggaacacat gtaagcgacg gatgtggcaa    32160
aagtgacgtt tttggtgtgc gccggtgtac acaggaagtg acaattttcg cgcggtttta    32220
ggcggatgtt gtagtaaatt tgggcgtaac cgagtaagat ttggccattt tcgcgggaaa    32280
actgaataag aggaagtgaa atctgaataa ttttgtgtta ctcatagcgc gtaatactg    32339
```

IN VIVO AND EX VIVO GENE TRANSFER INTO RENAL TISSUE USING GUTLESS ADENOVIRUS VECTORS

This application is a continuation of U.S. patent application Ser. No. 12/778,360, filed on May 12, 2010, which is a continuation of U.S. patent application Ser. No. 12/320,434, filed on Jan. 26, 2009, which is a continuation-in-part of U.S. patent application Ser. No. 11/650,478, now U.S. Pat. No. 7,501,114, filed on Jan. 8, 2007, which is a continuation-in-part application of U.S. patent application Ser. No. 10/725,013, now U.S. Pat. No. 7,179,459, filed on Dec. 2, 2003, which claims priority from U.S. Provisional Application Ser. No. 60/430,099 filed on Dec. 2, 2002. The entirety of all of the aforementioned applications is incorporated herein by reference.

FIELD

The present invention is directed to methods and compositions for the gene transfer into renal tissues and, in particular, is directed to methods and compositions for in vivo or ex vivo gene transfer to renal tissue using gutless adenovirus vector.

BACKGROUND

Kidney-targeted gene transfer has the potential to revolutionize the treatment of renal diseases. Transplanted kidneys also provide an ideal setting for ex vivo gene transfer. Several in vivo gene transfer methods have been attempted to target certain renal structures, for example, the HVJ-liposome method and renal perfusion of adenovirus for glomerular cells, intravenous injection of oligonucleotides (ODNs) for proximal tubule, intra-arterial injection of adenovirus followed by cold incubation with a vasodilator for interstitial vasculature of the outer medulla and adenoviral injection into the renal pelvis for the inner medullary collecting duct. As an ex vivo gene transfer method targeting the glomerulus, the transfusion of genetically-modified mesangial cells has been attempted. Implantation of genetically-modified tubular epithelial cells into the subcapsular region has been employed for ex vivo transfection to the interstitium.

However, although gene therapy theoretically has the distinct potential to treat renal disease at the most fundamental level, its application has been limited by the availability of an adequate system for long term gene delivery to the kidney. There still exists a need for improved gene transfer techniques, especially gene transfer vectors that are capable of mediating effective gene transfer into renal tissues with low toxicity.

SUMMARY

One aspect of the present invention relates to methods for treating a renal disease in a mammal. In one embodiment, the method comprises the step of infusing the kidney with a gutless adenoviral vector comprising a polynucleotide encoding a therapeutic agent and a regulatory element operably linked to the polynucleotide, wherein the gutless adenoviral vector comprises the nucleotide sequence of SEQ ID NO:13 or SEQ ID NO:15. In a related embodiment, the gutless adenovirus vector is infused through the vena renalis. In another related embodiment, the gutless adenovirus vector is infused through the superior mesenteric artery.

In another embodiment, the method comprises the steps of: administering a therapeutically effective amount of a gutless adenovirus vector into a segment of a renal blood vessel in vivo, wherein the gutless adenovirus vector comprises the nucleotide sequence of SEQ ID NO:13 or SEQ ID NO:15, and is capable of expressing a therapeutic agent. In a related embodiment, the gutless adenovirus vector is administered using a stent.

Another aspect of the present invention pertains to a method for improving allograft survival. The method comprises the steps of: perfusing a kidney harvested from an organ donor with a gutless adenovirus vector carrying a nucleotide sequence encoding a immune modulator and a regulatory element operably linked to the nucleotide sequence; and transplanting the perfused kidney into a subject. In a related embodiment, the immune modulator is indoleamine dioxygenase.

Another aspect of the present invention pertains to a gutless adenovirus vector comprising a polynucleotide encoding a therapeutic protein, a renal tissue specific regulatory element operably linked to the polynucleotide sequence; and a stuffer comprising the nucleotide sequence of SEQ ID NO:13 or SEQ ID NO:15.

Another aspect of the present invention pertains to a gutless adenovirus vector comprising a polynucleotide encoding an indoleamine dioxygenase, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a renal vascular disease, comprising the gutless adenovinis vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
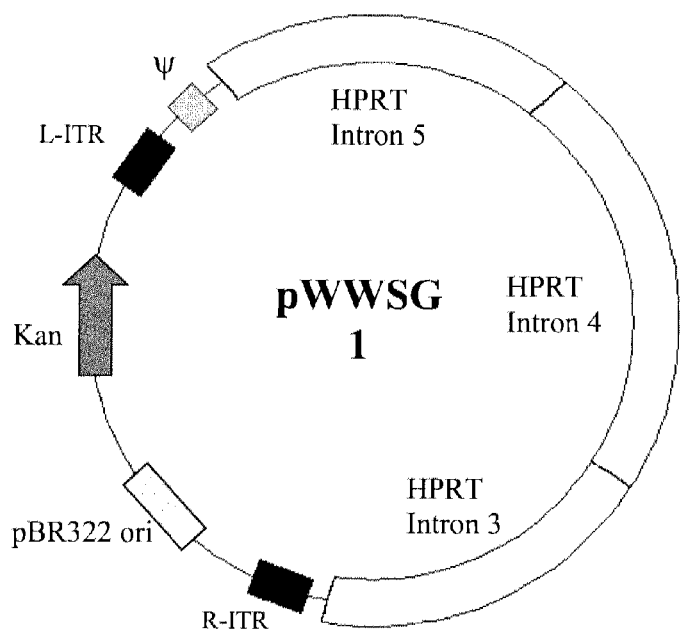
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating renal diseases and improving kidney allograft survival using gene transfer technologies. One aspect of the present invention relates to a method for treating a renal disease by infusing the kidney in vivo with an effective amount of gutless adenovirus vector carrying a DNA sequence encoding a therapeutic agent. The virus-mediated expression of the therapeutic agent in renal tissue ameliorates symptoms of the renal diseases. This local approach eliminates the need to inject a large quantity of virus into a patient and hence significantly reduces the viral-related toxicity.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The Gutless Adenovirus Vector

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The genome of an adenovirus can be manipulated such that it encodes and expresses a gene product of interest but is inactivated in terms of its ability to replicate in a normal lyric viral life cycle (Curie D T, *Ann NY Acad Sci* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells, muscle cells and renal cells Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

The so-called "gutless" adenovirus vectors contain a minimal amount of adenovirus DNA (i.e., the inverted terminal repeats and encapsidation signal) and are incapable of expressing any adenovirus antigens (hence the term "gutless"). The gutless adenovirus vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., *J. Virol.* 70:8944-8960 (1996).

The "inverted terminal repeats (ITRs)" of adenovirus are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward. The "encapsidation signal" or "packaging sequence" of adenovirus refers to the ψ sequence which comprises five (AI-AV) packaging signals and is required for encapsidation of the mature linear genome; the packaging signals are located from about 194 to 358 bp in the Ad genome (about 0.5-10 mμ).

In one embodiment, a viral backbone shuttle vector is used for the construction of gutless adenovirus vectors. The viral backbone shuttle vector contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb (SEQ ID NO: 1). In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1. In another embodiment, the viral backbone shuttle vector of the present invention comprises the nucleotide sequence of SEQ ID NO:13 or SEQ ID NO:15.

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may contain coding sequence for a protein, an iRNA agent, or an antisense RNA. The foreign DNA may further contain regulatory elements operably linked to the coding sequence. The term "operably linked," as used herein, refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence. Similarly, intervening untranscribed sequences can be present between an enhancer sequence and the coding sequence and the enhancer sequence can still be considered "operably linked" to the coding sequence.

Examples of regulatory elements include, but are not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human origin.

Renal Specific Expression

In one embodiment, the therapeutic agent is expressed in a tissue-specific manner either using a renal-specific regulatory element or using an inducible regulatory element combined with kidney-specific induction. Examples of renal-specific regulatory element include, but are not limited to, high-capacity (type 2) Na+/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

Examples of inducible regulatory elements include, but are not limited to, regulatory elements that responded to exogenous signals or stresses, such as heat, hormones, hypoxia, cytokines or metal ions, as well as artificial inducible systems such as the tetracycline inducible system; the FK506/rapamycin inducible system, the RU486/mifepristone inducible system, and the ecdysone inducible system. These systems are briefly described below.

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

In one embodiment, a kidney tissue is infected with a gutless virus containing an inducible regulatory element. The infected tissue is then exposed to an inducing agent, such as tetracycline or rapamycin, or an inducing condition such as local heating or hypoxia, to induce expression of the therapeutic agent. The inducible system thus allows kidney specific expression of the therapeutic agent and minimizes the side effect of the therapeutic agent. In addition, the level and duration of the therapeutic agent expression may also be controlled by the dose of the inducing agent and the frequency of inducing agent administration. In one embodiment, the coding sequence of the therapeutic agent is controlled by the tet-on system and the expression of the therapeutic agent can be induced by an oral dose of tetracycline.

The Renal Diseases

The renal disease can be any disease or disorder that affects the function of the kidneys and for which a therapeutic gene or genes have been identified. Examples of the renal diseases include, but are not limited to, glomerulonephritis, renal vein thrombosis, diabetic nephropathy, ischemia/reperfusion injury (shock kidneys), hypertension, proteinuric kidney diseases (post glomerulonephritis), ischemic nephropathy, obstruction nephropathy, atheroembolic renal disease, chronic nephritis, congenital nephrotic syndrome, interstitial nephritis, lupus nephritis, membranoproliferative glomerulonephritis, membranous nephropathy, minimal change disease, necrotizing glomerulonephritis, nephropathy—IgA, nephrosis (nephrotic syndrome), post-streptococcal GN, reflux nephropathy, renal artery embolism, renal artery stenosis, and renal underperfusion.

The Therapeutic Agents

The therapeutic agent can be any molecule that is, when expressed in a renal tissue or in the proximity of a renal tissue, capable of ameliorating symptoms of a renal disease. The therapeutic agents include, but are not limited to, proteins, iRNA agents and antisense RNA. The term "expression," as used herein, refers to the process of transcription of mRNA from a coding sequence and/or translation of mRNA into a polypeptide.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA.

Protein as a Therapeutic Agent

In one embodiment, the therapeutic agent is a protein or peptide capable of ameliorates symptoms of the renal disease. For example, the therapeutic agent can be thrombomodulin for treating renal vein thrombosis (RVT) or an antibody that binds specifically to a target molecule which is involved in a renal disease (e.g., an inflammatory cytokine which has been found to be associated with the chronic kidney disease (CKD)).

The term "antibody", as used herein, is defined as an immunoglobulin that has specific binding sites to combine with an antigen. The term "antibody" is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, a humanized antibody and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), F(ab')$_2$, Fv fragment, diabody, linear antibody, single-chain antibody molecule, multispecific antibody, and/or other antigen binding sequences of an antibody.

Examples of the therapeutic protein include, but are not limited to, thrombomodulin (TM), cytokines such as IL-1, IL-2, IL-3, IL-4, IL-5, IL-6, IL-7, IL-8, IL-9, IL-10, IL-11, IL-12, IL-13, IL-14, IL-15 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-α, TGF-β, and VEGF; antiviral cytokines such as interferons, antiviral proteins induced by interferons, TNF-α, and TNF-β; proteins involved in immune responses such as antibodies, CTLA4, hemagglutinin, MHC proteins, VLA-4, and kallikrein-kininogen-kinin system; ligands such as CD4; growth factor receptors including EGFR, PDGFR, FGFR, and NGFR, GTP-binding regulatory proteins, interleukin receptors, ion channel receptors, leukotriene receptor antagonists, lipoprotein receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb, and variants thereof.

A "variants" of a polypeptide is a polypeptide that differs from a native polypeptide in one or more substitutions, deletions, additions and/or insertions, such that the bioactivity of the native polypeptide is not substantially diminished or enhanced. In other words, the bioactivity of a variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

A variant preferably exhibits at least about 70%, more preferably at least about 90% and most preferably at least about 95% sequence homology to the original polypeptide.

The term "variant' also includes a polypeptides that is modified from the original polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In one embodiment, the therapeutic protein is a native TM or a TM variant for the treatment of renal vein thrombosis (RVT). RVT has numerous etiologies, it occurs most commonly in patients with nephrotic syndrome (i.e., >3 g/d protein loss in the urine, hypoalbuminemia, hypercholesterolemia, edema). The syndrome is responsible for a hypercoagulable state. The excessive urinary protein loss is associated with decreased antithrombin III, a relative excess of fibrinogen, and changes in other clotting factors; all lead to a propensity to clot. Numerous studies have demonstrated a direct relationship between nephrotic syndrome and both arterial and venous thromboses. Why the renal vein is susceptible to thrombosis is unclear. The renal vein also may contain thrombus after invasion by renal cell cancer. Other less common causes include renal transplantation, Behçet syndrome, hypercoagulable states, and antiphospholipid antibody syndrome.

Thrombomodulin (TM) is an integral membrane glycoprotein expressed on the surface of endothelial cells (Sadler et al., *Trhomb Haemost.*, 78:392-95 [1997]). It is a high affinity thrombin receptor that converts thrombin into a protein C activator. Activated protein C then functions as an anticoagulant by inactivating two regulatory proteins of the clotting system, namely factors Va and VI[I]a (Esmon et al., *Faseb J.*, 9:946-55 [1995]). The latter two proteins are essential for the function of two of the coagulation proteases, namely factors IXa and Xa. TM thus plays an active role in blood clot formation in vivo and can function as a direct or indirect anticoagulant.

TM and several other proteins or enzymes have been shown to reduce the process of intimal hyperplasia, whose evolution is the causes of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet*, 353:1729-34 [1999]; Palmer et al., *Nature*, 327:524-26 [1987]; Kubes et al., *PNAS USA.*, 88:4651-5 [1991]).

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

siRNA as the Therapeutic Agent

In another embodiment, short interfering RNAs (siRNA) are used as a therapeutic agent to inhibit a disease-related gene expression. For example, elevated levels of transforming growth factor-$\beta_1$ (TGF-$\beta_1$) and platelet-derived growth factor (PDGF) have been associated with the development of glomerular injury. Therefore, inhibition of the expression of TGF-$\beta_1$ and/or PDGF in kidney tissues may be used to prevent or reduce glomerular injury.

siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

siRNAs can be expressed in vivo from adenovirus vectors. This approach can be used to stably express siRNAs in kidney tissues. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database. Any target sequences with more than 16-17 contiguous base pairs of homology to other coding sequences may be eliminated from consideration in certain cases.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., *Proc. Natl. Acad. Sci*. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., *Nature Biotechnology* 20:500-505, 2002).

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

Route of Administration

The gutless adenovirus may be introduced into the kidney by intravenous, intrarterial, or retrograde infusion. In one embodiment, the virus is infused through the vene renalis. In another embodiment, the virus is infused through the superior mesenteric artery. In yet another embodiment, the virus is infused through a retrograde catheter into the pyelic cavity. Since only a relatively small amount of virus is needed for the kidney infusion, the virus-related toxicity is reduced. In yet another embodiment, the kidney is perfused with the virus, i.e., the virus enters the kidney through the vene renalis or the superior mesenteric artery, and is collected through the superior mesenteric artery or vene renalis. Since the leftover virus does not enter the blood circulation, a large amount of virus may be used for the perfusion. In addition, a close-circuit perfusion allows constant exposure to virus over an extended period of time (e.g., 10-60 minutes) and hence significantly increases the number of infected cells.

In another embodiment, the virus is administered into a segment of a renal blood vessel in vivo. In a related embodiment, the gutless adenovirus vector is administered using a stent. The viral vector is embedded in the stent and is released only at a treatment site. Since the viral infection is restricted at the treatment site and the surrounding area, only a small amount of the virus is needed and the virus-related toxicity is reduced.

Another aspect of the present invention relates to a method for improving allograft survival. The method comprises the steps of perfusing a kidney harvested from an organ donor with a gutless adenovirus vector carrying a nucleotide sequence encoding an immune modulator and a regulatory element operably linked to the nucleotide sequence; and transplanting the perfused kidney into a subject. The term "immune modulator," as used herein, refers to a polypeptide or a polynucleotide capable of modulating an immune response and improving allograft survival.

In one embodiment, the immune modulator is indoleamine dioxygenase (IDO). IDO is an enzyme that is expressed in the placenta and plays an important role in foeto-maternal tolerance. IDO metabolizes the amino acid tryptophan. The function of T cells, the most important cell-type involved in organ transplant rejection, is dependent on tryptophan. In addition, the metabolites of tryptophan (kynurenines) are toxic to T-cells. It has been shown that over-expression of IDO in renal tissues protects against renal transplant damage.

Typically, kidneys must be preserved prior to transplantation to obtain proper pathology assessment of the suitability of the organ for transplantation. Lack of proper preservation leads to degradation of organ function due to thrombosis (blood clotting), ischemia (lack of oxygen), or ischemia followed by reperfusion (the restoration of blood flow upon transplantation). These events bring about inflammation, cell death, and eventually failure of the organ. Kidney preservation is a process in which the renal artery is connected to a kidney perfusion machine in order to simulate the normal process by which nutrients are supplied to the kidney. A solution is continuously perfused through a closed circuit which includes the kidney, which is typically maintained at a low temperature (e.g., 5° C.) to reduce the cell metabolic rate and oxygen consumption. During the perfusion process, the perfusion pressure, flow, and vascular resistance, as well as the organ's chemistries, including base excess, oxygen saturation, calcium, potassium, hematocrit, $pO_2$, pH, and bicarbonate, are monitored closely to prevent tissue damage. The adenovirus vectors can be added to the perfusion solution and infect the kidney tissue during the perfusion period. Kidney perfusion solutions are commercially available. In one embodiment, the kidney perfusion solution is Lactated Ringer's solution.

In one embodiment, the regulatory element is a constitutive promoter, such as CMV or RSV promoter. In another embodiment, the gutless adenovirus contains the nucleotide sequence of SEQ ID NO:25 or SEQ ID NO:26.

In another embodiment, the gutless adenovirus is suspended in the perfusion solution to a final concentration of $10^9$-$10^{12}$ particles/ml and perfused for a period of 10-120 minutes.

Another aspect of the present invention pertains to a gutless adenovirus vector comprising a polynucleotide encoding a therapeutic agent, a renal-specific regulatory element or inducible regulatory element operably linked to the polynucleotide sequence; and a stuffer comprising the nucleotide sequence of SEQ ID NO:13 or SEQ ID NO:15.

In one embodiment, the renal-specific regulatory element is selected from the group consisting of high-capacity (type 2) Na+/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

In another embodiment, the inducible regulatory element is selected from the group consisting of heat inducible regulatory elements, hormone inducible regulatory elements, hypoxia inducible regulatory elements, cytokine inducible regulatory elements, metal ion inducible regulatory elements, and artificial inducible regulatory elements.

Yet another aspect of the present invention pertains to a pharmaceutical composition for treating a renal vascular disease, comprising the gutless adenovirus vector described above and a pharmaceutically acceptable carrier. As used herein, a "pharmaceutically acceptable carrier" is intended to include any and all solvents, solubilizers, stabilizers, absorbents, bases, buffering agents, controlled release vehicles, diluents, emulsifying agents, humectants, dispersion media, antibacterial or antifungal agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition is formulated to be compatible with its intended route of administration. Solutions or suspensions used for parenteral application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

It is especially advantageous to formulate parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At by 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1).

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)—1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV.

pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]). The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)—2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at by 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)—3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                              (SEQ ID NO: 8)
5'-gtaacactgg cccaggaggc ctttctggtg acccc-3'

(SEQ ID NO: 9)
3'-tgacc gggtcctccg gaaagaccac tggggatt-5'
```

Creation of pTMadap-Stuffer1

Based on the published sequence HSU71148 of the human X chromosome region q28 the following PCR primers were synthesized:

```
                                              (SEQ ID NO: 10)
Forward: 5' TAGTTCCTTCTGCCTGGAATAC 3'

(SEQ ID NO: 11)
Reverse: 5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BstEII and SfiI sites of pTMadap, resulting in pTMadap-stuffer1.

2(a)—4 Creation of pTMadap-Stuffer1-Short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO: 13.

2(a)—5 Creation of pTMadap-Stuffer1-Short-Stuffer2

The plasmid p2-2 (SEQ ID NO: 14, obtained from Gen-Bank) was cut with NotI and the resulting fragment of approximately 5954 bp (stuffer 2, SEQ ID NO: 15) was inserted into the NotI site of pTMadap-stuffer1 short, resulting in pTMadap-stuffer1-short-stuffer2.

2(a)—6 Removal of PacI Site from pTMadap-Stuffer1-Short-Stuffer2

Figure 2:
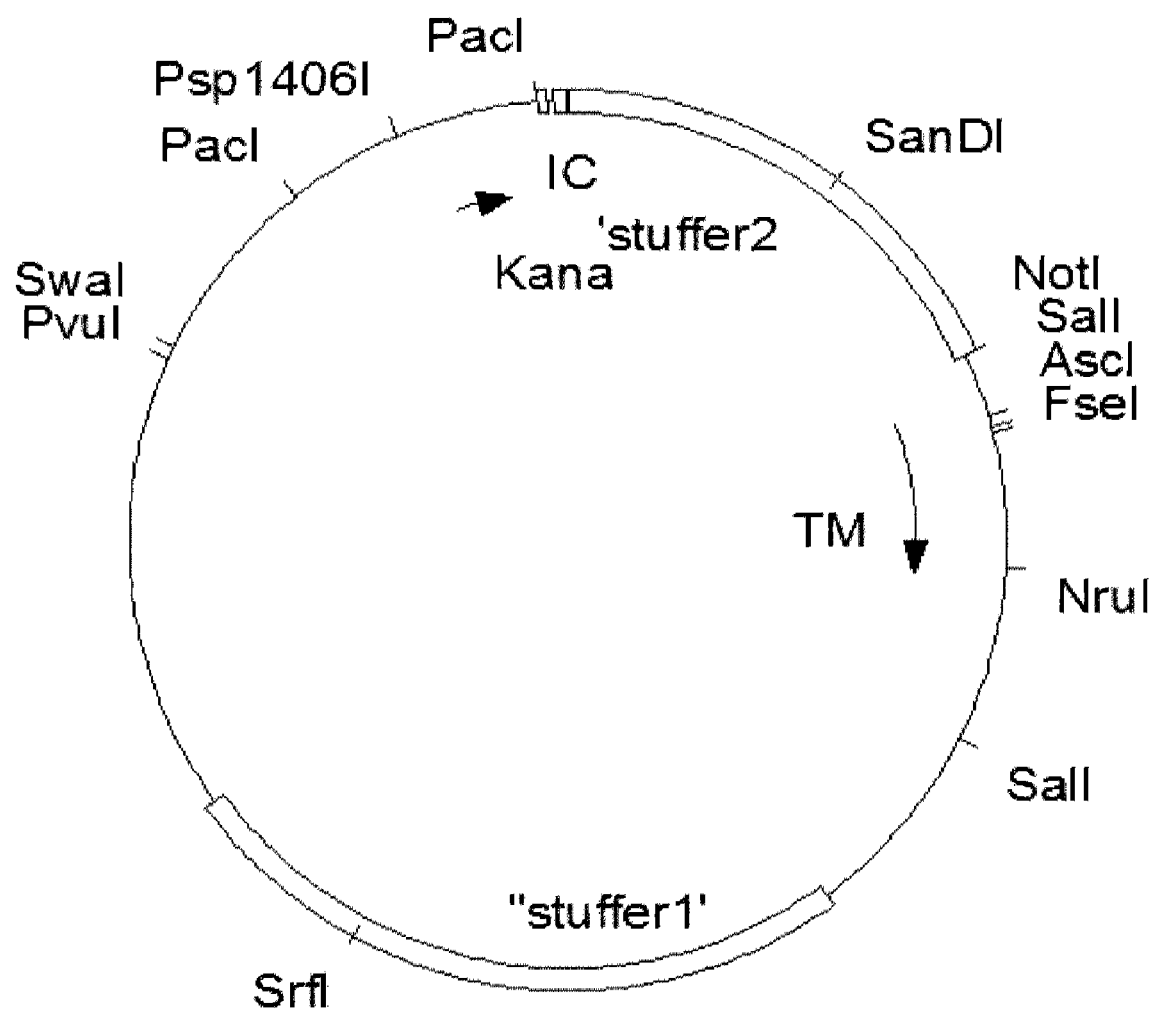
FIG. 2 is a schematic drawing of an embodiment of the full length backbone vector pTM-final.

Plasmid pTMadap-stuffer1-short-stuffer2 was cut with AclI and BsiWI. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 µg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl-Density 1.25, and 2.5 mL CsCl-Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/mL. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris-pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 µg/ml. (BSA is fine). Sample cuvettes were prepared using 1-10 µl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer:

$$[12.956+224.15(\mu g/ml)] \times 10^8.$$

EXAMPLE 4

Figure 3:
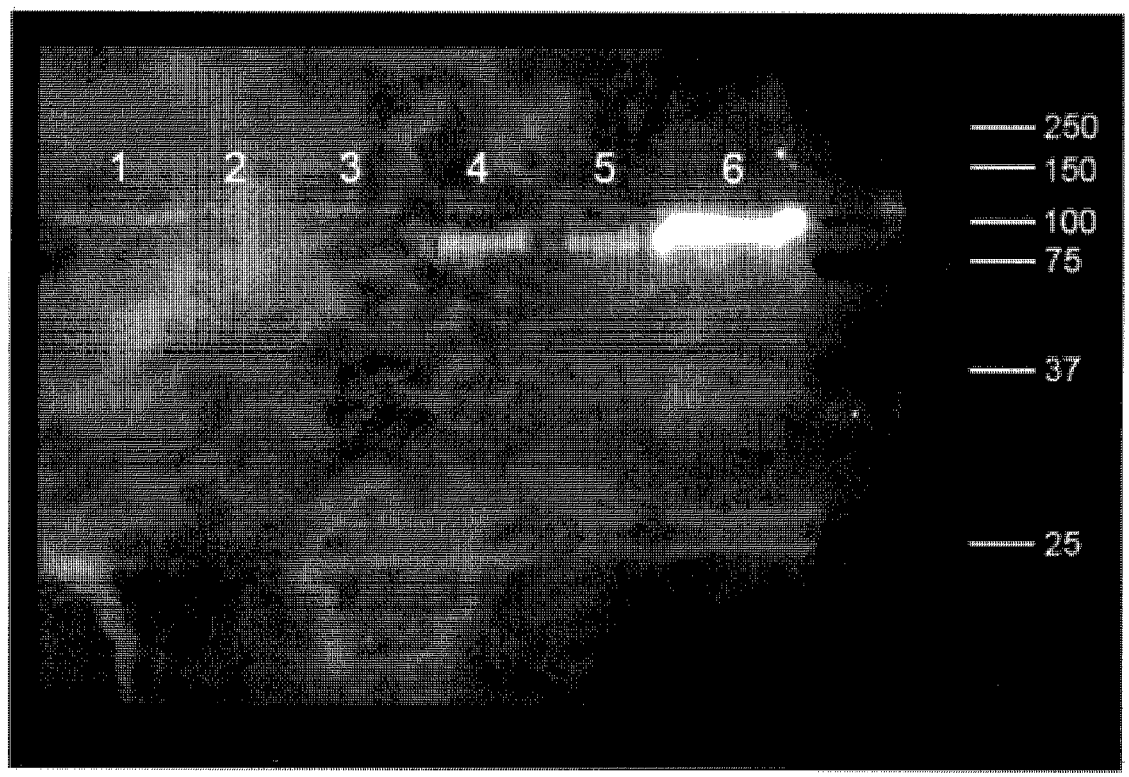
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 µg of pTM-final. After 24 hours, the cells were washed with PBS and lysed in 125 µl RIPA buffer with protease inbitors Protein samples (16 µl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 µl Igepal ca-630, 50 mg sodium deoxycholate, 500 µl 20% SDS, 10 mM β-mercapto ethanol, and 1 ml 10×PBS, and add water to a final volume of 10 ml at room temperature. A cocktail of protease inhibitors containing 11.5 µl PMSF (from 34.8 mg/ml in isopropanol, 64 µl Benzamidine (from 15.6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(B) Expression of hTM in P2 Lysate of 293FLP Cells

Figure 4:
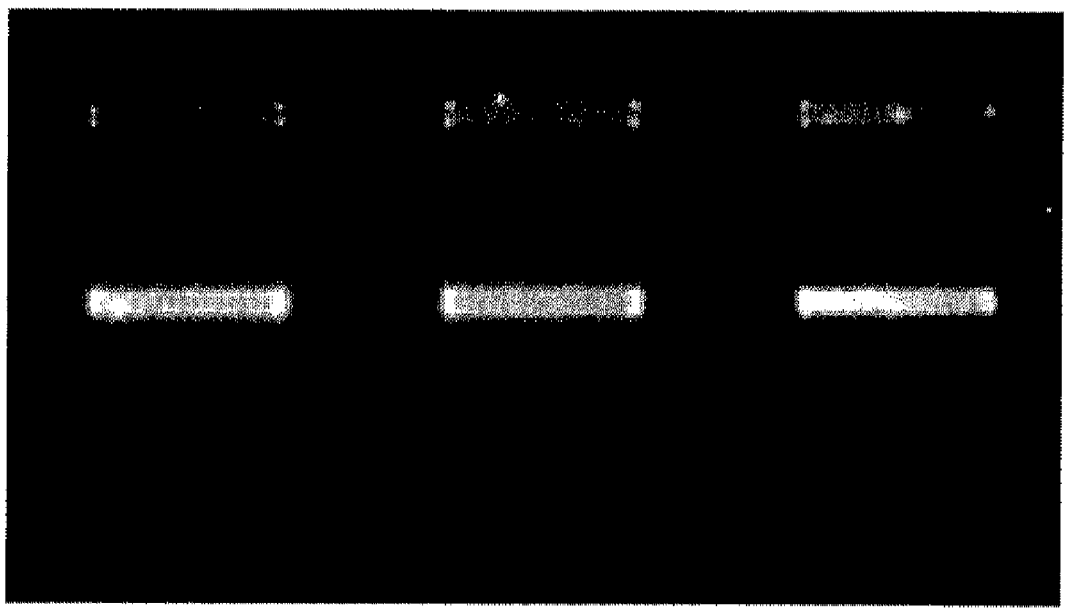
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 µl RIPA buffer. 7 ul of 5× loading buffer was added to 35 µl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 µl PMSF (from 34, 8 mg/ml in isopropanol, 64 µl Benzamidine (from 15, 6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
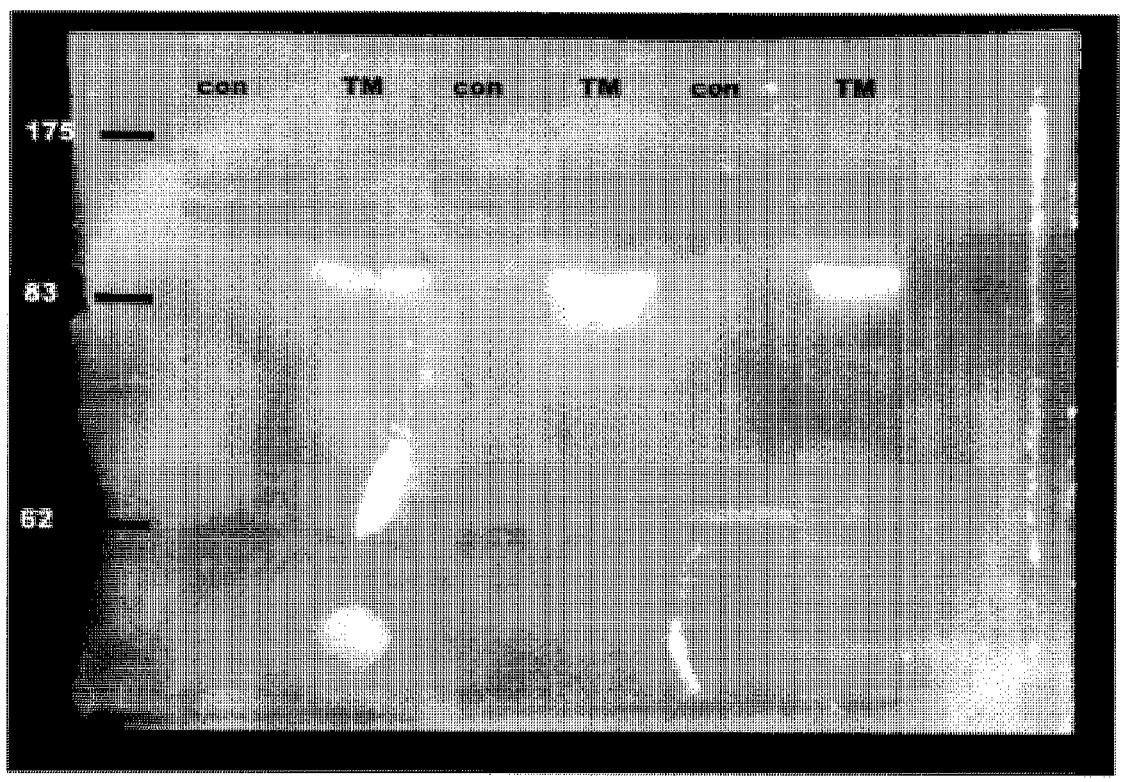
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 µg of PacI digested TM-vector backbone. After 24 hours, 2% DMEM-Fl 2 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
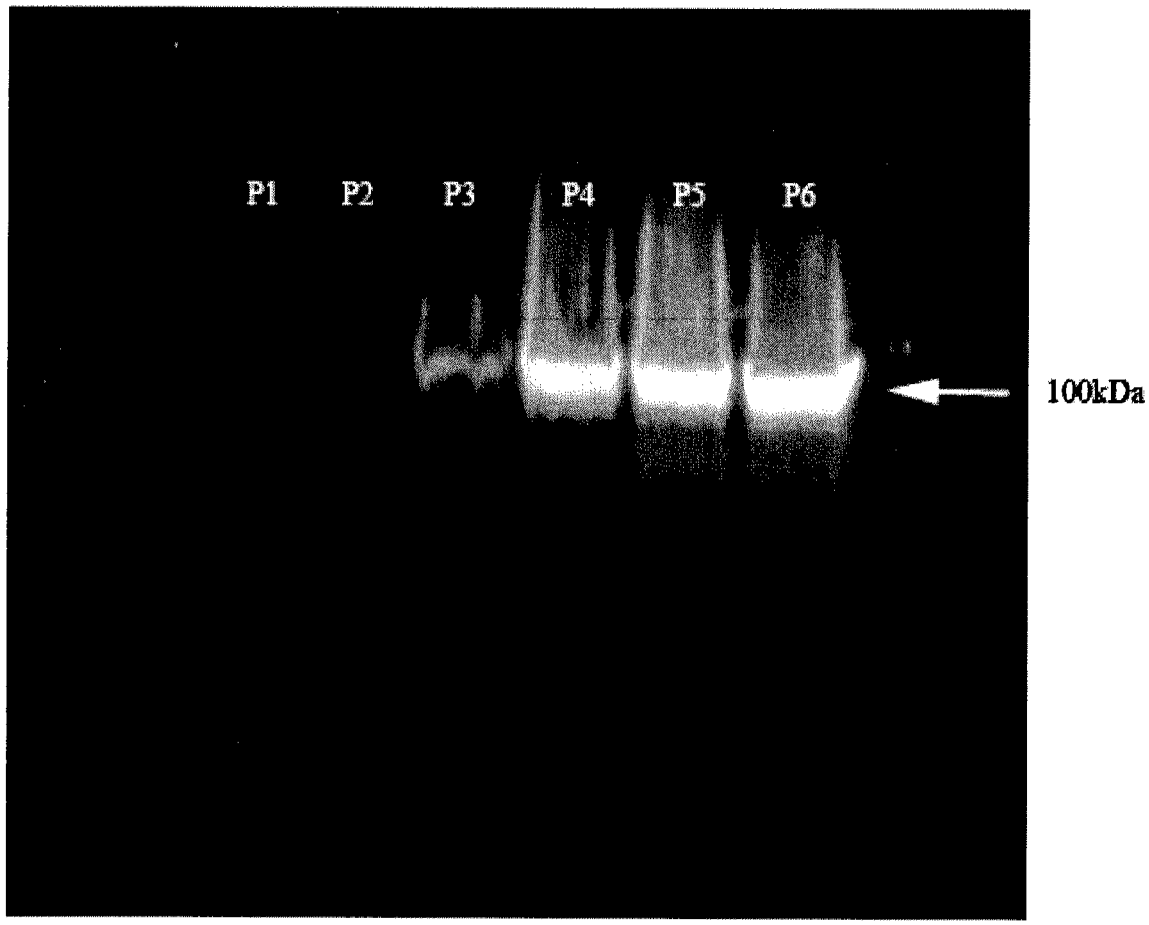
FIG. 6 is a picture of a Western bolt showing TM expression in CRE cells at passage number 1-6 (P1-P6).
Figure 7A:
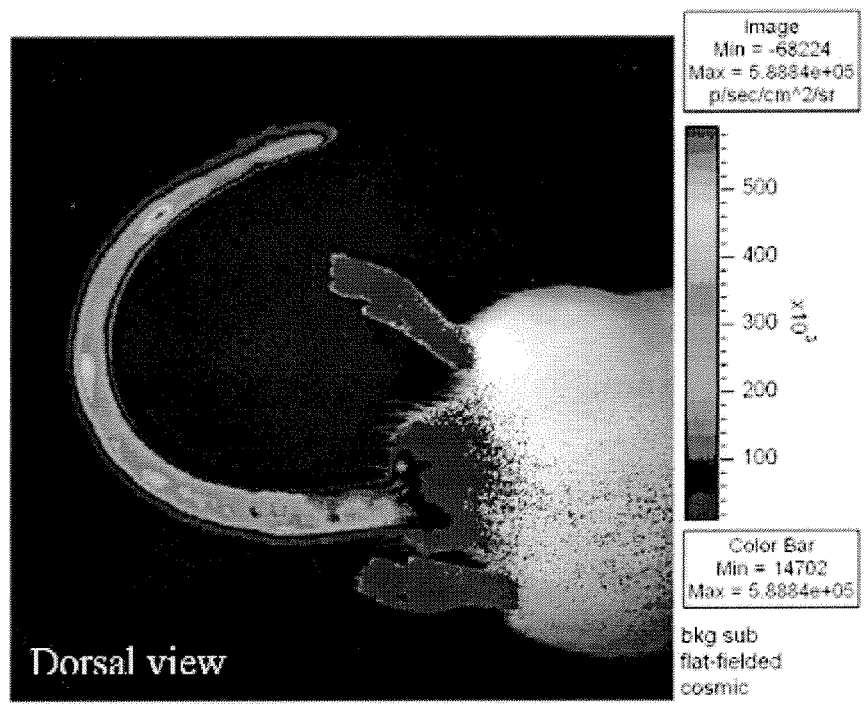
FIGS. 7A-7C is a composite of images showing gutless adenovirus-mediated luciferase expression in rat tail vein.
Figure 7A:
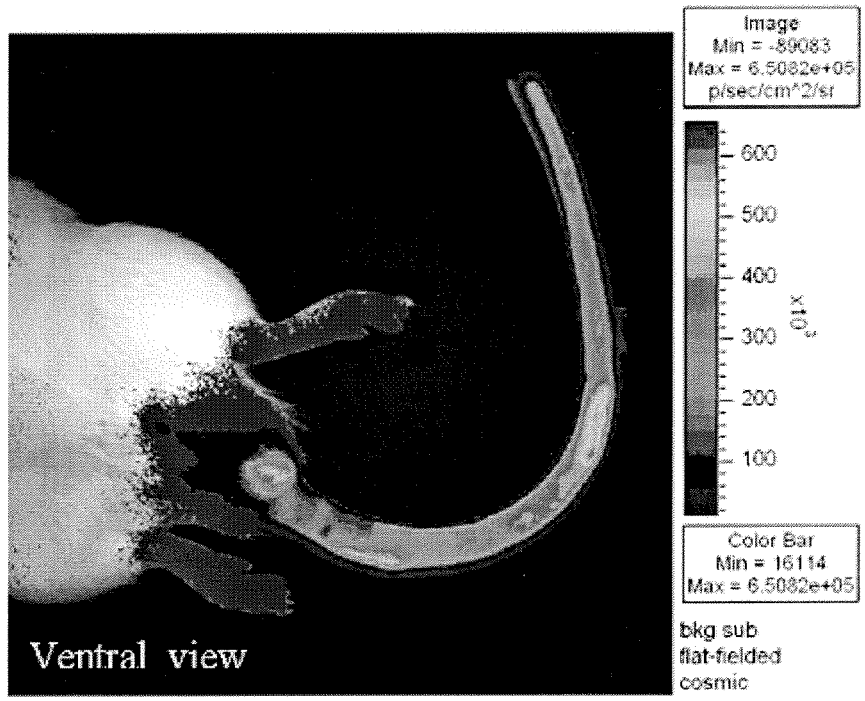
Figure 7B:
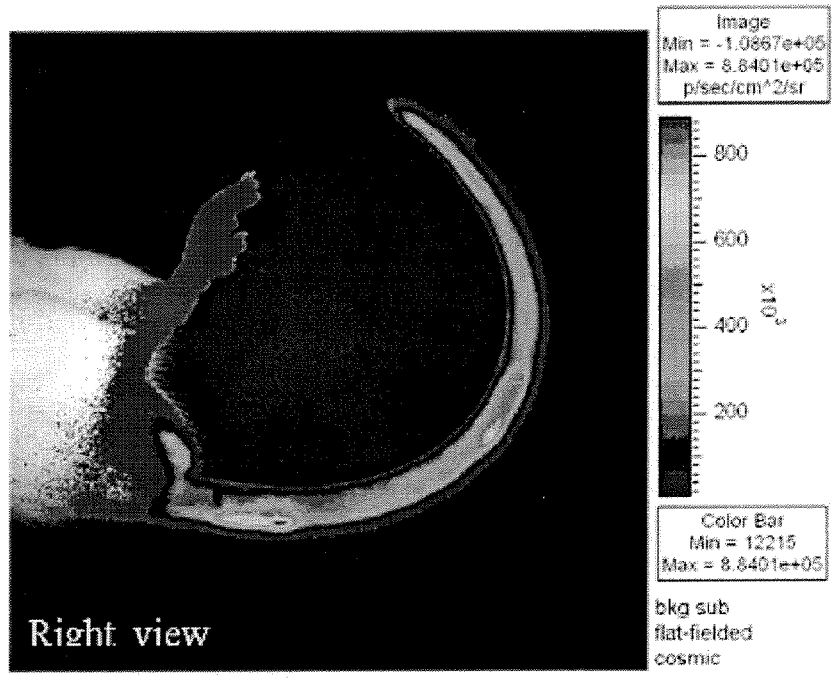
Figure 7B:
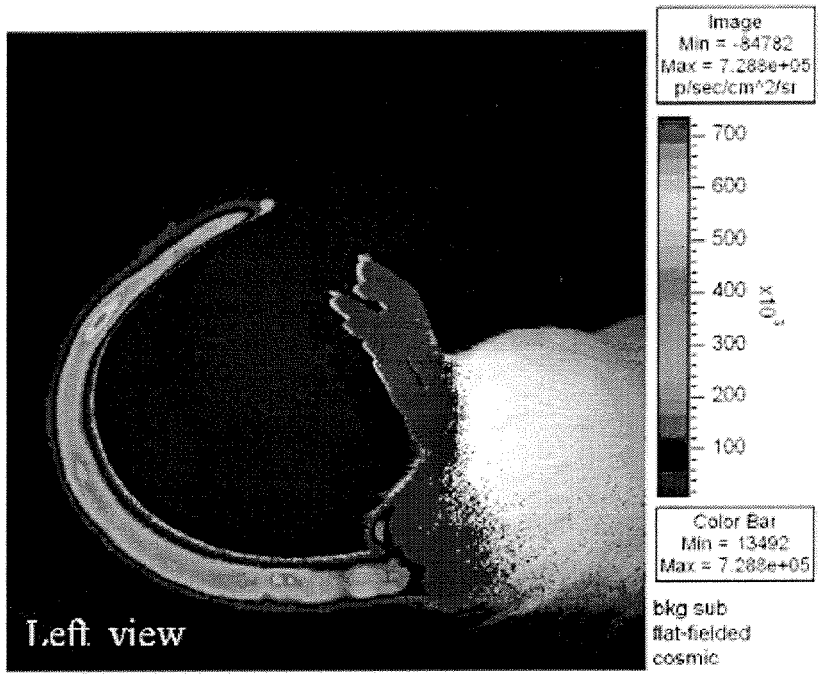
Figure 7C:
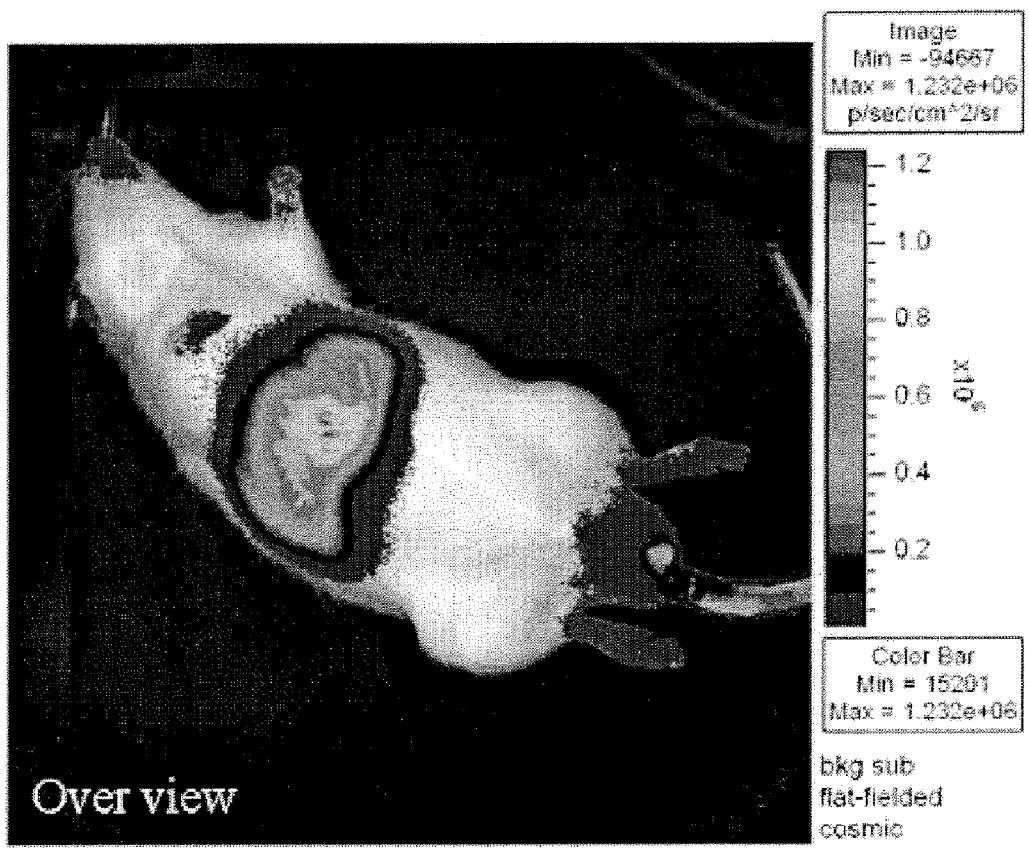

HEK 293 cells were cultured in a 6 well cluster and transfected with 200 µl of TM gutless virus of passage 1-6. After 24 hours, the cells were washed with PBS and lysed in 125 µl RIPA buffer. Protein samples (16 µl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 µl Igepal ca-630, 50 mg sodium deoxycholate, 500 µl 20% SDS, 10 mM β-mercapto ethanol, 1 ml 10×PBS, add water to make up 10 ml. Immediately before use, the following protease inhibitors were added to the RIPA buffer: 115 µl PMSF (from 34.8 mg/ml in isopropanol), 64 µl Benzamidine (from 15.6 mg/ml stock), 100 µl sodium orthovanadate (100 mM), 5 µl pepstatin (from 1 mg/ml stock), 1 µl leupeptin (from 5 mg/ml stock), 1 µl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Viva Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Expression of TM by Intravenous Infusion of Viral Vectors

Material and Methods

Infection with gutless TM virus: 3 male Wistar rats weighing approximately 300 grams were intravenously injected in the tail vein with a low dose of gutless TM virus (approximately $2 \times 10^{10}$ viral particles) in a total volume of 500 ul of sucrose buffer. After three weeks, the animals were sacrificed and liver tissue and blood plasma was collected and immediately frozen in liquid nitrogen.

TM expression in the liver was determined by western blotting. Approximately 500 mg of liver tissue was homogenized in 2 ml of RIPA buffer. Liver protein samples (20 µg) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins.

Detection of rat Anti-TM antibodies in the plasma of TM infected rats: HEK 293 cells were cultured in a 6 well cluster. 3 wells were infected with 100 µl of TM gutless virus (approximately $4 \times 10^9$ virus particles) and 3 wells received no virus. After 24 hours, non-infected and TM infected cells were washed with PBS and lysed in 125 µl RIPA buffer. Protein samples (16 µl) were separated on a 7.5% polyacrylamide/SDS gel and transferred to nitrocellulose membrane. Blots containing protein from both TM expressing cells and non-infected cells were incubated with primary antibody TM (c-17) (1:2000, Santa Cruz) or plasma from TM infected rats (1:20, 1:100 and 1:1000 dilution). Detection of primary antibodies was performed using Polyclonal Rabbit Anti-Goat Immunoglobulins/HRP (1:4000, DakoCytomation) and Polyclonal Rabbit Anti-Rat Immunoglobulins/HRP (1:4000, DakoCytomation), respectively. RIPA buffer was prepared as described in Example 4.

Figure 8:
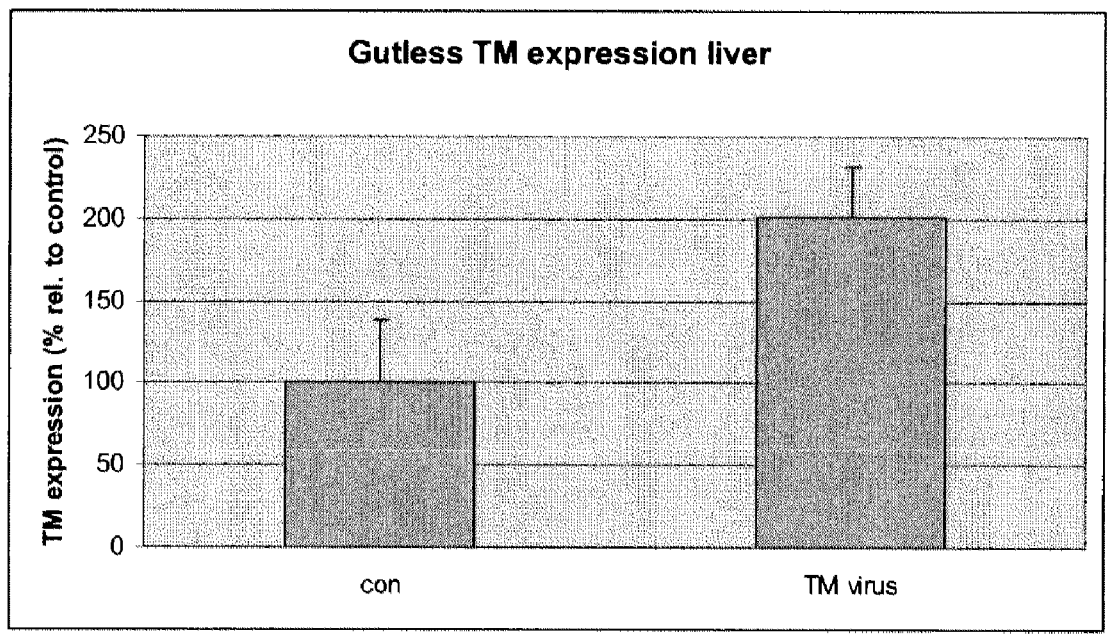
FIG. 8 is a diagram showing TM expression in livers of non-infected rats (con) and TM gutless virus infected rats (TM virus).

TM expression in the liver: No adverse effects of the injection of gutless TM virus could be detected. Animals displayed normal growth characteristics and did not suffer from excessive bleeding. Three weeks after injection, animals were sacrificed and no internal bleeding could be detected. Liver TM expression was evaluated using western-blot. TM expression was elevated two-fold above background levels, indicating modest over-expression of TM gutless virus in the liver three weeks after infection (FIG. 8).

Figure 9:
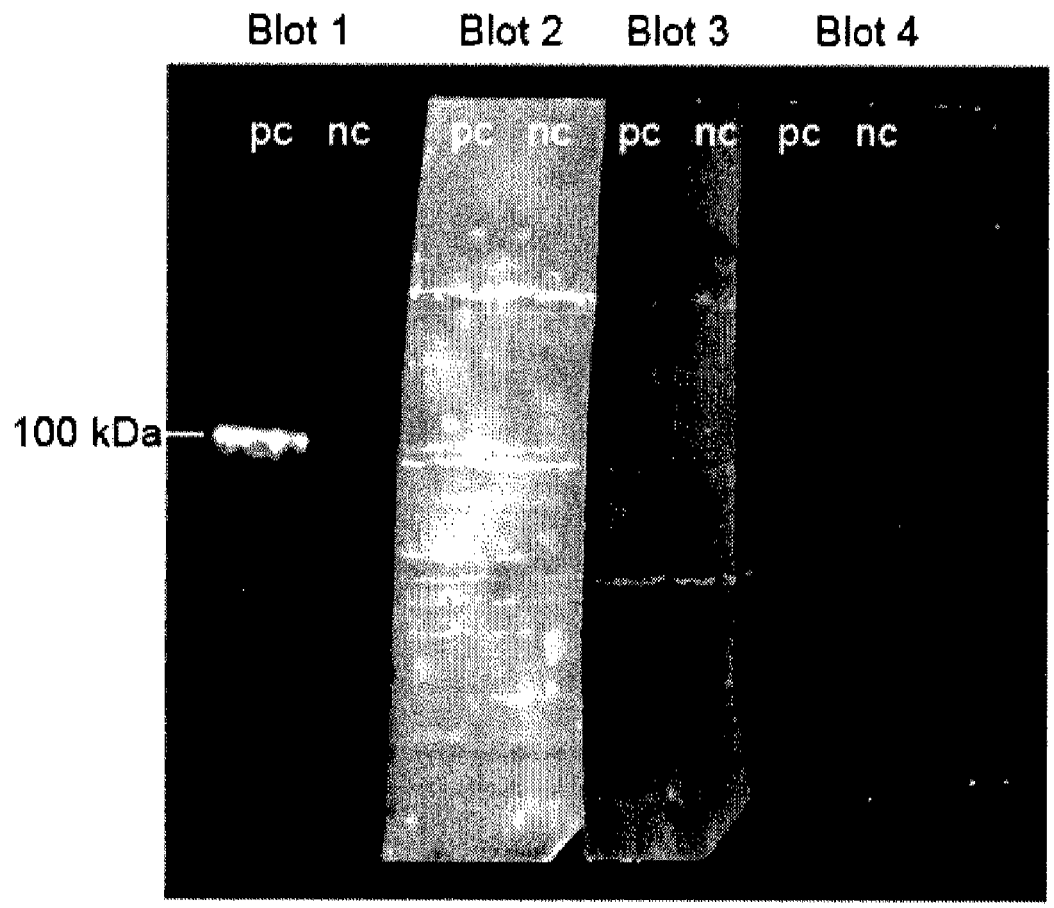
FIG. 9 is a picture of Western blots using a anti-TM antibody (blot 1) and plasma from animals infected with TM virus (blots 2-4).

To detect TM antibodies in the plasma of rats infected with the gutless TM virus, four western blots were made. Each blot contains a protein sample from human cells expressing TM (positive control) and a sample from the same cells that do not produce TM (negative control). Blot 1 was probed with a commercial antibody against TM (FIG. 9, blot 1), indicating the presence of human TM only in the positive control lane. Blots 2, 3 and 4 were probed with plasma from animals infected with TM virus in the dilution 1:20, 1:100 and 1:1000, respectively. Although some immunoreactivity is observed, the plasma of rats did not lead to the specific detection of TM in the positive control lane. Therefore, the plasma of these rats do not contain detectable levels of rat IgG antibodies against human TM.

Conclusion: Intravenous administration of low dose gutless TM virus into rat tail vein resulted in modest expression of TM in the liver of the recipient rats three weeks after injection. The viral injection did not result in the production of IgG antibodies against TM.

EXAMPLE 9

Adenovirus-Mediated In Vivo Gene Transfer to Vena Cava

Inbred male Brown Norway rats (BN/rijHsd, Harlan, Netherlands) with an age of 11 weeks were used. Animals were housed in a light and temperature controlled environment and fed standard rodent chow and water ad libitum. Rats were anaesthetized with isoflurane (3% in $O_2$). The vene cava with the branches was exposed by a mid-line incision. The vene cava was clamped just below the vene renalis of the left kidney. All accessible sidebranches of the vena cava in the region between the vena renalis and the bifurcation were also clamped. The virus particles were administered through an insulin syringe (29-gauge needle) with a volume of 290 ul containing $2\times10^{11}$ virus particles. After injection of the viral solution, the syringe with needle was not removed from the vena cava but remained in place during the following incubation period of 20 minutes. Subsequently, the clamps on the sidebranches of the vene cava were removed. The transfected segment of vena cava was washed by making a puncture with a needle 25-gauge needle just below the clamp near the vena renalis. The expelled blood containing excess virus was absorbed with a cotton bud. After bleeding a volume of approximately 0.5 ml, the bleeding was stopped by applying a pressure on the puncture site with a cottonswab. Subsequently, the clamp near the vene renalis was released and the abdomen was sutured. For post-operative pain relief, the rats received buprenorphin (Temgesic®) 10 µg/kg subcutaneously. The rats were allowed to recover with access to water and food ad libitum.

Two days after the transfection procedure, rats were anaesthetized with isoflurane (3% in $O_2$). The vene cava was exposed by a mid-line incision and clamped just below the vena renalis of the left kidney. The abdomen was temporarily closed during the incubation time of 2 hours. Subsequently, the abdomen was reopened and blood was collected from the aorta. The vena cava was harvested from the bifurcation till above the clamp. The vene cava was opened longitudinally and the thrombus was removed and placed in saline for size evaluation. The results of the experiment were summarized in Table I.

TABLE I

Vena cava thrombus in the experimental animals

| Group | Thrombus size in individual animals |
|---|---|
| sucrose | 1623.98 |
|  | 1507.23 |
|  | 239.84 |
|  | 398.25 |
|  | 107.97 |
|  | 32.24 |
|  | 85.40 |
| gfp virus | 97.00 |
|  | 107.13 |
|  | 158.93 |
|  | 0.00 |
|  | 89.04 |
|  | 87.63 |
|  | 1281.56 |
|  | 137.13 |
| TM virus | 0.00 |
|  | 280.04 |
|  | 0.00 |
|  | 0.00 |
|  | 140.21 |
|  | 60.65 |
|  | 0.00 |
|  | 108.69 |

EXAMPLE 10

Adenovirus-Mediated Gene Transfer to Kidney via Intravenous Infusion

This example describes the procedure for slowly infusing a recombinant adenovirus into the renal circulation. Male Sprague-Dawley rats (100-150 g) were injected intramuscularly with 20,000 units of penicillin, anesthetized with ketamine (70 mg/kg, ip) and xylazine (7 mg/kg, ip) and underwent surgical exposure of the right kidney, the aorta and the right renal blood vessels. The right renal blood flow was interrupted by clamping the aorta above and below the right renal artery and the superior mesenteric artery (SMA). This setting selectively excluded the right kidney without interrupting the blood circulation through the left kidney and allowed infusion of virus into the right kidney through the SMA. A 27-gauge winged infusion needle was inserted into the SMA and fixed in place with a microaneurism clamp. 1.5 ml of recombinant adenovirus in phosphate buffered saline (PBS) containing 5 units of heparin/ml were slowly infused into the right kidney with a Razel A-99 syringe pump at a flow rate of 0.1 ml/min. The right kidney was packed with ice during the infusion to minimize ischemic damage. Renal circulation was reestablished at the end of infusion. The abdominal cavity was closed with sutures. The animal was placed on a warm pad to recover from the anesthesia and was returned to its cage after recovery.

EXAMPLE 11

Adenovirus-Mediated Gene Transfer to Kidney via Balloon Catheter

In this application, a catheter is inserted in a vein near or in the kidney. Both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 12

In Vivo Treatment with Virus Containing Stent

In this application, a virus-coated stent is placed at a treatment site in or near the kidney. Alternatively, the virus may be embedded in the stent and is releases gradually through a time-releasing mechanism well-known to one skilled in the art.

EXAMPLE 13

Construction of Gutless Adenovirus Vectors Carrying the IDO Gene

Rat and human IDO cDNA were amplified by RT-PCR using the following set of primers:

```
Forward primer
(containing a FseI restriction site):
                                        (SEQ ID NO: 17)
5'-TATTTATTGGCCGGCCGCGTTAAGATACATTGATGAG-3'

Reverse primer
(containing a SbfI restriction site):
                                        (SEQ ID NO: 18)
5'-TATTTATTCCTGCAGGTCGTAGGTCAAGGTAGTAGA-3'.
```

The amplified rat IDO cDNA (SEQ ID NO:19) and human IDO cDNA (SEQ ID NO:20) were cloned into expression plasmids pAdTrackCMV-rIDO and pAdTrackCMV-hIDO, respectively.

Expression cassettes comprising a CMV promoter, IDO cDNA and poly-adenylation signal were constructed using PCR. PCR primers were equipped with additional restriction enzyme sites to facilitate cloning into the gutless backbone vector.

```
Forward primer
(containing a FseI restriction site):
                                        (SEQ ID NO: 17)
tatttattggccggcCGCGTTAAGATACATTGATGAG Reverse primer
(containing a SbfI restriction site):
                                        (SEQ ID NO: 18)
tatttattcctgcaggTCGTAGGTCAAGGTAGTAGA
```

Figure 10:
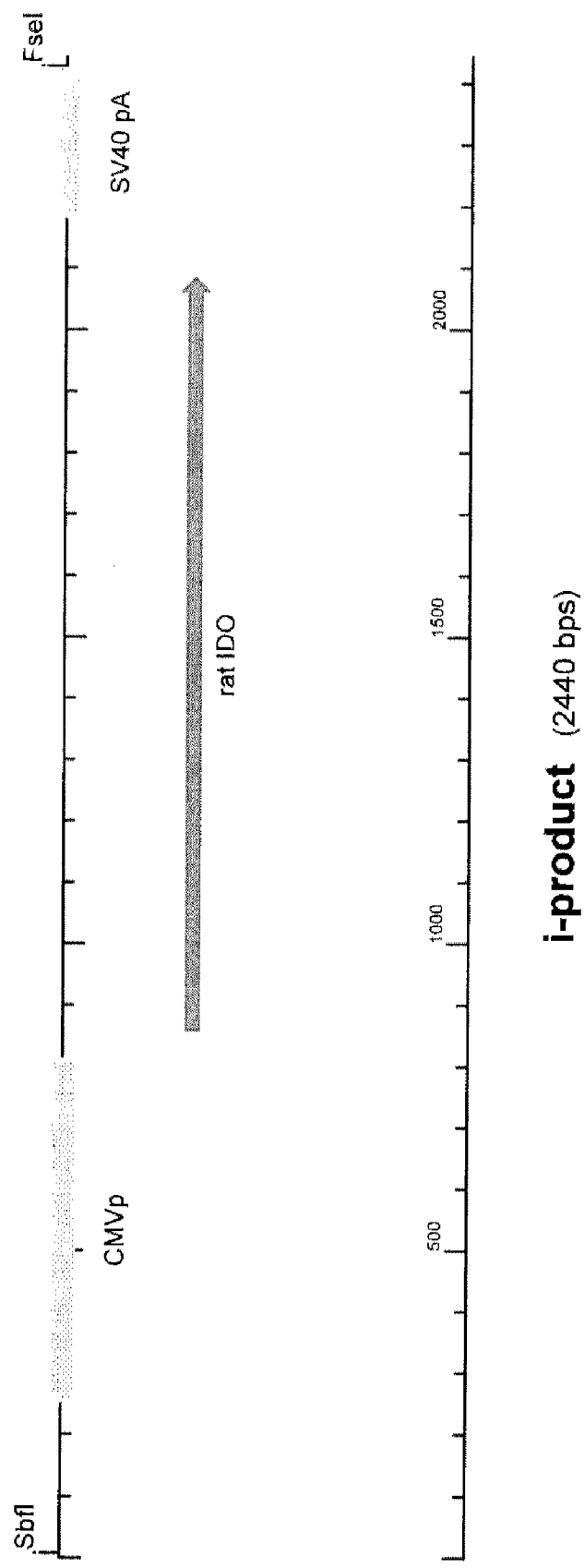
FIG. 10 is a schematic drawing of an embodiment of the rat IDO expression cassette.
Figure 11:
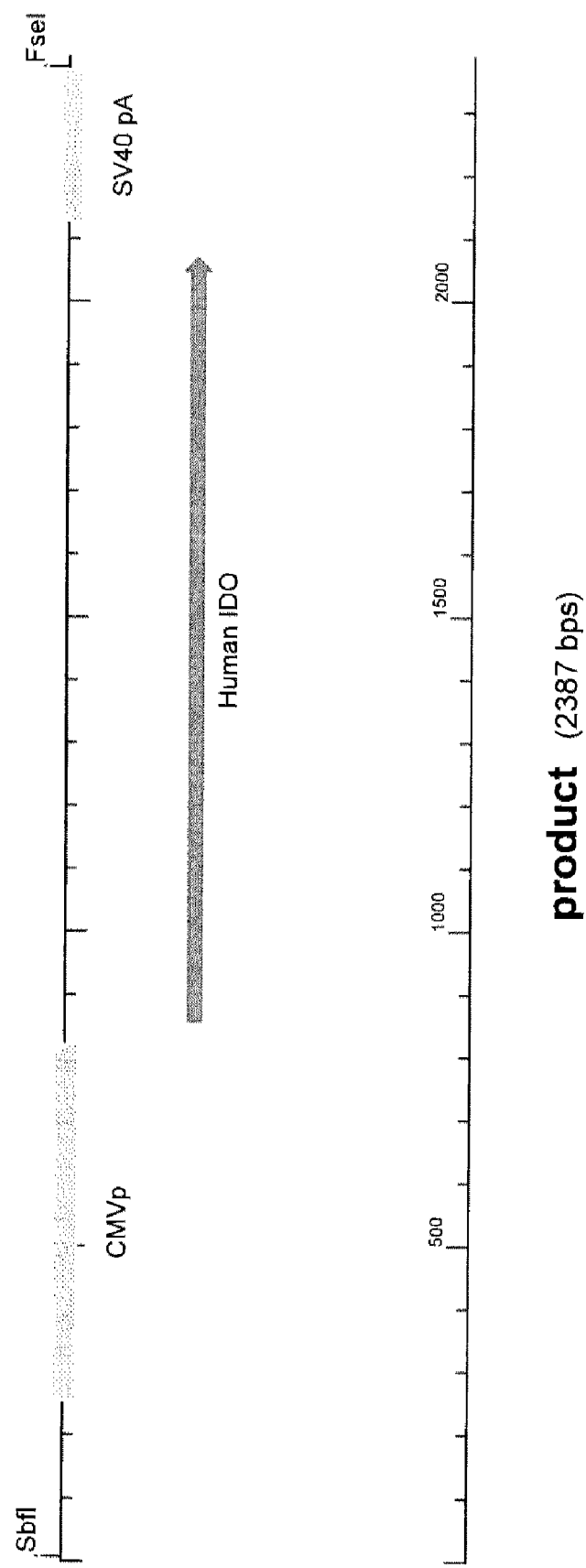
FIG. 11 is a schematic drawing of an embodiment of the human IDO expression cassette.

The resulting PCR fragments were cloned into pGEM-T-EASY for sequencing and cloning. Sequencing confirmed the presence of rat IDO expression cassette (FIG. 10, SEQ ID NO:21) and human IDO expression cassette (FIG. 11, SEQ ID NO:22).

Figure 12:
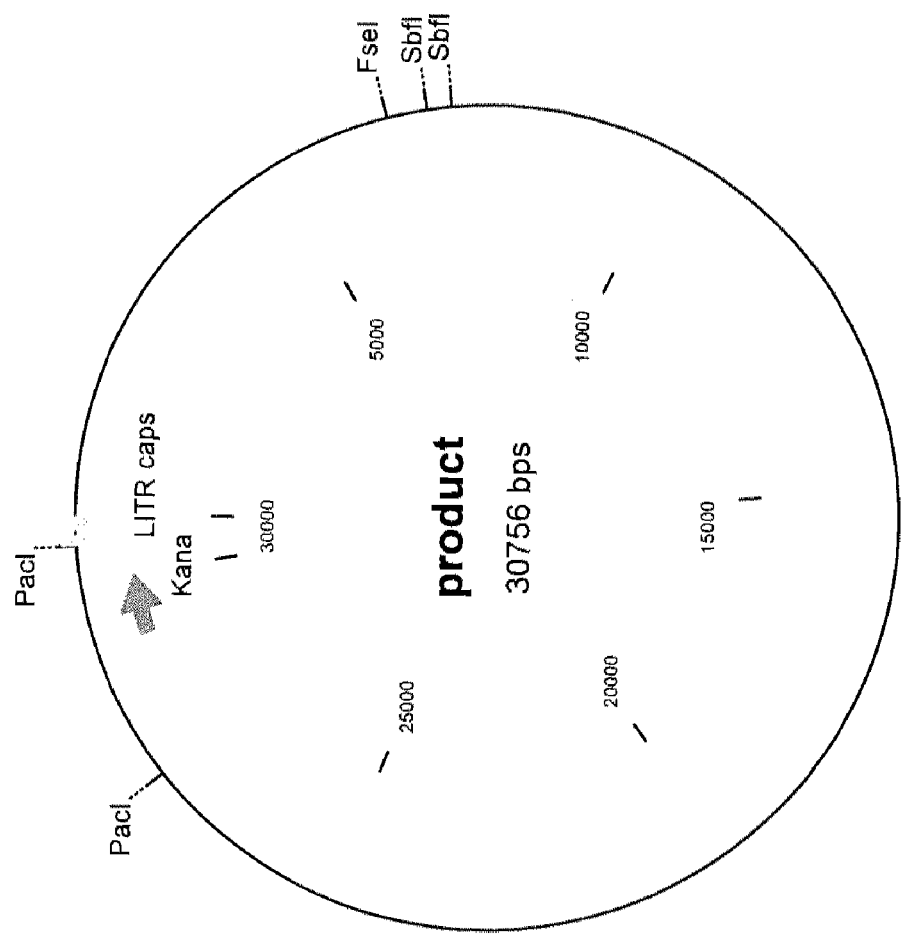
FIG. 12 is a schematic drawing of a gutless backbone vector.
Figure 13:
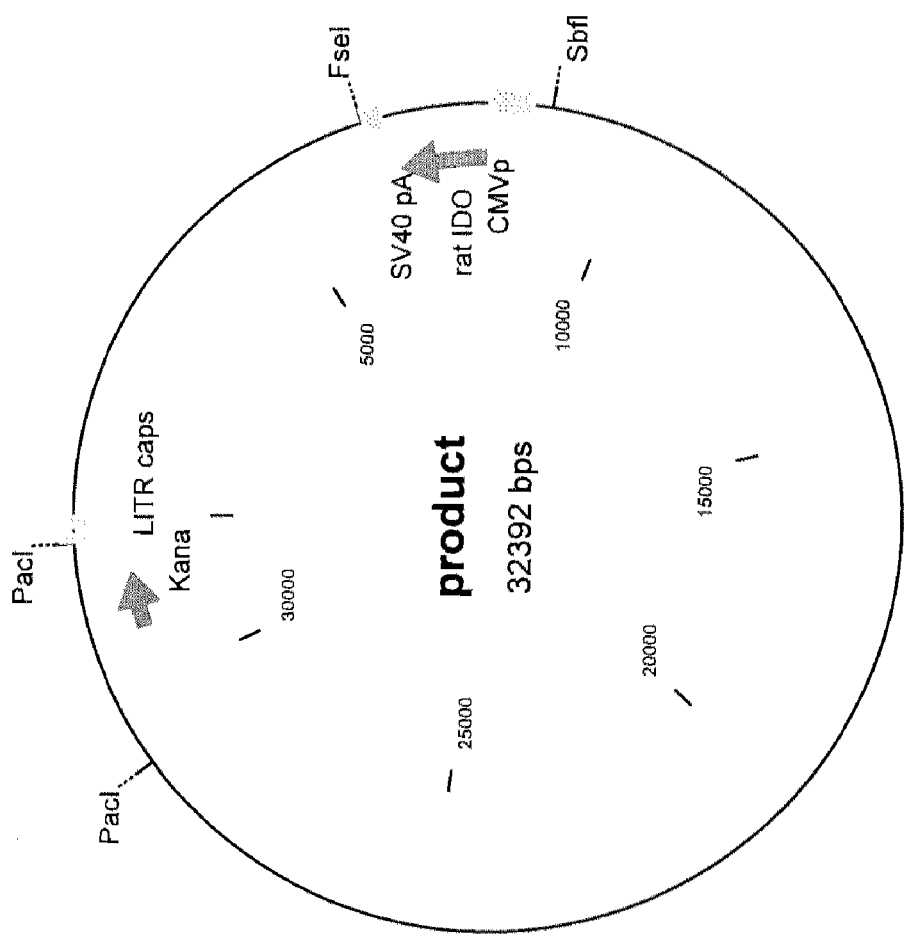
FIG. 13 is a schematic drawing of an embodiment of the rat gutless IDO backbone vector.
Figure 14:
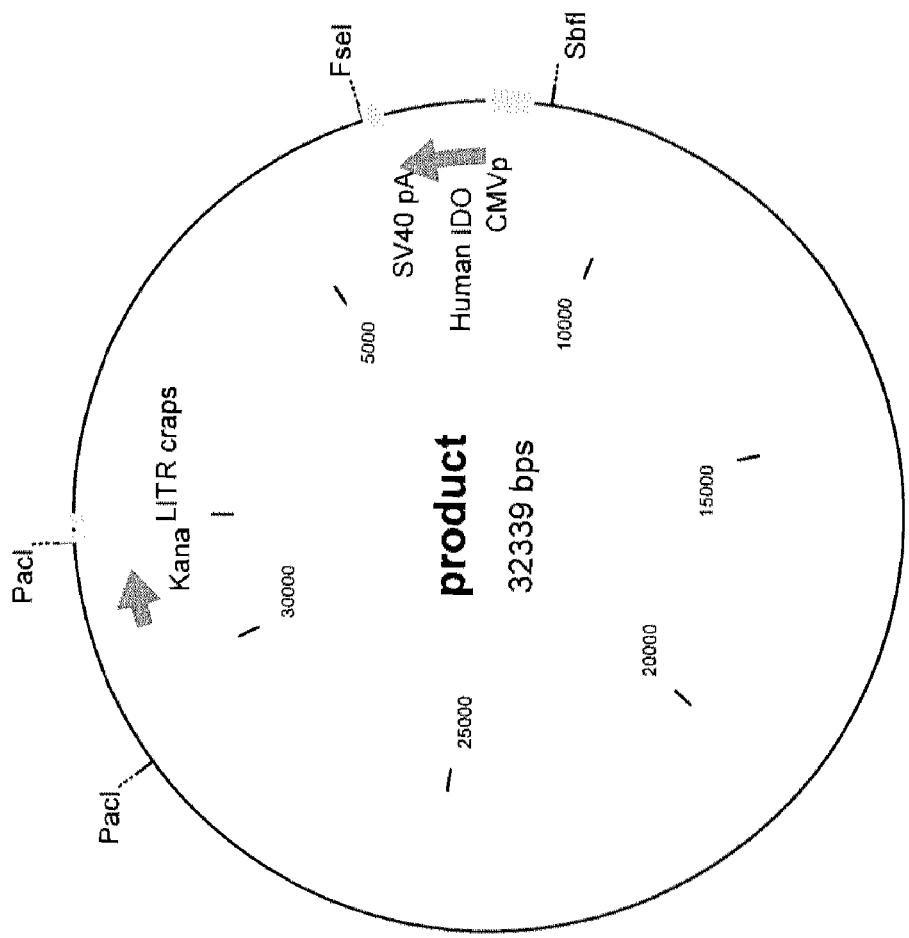
FIG. 14 is a schematic drawing of an embodiment of the human gutless IDO backbone vector.

The gutless backbone (SEQ ID NO:23, FIG. 12) was cut with SbfI and FseI to release the TM expression cassette. The backbone was subsequently dephosphorylated to prevent vector self-ligation. Rat and human IDO expression cassettes were released from pGEM-T-Easy by digestion with FseI and SbfI and ligated into the FseI and SbfI sites of the gutless backbone. The resulting constructs prIDO-final (FIG. 13, SEQ ID NO:24) and phIDO-final (FIG. 14, SEQ ID NO:25) were cloned in *E-coli* DH5α. DNA midipreps were generated for the production of high quality plasmid DNA. Gutless adenovirus containing rat IDO or human IDO was produced using the procedure described in Example 3.

EXAMPLE 14

Perfusion of Kidney Transplant with Gutless Adenovirus Vectors Carrying the IDO Gene The experiment was carried out in Fisher-Lewis kidney transplantation model. Gutless adenoviruses carrying the IDO gene (Ad.TIDO) or luciferase gene (Ad.TL) were surface-modified with cyclic arginine-glycine-aspartic acid (RGD) peptides through a bifunctional poly(ethyleneglycol) linker for integrin alpha(v)beta(3) specific delivery. The resulting RGD modified viruses were designated RGD-Ad.TIDO and Ad.TL. The transplanted kidneys were incubated with either RGD-AdTIDO (n=6) or RGD-AdTL (n=5) at 4° C. for 20 min with saline. The transplanted animals were sacrificed at day 7. The transplanted kidneys were isolated and subjected to Western blot and immunohistological examination.

Figure 15:
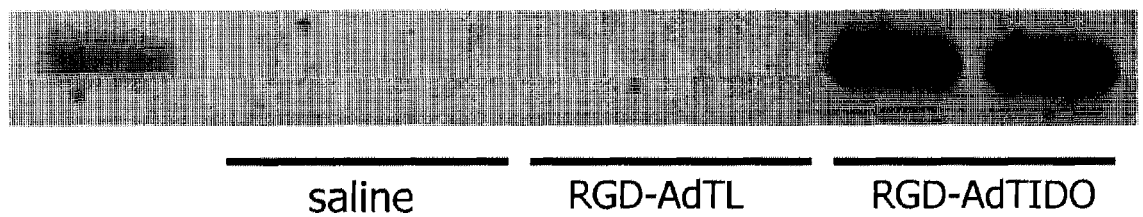
FIG. 15 is a picture of a Western blot showing gutless adenovirus mediated IDO expression in transplanted kidney (lane 1=hIDO control, other lanes as indicated)
Figure 16A:
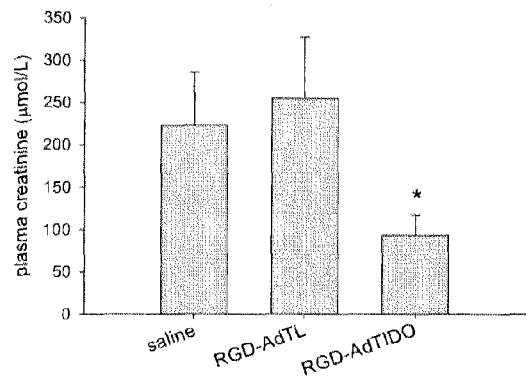
FIG. 16 is a composite of graphs showing reduction of plasma creatinin levels (panel A), ED-1 staining (panel B), CD8 staining (panel C) and smooth muscle actin score (panel D) in kidney tissue infected by gutless adenovirus carrying the IDO gene.
Figure 16B:
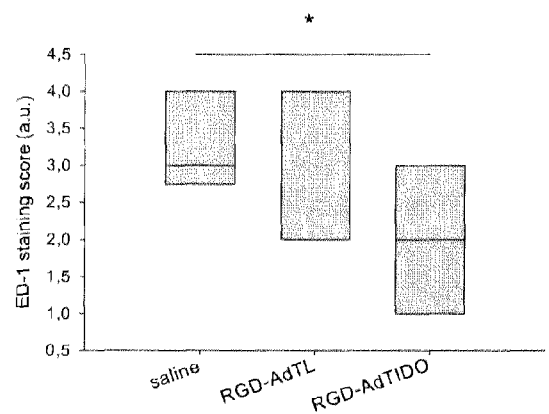
Figure 16C:
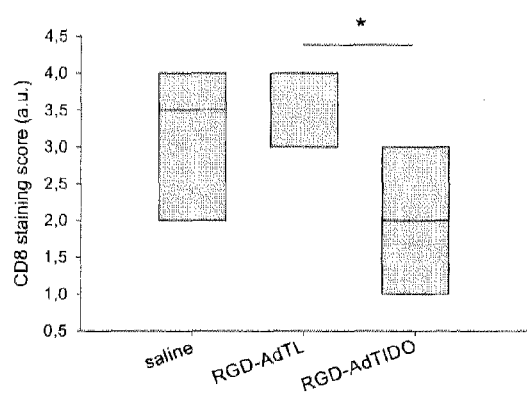
Figure 16D:
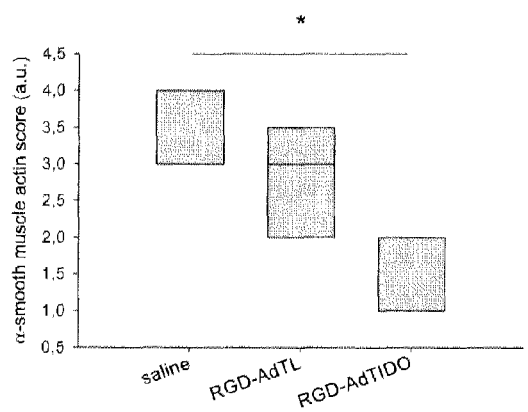

As shown in FIG. 15, IDO expression was detected in the kidneys infected with RGD-AdTIDO but not in kidneys infected with RGD-AdTL. FIGS. 16A-16D shows that, comparing to kidneys perfused with saline or control virus (RGD-AdTL), kidneys infected with RGD-AdTIDO showed reduced plasma creatinin levels (FIG. 16A). Kidneys infected with RGD-AdTIDO also showed reduced tissue damage, as evidenced by the reduced ED-1 staining (FIG. 16B), reduced macrophage influx (FIG. 16C, CD-8 staining for T-lymphocytes), and reduced fibrotic response (FIG. 16D, staining for smooth muscle actin).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

LIST OF THE SEQUENCES

SEQ ID NO:1 (pShuttle-ITR/HPRT)
SEQ ID NO:2 (human TM amino acid sequence)
SEQ ID NO:3 (human TM nucleotide sequence)
SEQ ID NO:4 (CMV promoter)
SEQ ID NO:5 (hTM cDNA)
SEQ ID NO:6 (CMV-hTM expression cassette)
SEQ ID NO:7 (pTMadap)
SEQ ID NO:8 (BstII linker)
SEQ ID NO:9 (SfiI linker)
SEQ ID NO:10 (Forward PCR primer)
SEQ ID NO:11 (Reverse PCR primer)
SEQ ID NO:12 (Stuffer1)
SEQ ID NO: 13 (Stuffer 1-Short)
SEQ ID NO:14 (p2-2)
SEQ ID NO:15 (Stuffer 2)
SEQ ID NO:16 (pTM-final)
SEQ ID NO: 17: IDO RT-PCR forward primer (containing a FseI restriction site)
SEQ ID NO: 18: IDO RT-PCR reverse primer (containing a SbtI restriction site)
SEQ ID NO:19: rat IDO cDNA
SEQ ID NO:20: human IDO cDNA
SEQ ID NO:21: rat IDO expression cassette SEQ ID NO:22: human IDO expression cassette
SEQ ID NO:23: gutless backbone vector
SEQ ID NO:24: prIDO-final
SEQ ID NO:25: phIDO-final

What is claimed is:

1. A gutless adenovirus vector, comprising
a polynucleotide encoding a therapeutic agent;
a renal-specific regulatory element operably linked to said polynucleotide sequence; and
a stuffer comprising the nucleotide sequence of SEQ ID NO:13 or SEQ ID NO:15,
wherein said therapeutic agent is thrombomodulin.

2. The gutless adenovirus vector of claim 1, wherein said renal-specific regulatory element is selected from the group consisting of high-capacity (type 2) Na$^+$/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

3. The gutless adenovirus vector of claim 1, wherein said stuffer comprises the nucleotide sequences of SEQ ID NO:13 and SEQ ID NO:15.

4. The gutless adenovirus vector of claim 1, wherein said thrombomodulin is human thrombomodulin or a variant thereof.

5. The gutless adenovirus vector of claim 4, wherein said thrombomodulin is human thrombomodulin.

6. The gutless adenovirus vector of claim 2, wherein said renal-specific regulatory element is high-capacity (type 2) Na$^+$/glucose cotransporter gene (Sglt2) promoter.

7. The gutless adenovirus vector of claim 2, wherein said renal-specific regulatory element is Ksp-cadherin promoter.

8. The gutless adenovirus vector of claim 2, wherein said renal-specific regulatory element is ClC-K1 chloride channel gene promoter.

9. The gutless adenovirus vector of claim 2, wherein said renal-specific regulatory element is uromodulin promoter.

10. The gutless adenovirus vector of claim 2, wherein said renal-specific regulatory element is Nkcc2/Slc12a1 gene promoter.

11. The gutless adenovirus vector of claim 2, wherein said renal-specific regulatory element is the p1 promoter of the parathyroid hormone (PTH)/PTH-related peptide receptor gene.

* * * * *